United States Patent
Hutchinson et al.

(10) Patent No.: US 7,671,190 B2
(45) Date of Patent: Mar. 2, 2010

(54) RECOMBINANT POLYNUCLEOTIDES ENCODING PRO-GELDANAMYCIN PRODUCING POLYKETIDE SYNTHASES AND ACCESSORY PROTEINS, AND USES THEREOF

(75) Inventors: Richard C. Hutchinson, San Mateo, CA (US); Ralph C. Reid, San Rafael, CA (US); Zhihao Hu, Castro Valley, CA (US); Andreas Rascher, San Francisco, CA (US); Andreas Schirmer, Hayward, CA (US); Robert McDaniel, Palo Alto, CA (US)

(73) Assignee: Kosan Biosciences Incorporation, Princeton, NJ (US)

( * ) Notice: Subject to any disclaimer, the term of this patent is extended or adjusted under 35 U.S.C. 154(b) by 520 days.

(21) Appl. No.: 11/654,485

(22) Filed: Jan. 16, 2007

(65) Prior Publication Data

US 2007/0269855 A1    Nov. 22, 2007

Related U.S. Application Data

(63) Continuation of application No. 10/461,194, filed on Jun. 13, 2003, now Pat. No. 7,189,549, which is a continuation-in-part of application No. 10/212,962, filed on Aug. 5, 2002, now Pat. No. 6,872,715.

(60) Provisional application No. 60/389,255, filed on Jun. 14, 2002, provisional application No. 60/393,929, filed on Jul. 3, 2002, provisional application No. 60/395,275, filed on Jul. 12, 2002, provisional application No. 60/415,326, filed on Sep. 30, 2002, provisional application No. 60/420,820, filed on Oct. 24, 2002, provisional application No. 60/433,130, filed on Dec. 13, 2002.

(51) Int. Cl.
C12N 15/53 (2006.01)
C12N 15/74 (2006.01)
C12N 15/76 (2006.01)
C12N 15/31 (2006.01)
C12N 9/06 (2006.01)

(52) U.S. Cl. ............... 536/23.2; 435/189; 435/69.1; 435/252.3; 435/252.35; 435/320.1; 536/24.32

(58) Field of Classification Search .................. None
See application file for complete search history.

(56) References Cited

U.S. PATENT DOCUMENTS 6,495,348 B1 * 12/2002 Sherman et al. ............... 435/76

(Continued)

FOREIGN PATENT DOCUMENTS

WO    WO 97/02358 A1 *  1/1997

(Continued)

OTHER PUBLICATIONS

Deboer et al., "Geldanamycin, a new antibiotic," The Journal of Antibiotics, 23: 442-447 (1970).*

(Continued)

Primary Examiner—Anand U Desai
Assistant Examiner—William W Moore
(74) Attorney, Agent, or Firm—Stephen C. D'Amico

(57) ABSTRACT

The invention relates to recombinant polyketide synthase enzymes, polyketide modifying proteins, and other proteins involved in polyketide biosynthesis or function. The invention provides domains of geldanamycin and herbimycin polyketide synthases, polynucleotides that encode such enzymes, and to host cells in which such encoding polynucleotides can be advantageously expressed.

10 Claims, 11 Drawing Sheets

U.S. PATENT DOCUMENTS

| | | | |
|---|---|---|---|
| 6,872,715 B2 * | 3/2005 | Santi et al. | 514/183 |
| 7,189,549 B2 * | 3/2007 | Hutchinson et al. | 435/190 |
| 2006/0084141 A1 * | 4/2006 | Floss et al. | 435/69.1 |
| 2008/0188450 A1 | 8/2008 | Ashley et al. | |

FOREIGN PATENT DOCUMENTS

| | | | |
|---|---|---|---|
| WO | WO 03/013430 A2 * | 2/2003 | |
| WO | WO 98/49315 A2 * | 2/2003 | |
| WO | 2006069610 A2 | 7/2006 | |
| WO | 2007087815 A2 | 8/2007 | |

OTHER PUBLICATIONS

Deboer et al., "The description and antibiotic production of *Streptomyces hygoscopicus* var *geldanus*," The Journal of Antibiotics, 29: 1182-1188 (1976).*

Omura et al., "Herbimycin, a new antibiotic produced by a strain of*Streptomyces*," The Journal of Antibiotics, 32: 255-261 (1979).*

McDaniel et al., "Engineered biosynthesis of novel polyketides," Science, 262: 1546-1550 (1993).*

Allen et al., "Cloning and analysis of DNA sequences from *Streptomyces hygroscopicus* encoding geldanamycin biosynthesis," Molecular and General Genetics, 243(5): 593-599 (1994).*

Kim et al., "3-Amino-5-hydroxybenzoic acid synthase, the terminal enzyme in the formation of the precursor of mC7N units in rifamycin and related antibiotics," The Journal of Biological Chemistry, 273: 6030-6040 (1998).*

August et al., "Biosynthesis of the ansamycin antibiotic rifamycin: deductions from the molecular analysis of the rif biosynthetic gene cluster of *Amycolatopsis mediterranei* S699," Chemistry & Biology, 5: 69-79 (1998).*

Eads et al., "Crystal Structure of 3-amino-5-hydroxybenzoic acid (AHBA) synthase", Biochemistry, 38: 9840-9849.*

Chen et al., "Biosynthesis of ansatrienin (mycotrienin) and naphthomycin. Identification and analysis of two separate biosynthetic gene clusters in *Streptomyces collinus* Tu1892," European Journal of Biochemistry, 261: 98-107 (1999).*

Yu et al., "The biosynthetic gene cluster of the maytansinoid antitumor agent ansamitocin from *Actinosynnema pretiosum*," PNAS, USA, 99: 7968-7973 (2002).*

Rascher et al., "Links Cloning and characterization of a gene cluster for geldanamycin production in *Streptomyces hygroscopicus* NRRL 3602," FEMS Microbiol. Lett., 218(2): 223-230 (2003).*

* cited by examiner

Geldanamycin

Reblastatin

Herbimycin A ($R_1$=OCH$_3$, $R_2$=CH$_3$)
Herbimycin C ($R_1$=OCH$_3$, $R_2$=H)
Macbecin I ($R_1$=CH$_3$, $R_2$=CH$_3$)
Macbecin II = Macbecin I hydroquinone Herbimycin B

TAN 420A

Ansamitocins
($R_1$=esters)

RECOMBINANT POLYNUCLEOTIDES ENCODING PRO-GELDANAMYCIN PRODUCING POLYKETIDE SYNTHASES AND ACCESSORY PROTEINS, AND USES THEREOF

CROSS REFERENCE TO RELATED APPLICATIONS

This application claims the benefit of U.S. provisional patent application Nos. 60/389,255 (filed Jun. 14, 2002), 60/393,929 (filed Jul. 3, 2002), 60/395,275 (filed Jul. 12, 2002), 60/415,326 (filed Sep. 30, 2002), 60/420,820 (filed Oct. 24, 2002), 60/433,130 (filed Dec. 13, 2002), and is a Continuation-in-Part of U.S. patent application Ser. No. 10/212,962 (filed Aug. 5, 2002). The entire contents of each of these applications is incorporated herein by reference.

STATEMENT OF GOVERNMENT INTEREST

This invention was made in part with government support under SBIR Grant no. 1 R43 CA/GM96262-01, awarded by the National Institutes of Health, Department of Health and Human Services. The United States government may have certain rights in the invention.

REFERENCE TO SEQUENCE LISTING

The appended sequence listing is part of, and incorporated into, the specification.

FIELD OF THE INVENTION

The present invention relates to the fields of molecular biology, chemistry, recombinant DNA technology, medicine, animal health, and agriculture.

BACKGROUND OF THE INVENTION

Polyketides represent a large family of diverse compounds synthesized from 2 carbon units through a series of condensations and subsequent modifications. Polyketides occur in many types of organisms including fungi and mycelial bacteria, in particular the actinomycetes. An appreciation for the wide variety of polyketide structures and for their biological activities may be gained upon review of the extensive art, for example, published International Patent Specification WO 95/08548; U.S. Pat. Nos. 5,672,491 and 6,303,342; Fu et al., 1994, *Biochemistry*, 33:9321-26; McDaniel et al., 1993, *Science*, 262:1546-50; and Rohr, 1995, *Angew. Chem. Int. Ed. Engl.* 34:881-88.

Polyketides are synthesized in nature by polyketide synthases ("PKS"). These synthase enzymes are complexes of multiple enzyme activities. Two major types of PKS are known and differ in their mode of synthesis. These are commonly referred to as Type I or "modular" and Type II "iterative." The Type I or modular PKSs, as commonly found in bacteria but not in fungi, comprise a set of separate catalytic active sites; the portion of the protein that encompasses each active site region is termed a "domain", and a set thereof is termed a "module". One module exists for each cycle of carbon chain elongation and modification. FIG. 9 of aforementioned WO95/08548 depicts a typical Type I PKS, in this case 6-deoxyerythronolide B synthase ("DEBS") which is involved in the production of erythromycin. Six separate modules, each catalyzing a round of condensation and modification of a 3-carbon unit, are present in DEBS. The number and type of catalytic domains that are present in each module varies based on the needed chemistry, and the total of 6 modules is provided on 3 separate polypeptides (designated DEBS-1, DEBS-2, and DEBS-3, with 2 modules per each polypeptide). Each of the DEBS polypeptides is encoded by a separate open reading frame (gene), see Caffrey et al., 1992, *FEBS Letters*, 304:205. DEBS provides a representative example of a modular Type I PKS. In DEBS, modules 1 and 2 reside on DEBS-1, modules 3 and 4 on DEBS-2, and modules 5 and 6 on DEBS-3, wherein module 1 is defined as the first module to act on the growing polyketide backbone, and module 6 the last.

The minimal PKS module is typified by module 3 of DEBS which contains a ketosynthase ("KS") domain, an acyltransferase ("AT") domain, and an acyl carrier protein ("ACP") domain. These three enzyme activities are sufficient to activate a 2, 3, or more -carbon extender unit and attach it to the growing polyketide molecule. Additional domains that may be included in a module relate to reactions other than the actual condensation, and include domains for a ketoreductase activity ("KR"), a dehydratase activity ("DH"), and an enoylreductase activity ("ER") and a methyltransferases activity. With respect to DEBS-1, the first module thereof also contains additional AT and ACP domains because that module catalyzes the initial condensation, and so begins with a "loading di domain" (sometimes referred to as a loading module) that contains an AT and ACP, that bind the starter unit. The "finishing" of the 6-deoxyerythronolide molecule is regulated by a thioesterase activity ("TE") in module 6 that catalyzes cyclization of the macrolide ring during release of the product of the PKS.

In PKS polypeptides, the regions that encode enzymatic activities (domains) are separated by linker or "scaffold"-encoding regions. These scaffold regions encode amino acid sequences that space the enzymatic activities (domains) at the appropriate distances and assure the correct order of modules in the PKS. Thus, these linker regions collectively can be considered to encode a scaffold into which the various domains (and thus modules) are placed in a particular order and spatial arrangement. Generally, this organization permits PKS domains of different or identical substrate specificities to be substituted (usually at the level of encoding DNA) from other PKS by various available methodologies. Thus, there is considerable flexibility in the design of a new PKS to produce a novel polyketide. An additional level of structural complexity in the resultant polyketides may be introduced by subsequent P450 oxidation, methylation, glycosylation or other enzymes that catalyze post-PKS reactions.

Geldanamycin is a polyketide produced by a modular PKS and was the first of four benzoquinone ansamycins isolated from microorganisms (see FIG. 1) to have been evaluated extensively as an antitumor drug. Although originally discovered by screening microbial extracts for antibacterial and antiviral activity [DeBoer, et al. (1970), Sasaki, et al. (1970); full citations of all references cited herein by the author and year of publication are provided below], geldanamycin was later found to be cytotoxic to tumor cells in vitro [Sasaki et al. (1979)] and to reverse the morphology of cells transformed by the Rous sarcoma virus to the normal state [Uehara et al. (1986)]. Subsequent discoveries of the herbimycins [Omura et al. (1979)], macbecins [Muroi et al. (1980)] and TAN 420A [Shibata et al. (1986)] expanded this class of antitumor natural products. Ansamycins like the ansamitocins are usually included in this class of microbial products. Reblastatin, isolated from the geldanamycin producer, was recently found to have interesting biological activities [Takatsu et al. (2000), Stead et al. (2001)].

Geldanamycin's nanomolar potency and apparent specificity for aberrant protein kinase dependent tumor cells, as well as the discovery that its primary target in mammalian cells is the ubiquitous Hsp90 protein chaperone, has stimulated interest in its development as an antitumor drug [Neckers et al. (2002); Blagosklonny, 2002]. Severe hepatotoxicity [Supko et al. (1995)] led to its withdrawal from Phase I clinical trials in 1995. Nonetheless, during the 1990's considerable information was obtained about the structure-activity relationships (SAR) of geldanamycin, herbimycin and reblastatin [Neckers et al. (2002), Schnur et al. (1995)]. In late 1999, 17-allylamino-17-desmethoxygeldanamycin entered Phase I clinical trials [Egorin et al. (2001), Wilson et al. (2001), Erlichman et al. (2001)] sponsored by the National Cancer Institute in the US and the Cancer Research Campaign in the UK because this analog had exhibited good in vivo activity [Wilson, et al. (2001), Erlichman, et al. (2001)], better pharmacokinetics and lower toxicity than geldanamycin [Egorin et al. (2001)] during preclinical development. The maximum tolerated dose is 40 mg/m$^2$ [Wilson et al. (2001)], and micromolar serum concentrations are achieved without overt toxicity. Efficacy in inhibiting signal transduction pathways has been demonstrated in peripheral blood lymphocytes.

There is therefore a need for recombinant nucleic acids, host cells, and methods of expressing those nucleic acids in host cells to produce geldanamycin at a commercially useful scale and to make geldanamycin analogs. These and other needs are met by the materials and methods provided by the present invention.

The following articles provide additional background information relating to the invention and are incorporated herein by reference. DeBoer et al. "Geldanamycin, a new antibiotic" *J Antibiot (Tokyo)* (1970) 23:442-7. Sasaki et al. "Geldanamycin. I. Structure assignment" *J Am Chem Soc* (1970) 92:7591-3. Blagosklonny, 2002, "Hsp-90-associated oncoproteins: multiple targets of geldanamycin and its analogs" *Leukemia* 16:455-62. Sasaki et al. "Growth inhibition of virus transformed cells in vitro and antitumor activity in vivo of geldanamycin and its derivatives" *J Antibiot (Tokyo)* (1979) 32:849-51. Uehara et al. "Phenotypic change from transformed to normal induced by benzoquinonoid ansamycins accompanies inactivation of p60src in rat kidney cells infected with Rous sarcoma virus" *Mol Cell Biol* (1986) 6:2198-206. Omura et al. "Herbimycin, a new antibiotic produced by a strain of *Streptomyces*." *J Antibiot (Tokyo)* (1979) 32:255-61. Iwai et al. "Herbimycin B, a new benzoquinonoid ansamycin with anti-TMV and herbicidal activities" *J. Antibiot (Tokyo)* (1980) 33:1114-9. Muroi et al. "Macbecins I and II, new antitumor antibiotics. II. Isolation and characterization" *J Antibiot (Tokyo)* (1980) 33:205-12. Shibata et al. "The structure and cytocidal activity of herbimycin C." *J Antibiot (Tokyo)* (1986) 39:1630-3. Takatsu et al. "Eblastatin, a novel benzenoid ansamycin-type cell cycle inhibitor." *J. Antibiot.* (2000) 53:1310-1312. Stead et al. "Discovery of novel ansamycins possessing potent inhibitory activity in a cell-based oncostatin M signalling assay. *J. Antibiot (Tokyo)* 53:657-663. Neckers, L. "Hsp90 inhibitors as novel cancer chemotherapy agents." *Tr. Molec. Med.* (2002) 8:S55-S61. Supko et al. "Preclinical pharmacologic evaluation of geldanamycin as an antitumor agent." *Cancer Chemother Pharmacol* (1995) 36:305-15. Schnur, et al. "erbB-2 Oncogene inhibition by geldanamycin derivatives: synthesis, mechanism of action, and structure-activity relationships." *J. Med. Chem.* (1995) 38:3813-20. Egorinet et al. "Plasma pharmacokinetics and tissue distribution of 17-(allylamino)-17-demethoxygeldanamycin (NSC 330507) in CD2F1 mice." *Cancer Chemother Pharmacol* (2001) 47:291-302. Wilson et al. "Phase I pharmacologic study of 17-AAG in adult patients with advanced solid tumors." *Amer Soc of Clin Oncol*, (2001) Abstract 325; Erlichman et al. "A phase I trial of 17-AAG in patients with advanced cancer." *Proceedings of the AACR* (2001) Abstract. Guo J, Frost J W. "Biosynthesis of 1-deoxy-1-imino-D-erythrose 4-phosphate: (2002). A defining metabolite in the aminoshikimate pathway." (2002) *J Am Chem Soc.* 124, 528-9. Yu et al. (2002). "The biosynthetic gene cluster of the maytansinoid antitumor agent ansamitocin from *Actinosynnema pretiosum*." *Proc Natl Acad Sci USA.* 99, 7968-73. August et al. (1998). "Biosynthesis of the ansamycin antibiotic rifamycin: deductions from the molecular analysis of the rif biosynthetic gene cluster of *Amycolatopsis mediterranei* S699." *Chem Biol* 5, 69-79; Leistner E (1999). "Biosynthesis of ansatrienin (mycotrienin) and naphthomycin. Identification and analysis of two separate biosynthetic gene clusters in *Streptomyces collinus* Tu1892." *Eur J Biochem* 261, 98-107; DeBoer C, Dietz A. (1976). "The description and antibiotic production of *Streptomyces hygoscopicus* var. *geldanus*." *J Antibiot* 29, 1182-8. Kunkel, T. A. *Proc Natl Acad Sci USA* (1985) 82:448. Geisselsoder et al. *BioTechniques* (1987) 5:786. Zoller and Smith, *Methods in Enzymology* (1983) 100:468. Dalbie-McFarland et al. *Proc Natl Acad Sci USA* (1982) 79:6409.

SUMMARY OF THE INVENTION

In one aspect, the invention relates to polyketide synthases (PKSs) that produce progeldanamycin, and polynucleotides encoding domains, modules and proteins of such synthases. The structure, sequences and characteristics of the geldanamycin PKS gene cluster and herbimycin PKS gene cluster are disclosed, along with other genes and proteins that participate in polyketide biosynthesis or have other functions. The geldanamycin PKS gene cluster was cloned from *S. hygroscopicus* var. *geldanus* NRRL 3602 and, in one embodiment of the invention, is encoded in SEQ ID NO:1. The herbimycin PKS gene cluster sequence was cloned from *S. hygroscopicus* AM-3672 and, in one embodiment of the invention, is encoded in SEQ ID NO:2.

In one aspect, the invention provides a method of producing a polyketide by culturing a cell under conditions under which the cell produces the polyketide, wherein the cell comprises a recombinant polynucleotide that hybridises under stringent conditions to the polyketide synthase-encoding region of SEQ ID NO:1 and/or SEQ ID NO:2 and encodes at least one core polyketide synthase protein, and where the cell is unable to make the polyketide in the absence of the recombinant polynucleotide. The recombinant polynucleotide can be an expression vector. In one embodiment the polyketide is pro-geldanamycin, and in related embodiments the cell produces geldanamycin or herbimycin. In one embodiment, the cell is not a *Streptomyces* cell. In a related aspect, the invention provides a recombinant host cell (e.g., which may be a other than a *Streptomyces* cell) comprising one or more expression vectors that drive expression of polyketide synthase enzymes capable of making pro-geldanamycin in the cell, where the host cell produces progeldanamycin and where the host cell does not produce progeldanamycin in the absence of the expression vector(s).

In another aspect the invention provides a recombinant DNA molecule encoding a domain of a geldanamycin polyketide synthase (PKS) or a herbimycin PKS. In one embodiment, the recombinant DNA molecule encodes one or more modules or polypeptides (open reading frames) of a chimeric PKS. The recombinant DNA molecule can encode a module of geldanamycin PKS and may comprise one or more open reading frames (ORFs) selected from gdmAI, gdmAII and gdmAIII. In an embodiment, the recombinant DNA molecule differs from the corresponding region of native geldanamycin PKS by inactivation of at least one geldanamycin PKS domain. The recombinant DNA molecule can encode a module of a herbimycin PKS and may comprise one or more ORFs selected from hbmAI, hbmAII and hbmAIII. In an embodiment, the recombinant DNA molecule differs from the corresponding region of native herbimycin PKS by inactivation of at least one herbimycin PKS domain. In one embodiment, the recombinant DNA molecule hybridizes under stringent conditions to a nucleic acid having a nucleotide sequence of SEQ. ID NO:1 and/or SEQ. ID NO:2. In related embodiments, a recombinant DNA expression vector comprising the DNA molecule operably linked to a promoter (which can be a promoter is derived from a cell other than *Streptomyces*) is provided.

In another aspects, a recombinant DNA molecule encoding a geldanamycin modification enzyme involved in the conversion of progeldanamycin to geldanamycin or a herbimycin modification enzyme involved in the conversion of proherbimycin to herbimycin is provided.

The invention also provides a host cell comprising a recombinant DNA molecule or vector described above or elsewhere herein. In one embodiment, the host cell is a *S. hygroscopicus* cell. In other embodiments, the host cell is not a *S. hygroscopicus* cell or is not an *S. hygroscopicus* var. *geldanus* NRRL 3602 cell.

The invention further provides a method of producing a polyketide by growing a host cell, as described above or elsewhere herein, under conditions where a polyketide synthesized by a PKS comprising a protein encoded by the recombinant DNA molecule is produced in the cell, optionally, recovering the synthesized polyketide, and optionally chemically modifying the polyketide and/or formulating the polyketide for administration to a mammal.

The invention further provides an isolated polypeptide encoded by a recombinant DNA molecule described above or elsewhere herein, as well as (1) a chimeric PKS that is composed of at least a portion of a geldanamycin PKS and at least a portion of a second PKS for a polyketide other than geldanamycin and (2) a chimeric PKS that is composed of at least a portion of a herbimycin PKS and at least a portion of a second PKS for a polyketide other than herbimycin. In one embodiment, the second PKS is from a narbonolide PKS, an oleandolide PKS, a DEBS PKS or a rapamycin PKS.

In another aspect, the invention provides a method of producing a polyketide comprising by recombinantly modifying a gene in the geldanamycin PKS gene cluster of a *Streptomyces* cell that comprises the gene cluster to produce a recombinant cell, or obtaining a progeny of the recombinant cell, and growing the recombinant cell or progeny under conditions whereby a polyketide other than geldanamycin is synthesized by the cell, optionally, recovering the synthesized polyketide and, optionally, chemically modifying the polyketide and/or formulating the polyketide for administration to a mammal. In one embodiment of this method, the cell is *S. hygroscopicus* var. *geldanus* NRRL 3602. In one embodiment the cell does not produce geldanamycin.

In another aspect, the invention provides a method of producing a polyketide by recombinantly modifying a gene in the herbimycin PKS gene cluster of a *Streptomyces* cell that comprises the gene cluster to produce a recombinant cell, or obtaining a progeny of the recombinant cell, and growing the recombinant cell or progeny under conditions whereby a polyketide other than herbimycin is synthesized by the cell, optionally, recovering the synthesized polyketide cell, and, optionally, chemically modifying the polyketide and/or formulating the polyketide for administration to a mammal. In one embodiment of this method, the cell is *S. hygroscopicus* AM-3672. In one embodiment the cell does not produce herbimycin.

In various embodiments of these methods, the modifying involves (1) substitution of a geldanamycin AT domain with an AT domain having a different specificity; (2) inactivation of a domain, wherein the domain is selected from the group consisting of a KS domain, an AT domain, an ACP domain, a KR domain, a DH domain, and an ER domain; and/or (3) substitution of KS domain, an ACP domain, a KR domain, a DH domain, or an ER domain with a domain having a different specificity.

In another aspect, the invention provides a recombinant DNA molecule comprising one or more open reading frames (ORFs) of SEQ ID NO:3 as well as a host cell comprising the DNA. In one embodiment, the ORF comprises basepairs 5263-6345; 6575-7270; 2427-3224; 1364-2413; 3397-3846; 4058-5224; and 428-1252. In a related embodiment, the invention provides a recombinant DNA expression vector comprising the above-described DNA molecule operably linked to a promoter as well as a host cell comprising the vector.

In one aspect, the present invention provides recombinant nucleic acids encoding polyketide synthases that produce geldanamycin or geldanamycin analogs in host cells.

In an embodiment of the present invention, there are provided polynucleotides that comprise a coding sequence for one or more domains of geldanamycin polyketide synthase. In another embodiment, the polynucleotide also comprises a coding sequence for one or more domains of another polyketide synthase. In another embodiment, a coding sequence for a domain (or portion thereof) of geldanamycin synthase is combined with coding sequence from another PKS to make a novel PKS that produces a polyketide. Expression of such DNAs, in suitable host cells leads to the production of synthases capable of producing useful polyketides.

Accordingly, there is provided a recombinant PKS wherein at least 10, 15, 20, or more consecutive amino acids in one or more domains of one or more modules thereof are derived from one or more domains of one or more modules of geldanamycin polyketide synthase. Preferably at least an entire domain of a module of geldanamycin synthase is included. Representative geldanamycin PKS domains useful in this aspect of the invention include, for example, KR, DH, ER, AT, ACP and KS domains. In one embodiment of the invention, the PKS is assembled from polypeptides encoded by DNA molecules that comprise coding sequences for polyketide synthase domains, wherein at least one encoded domain corresponds to a domain of geldanamycin polyketide synthase. In such DNA molecules, the coding sequences are operably linked to control sequences so that expression therefrom in host cells is effective.

In another embodiment of the present invention, there is provided a PCR based method to rapidly query the genomic DNA for the presence of type I modular PKS genes, then the number of these genes and their individual characteristics can be established by DNA sequence and bioinformatics analysis of short PKS gene amplimers. This method of the present invention is more reliable and informative than methods involving DNA hybridization, and much less costly than approaches based on whole genome sequencing. This method of the present invention was applied to identify the PKS and tailoring enzymes of the geldanamycin PKS and the genes responsible for the biosynthesis of the ansamycin and geldanamycin starter unit AHBA (3-amino-5-hydroxy benzoic acid).

Accordingly there are provided recombinant polynucleotides that comprise a coding sequence for one or more domains of the geldanamycin starter unit AHBA synthetic enzymes. Expression of such DNAs, in suitable host cells leads to the production of the AHBA starter unit.

BRIEF DESCRIPTION OF THE DRAWINGS

FIG. 2 shows the functions and products of the geldanamycin and herbimycin synthases.

FIG. 3 shows PKS gene clusters and flanking genes.

DETAILED DESCRIPTION OF THE INVENTION

Definitions and Methods

Figure 1:
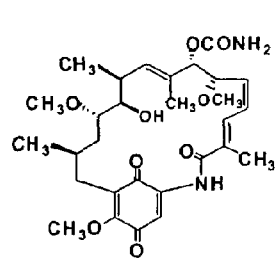
FIG. 1 shows the structure of naturally occurring benzoquinone ansamycins, including geldanamycin and herbimycins A-C.
Figure 1:
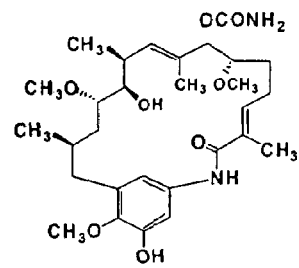
Figure 1:
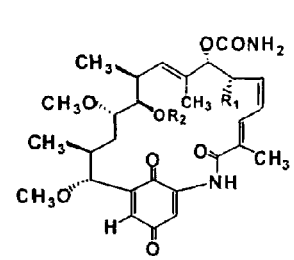
Figure 1:
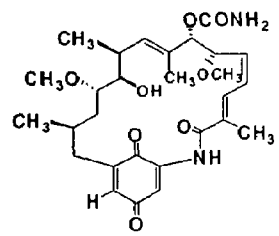
Figure 1:
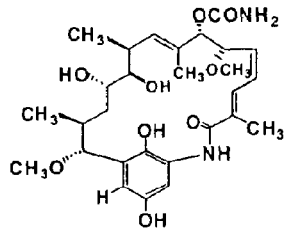
Figure 1:
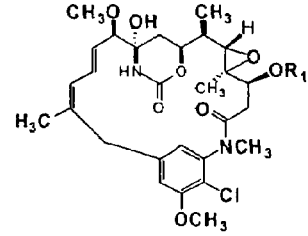

This section provides definitions of selected terms and abbreviations used in this disclosure, as well as resources useful in the practice of the invention. Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art.

As used herein, the terms "tailoring enzyme" and "modification enzyme" are used interchangably and mean an enzyme that modifies the product of a PKS (e.g., progeldanamycin). Exemplary tailoring proteins include oxygenases, glycosyl- and methyltransferases, acyltransferases, halogenases, cyclases, aminotransferases, hydroxylases, and others known in the art.

As used herein, "core" polyketide synthase genes are genes encoding the loading and extendor modules of the PKS. The "core PKS" genes in the geldanamycin PKS cluster are gdmAI, gdmAII, and gdmAIII. The "core PKS" genes in the herbimycin PKS cluster are hbmAI, hbmAII, and hbmAIII. As used herein, a "core" polyketide synthase protein is a protein encoded by a core PKS gene. As used herein, a "polyketide synthase-encoding region" of a polynucleotide refers to the region encoding the core PKS genes.

As used herein, "polyketide synthase biosynthetic gene cluster" refers generally to section of the chromosome comprising the core PKS genes and other genes that play a role in polyketide biosynthesis.

As used herein, a PKS "accessory" protein is a protein, other than a PKS protein, that plays a role in the biosynthesis, modification, or activity of a polyketide. Exemplary accessory proteins include tailoring enzymes, enzymes involved in biosynthesis of polyketide starter units (e.g., AHBA) or extender units (e.g., malonate, 2-methylmalonate and 2-methoxymalonate), CoA-ligases, and transcription regulatory proteins. In general, genes encoding accessory proteins are named "gdm_____" or "hdm_____."

As used herein, PKS "ancillary" proteins refers to proteins disclosed herein that are encoded in the *S. hygroscopicus* genome by genes located near the geldanamycin or herbimycin PKS gene clusters that are not accessory proteins or PKS proteins. In general, genes encoding ancillary proteins are named "ORF_____."

It will be appreciated that the terms "gene cluster," "accessory protein," and "ancillary proteins" are used for convenience and are not intended to precisely define the function of a gene or protein.

As used herein an "active fragment" of a polypeptide or domain (or a polynucleotide encoding a polypeptide) has the activity of polypeptide or domain from which it is derived, when intergrated into an appropriate PKS framework using methods known in the art.

As used herein the term "geldanamycin" sometimes refers to "progeldanamycin," as will be clear from context.

As used herein the term "recombinant" refers to a polynucleotide synthesized or otherwise manipulated in vitro, or to methods of using recombinant polynucleotides to produce gene products in cells or other biological systems. Thus, a "recombinant" polynucleotide is defined either by its method of production or its structure. In reference to its method of production, the process is use of recombinant nucleic acid techniques, e.g., involving human intervention in the nucleotide sequence, typically selection or production. Alternatively, a recombinant polynucleotide can be a polynucleotide made by generating a sequence comprising fusion of two fragments which are not naturally contiguous to each other, but is meant to exclude products of nature. Thus, for example, products made by transforming cells with any non-naturally occurring vector is encompassed, as are polynucleotides comprising sequence derived using any synthetic oligonucleotide process, as are polynucleotides from which a region has been deleted. A recombinant polynucleotide can also be a coding sequence that has been modified in vivo using a recombinant oligo or polynucleotide (such as a PKS in which a domain is inactivated by homologous recombination using a recombinant polynucleotide). A "recombinant" polypeptide is one expressed from a recombinant polynucleotide.

As used herein, "isolated" means that a substance is either present in a preparation at a concentration higher than that substance is found in nature or in its naturally occurring state or that the substance is present in a preparation that contains other materials with which the substance is not associated with in nature. As an example of the latter, an isolated geldanamycin PKS protein includes a geldanamycin PKS protein expressed in a *Myxococus* or *Streptomyces lividans* host cell.

"Stringent hybridization conditions" refers to conditions in a range from about 5° C. to about 20° C. or 25° C. below the melting temperature (Tm) of the target sequence and a probe with exact or nearly exact complementarity to the target. As used herein, the melting temperature is the temperature at which a population of double-stranded nucleic acid molecules becomes half-dissociated into single strands. Methods for calculating the Tm of nucleic acids are well known in the art (see, e.g., Berger and Kimmel, 1987, Methods In Enzymology, Vol. 152: Guide To Molecular Cloning Techniques, San Diego: Academic Press, Inc. and Sambrook et al., 1989, Molecular Cloning: A Laboratory Manual, 2nd Ed., Vols. 1-3, Cold Spring Harbor Laboratory). Typically, stringent hybridization conditions are salt concentrations less than about 1.0 M sodium ion, typically about 0.01 to 1.0 M sodium ion at pH 7.0 to 8.3, and temperatures at least about 60° C. for probes greater than 50 nucleotides. As noted, stringent conditions may also be achieved with the addition of destabilizing agents such as formamide, in which case lower temperatures may be employed.

The term substantially identical or homologous or similar varies with the context as understood by those skilled in the relevant art and generally means at least 70%, preferably means at least 80%, more preferably at least 90%, and most preferably at least 95% identity. To determine identity, optimal alignment of sequences for comparison can be conducted, e.g., by the local homology algorithm of Smith & Waterman, 1981, *Adv. Appl. Math.* 2:482, by the search for similarity method of Pearson & Lipman, 1988, *Proc. Natl. Acad. Sci. USA* 85:2444, using the CLUSTAL W algorithm of Thompson et al., 1994, *Nucleic Acids Res* 22:467380, by computerized implementations of these algorithms (GAP, BESTFIT, FASTA, and TFASTA in the Wisconsin Genetics Software Package, Genetics Computer Group, 575 Science Dr., Madison, Wis. The BLAST algorithm (Altschul et al., 1990, *Mol. Biol.* 215:403-10) for which software may be obtained through the National Center for Biotechnology Information (http://www.ncbi.nlm.nih.gov/) can also be used. When using any of the aforementioned algorithms, the default parameters for "Window" length gap penalty, etc., are used.

As used herein, "substantially identical" to a product means sufficiently similar so that the property of interest is sufficiently unchanged so that the substantially identical product can be used in place of the product.

As used herein, "vector" refers to polynucleotide elements that are used to introduce recombinant nucleic acid into cells for either expression or replication. Selection and use of such vehicles is routine in the art. An "expression vector" includes vectors capable of expressing DNAs that are operatively linked with regulatory sequences, such as promoter regions. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those which integrate into the host cell genome.

The following abbreviations are used in this disclosure: 1) ACP, acyl carrier protein; 2) Aden, adenylation; 3) AT, acyltransferase; 4) DH, dehydratase; 5) ER, enoylreductase; 6) KR, ketoreductase; 7) KS, ketosynthase; 8) LDD, loading didomain; 9) NRPS, non-ribosomal peptide synthetase; 10) m, malonylCoA; 11) mm, 2-methylmalonylCoA; 12) moxm, 2-methoxymalonyl-ACP; 13) mod, module; 14) CT carbamoyltransferase; 15) PKS, polyketide synthase; 16) AHBA, 3-amino-5-hydroxy benzoic acid. The following convention is used to refer to domains in a PKS: the number following an abbreviation for a PKS domain refers to the module from which that domain originated. For example, "AT2" refers to the AT domain of module 2. When referring to plasmids, "periods" and "hyphens" are sometimes used interchangably (e.g., pKOS205-110-12 and pKOS205-110.12 are the same).

The practice of the present invention will employ, unless otherwise indicated, conventional techniques of molecular biology (including recombinant techniques), microbiology, cell biology, biochemistry, nucleic acid chemistry, and immunology, which are within the skill of the art. Such techniques are explained fully in the literature, such as *Current Protocols in Molecular Biology* (F. M. Ausubel et al., eds., 1987, including supplements through 2001); *Molecular Cloning: A Laboratory Manual*, third edition (Sambrook and Russel, 2001); *PCR: The Polymerase Chain Reaction*, (Mullis et al., eds., 1994); *Current Protocols in Immunology* (J. E. Coligan et al., eds., 1999, including supplements through 2001). Methods for the genetic manipulation of *Streptomyces* are described in Kieser et al, 2000, "Practical *Streptomyces* Genetics," The John Innes Foundation, Norwich.

DESCRIPTION OF THE INVENTION

Figure 2A:
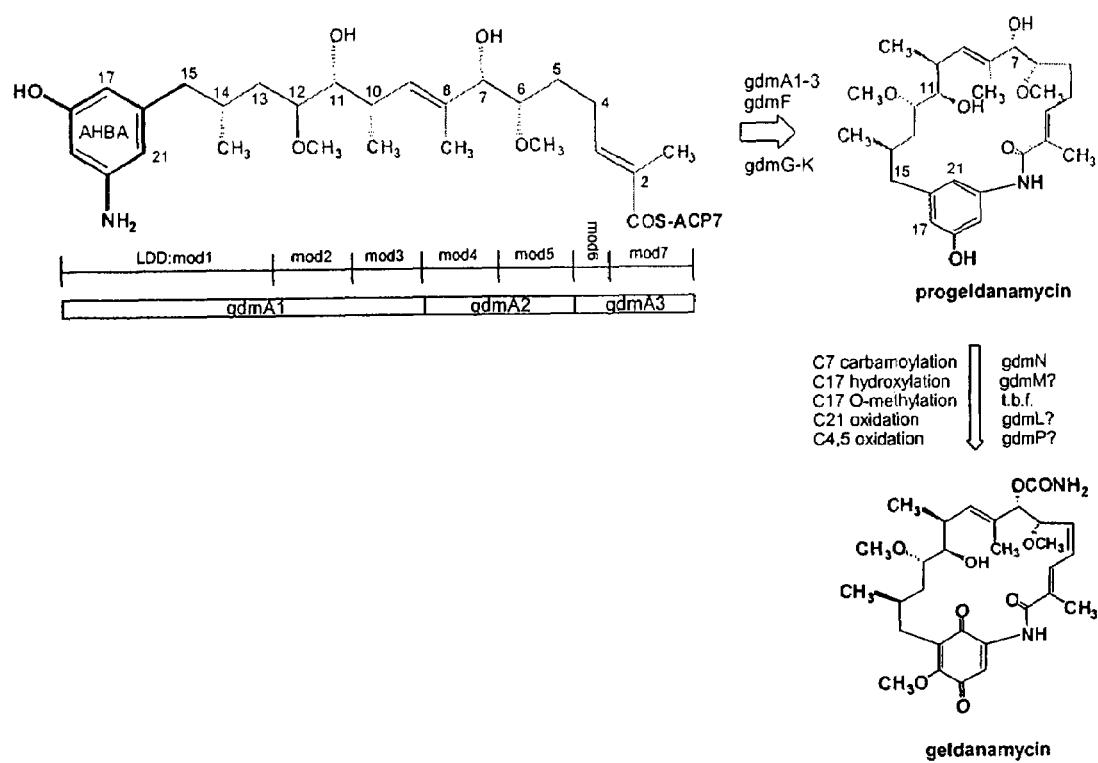
FIG. 2A shows the predicted functions and product of the PKS for geldanamycin biosynthesis. The schematic shows the enzyme-bound product assembled from AHBA and carbon chain extender substrates malonyl-CoA, 2-methoxymalonate and 2-methylmalonyl-CoA by the PKS modules indicated beneath the product structure. Progeldanamycin, produced by the PKS from the 3-amino-5-hydroxybenzoic acid starter unit (AHBA) is converted to geldanamycin by three oxidations, O-methylation, and O-carbamoylation. Panel A shows reduction of the unusual α-methoxy C=C during the second carbon chain extension cycle. Panel B shows creation of the 4,5 cis C=C by oxidation of the saturated system after formation of the ansamycin framework.

Geldanamycin and herbimycin are structurally related polyketides produced by *Streptomyces hygroscopicus*. Geldanamycin was originally identified as a product of *S. hygroscopicus* var. *geldanus* NRRL 3602, and herbimycin was first identified in *S. hygroscopicus* AM-3672. FIG. 2A and FIGURE B show the predicted synthetic pathways for geldanamycin and herbimycin. The geldanamycin polyketide synthase (in *S. hygroscopicus* var. *geldanus* NRRL 3602) and the herbimycin polyketide synthase (in *S. hygroscopicus* AM-3672) produce identical polyketide products, referred to as progeldanamycin or proherbimycin. As a result of post-PKS processing, herbimycin differs from geldanamycin by having a methoxy group at the C15 position instead of at the C17 position, and may also have a hydroxyl or methoxy group at the C11 position.

Given the valuable pharmaceutical properties of geldanamycin and other ansamycins, means to produce pharmaceutically useful quantities of this and related polyketides are useful. The genes encoding the geldanamycin and herbimycin polyketide synthases, as well as genes encoding tailoring enzymes, biosynthetic proteins, regulatory proteins, and other polypeptides have now been cloned, sequenced, and characterized. This information, along with the disclosure below, provides new methods for expressing PKS enzymes and polyketide modification enzymes derived in whole and in part from the geldanamycin and herbimycin gene clusters in recombinant host cells, resulting in the biosynthesis of progeldanamycin, geldanamycin, herbimycins, derivatives and analogs of progeldanamycin, geldanamycin and herbimycin, and other polyketides in host cells. Various aspects of the invention are described in detail in the following sections.

Figure 3A:
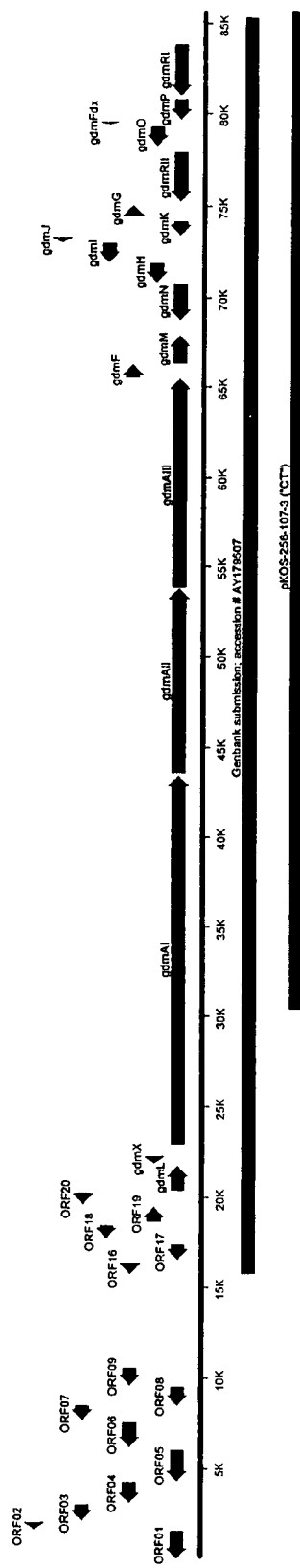
FIG. 3A is a schematic of BAC clones pKOS256-154-1 (KS) and pKOS-256-107-3 (CT) encompassing the geldanamycin PKS gene cluster with flanking genes.
Figure 3B:
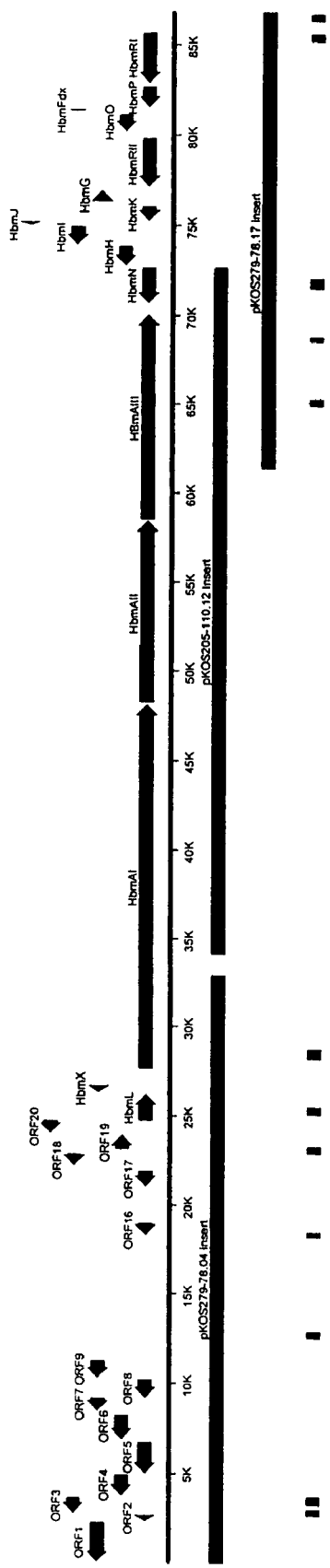
FIG. 3B shows is a schematic of BAC clones pKOS279-78.04, pKOS279-78.17, and pKOS205-110.12, encompassing the herbimycin PKS gene cluster with flanking genes.

The geldanamycin and herbimycin PKS gene clusters are similar at both the sequence and organizational levels (see FIG. 3A and FIG. 3B). TABLE 1, below, summarizes the organization of the gene clusters.

The geldanamycin PKS contains seven modules and produces progeldanamycin. As noted above, this ansamycin is formed from the starter unit 3-amino-5-hydroxybenzoic acid (AHBA) and three different α-carboxy acid chain extender units: malonate, 2-methymalonate and 2-methoxymalonate. (AHBA is formed by the products of AHBA-biosynthetic genes of the geldanamycin gene cluster, which are discussed below.) Module 1 of the geldanamycin PKS contains the loading didomain, which is homologous to the corresponding portion of the rifamycin and ansamitocin PKSs, and consists of a domain for activation of AHBA via formation of its thioester and an ACP domain for subsequent attachment of the activated starter unit to the PKS. This module also contains the six domains required for selection of the first chain extender substrate, 2-methylmalonyl-CoA, and its loading onto the ACP1 domain, followed by condensation of the starter and extender unit catalyzed by the KS1 domain, then reduction, dehydration and double bond reduction catalyzed by the KR1, DH1 and ER1 domains acting in sequo. The domain organization and functions of the six other modules in the geldanamycin PKS are listed in FIG. 2A. The AT2 and AT5 domains (of modules 2 and 5) recognize and load 2-methoxymalonate, a comparatively rare substrate in polyketide synthesis whose formation is governed by five genes in the geldanamycin gene cluster that are homologous to the corresponding FK520 and ansamitocin genes (see WO 00/20601). Modules 3, 4 and 7 utilize 2-methylmalonate, and module 6 uses methylmalonate. These six modules also contain KR, DH and/or ER domains that establish the functionality at positions 2, 4, 7, 9, 11 and 13 in the product of the PKS.

Modification of progeldanamycin to produce geldanamycin involves at least four and perhaps five or six enzymatic reactions: C7 carbamoylation; C17 hydroxylation; C17 O-methylation, C21 oxidation, and perhaps either C4,5 desaturation (oxidation) or C4 or C5 hydroxylation plus dehydration. C7 carbamoylation is believed to be carried out by the gdmN gene product. The oxidation steps, including the hydroxylation, are believed to involve the activities of a subset of the gene products of gdmL, gdmM, gdmP (with gdmFdx) and ORF4P450.

Figure 2B:
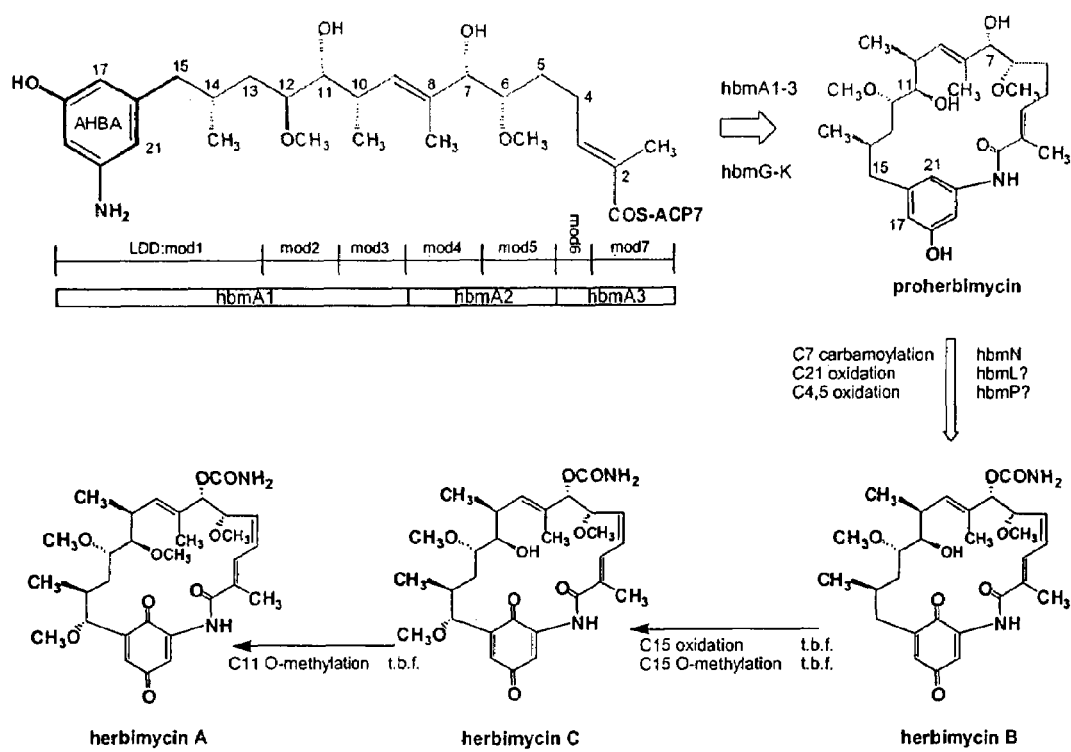
FIG. 2B shows the predicted functions and product of the PKS effecting herbimycin biosynthesis. Proherbimycin, produced by the PKS from the AHBA starter unit, is converted to herbimycin by hydroxylation at C15, O-methylation at C15 and C11, oxidation at C21, and O-carbamoylation at C7.

As noted above, the organization of the herbimycin PKS is similar to that of the geldanamycin gene cluster. The herbimycin PKS contains seven modules and produces progeldanamycin from an AHBA starter unit and malonate, 2-methymalonate and 2-methoxymalonate extender units. Module 1 of the herbimycin PKS contains the loading didomain, and consists of a domain for activation of AHBA via formation of its thioester and an ACP domain for subsequent attachment of the activated starter unit to the PKS. This module also contains the six domains required for selection of the first chain extender substrate, 2-methylmalonyl-CoA, and its loading onto the ACP1 domain, followed by condensation of the starter and extender unit catalyzed by the KS1 domain, then reduction, dehydration and double bond reduction catalyzed by the KR1, DH1 and ER1 domains acting in sequo. The domain organization and functions of the six other modules in the herbimycin PKS are shown in FIG. 2B. The AT2 and AT5 domains (of modules 2 and 5) recognize and load 2-methoxymalonate, a comparatively rare substrate in polyketide synthesis whose formation is governed by five non-PKS genes in the herbimycin gene cluster that are homologous to the corresponding FK520 and ansamitocin genes. Modules 3, 4 and 7 utilize 2-methylmalonate, and module 6 uses malonate. These six modules also contain KR, DH and/or ER domains that establish the functionality at positions 2, 4, 7, 9, 11 and 13 in the product of the PKS.

Modification of progeldanamycin to produce herbimycin involves five enzymatic reactions: C7 carbamoylation, C11 O-methylation, C15 hydroxylation, C15 O-methylation, C21 oxidation, and perhaps either C4,5 desaturation (oxidation) or C4 or C5 hydroxylation plus dehydration. C7 carbamoylation is believed to be carried out by the hbmN gene product. C11 and/or C15 O-methylation may involve the hbmG gene product. The oxidation steps, including the hydroxylation, are believed to involve the activities of a subset of the gene products of hbmL, hbmM, hbmP (with hbmFdx) and ORF4P450.

TABLE 1

PKS AND MODIFYING GENE CLUSTER ORFS OF GELDANAMYCIN (SEQ ID NO: 1) AND HERBIMYCIN (SEQ. ID NO: 2)

| GELDANAMYCIN | | | HERBIMYCIN | |
| --- | --- | --- | --- | --- |
| ORF BOUNDARIES- | ORF NAME | PROPOSED FUNCTION | ORF NAME | ORF BOUNDARIES- |
| 1-1652 (N-terminus only) | ORF01 | homolog of S. coelicolor SC0860c & S. avermitilis SAV617; probable cation-transporting ATPase | ORF01 | 71-2359 |

TABLE 1-continued

PKS AND MODIFYING GENE CLUSTER ORFS OF GELDANAMYCIN (SEQ ID NO: 1) AND HERBIMYCIN (SEQ. ID NO: 2)

| GELDANAMYCIN | | | HERBIMYCIN | |
|---|---|---|---|---|
| ORF BOUNDARIES- | ORF NAME | PROPOSED FUNCTION | ORF NAME | ORF BOUNDARIES- |
| 1652-2083 | ORF02 | homolog of S. coelicolor SC0861c & S. avermitilis SAV618; putative secreted protein | ORF02 | 2359-2775 |
| 2070-3053 | ORF03 | homolog of PvcA (Pseudomonas aeruginosa PA2234); & of V. cholerae VC1949) | ORF03 | 2762-3745 |
| 3057-4313 | ORF04 | P450 | ORF04 | 3757-5013 |
| 4326-6152 | ORF05 | asparagine synthase family | ORF05 | 5026-6852 |
| 6187-7617 | ORF06 | transmembrane efflux protein | ORF06 | 6887-8317 |
| 7723-8526 | 0RF07 | homolog of FtrE, S. coelicolor SC0998; permease (Fe) | ORF07 | 8437-9240 |
| 8490-9572 | ORF08 | homolog of FtrD, S. coelicolor SC0997 | ORF08 | 9204-10286 |
| 9572-10648 | ORF09 | lipoprotein | ORF09 | 10286-11362 |
| 15732-16415 | ORF16 | RhtB family transporter | ORF16 | 18360-19043 |
| 16502-17404 | ORF17 | secreted protein | ORF17 | 21063-21965 |
| 17676-18467 | ORF18 | hydrolase | ORF18 | 22155-22946 |
| 18621-19505 | ORF19 | transcriptional regulator (AraC family) | ORF19 | 23100-23984 |
| 19555-20316 | ORF20 | transcriptional regulator (TetR family) | ORF20 | 24036-24797 |
| 20357-21796 | GdmL | flavin-dependent monooxygenase | HbmL | 24781-26277 |
| 21838-22308 | GdmX | Conserved JadX and MmyY homolog | HbmX | 26325-26795 |
| 22939-43464 | GdmAI Loading Module Module 1 Module 2 Module 3 | PKS modules 0-3 AL0 X ACP0 KS AT DH ER KR ACP KS AT DH ER KR ACP KS AT KR ACP | HbmAI Loading Module Module 1 Module 2 Module 3 | 27677-48139 |
| 43525-53829 | GdmAII Module 4 Module 5 | PKS modules 4-5 KS AT DH KR ACP KS AT KR ACP | HbmAII Module 4 Module 5 | 48197-58492 |
| 53859-65546 | GdmAIII Module 6 Module 7 | PKS modules 6-7 KS AT DH ER KR ACP KS AT DH KR ACP | HbmAIII Module 6 Module 7 | 58519-70125 |
| 6558-66331 | GdmF | amide synthase | none* | |
| 66328-67962 | GdmM | flavin-dependent monooxygenase | none | |
| 68782-70791 | GdmN | carbamoyltransferase | HbmN | 70662-72719 |
| 70853-71965 | GdmH | methoxymalonyl-ACP biosynthesis pathway | HbmH | 72781-73893 |
| 71962-73074 | GdmI | methoxymalonyl-ACP biosynthesis pathway | HbmI | 73890-75002 |
| 73071-73346 | GdmJ | ACP in methoxymalonyl-ACP biosynthesis pathway | HbmJ | 74999-75274 |
| 73343-74209 | GdmK | methoxymalonyl-ACP biosynthesis pathway | HbmK | 75271-76137 |
| 74453-75019 | GdmG | O-methyltransferase in methoxymalonyl-ACP biosynthesis | HbmG | 76381-77037 |
| 75234-78014 | GdmRII | LuxR-type transcriptional regulator | HbmRII | 77137-79917 |
| 78289-79353 | GdmO | AminoDHQsynthase | HbmO | 80193-81257 |
| 79434-79628 | GdmFdx | ferredoxin | HbmFdx | 81334-81528 |
| 79671-80864 | GdmP | P450 | HbmP | 81571-82764 |
| 81021-83909 | GdmRI | LuxR-type transcriptional regulator | HbmRI | 82921-86764 |
| 84662-85375 | ORF22 | Hydrolase | none | |

*"none" indicates the absence of a homolog in this section of the herbimycin genome.

The reader skilled in the art of molecular biology and polyketide biosynthesis will understand, guided by this disclosure, that the polynucleotide sequences and other teachings of the specification and figures make possible a wide variety of applications. These applications include, but are not limited to, applications in which core PKS genes, accessory genes, and ancillary genes are modified and/or expressed using recombinant methods.

The present invention provides, for example, (1) recombinant polynucleotides that comprise sequences encoding a PKS protein, module, domain or fragment thereof, and/or encode an accessory protein or fragment thereof; (2) recombinant polypeptides comprising the sequence of a PKS protein, module, domain or fragment thereof or comprising the sequence of an accessory protein or fragment thereof; and (3) cells comprising a recombinant polynucleotide or polypeptide of the invention. The following sections describe these and other aspects of the invention. However, it will be understood that the embodiments discussed below are for illustration, and are not intended to limit the invention.

In one aspect, the invention provides recombinant polynucleotides that encode a PKS protein, module, domain or fragment thereof, and/or encode an accessory protein or fragment thereof. The polynucleotides of the invention are useful for expression of recombinant proteins (e.g., chimeric PKS proteins), as tools for manipulation of PKS and accessory genes (e.g., vectors for homologous recombination for mutation or deletion of PKS and accessory genes), as probes and primers, and a variety of other uses. It is contemplated that a polynucleotide of the invention can be in any of a variety of forms, depending on its intended function: e.g., integrated into a host cell genome (whether episomal or chromosomal), encoded by a recombinant vector (such as an expression vector), as a linear oligomer (such as a probe or primer), and other forms. In one aspect, the polynucleotide compounds of the invention are used in recombinant procedures for production of desired portions of the geldanamycin or herbimycin synthases. Optionally these portions are fused to, or expressed in conjunction with, all or a portion of a heterologous PKS protein(s), or are modified to change activity. Optionally, recombinant geldanamycin or herbimycin PKS protein, or a chimeric PKS of the invention, is co-expressed with one or more polyketide modification enzymes that modify the polyketide product of the geldanamycin or herbimycin or a chimeric PKS.

In one embodiment, the invention is directed to recombinant materials comprising nucleic acids with nucleotide sequences encoding at least one domain, at least one module, or least one polypeptide encoded by a geldanamycin or herbimycin PKS gene. In one embodiment, purified and isolated DNA molecules are provided that comprise one or more coding sequences for one or more domains or modules of geldanamycin synthase or herbimycin synthase. In one embodiment of the invention, the DNA compounds of the invention comprise a coding sequence for at least two, at least three, at least four, or more, of the domains of the loading module and extender modules 1 through 7, inclusive, of the geldanamycin/herbimycin PKS, or at least one, at least two, or three of the modules of the geldanamycin/herbimycin PKS gene. Examples of such encoded domains include geldanamycin synthase KR, DH, ER, AT, ACP, and KS domains and herbimycin synthase KR, DH, ER, AT, ACP, and KS domains. Examples of such modules include the PKS modules of the geldanamycin PKS and the PKS modules of the herbimycin PKS.

In one embodiment, the invention provides an isolated nucleic acid fragment which hybridizes to a nucleic acid having a nucleotide sequence set forth in the SEQ. ID NO:1, SEQ. ID NO:2, or SEQ. ID NO:3 under stringent conditions. In an embodiment, the nucleic acid fragment comprises, consists or consists essentially of a nucleic acid having a nucleotide sequence set forth in SEQ. ID NO:1, SEQ. ID NO:2, or SEQ. ID NO:3. Encoding sequences for geldanamycin and herbimycin polyketide synthase proteins and accessory proteins may comprise substitutions, additions or deletions relative to SEQ. ID NO:1, SEQ. ID NO:2, or SEQ. ID NO:3 that provide for functionally equivalent molecules. For example, the invention provides, due to the degeneracy of the genetic code, a large number of DNA sequences that encode the amino acid sequences of the domains, modules, and proteins of the geldanamycin and herbimycin PKSs as well as the accessory enzymes. The PKS and accessory genes include those with nucleotide sequences encoding substantially the same amino acid sequences as found in native PKS and accessory genes biosynthetic enzyme proteins, and those encoding amino acid sequences with functionally equivalent amino acids, as well as PKS and accessory genes biosynthetic enzyme derivatives or analogs as described herein. These include but are not limited to nucleotide sequences comprising all or portions of SEQ ID NO:1, 2 or 3 genes that are altered by the substitution of different codons that encode the amino acid residue within the sequence, thus producing a silent change, or in which functionally equivalent amino acid residues are substituted for residues within the sequence resulting in a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

In specific embodiments, the biosynthetic nucleic acids encoding PKS and accessory proteins comprise the sequence of SEQ. ID NO:1, SEQ. ID NO:2, or SEQ. ID NO:3, or the coding regions thereof, or nucleotide sequences encoding, in whole or in part, a PKS and accessory genes biosynthetic enzyme protein. The isolated nucleic acids typically consists of at least 25 (continuous) nucleotides, 50 nucleotides, 100 nucleotides, 150 nucleotides, or 200 nucleotides of PKS and accessory genes biosynthetic nucleic acid sequence, or a full-length PKS and accessory genes biosynthetic coding sequence. In another embodiment, the nucleic acids are smaller than 35, 200, or 500 nucleotides in length. Nucleic acids can be single or double stranded. Nucleic acids that hybridize to or are complementary to the foregoing sequences, in particular the inverse complement to nucleic acids that hybridize to the foregoing sequences (i.e., the inverse complement of a nucleic acid strand has the complementary sequence running in reverse orientation to the strand so that the inverse complement would hybridize without mismatches to the nucleic acid strand) are also provided. In specific aspects, nucleic acids are provided which comprise a sequence complementary to (specifically are the inverse complement of) at least 10, 25, 50, 100, or 200 nucleotides or the entire coding region of a PKS and accessory genes biosynthetic gene.

In one important aspect, the invention provides a modified and/or chimeric (also called "hybrid") polyketide synthases. A "modified" PKS is a PKS in which a domain or module has been deleted (including deletion by replacement with a different domain) or mutated to change or eliminate the enzymatic activity of the domain (e.g., inactivation of the domain). Further, reference herein to an "inactivated" domain is intended to encompass a domain that does not function in a PKS because it is partially or completely deleted. As will be apparent to the reader, "modifying" polynucleotides or proteins, as used herein, refers to recombinantly modifying said polynucleotides or proteins, in contrast to, for example, random changes induced by radiation, chemical mutagens, or the like.

A "chimeric" PKS is a PKS protein (or encoding gene) that expresses modules, domains, or portions of domains from two different PKS proteins (either as a fusion protein or by coexpression). Recombinant methods for manipulating modular PKS genes to make hybrid PKS enzymes are described in U.S. Pat. Nos. 5,672,491; 5,843,718; 5,830,750; and 5,712,146; and in WO 98/49315 and WO 97/02358. A number of genetic engineering strategies have been used with DEBS to demonstrate that the structures of polyketides can be manipulated to produce novel natural products, primarily analogs of the erythromycins (see the patent publications referenced supra and Hutchinson, 1998, *Curr Opin Microbiol.* 1:319-329, and Baltz, 1998, *Trends Microbiol.* 6:76-83).

It will be appreciated that a PKS that is chimeric is also modified and, moreover, that these characterizations are used for convenience and not limitation.

In constructing novel PKS proteins, a number of general principles are known, some of which are summarized here. There are at least six degrees of freedom for constructing a polyketide synthase in terms of the polyketide that will be produced. First, the polyketide chain length will be determined by the number of modules in the PKS. Second, the nature of the carbon skeleton of the PKS will be determined by the specificities of the acyl transferases which determine the nature of the extender units at each position—e.g., malonyl, methyl malonyl, ethyl malonyl, etc. Third, the loading domain specificity will also have an effect on the resulting carbon skeleton of the polyketide. Thus, the loading domain may use a different starter unit, such as acetyl, propionyl, ahba, and the like. Fourth, the oxidation state at various positions of the polyketide will be determined by the dehydratase and reductase portions of the modules. This will determine the presence and location of ketone, alcohol, alkene or alkane substituents at particular locations in the polyketide. Fifth, the stereochemistry of the resulting polyketide is a function of three aspects of the synthase. The first aspect is related to the AT/KS specificity associated with substituted malonyls as extender units, which affects stereochemistry only when the reductive cycle is missing or when it contains only a ketoreductase since the dehydratase would abolish chirality. Also, the specificity of the ketoreductase will determine the chirality of the corresponding hydroxyl group. Also, the enoyl reductase specificity for substituted malonyls as extender units will influence the result when there is a complete KR/DH/ER available. Sixth, the presence and position of PKS methyl transferase domain(s) in PKS module(s) will determine the presence of methyl functions in the polyketide.

Recombinant methods for manipulating modular PKS genes to make chimeric PKS enzymes are described in U.S. Pat. Nos. 5,672,491; 5,843,718; 5,830,750; and 5,712,146; and in PCT publication Nos. 98/49315 and 97/02358. A number of genetic engineering strategies have been used with DEBS to demonstrate that the structures of polyketides can be manipulated to produce novel natural products, primarily analogs of the erythromycins (see the patent publications referenced supra and Hutchinson, 1998, *Curr Opin Microbiol.* 1:319-329, and Baltz, 1998, *Trends Microbiol.* 6:76-83). In general, these techniques include: (i) deletion or insertion of modules to control chain length, (ii) inactivation of reduction/dehydration domains to bypass beta-carbon processing steps, (iii) substitution of AT domains to alter starter and extender units, (iv) addition of reduction/dehydration domains to introduce catalytic activities, and (v) substitution of ketoreductase KR domains to control hydroxyl stereochemistry. In addition, engineered blocked mutants of DEBS have been used for precursor directed biosynthesis of analogs that incorporate synthetically derived starter units and it is contemplated that the analogous biosynthesis is carried out by a geldanamycin/herbimycin based PKS.

Thus, further aspects of the invention include: (1) encoding DNA for a chimeric PKS that is substantially patterned on a non-geldanamycin producing enzyme, but which includes one or more functional domains or modules of geldanamycin PKS; (2) encoding DNA for a chimeric PKS that is substantially patterned on the geldanamycin PKS, but which includes one or more functional domains or modules of another PKS or NRPS; (3) encoding DNA for a modified PKS that is substantially patterned on a geldanamycin producing enzyme, but in which one or more domains or modules has been deleted or inactivated; (4) methods for making geldanamycin analogs and derivatives; (5) encoding DNA for a chimeric PKS that is substantially patterned on a non-herbimycin producing enzyme, but which includes one or more functional domains or modules of herbimycin PKS; (6) encoding DNA for a chimeric PKS that is substantially patterned on the herbimycin PKS, but which includes one or more functional domains or modules of another PKS or NRPS; (7) encoding DNA for a modified PKS that is substantially patterned on a herbimycin producing enzyme, but in which one or more domains or modules has been deleted or inactivated; and (8) methods for making herbimycin analogs and derivatives.

With respect to items (1) and (5) above, preferred examples include chimeric PKS enzymes wherein the genes for the erythromycin PKS or rapamycin PKS function as accepting genes, and one or more of the above-identified coding sequences for geldanamycin or herbimycin PKS domains or modules are inserted as replacements for domains or modules of comparable function. With respect for (2) and (6) above, a number of other PKS coding sequences that can be used to prepare chimeric domains or molecules are known which are can be used in conjunction with geldanamycin and/or herbimycin PKS encoding sequences to construct a chimeric molecule. A partial list, for illustration and not limitation, includes Avermectin (U.S. Pat. No. 5,252,474; MacNeil et al., 1993, Industrial Microorganisms: Basic and Applied Molecular Genetics, Baltz, Hegeman, & Skatrud, eds. (ASM), pp. 245-256; MacNeil et al., 1992, *Gene* 115: 119-25); Candicidin (FRO008) (Hu et al., 1994, *Mol. Microbiol.* 14: 163-72); Epothilone (U.S. Pat. No. 6,303,342); Erythromycin (WO 93/13663; U.S. Pat. No. 5,824,513; Donadio et al., 1991, *Science* 252:675-79; Cortes et al., 1990, *Nature* 348:176-8); FK-506 (Motamedi et al., 1998, *Eur. J. Biochem.* 256:528-34; Motamedi et al., 1997, *Eur. J. Biochem.* 244:74-80); FK-520 (U.S. Pat. No. 6,503,737; see also Nielsen et al., 1991, *Biochem.* 30:5789-96); Lovastatin (U.S. Pat. No. 5,744,350); Nemadectin (MacNeil et al., 1993, supra); Niddamycin (Kakavas et al., 1997, *J. Bacteriol.* 179:7515-22); Oleandomycin (Swan et al., 1994, *Mol. Gen. Genet.* 242:358-62; U.S. Pat. No. 6,388,099; Olano et al., 1998, *Mol. Gen. Genet.* 259:299-308); Platenolide (EP Pat. App. 791,656); Rapamycin (Schwecke et al., 1995, *Proc. Natl. Acad. Sci. USA* 92:7839-43); Aparicio et al., 1996, *Gene* 169:9-16); Rifamycin (August et al., 1998, *Chemistry & Biology*, 5: 69-79); Soraphen (U.S. Pat. No. 5,716,849; Schupp et al., 1995, *J. Bacteriology* 177: 3673-79); Spiramycin (U.S. Pat. No. 5,098,837); Tylosin (EP 0 791,655; Kuhstoss et al., 1996, *Gene* 183:231-36; U.S. Pat. No. 5,876,991). Additional suitable PKS coding sequences remain to be discovered and characterized, but will be available to those of skill (e.g., by reference to GenBank).

In a related embodiment, a domain in a PKS gene is replaced with a domain or domains from a different location (e.g., different module) from same PKS gene. In another embodiment, portions of more than two or more than three PKS genes are combined to produce a chimeric gene and protein.

As noted, construction of such enzymes is most effectively achieved by construction of appropriate encoding polynucleotides. In this example of the invention, it is not necessary to replace an entire domain or module accepting of the PKS with an entire domain or module of geldanamycin PKS, rather peptide subsequences of a PKS domain or module that correspond to a peptide subsequence in an accepting domain or module, or which otherwise provide useful function, may be used as replacements. Accordingly, appropriate encoding DNAs for construction of such chimeric PKS include those that encode at least 5, 10, 15, 20 or more amino acids of a selected geldanamycin domain or module. Those of skill in the art will recognize that all or part of a PKS sequence in a chimeric PKS of the invention need not be isolated from a naturally occurring source. For example, only a small portion of an AT domain determines its specificity. See WO US99/15047, and Lau et al., *Biochemistry* 38:1643-51. The state of the art in DNA synthesis allows the artisan to construct de novo DNA compounds of size sufficient to construct a useful portion of a PKS module or domain. Thus, the desired derivative coding sequences can be synthesized using standard solid phase synthesis methods such as those described by Jaye et al., 1984, *J. Biol. Chem.* 259: 6331, and instruments for automated synthesis are available commercially from, for example, Applied Biosystems, Inc. For purposes of the invention, such synthetic DNA compounds are deemed to be a portion of a PKS.

In addition to providing mutated forms of regions encoding enzymatic activity, regions encoding corresponding activities from different PKS or from different locations in the same PKS can be recovered, for example, using PCR techniques with appropriate primers. By "corresponding" activity encoding regions is meant those regions encoding the same general type of activity—e.g., a ketoreductase activity in one location of a gene cluster would "correspond" to a ketoreductase-encoding activity in another location in the gene cluster or in a different gene cluster; similarly, a complete reductase cycle could be considered corresponding—e.g., KR/DH/ER could correspond to KR alone.

If replacement of a particular target region in a host polyketide synthase is to be made, this replacement can be conducted in vitro using suitable restriction enzymes or can be effected in vivo using recombinant techniques involving homologous sequences framing the replacement gene. One such system involving plasmids of differing temperature sensitivities is described in WO 96/40968.

A particularly useful method for modifying a PKS gene (e.g., making domain substitutions or "swaps") is a RED/ET cloning procedure developed for constructing domain swaps or modifications in an expression plasmid without first introducing restriction sites. The method is related to ET cloning methods (see, Datansko & Wanner, 2000, *Proc. Natl. Acad. Sci. U.S.A.* 97, 664045; Muyrers et al, 2000, *Genetic Engineering* 22:77-98) and is described in Example 8, infra. The RED/ET cloning procedure is used to introduce a unique restriction site in the recipient plasmid at the location of the targeted domain. This restriction site is used to subsequently linearize the recipient plasmid in a subsequent ET cloning step to introduce the modification. This linearization step is necessary in the absence of a selectable marker, which cannot be used for domain substitutions. An advantage of using this method for PKS engineering is that restriction sites do not have to be introduced in the recipient plasmid in order to construct the swap, which makes it faster and more powerful because boundary junctions can be altered more easily.

As noted supra, mutations can be introduced into PKS genes such that polypeptides with altered activity are encoded. Polypeptides with "altered activity" include those in which domains are inactivated or deleted, or in which a mutation changes the substrate specificity of a domain, as well as other alterations in activity. Mutations can be made to the native sequences using any number of conventional techniques. The substrates for mutation can be an entire cluster of genes or only one or two of them; the substrate for mutation may also be portions of one or more of these genes. Techniques for mutation include preparing synthetic oligonucleotides including the mutations and inserting the mutated sequence into the gene encoding a PKS subunit using restriction endonuclease digestion (see, e.g., Kunkel, 1985, *Proc Natl Acad Sci USA* 82:448; Geisselsoder et al., 1987, *BioTechniques* 5:786). Alternatively, the mutations can be effected using a mismatched primer (generally 10-20 nucleotides in length) which hybridizes to the native nucleotide sequence (generally cDNA corresponding to the RNA sequence), at a temperature below the melting temperature of the mismatched duplex. The primer can be made specific by keeping primer length and base composition within relatively narrow limits and by keeping the mutant base centrally located. (See Zoller and Smith, 1983, *Methods in Enzymology* 100:468). Primer extension is effected using DNA polymerase. The product of the extension reaction is cloned, and those clones containing the mutated DNA are selected. Selection can be accomplished using the mutant primer as a hybridization probe. The technique is also applicable for generating multiple point mutations (see, e.g., Dalbie-McFarland et al., 1982, *Proc Natl Acad Sci USA* 79:6409). PCR mutagenesis can also be used for effecting the desired mutations.

It will be apparent that, as described above, a large number of other chimeric and/or modified PKSs can be made. Examples of chimeric polyketide synthases are provided in Examples 6 and 7, below. Example 6 shows substitution of the geldanamycin AT7domain with the AT2 domain of the rapamycin PKS, and Example 7 shows substitution of geldanamycin AT5 domain with the rapamycin AT2 domain. For illustration (and not limitation) several additional examples are provided in the paragraphs A-H, below.

A. Substitution of the Geldanamycin PKS AT1 Domain with an AT Domain Specific for Malonyl-CoA One illustrative recombinant host cell provided by the present invention expresses a recombinant geldanamycin PKS in which the acyltransferase domain in module 1 of the geldanamycin PKS gene is replaced with an AT domain specific for malonyl-CoA instead of 2-methylmalonyl-CoA. The domain substitution is created by introducing a malonyl-CoA specific acyltransferase domain from a heterologous PKS gene, for example from the rapamycin, tylosin, or FK520 PKS genes or the like, into the geldanamycin PKS locus by homologous recombination into a geldanamycin-producing strain, aided by a selectable antibiotic resistance gene, then isolating the recombinants resulting from double crossover events in which the wild-type acyltransferase domain is replaced with one specific for malonyl-CoA. The AT domain of module 1 is encoded by nucleotides 27864 through 28908, approximately, of SEQ ID-NO:1. This sequence information together with the methods described in U.S. Pat. Nos. 6,399,789; 6,403,775; and 5,962,290 allows one skilled in the art to construct recombination vectors that result in replacement of the native AT domain of module 1 with an AT domain having a specificity for malonyl-CoA. Suitable examples of AT domains with specificity for malonyl-CoA may be found in the rapamycin PKS genes (modules 2, 5, 8, 9, 11, 12, and 14), as described in U.S. Pat. No. 6,399,789, as well as the tylosin PKS genes (modules 3 and 7) as described in U.S. Pat. No. 5,876,991; the spiramycin genes (modules 1-3 and 7), as described in U.S. Pat. No. 5,945,320; the FK520 genes (modules 3 and 10), as described in WO 00/20601; the pikromycin genes (module 2) as described in WO 99/61599; the narbomycin genes (module 2), as described in U.S. Pat. No. 6,303,767; the avermectin genes (module 2), and others. Fermentation of a host cell comprising the resulting hybrid PKS together with the remaining geldanamycin biosynthetic genes under conditions wherein the native strain produces geldanamycin, provides novel compounds.

B. Mutagenesis of Geldanamycin AT1

One illustrative recombinant host cell provided by the present invention expresses a recombinant geldanamycin PKS in which the AT1 domain of the geldanamycin PKS gene is mutagenized by site-directed mutagenesis to alter the substrate specificity of the AT domain. The AT1 domain can be mutagenized by art-known methods, such as methods described in Reeves et al., "Alteration of the substrate specificity of a modular polyketide synthase acyltransferase domain through site-directed mutagenesis," *Biochemistry* 2001, 40: 15464-70, and in WO 03/014312. The amino acid sequence Tyr-Ala-Ser-His (SEQ ID NO:81), encoded by nucleotide sequence TAC-GCC-TCC-CAC (SEQ ID NO:82) at positions 56052 to 56063 in SEQ ID NO:1, is mutagenized using methods known to one skilled in the art to generate the mutant amino acid sequence His-Ala-Phe-His (SEQ ID NO:83), for example by mutagensis of the nucleotide sequence to CAC-GCC-TTC-CAC (SEQ ID NO:84) as described in the Reeves et al. reference cited above. Fermentation of a host cell comprising the resulting mutagenized PKS together with the remaining geldanamycin biosynthetic genes under conditions wherein the native strain produces geldanamycin, followed by extraction of the broth and purification provides novel compounds.

C. Substitution of KR Domain for the Reduction Cassette of Geldanamycin PKS Module 6 (DH6+KR6)

One illustrative recombinant host cell provided by the present invention expresses a recombinant geldanamycin PKS in which the coding sequence for the reduction cassette of module 6, which has both DH and KR domains, is replaced with a coding sequence for a reduction cassette that has only a KR domain.

The coding sequence for the reduction cassette of module 6, which has both DH and KR domains, is replaced with a coding sequence for a reduction cassette that has only a KR domain. The reduction cassette is contained in the sequence between the end of the AT domain, at approximately nucleotide position 56663 of SEQ ID NO:1, and the beginning of the ACP domain, at approximately nucleotide position 59886 of SEQ ID NO:1. This sequence information together with the methods described in U.S. Pat. Nos. 6,399,789; 6,403,775; and 5,962,290 allows one skilled in the art to construct recombination vectors that result in replacement of the native reduction cassette of module 6 with a cassette encoding only a KR domain. Suitable examples of cassettes encoding only a KR domain may be found in the erythromycin and rapamycin PKS genes, as described in U.S. Pat. No. 6,399,789. Fermentation of a host cell comprising the resulting hybrid PKS together with the remaining geldanamycin biosynthetic genes under conditions wherein the native strain produces geldanamycin, followed by extraction of the broth and purification provides 4,5-dihydro-5-hydroxy-geldanamycin.

D. Inactivation of DH6

One illustrative recombinant host cell provided by the present invention expresses a recombinant geldanamycin PKS in which the dehydratase domain in module 6 is inactivated by site-specific mutation.

Inactivation of the dehydratase domain in module 6 of the geldanamycin PKS gene by site-specific mutation of the wild-type domain results in production of 4,5-dihydro-5-hydroxygeldanamycin. The DH domain of module 6 is encoded by nucleotides 56663 to 59886, approximately, of SEQ ID NO:1. Two particular sequences may be targeted for mutational inactivation of the DH domain. In one embodiment, the DNA sequence encoding the DH peptide motif His-Val-Ile-Ser-Gly-Ala-Val-Leu-Val-Pro (SEQ ID NO:7), nucleotides 56814 to 56843 of SEQ ID NO:1, is mutated so as to produce a peptide having an amino acid other than histidine at the first position. The CAC codon encoding histidine is mutated, for example to CAA or CAG to encode a glutamine. Fermentation of a host cell comprising the resulting mutagenized PKS together with the remaining geldanamycin biosynthetic genes under conditions wherein the native strain produces geldanamycin, followed by extraction of the broth and purification, provides 4,5-dihydro-5-hydroxy-geldanamycin.

E. Deletion of DH6+ER6

One illustrative recombinant host cell provided by the present invention expresses a recombinant geldanamycin PKS in which a substantial portion of the nucleotide sequence between the end of the AT6 and KR6 domain is deleted.

A portion of the nucleotide sequence in module 6 between the end of the AT domain (approximately nucleotide 56663 of SEQ ID NO:1) and the start of the KR domain (approximately nucleotide 57128 of SEQ ID NO:1) is deleted, resulting in deletion of the dehydratase and enol-reductase domains. This leaves a linker region between the AT and KR domains of approximately 465 amino acids.

F. Reductive Domain Swap

One illustrative recombinant host cell provided by the present invention expresses a recombinant geldanamycin PKS in which the dehydratase domain of module 1 is replaced or inactivated by site-specific mutation.

The reduction cassette in module 1 is encoded by the sequence between the end of the AT domain, at approximately nucleotide position 28908 of SEQ ID NO:1, and the beginning of the ACP domain, at approximately nucleotide position 32133 of SEQ ID NO:1. This sequence information together with the methods described in U.S. Pat. Nos. 6,399,789; 6,403,775; and 5,962,290 allows one skilled in the art to construct recombination vectors that result in replacement of the native reduction cassette of module 1 with a cassette encoding only a KR domain. Suitable examples of cassettes encoding only a KR domain may be found in the erythromycin and rapamycin PKS genes, as described in U.S. Pat. No. 6,399,789. Fermentation of a host cell comprising the resulting hybrid PKS together with the remaining geldanamycin biosynthetic genes under conditions wherein the native strain produces geldanamycin, followed by extraction of the broth and purification, provides 15-hydroxy-geldanamycin.

G. Inactivation of DH1

One illustrative recombinant host cell provided by the present invention expresses a recombinant geldanamycin PKS in which the dehydratase domain of module 1 is inactivated by site-specific mutation of the wild-type domain.

Inactivation of the dehydratase domain in module 1 of the geldanamycin PKS gene by site-specific mutation of the wild-type domain results in production of 15-hydroxygeldanamycin. The DH domain of module 1 is encoded by nucleotides 28908 to 30378 approximately, of SEQ ID NO:1.

Two particular sequences may be targeted for mutational inactivation of the DH domain. In one embodiment, the DNA sequence encoding the DH peptide motif His-Ala-Val-Ser-Gly-Thr-Val-Leu-Leu-Pro (SEQ ID NO:9), nucleotides 29088 through 29059 of SEQ ID NO:1, is mutated so as to produce a peptide having an amino acid other than histidine at the first position. The CAC codon encoding histidine is mutated, for example to CAA or CAG to encode a glutamine. Fermentation of a host cell comprising the resulting mutagenized PKS together with the remaining geldanamycin biosynthetic genes under conditions wherein the native strain produces geldanamycin, followed by extraction of the broth and purification provides 15-hydroxy-geldanamycin.

H. Inactivation of KS Domain

One illustrative recombinant host cell provided by the present invention expresses a recombinant geldanamycin PKS in which the module 1 KS domain is inactivated by deletion or other mutation. In one version, the inactivation results from a change in the KS domain that renders it incapable of binding substrate (called a KS1° mutation). This inactivation can be accomplished by a mutation in the codon for the active site cysteine that changes the codon to another codon, such as an alanine codon. Preferably the modified KS domain is in translational reading frame with extender modules 1 and 2 of the PKS. The host cells expressing a PKS comprising the protein encoded thereby can be fed or supplied with N-acylcysteamine thioesters of precursor molecules to prepare a polyketide of interest. See U.S. patent application Ser. No. 09/492,773 (published as U.S. Pat. No. 6,492,562) and WO 00/44717.

Examples of compounds that can be produced using geldanamycin-based chimeric PKSs, for illustration and not limitation, are described in WO 03/013430 ("Benzoquinone Ansamycins," published Feb. 20, 2003).

In an aspect, the invention provides chimeric and/or modified polyketide synthases based on the geldanamycin or herbimycin PKSs or containing a portion (e.g., domain) of geldanamycin or herbimycin PKS. Regardless of the naturally occurring PKS gene used as an acceptor, the invention provides libraries of polyketides by generating modifications in, or using a portion of, the geldanamycin or herbimycin PKS so that the protein complexes produced by the cluster have altered activities in one or more respects, and thus produce polyketides other than the natural product of the PKS. Novel polyketides may thus be prepared, or polyketides in general prepared more readily, using this method. By providing a large number of different genes or gene clusters derived from a naturally occurring PKS gene cluster, each of which has been modified in a different way from the native cluster, an effectively combinatorial library of polyketides can be produced as a result of the multiple variations in these activities.

As used herein, a polyketide synthase "derived from" a naturally occurring PKS contains the scaffolding encoded by all the portion of the naturally occurring synthase gene used, contains at least two modules that are functional, and contains mutations, deletions, or replacements of one or more of the activities of these functional modules so that the nature of the resulting polyketide is altered. This definition applies both at the protein and genetic levels. Particularly preferred embodiments include those wherein a KS, AT, KR, DH, NRPS, or ER has been deleted or replaced by a version of the activity from a different PKS or from another location within the same PKS. Also preferred are derivatives where at least one non-condensation cycle enzymatic activity (KR, DH, or ER) has been deleted or wherein any of these activities has been mutated so as to change the ultimate polyketide synthesized.

In one aspect, the invention provides libraries of recombinant cells producing polyketides wherein the polyketides are synthesized by a PKS derived from naturally occurring PKSs. Generally, many members of these polyketide libraries may themselves be novel compounds, and the invention further includes novel polyketide members of these libraries.

Expression vectors containing nucleotide sequences encoding a variety of PKS systems for the production of different polyketides can be introduced by transformation into the appropriate host cells to construct a polyketide library. In one approach, a mixture of such vectors is transformed into the selected host cells and the resulting cells plated into individual colonies and selected for successful transformants. Each individual colony has the ability to produce a particular PKS synthase and ultimately a particular polyketide. Typically, there will be duplications in some of the colonies; the subset of the transformed colonies that contains a different PKS in each member colony can be considered the library. Alternatively, the expression vectors can be used individually to transform hosts, which transformed hosts are then assembled into a library. A variety of strategies might be devised to obtain a multiplicity of colonies each containing a PKS gene cluster derived from the naturally occurring host gene cluster so that each colony in the library produces a different PKS and ultimately a different polyketide. The number of different polyketides that are produced by the library is typically at least four, more typically at least ten, and preferably at least 20, more preferably at least 50, reflecting similar numbers of different altered PKS gene clusters and PKS gene products. The number of members in the library is arbitrarily chosen; however, the degrees of freedom outlined above with respect to the variation of starter, extender units, stereochemistry, oxidation state, and chain length is quite large. The polyketide producing colonies can be identified and isolated using known techniques and the produced polyketides further characterized. The polyketides produced by these colonies can be used collectively in a panel to represent a library or may be assessed individually for some kind of chemical or biological activity.

The libraries can thus be considered at four levels: (1) a multiplicity of colonies each with a different PKS encoding sequence encoding a different PKS cluster but all derived from a naturally occurring PKS cluster; (2) colonies which contain the proteins that are members of the PKS produced by the coding sequences; (3) the polyketides produced; and (4) compounds derived from the polyketides. Of course, combination libraries can also be constructed wherein members of a library derived, for example, from the erythromycin PKS can be considered as a part of the same library as those derived from, for example, the rapamycin PKS cluster.

Colonies in the library are induced to produce the relevant synthases and thus to produce the relevant polyketides to obtain a library of candidate polyketides. The polyketides secreted into the media can be screened for binding to desired targets, such as receptors, signaling proteins, and the like. The supernatants per se can be used for screening, or partial or complete purification of the polyketides can first be effected. Typically, such screening methods involve detecting the binding of each member of the library to a receptor or other target molecule or complex of molecules. Binding can be detected either directly or through a competition assay. Means to screen such libraries for binding are well known in the art. Alternatively, individual polyketide members of the library can be tested against a desired target. In this event, screens wherein the biological response of the target is measured can be included.

In one version, libraries of polyketides are produced by cloning PKS genes as a set of three or more mutually selectable plasmids, each carrying a different wild-type or mutant PKS gene, then introducing all possible combinations of the plasmids with wild-type, mutant, and hybrid PKS coding sequences into the same host (see WO 00/63361 and WO 98/27203).

In aspects of the invention, accessory genes and proteins disclosed herein are used for production of novel polyketides (e.g., by post-PKS tailoring of polyketides), more efficient production of known polyketides (e.g., increased and/or heterologous biosynthesis of a desired polyketide), increased and/or heterologous biosynthesis of PKS substrates (such as AHBA, malonyl-CoA, 2-methoxymalonate and 2-methylmalonyl-CoA), regulation of protein biosynthesis (e.g., transcriptional regulation of genes encoding PKS and accessory proteins, increased and/or heterologous transport of polyketides), drug resistance (e.g., resistance to geldanamycin and/or herbimycin), and other uses. These and other results are accomplished by heterologous expression of one or more accessory proteins and/or inactivation of one or more accessory proteins and/or modification of one or more accessory proteins. Similarly, genes denoted as ancillary genes encode useful proteins and can be expressed and/or modified in a host cell, used for targeting, and the like.

One useful set of accessory proteins are the AHBA biosynthetic proteins described in EXAMPLE 4, infra. The genes encoding these proteins can be expressed alone or in combination with AHBA biosynthetic genes from other sources (see, e.g., Yu et al., 2002 *Proc Natl Acad Sci USA.* 99:7968-73; August et al., 1998 *Chem Biol* 5: 69-79; and Kim et al., 1998, *J. Biol. Chem.* 273:6030-40) to produce AHBA in a heterologous cell. Alternatively, one or more genes in the AHBA synthetic pathway can be inactivated by recombinant means. Such inactivation can be employed, for example, to facilitate production of polyketides modified or that use starter units other than AHBA, such as modified AHBA derivatives or diketides, including polyketides expressed by modified or chimeric PKSs.

Sequences of the geldanamycin (or herbimycin) gene cluster or mutated versions of the geldanamycin gene cluster prepared according to the methods of the invention can be expressed in the native geldanamycin (or herbimycin) producer or in heterologous systems. Methods for heterologous expression of PKS genes and host cells suitable for expression of these genes and production of polyketides are described, for example, in U.S. Pat. Nos. 5,843,718 and 5,830,750; WO 01/31035, WO 01/27306, and WO 02/068613; and U.S. patent application Ser. Nos. 10/087,451; 60/355,211; and 60/396,513.

Particularly preferred host cells for purposes of the present invention are *Streptomyces, Myxococcus,* and *Saccharopolyspora* host cells. Preferred hosts include fungal systems such as yeast, and procaryotic hosts; mammalian cells could also be used. As disclosed in U.S. Pat. No. 6,033,883, a wide variety of hosts can be used, even though some hosts natively do not contain the appropriate post-translational mechanisms to activate the acyl carrier proteins of the synthases. These hosts can be modified with the appropriate recombinant enzymes to effect these modifications. Suitable host cells include *Streptomyces* spp., *E. coli*, yeast, and other procaryotic hosts which use control sequences compatible with *Streptomyces* spp.

Similarly, host cells can be selected, or engineered, for expression of polyketide biosynthetic activities, such as glycosylatation apparatus (discussed below), amide synthases, (see, for example, U.S. provisional patent application 60/396,513 "Metabolic Pathways For Starter Units in Polyketide Biosynthesis in *E. coli*"). In one embodiment herbimycin PKS genes are co-expressed with a heterologous amide synthase, such as the synthase encoded by gdmF. In a related embodiment, gdmF is expressed in the herbimycin producer *S. hygroscopicus* AM-3672.

The vectors used to perform the various operations to replace the enzymatic activity in the host PKS genes or to support mutations in these regions of the host PKS genes may be chosen to contain control sequences operably linked to the resulting coding sequences in a manner that expression of the coding sequences may be effected in an appropriate host. If the cloning vectors employed to obtain PKS genes encoding a derived PKS lack control sequences for expression operably linked to the encoding nucleotide sequences, the nucleotide sequences are inserted into appropriate expression vectors. This need not be done individually, but a pool of isolated encoding nucleotide sequences can be inserted into host vectors, the resulting vectors transformed or transfected into host cells and the resulting cells plated out into individual colonies.

Preferred host cells for purposes of selecting vector components for expression vectors of the present invention include fungal host cells such as yeast and procaryotic host cells such as *E. coli* and *Streptomyces*, but mammalian host cells can also be used. Suitable control sequences include those which function in eucaryotic and procaryotic host cells.

Suitable control sequences for single cell cultures of various types of organisms are well known in the art. Control systems for expression in yeast are widely available and are routinely used. Control elements include promoters, optionally containing operator sequences, and other elements depending on the nature of the host, such as ribosome binding sites. Particularly useful promoters for procaryotic hosts include those from PKS gene clusters which result in the production of polyketides as secondary metabolites, including those from Type I or aromatic (Type II) PKS gene clusters. Examples are act promoters, tcm promoters, spiramycin promoters, and the like. However, other bacterial promoters, such as those derived from sugar metabolizing enzymes, such as galactose, lactose (lac) and maltose, are also useful. Additional examples include promoters derived from biosynthetic enzymes such as for tryptophan (trp), the β-lactamase (bla) bacteriophage lambda PL, and T5. In addition, synthetic promoters, such as the tac promoter (U.S. Pat. No. 4,551,433) can be used.

As noted, particularly useful control sequences are those which themselves, or with suitable regulatory systems, activate expression during transition from growth to stationary phase in the vegetative mycelium. The system contained in the plasmid identified as pCK7, i.e., the actI/actIII promoter pair and the actII-ORF4 (an activator gene), is particularly preferred. Particularly preferred hosts are those which lack their own means for producing polyketides so that a cleaner result is obtained. Illustrative control sequences, vectors, and host cells of these types include the modified *S. coelicolor* CH999 and vectors described in PCT publication WO 96/40968 and similar strains of *S. lividans*. See U.S. Pat. Nos. 5,672,491; 5,830,750, 5,843,718; and 6,177,262.

Other regulatory sequences may also be desirable which allow for regulation of expression of the PKS sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

Selectable markers can also be included in the recombinant expression vectors. A variety of marker genes are known which are useful in selecting for transformed cell lines and generally comprise a gene whose expression confers a selectable phenotype on transformed cells when the cells are grown in an appropriate selective medium. Such markers include, for example, genes which confer antibiotic resistance or sensitivity to the plasmid. Alternatively, several polyketides are naturally colored, and this characteristic provides a built-in marker for screening cells successfully transformed by the present constructs.

The various PKS nucleotide sequences, or a mixture of such sequences, can be cloned into one or more recombinant vectors as individual cassettes, with separate control elements or under the control of a single promoter. The PKS subunits or components can include flanking restriction sites to allow for the easy deletion and insertion of other PKS subunits so that hybrid or chimeric PKSs can be generated. The design of such restriction sites is known to those of skill in the art and can be accomplished using the techniques described above, such as site-directed mutagenesis and PCR. Methods for introducing the recombinant vectors of the present invention into suitable hosts are known to those of skill in the art and typically include the use of $CaCl_2$ or other agents, such as divalent cations, lipofection, DMSO, protoplast transformation, and electroporation.

When such DNA molecules are introduced into a host cell and the host cell is cultured under conditions that lead to the expression of the geldanamycin (or herbimycin), or chimeric PKS proteins, geldanamycin (or herbimycin) and/or its analogs or derivatives may be produced. In one embodiment, the expression control sequences are those normally associated with a module of the S. hygroscopicus geldanamycin or herbimycin polyketide synthase gene cluster.

The native, chimeric or modified PKS genes can be expressed in a cell that also expresses other proteins involved in polyketide biosynthesis or modification. These other proteins can be endogenous proteins (normally expressed in the host cell), heterologous recombinant proteins (encoded by a sequence not normally expressed in the host cell), or combinations of both.

In hosts such as yeasts, plants, or mammalian cells that ordinarily do not produce polyketides, it may be necessary to provide, also typically by recombinant means, suitable holo-ACP synthases to convert the recombinantly produced PKS to functionality. Provision of such enzymes is described, for example, in WO 97/13845 and WO 98/27203.

For example and not limitation, the host cell can contain the desosamine, megosamine, and/or mycarose biosynthetic genes, corresponding glycosyl transferase genes, and hydroxylase genes (e.g., picK, megK, eryK, megF, and/or eryF). Methods for glycosylating polyketides are generally known in the art and can be applied in accordance with the methods of the present invention; the glycosylation may be effected intracellularly by providing the appropriate glycosylation enzymes or may be effected in vitro using chemical synthetic means as described herein and in WO 98/49315, incorporated herein by reference. Glycosylation with desosamine, mycarose, and/or megosamine is effected in accordance with the methods of the invention in recombinant host cells provided by the invention. Alternatively and as noted, glycosylation may be effected intracellularly using endogenous or recombinantly produced intracellular glycosylases. In addition, synthetic chemical methods may be employed.

Alternatively, the aglycone compounds can be produced in the recombinant host cell, and the desired modification (e.g., glycosylation and hydroxylation) steps carried out in vitro (e.g., using purified enzymes, isolated from native sources or recombinantly produced) or in vivo in a converting cell different from the host cell (e.g., by supplying the converting cell with the aglycone).

Suitable culture conditions for production of polyketides using the cells of the invention will vary according to the host cell and the nature of the polyketide being produced, but will be know to those of skill in the art. See, for example, WO 98/27203 "Production Of Polyketides In Bacteria And Yeast" and WO 01/83803 "Overproduction Hosts For Biosynthesis Of Polyketides."

The polyketide product produced by host cells of the invention can be recovered (i.e., separated from the producing cells and at least partially purified) using routine techniques (e.g., extraction from broth followed by chromatography).

The compositions, cells and methods of the invention may be directed to the preparation of an individual polyketide or a number of polyketides. The polyketide may or may not be novel, but the method of preparation permits a more convenient or alternative method of preparing it. It will be understood that the resulting polyketides may be further modified to convert them to other useful compounds. For example, an ester linkage may be added to produce a "pharmaceutically acceptable ester" (i.e., an ester that hydrolyzes under physiologically relevant conditions to produce a compound or a salt thereof). Illustrative examples of suitable ester groups include but are not limited to formates, acetates, propionates, butyrates, succinates, and ethylsuccinates.

The polyketide product can be modified by addition of a protecting group, for example to produce prodrug forms. A variety of protecting groups are disclosed, for example, in T. H. Greene and P. G. M. Wuts, Protective Groups in Organic Synthesis, Third Edition, John Wiley & Sons, New York (1999). Prodrugs are in general functional derivatives of the compounds that are readily convertible in vivo into the required compound. Conventional procedures for the selection and preparation of suitable prodrug derivatives are described, for example, in "Design of Prodrugs," H. Bundgaard ed., Elsevier, 1985.

Similarly, improvements in water solubility of a polyketide compound can be achieved by addition of groups containing solubilizing functionalities to the compound or by removal of hydrophobic groups from the compound, so as to decrease the lipophilicity of the compound. Typical groups containing solubilizing functionalities include, but are not limited to: 2-(dimethylaminoethyl)amino, piperidinyl, N-alkylpiperidinyl, hexahydropyranyl, furfuryl, tetrahydrofurfuryl, pyrrolidinyl, N-alkylpyrrolidinyl, piperazinylamino, N-alkylpiperazinyl, morpholinyl, N-alkylaziridinylmethyl, (1-azabicyclo [1.3.0]hex-1-yl)ethyl, 2-(N-methylpyrrolidin-2-yl)ethyl, 2-(4-imidazolyl)ethyl, 2-(1-methyl-4-imidazolyl)ethyl, 2-(1-methyl-5-imidazolyl)ethyl, 2-(4-pyridyl)ethyl, and 3-(4-morpholino)-1-propyl. In the case of geldanamycin analogs, solubilizing groups can be added by reaction with amines, which results in the displacement of the 17-methoxy group by the amine (see, Schnur et al., 1995, "Inhibition of the Oncogene Product $p_{185}^{erbB-2}$ in Vitro and in Vivo by Geldanamycin and Dihydrogeldanamycin Derivatives;", *J. Med. Chem.* 38, 3806-3812; Schnur et al., 1995 "erbB-2 Oncogene Inhibition by Geldanamycin Derivatives: Synthesis, Mechanism of Action, and Structure-Activity relationships," *J. Med. Chem.*

38, 3813-3820; Schnur et al., "Ansamycin Derivatives as Antioncogene and Anticancer Agents," U.S. Pat. No. 5,932, 655; all of which are incorporated herein by reference). Typical amines containing solubilizing functionalities include 2-(dimethylamino)-ethylamine, 4-aminopiperidine, 4-amino-1-methylpiperidine, 4-aminohexahydropyran, furfurylamine, tetrahydrofurfurylamine, 3-(aminomethyl)-tetrahydrofuran, 2-(amino-methyl)pyrrolidine, 2-(aminomethyl)-1-methylpyrrolidine, 1-methylpiperazine, morpholine, 1-methyl-2(aminomethyl)aziridine, 1-(2-aminoethyl)-1-azabicyclo-[1.3.0]hexane, 1-(2-aminoethyl)piperazine, 4-(2-aminoethyl)morpholine, 1-(2-amino-ethyl)pyrrolidine, 2-(2-aminoethyl)pyridine, 2-fluoroethylamine, 2,2-difluoroethylamine, and the like.

In addition to post synthesis chemical or biosynthetic modifications, various polyketide forms or compositions can be produced, including but not limited to mixtures of polyketides, enantiomers, diastereomers, geometrical isomers, polymorphic crystalline forms and solvates, and combinations and mixtures thereof can be produced Many other modifications of polyketides produced according to the invention will be apparent to those of skill, and can be accomplished using techniques of pharmaceutical chemistry.

Prior to use the PKS product (whether modified or not) can be formulated for storage, stability or administration. For example, the polyketide products can be formulated as a "pharmaceutically acceptable salt." Suitable pharmaceutically acceptable salts of compounds include acid addition salts which may, for example, be formed by mixing a solution of the compound with a solution of a pharmaceutically acceptable acid such as hydrochloric acid, hydrobromic acid, sulfuric acid, fumaric acid, maleic acid, succinic acid, benzoic acid, acetic acid, citric acid, tartaric acid, phosphoric acid, carbonic acid, or the like. Where the compounds carry one or more acidic moieties, pharmaceutically acceptable salts may be formed by treatment of a solution of the compound with a solution of a pharmaceutically acceptable base, such as lithium hydroxide, sodium hydroxide, potassium hydroxide, tetraalkylammonium hydroxide, lithium carbonate, sodium carbonate, potassium carbonate, ammonia, alkylamines, or the like.

Prior to administration to a mammal the PKS product will be formulated as a pharmaceutical composition according to methods well known in the art, e.g., combination with a pharmaceutically acceptable carrier. The term "pharmaceutically acceptable carrier" refers to a medium that is used to prepare a desired dosage form of a compound. A pharmaceutically acceptable carrier can include one or more solvents, diluents, or other liquid vehicles; dispersion or suspension aids; surface active agents; isotonic agents; thickening or emulsifying agents; preservatives; solid binders; lubricants; and the like. Remington's Pharmaceutical Sciences, Fifteenth Edition, E. W. Martin (Mack Publishing Co., Easton, Pa., 1975) and Handbook of Pharmaceutical Excipients, Third Edition, A. H. Kibbe ed. (American Pharmaceutical Assoc. 2000), disclose various carriers used in formulating pharmaceutical compositions and known techniques for the preparation thereof.

The composition may be administered in any suitable form such as solid, semisolid, or liquid form. See Pharmaceutical Dosage Forms and Drug Delivery Systems, $5^{th}$ edition, Lippicott Williams & Wilkins (1991). In an embodiment, for illustration and not limitation, the polyketide is combined in admixture with an organic or inorganic carrier or excipient suitable for external, enteral, or parenteral application. The active ingredient may be compounded, for example, with the usual non-toxic, pharmaceutically acceptable carriers for tablets, pellets, capsules, suppositories, pessaries, solutions, emulsions, suspensions, and any other form suitable for use. The carriers that can be used include water, glucose, lactose, gum acacia, gelatin, mannitol, starch paste, magnesium trisilicate, talc, corn starch, keratin, colloidal silica, potato starch, urea, and other carriers suitable for use in manufacturing preparations, in solid, semi-solid or liquified form. In addition, auxiliary stabilizing, thickening, and coloring agents and perfumes may be used.

In one aspect, the invention provides recombinant DNA molecules. In some embodiments, the invention provides a recombinant DNA molecule that contains an open reading frame of a polyketide synthase that includes an encoding sequence for a polyketide synthase domain, where the encoding sequence is SEQ ID NO:1-3, (or no:1' or 1") or a fraction thereof that encodes at least 10 consecutive amino acids of the polyketide synthase. In some embodiments, the invention provides a recombinant DNA molecule that comprises an encoding sequence for a geldanamycin synthase domain. In some of theses embodiments, the sequence is SEQ ID NO:1-3 (or no:1' or 1"). In some embodiments, the invention provides a recombinant DNA molecule encoding a geldanamycin PKS domain of at least 10 amino acids, where the DNA molecule includes a sequence contained in a sequence of SEQ ID NO:1-3 (or no:1' or 1").

In another aspect, the invention provides a recombinant expression system capable of producing a polyketide synthase domain in a host cell, where the system includes an encoding sequence for a geldanamycin polyketide synthase domain that is operably linked to control sequences effective in the host cell to produce RNA that is translated into the polyketide synthase domain. In a further aspect, the invention provides a host cell modified to contain the recombinant expression system.

In another aspect, the invention provides vectors. In some embodiments, the invention provides a vector containing geldanamycin PKS genes, where the vector is pKOS-256-144-1, pKOS-256-144-2, pKOS-256-144-3, pKOS-256-144-4, pKOS-256-154-1, pKOS-256-154-2, pKOS-256-154-3, pKOS-256-154-4, pKOS-256-154-5, pKOS-256-154-6, pKOS-256-154-7, pKOS-256-163-1, pKOS-256-163-2, pKOS-256-163-3, pKOS-256-107-1, pKOS-256-107-2, pKOS256-107-3, pKOS-256-107-4, pKOS-256-107-5, pKOS-256-107-6, or pKOS-256-107-7. In some embodiments, the invention provides a vector that includes an open reading frame of SEQ ID NO:1 (or no: 1' or 1"). In some embodiments, the invention provides a vector that comprises an open reading frame of SEQ ID NO:3. In some embodiments, the invention provides a pKOS256-116-10 vector.

In yet another aspect, the invention provides an isolated and purified nucleic acid encoding a geldanamycin PKS domain, where the sequence of the nucleic acid is one of the following sequences: SEQ ID NO:4, SEQ ID NO:5, SEQ ID NO:6, SEQ ID NO:7, SEQ ID NO:8, SEQ ID NO:9, SEQ ID NO:10, or SEQ ID NO:11. In another aspect, the invention provides an isolated and purified geldanamycin LDD domain comprising the amino acid sequence of SEQ ID NO:12.

In another aspect, the invention provides a recombinant DNA molecule that comprises an open reading frame of a polyketide synthase, where the open reading frame includes an encoding sequence for a polyketide synthase domain, where the encoding sequence contains a sequence that is the sequence one of SEQ ID NO:1-3 and 22-38 (or no:1' or 1"), or a fraction thereof that encodes at least 10 consecutive amino acids of the polyketide synthase.

In another aspect, the invention provides recombinant DNA molecules. In some embodiments, the invention provides a recombinant DNA molecule that contains an encoding sequence for a herbimycin synthase domain. In some embodiments, the recombinant DNA molecule of contains a sequence of SEQ ID NO:1-3 and 22-38 (or no:1' or 1"). In some embodiments, the invention provides a recombinant DNA molecule encoding a herbimycin PKS domain that includes at least 10 amino acids, where the DNA molecule contains a sequence contained in a sequence from the following group of sequences: SEQ ID NO:1-3 and 22-38 (or no:1' or 1").

In a further aspect, the invention provides a recombinant expression system capable of producing a polyketide synthase domain in a host cell, where the system contains an encoding sequence for a herbimycin polyketide synthase domain, and where the encoding sequence is operably linked to control sequences effective in the host cell to produce RNA that is translated into the polyketide synthase domain. In another aspect, the invention provides a host cell modified to contain this recombinant expression system.

In a yet further aspect, the invention provides vectors. In some embodiments, the invention provides a vector containing herbimycin PKS gene. In some embodiments, the invention provides a vector that contains an open reading frame of a herbimycin PKS clone, where the sequence of the open reading frame is one of SEQ ID NO:1-3 and 22-38 (or no:1' or 1"). In yet other embodiments, the invention provides a vector that contains an open reading frame of a herbimycin PKS cluster.

In another aspect, the invention provides an isolated and purified nucleic acid encoding a herbimycin PKS domain, where the sequence of the nucleic acid is from one of SEQ ID NO:1-3 and 22-38 (or no:1' or 1").

In a further aspect, the invention provides an isolated and purified herbimycin domain expressed from an isolated and purified nucleic acid whose sequence is from one of SEQ ID NO:1-3 and 22-38 (or no:1' or 1").

In one aspect, the invention provides recombinant DNA molecules, and vectors comprising those recombinant DNA molecules, that encode all or a portion of the geldanamycin PKS and that, when transformed into a host cell which is then cultured under conditions that lead to the expression of said geldanamycin PKS proteins, results in the production of geldanamycin and/or analogs or derivatives thereof in useful quantities. The present invention also provides recombinant host cells comprising those recombinant vectors. In a related aspect, the invention provides recombinant DNA molecules, and vectors comprising those recombinant DNA molecules, that encode all or a portion of the herbimycin PKS and that, when transformed into a host cell which is then cultured under conditions that lead to the expression of said herbimycin PKS proteins, results in the production of geldanamycin and/or analogs or derivatives thereof in useful quantities. The present invention also provides recombinant host cells comprising those recombinant vectors.

The invention provides the coding sequences for the proteins of the geldanamycin synthase complex, and DNA molecules in which the complete set of appropriately arranged geldanamycin PKS-encoding sequences are operably linked to expression control sequences that are effective in suitable host cells of the invention to produce geldanamycin and/or its analogs or derivatives. The invention similarly provides the coding sequences for the proteins of the herbimycin synthase complex, and DNA molecules in which the complete set of appropriately arranged herbimycin PKS-encoding sequences are operably linked to expression control sequences that are effective in suitable host cells of the invention to produce a herbimycin and/or its analogs or derivatives.

In a further aspect, the invention provides a method of identifying and isolating a PKS gene cluster from the genome of a host cell by: constructing a genomic library of the host cell into a vector, where the vector is a plasmid, cosmid, bacterial artificial chromosome, or yeast artificial chromosome; designing degenerate PCR primers homologous to a conserved region of the PKS gene cluster; performing PCR amplification using these degenerate primers and the host cell genome as template; cloning and sequencing the resulting PCR amplimers; comparing nucleotide sequences of the PCR amplimers to known homologs of the PKS gene cluster to create a sequence homology phylogenetic tree; analyzing the sequence homology data to deduce a most likely candidate PKS gene cluster; probing the host cell genomic library with the PCR amplimer as a probe; isolating genomic library clones that hybridize with the amplimer probe; and sequencing these positive genomic library clones.

EXAMPLES

Example 1

Identification of Nucleotide Sequences Encoding Domains of Geldanamycin Synthase from *Streptomyces hygrospcopicus* NRRL 3602

Genomic Library Generation and Screening. Genomic DNA of *Streptomyces hygroscopicus* 3602 was cloned into bacterial artificial chromosomes (BACs) to make a BAC library for screening. The particular BAC system was selected, because it allows genomic DNA fragments of up to approximately 50 Kb to be cloned into a single BAC, thus reducing the number of clones needed to encompass the *S. hygroscopicus* 3602 genome. Restriction fragment length analysis of the insert DNA in the BAC clones of the BAC library revealed that the average insert size was about 4045 Kb (BAC clone DNA was prepared as described in Example 2). An array of 5,000 BAC clones from the BAC library was generated for screening on a high density nylon filter array (Amplicon, Pullman, Wash.).

Analysis of the *S. hygroscopicus* 3602 genome by PCR using degenerate primers to amplify KS domain encoding sequences showed that the genome contains about 65 different ketosynthase coding sequences. Thus, in screening the BAC library, there was a need for a two-prong approach to distinguish clones containing geldanamycin PKS gene cluster sequences from clones containing KS domain encoding sequences from other clusters. The BAC library was screened first with $^{32}P$-labeled Carbamoyl O-Transferase (CT) nucleic acid probes, and then, positive clones from the CT screen were screened with $^{32}P$-labeled Ketosynthase (KS) nucleic acid probes.

Carbamoyl Transferase Probe Screening. CT degenerate primer set 1 (SEQ ID NO:14 and SEQ ID NO:16) was used to PCR amplify *S. hygroscopicus* 3602 genomic DNA, and 20 amplimers were identified and sequenced. The sequence data revealed that all amplimers were identical. Specific CT primer pair (SEQ ID NO:17 and SEQ ID NO:18) was then used to generate an 849 bp CT probe (SEQ ID NO:13). This CT probe was used to identify BAC clones on the high density filter that hybridized specifically to the probe. Twenty one clones were identified and subjected to a second round of PCR with primer set 2 (SEQ ID NO:14 and SEQ ID NO:15) to confirm that the clones contained the DNA; fifteen clones were positive by this test and used in the KS probe screen.

Ketosynthase Degenerate Primer PCR Screening. PCR with the KS degenerate primer pair (SEQ ID NO:19 and SEQ ID NO:20) was used to screen the CT-positive clones and to generate KS amplimers useful for sequencing and as probes. Nine of the fifteen clones contained sequences that amplified with the degenerate KS primers. Restriction mapping analysis of these clones and sequence analysis of the amplimers revealed that these clones contained coding sequences for no more than four different KS domains in addition to the CT sequences. Because the geldanamycin PKS was expected to contain at least seven different KS domains, this result suggested that the insert DNA of these nine clones did not span the entire geldanamycin biosynthetic gene cluster, and an effort to identify additional clones containing the missing portion of the gene cluster was undertaken.

Identification of Missing Portion of Geldanamycin PKS Gene Cluster and Probe Preparation. Because CT-positive BAC clones were isolated that did not contain KS domain coding sequences, it was expected that the CT sequences flanked the PKS encoding region. Restriction fragment length analysis revealed that the insert DNA of the nine clones containing both CT and KS coding sequences overlapped with the insert DNA of the clones that contained CT sequences but lacked KS sequences. Of the nine BAC clones containing both CT and KS coding sequences, the clone designated pKOS-256-107-3 had the longest insert (39 Kb), which was designated 5-CT.

Identification and Sequencing of BAC Clones Encompassing the Missing Portion of the Geldanamycin PKS Gene Cluster. Chromosome walking was performed to identify BAC clones having insert DNA overlapping the 5-CT insert and containing the missing portion of the geldanamycin PKS gene cluster. The KS PCR amplimers of the four different KS domain encoding sequences identified from the nine BAC clones that contained the CT and KS sequences were subcloned to obtain 4 different subclones: pKOS-256-144-1 through -4 (the KS domain coding sequences are shown in SEQ ID NO:4 through SEQ ID NO:7). These 4 amplimers were pooled and used as $^{32}$P radiolabeled KS probes in a hybridization at high stringency with the clones on the high density filter. Seven additional BAC clones, pKOS-256-154-1 through pKOS-256-154-7, were identified and found to contain three additional KS sequences.

Figure 4:
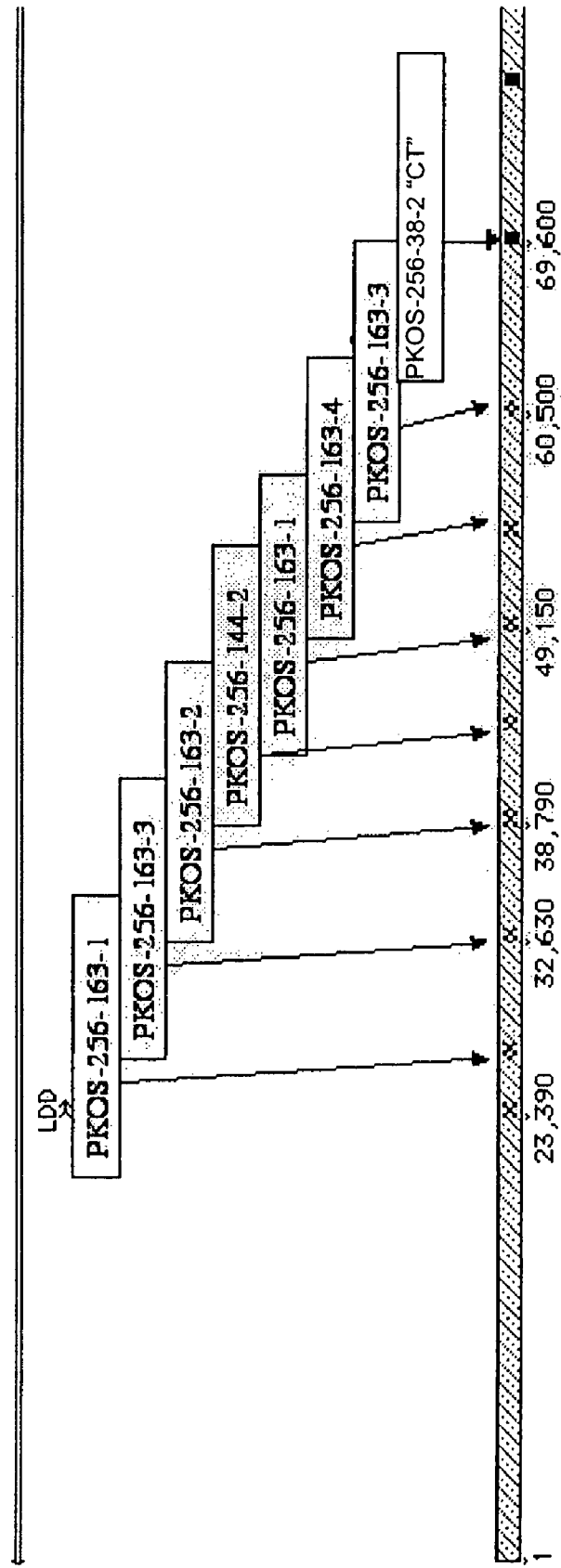
FIG. 4 is a schematic of the configuration of KS, CT, and LDD domains of geldanamycin PKS gene cluster and corresponding clones containing those domains.
Figure 8:
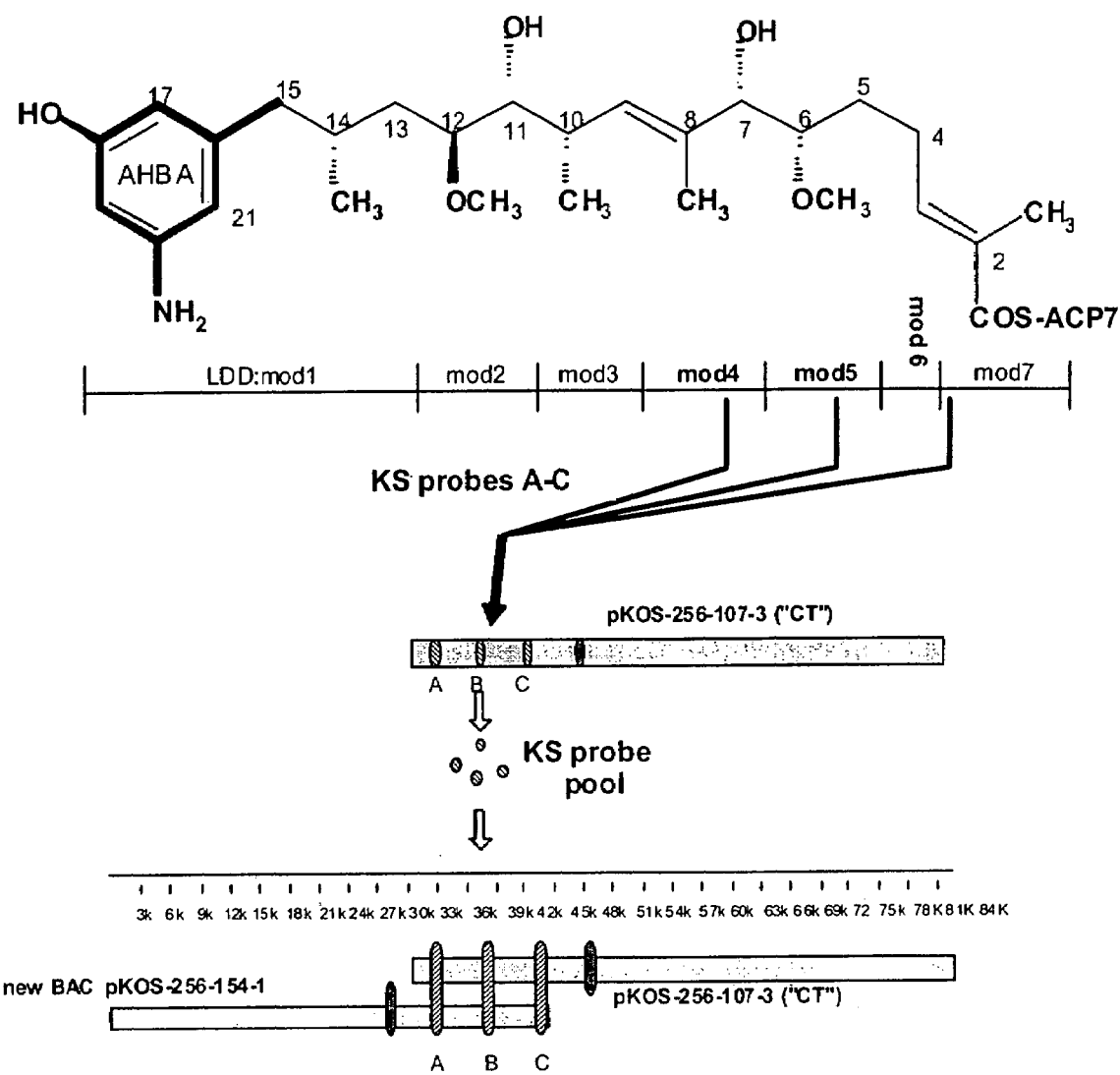
FIG. 8 is a schematic of the CT probe identified BAC showing overlap with KS probe hybridization sites of modules 4, 5 and 6.

One clone (pKOS-256-154-1) contained an insert, designated KS2, that overlapped with the 5-CT insert and contained all three of the additional KS domain coding sequences; the insert of this clone is shown on FIG. 3. Based on the structure of progeldanamyin (See FIG. 2), the geldanamycin PKS gene cluster was expected to have 7 modules. Thus, the geldanamycin PKS gene cluster and additional genes of the geldanamycin biosynthetic gene cluster can be assembled from BAC clones pKOS256-107-3 and pKOS256-154-1. The seven KS domain coding sequences of the geldanamycin PKS genes are shown in SEQ ID NO:4 through SEQ ID NO:10; these sequences were subcloned into vectors pKOS-256-144-1, pKOS-256-144-2, pKOS-256-144-3, pKOS-256-144-4, pKOS-256-163-1, pKOS-256-163-2, and pKOS-256-163-3. The KS domain coding sequences, corresponding vectors, and organization of the geldanamycin PKS gene cluster is shown in FIG. 4 and FIG. 8. The overlap of BAC clones pKOS256-107-3 and pKOS256-154-1 at the KS probe hybridization sites and overlap of the deduced geldanamycin PKS gene cluster organization is shown in FIG. 3A and FIG. 8.

The geldanamycin PKS gene cluster contig nucleotide sequence is provided in SEQ ID NO:1 below. Standard IUPAC ambiguity codes are used in the sequence. The insert of BAC clone pKOS256-154-1 ("KS2") corresponds to bases 1-44591 of SEQ ID NO:1. This subsequence of SEQ ID NO:1 is sometimes referred to herein as Sequence ID NO:1'. The insert of clone pKOS256-107-3 ("CT") corresponds to bases 30398-85692 of SEQ ID NO:1. This subsequence of SEQ ID NO:1 is sometimes referred to herein as Sequence ID NO:1'''. References herein to SEQ ID NO:1 or fragments thereof (e.g., fragments of at least 100 bp) or protein coding regions thereof are also intended to refer to Sequence ID NO:1' and Sequence ID NO:1''. Translations of selected ORFs in SEQ ID NO:1 are provided as SEQ ID NOS:115-146.

TABLE 1, above, provides open reading frame (ORF) boundaries corresponding to the nucleotide position in SEQ ID NO:1 of the geldanamycin PKS as well as the nucleotide sequences encoding enzymes involved in precursor synthesis and progeldanamycin modification.

Figure 7:
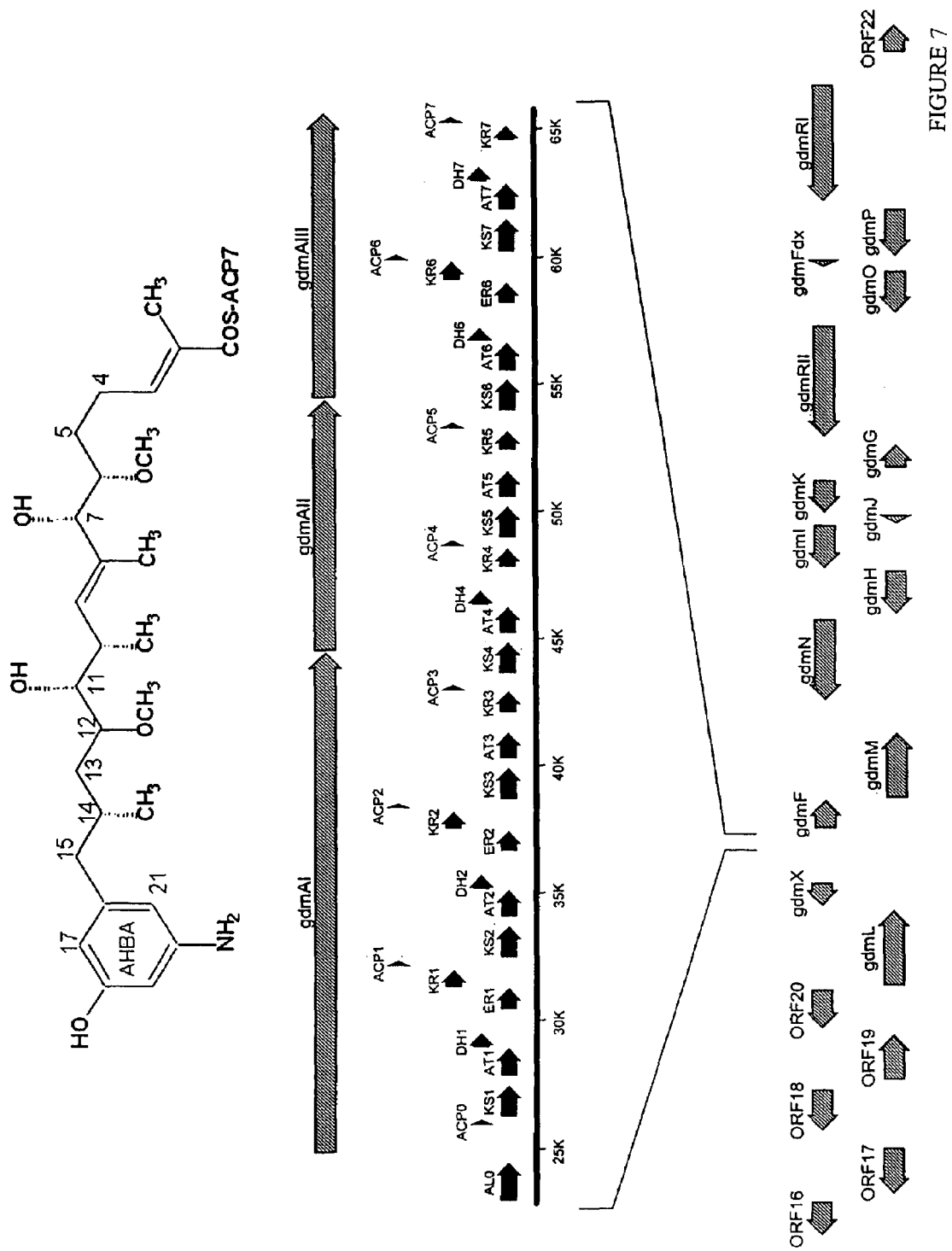
FIG. 7 is a schematic of the geldanamycin PKS gene cluster showing ORFs and modifying genes. Abbreviations: ORF 16: efflux (SC3C8.01); gdmL: oxred. (rifl9); gdmF: amide synthase (riff); ORF 17: secreted protein (SC3C8.01); gdmX: unknown (homolog of JadX MmyY); gdmM: flavin-dependent monooxygenase (rifl9); ORF 18: hydrolase (SCF1.09); gdmA1: PKS modules 0-3; gdmN: carbamoyltransferase; ORF 19: transcriptional regulation (AraC family); gdmA2: PKS modules 4-5; gdmH: methoxymalonyl-ACP biosynthesis; ORF 20: transcriptional regulation (tetR); gdmA3: PKS modules 6-7; gdmI: Methoxymalonyl-ACP biosynthesis; gdmJ: Methoxymalonyl-ACP biosynthesis; gdmFdx: ferredoxin; gdmP: P450; gdmK: Methoxymalonyl-ACP biosynthesis; gdmRI: transcriptional regulation; gdmG: Methoxymalonyl-ACP biosynthesis; ORF 22: hydrolase ns; gdmRII: transcriptional regulation; gdmO: aminoDHQ synthase; (ahba3) gdmP: Regulation 450.

In addition to the ORFs listed in TABLE 1 above, SEQ ID NO:1 includes additional open reading frames of genes encoding proteins that may be useful in the biosynthesis of progeldanamycin, geldanamycin, and geldanamycin analogs in certain host cells and/or have other uses. These include, for example and not limitation, the following ORFs (nucleotide boundaries): ORF10 (10864-11565), ORF11 (11987-12367), ORF12 (13068-13829), ORF13 (13909-14655), ORF14 (14564-15013), and ORF15 (15122-15700). FIG. 7 shows the Geldanamycin PKS gene cluster and upstream and downstream modifying genes and ORFs.

The geldanamycin biosynthetic gene cluster is believed to include all of the genes from ORF 19 on the left flanking region (thus, ORFs 12 through 18 are outside the cluster) through and beyond ORF22 (less than about five genes of the cluster are believed to extend beyond ORF22).

Example 2

BAC DNA Preparation

A 10 mL culture was inoculated with a single colony from the filter and grown at 37° C. overnight in LB medium with chloramphenicol selection (12.5 µg/mL). The cells were pelleted by centrifugation and resuspended in 300 µl of TE buffer (50 mM tris pH8/10 mM EDTA) and 300 µl of lysis solution (0.2 N NaOH/1% SDS) and mixed gently. The lysis solution was then neutralized with 300 µl of 3 M KOAc for precipitation and put on ice for 5 minutes. Following precipitation, a phenol extraction was done followed by an isopropanol precipitation. The DNA was centrifuged and resuspended in 250 µl of TE buffer (OD$_{260}$~10 µg/µl). RNAse digestion (Sigma Chemical Co., St. Louis, Mo.) was performed by adding RNAse to a concentration of 200 µg/ml and incubating at 37° C. for 30 min. DNAse digestion (Epicentre Technologies, Madison, Wis.) was done to eliminate non-plasmid DNA by incubation at 37° C. overnight. The DNAse was inactivated by heat incubation at 75° C. for 20 minutes. An isopropanol precipitation was performed by adding isopropanol and 3 M NaOAc to the sample and placed on ice for 10 minutes. The DNA was centrifuged at 4500 RPM for 45 minutes at room temperature. The DNA pellet was redissolved in TE buffer. The usual yield was about 50-100 µg/mL.

Example 3

Identification of Nucleotide Sequences Encoding Domains of Herbimycin Synthase from *Streptomyces hygrospcopicus* AM-3672

Genomic Library Generation and Screening. Genomic DNA of *Streptomyces hygroscopicus* AM-3672 was cloned into a pSET152 based plasmid-pKOS97-64c (see FIG. 10) as a vector. For library preparation, pKOS279-64C was cut with BglII and the genomic DNA was partially digested with Sau3AI to obtain DNA fragments about 38-43 kb. This ligation mixture of linearized DNA was packaged into cosmids with Gigapack® III XL Packaging Extract (Stratagene, Inc., LaJolla, Calif.) and then transfected into XLI-blue *E. coli* strain. A library of 2304 colonies was obtained and analyzed. The transfectants were grown on LB agar having apramycin at a final concentration of 60 mg/L. The transfectants were spread onto nylon-membranes to allow the cells to grow into the membrane structure. After alkaline cell wall disruption, the DNA was bound to the membrane by UV cross linking under standard conditions. These colony-blot membranes were then used to screen the library.

Genomic *Streptomyces hygroscopicus* AM-3672 cosmid library screening. Because the product of the PKS is usually modified by several tailoring steps in the biosynthetic pathways for the majority of bacterial polyketides, homologs of genes that are likely to be unique to the pathway of interest or to a particular class of compounds are targeted as probes for the desired PKS cluster. In the case of herbimycin, a geldanamycin homolog, the genes for formation of the C7 carbamoylation (CT) and also the CoA-ligase that activates the AHBA (3-Amino-5-hydroxy-benzoic acid) starter unit to be loaded on the first PKS module were used as the target genes for probe generation. Analysis of the *S. hygroscopicus* AM-3672 genome by PCR was performed using those two different sets of degenerate primers: one aimed at amplifying regions with homology to domains of the CoA-ligase-type from PKS sources ($AL_0$ Domain Probe); the other aimed at amplifying regions with homology to carbamoyltransferase (CT Probe). This two-prong approach was needed to distinguish clones containing herbimycin PKS gene cluster sequences from clones containing KS domain encoding sequences from other clusters.

Carbamoyl transferase gene fragments were amplified with degenerate forward primer degCT2F (5'-AARGT-SATGGGSYTSGCSCCSTA-3') (SEQ ID NO:41) and reverse primers degCT3R (5' CCSARSGCSCKSGGSC-CRAAYTC-3') (SEQ ID NO:44) using an annealing temperature of 55° C. This PCR reaction produces amplimers of 650 bp in length when using the *Streptomyces hygroscopicus* AM-3672 genome as a template. CoA-ligase gene fragments were amplified with degenerate forward primer LDDF1 (5'-GAY GAS CCS GCS TGG ATG YTS TA-3') (SEQ ID NO:43) and reverse primers LDDB2 (5'-CCR TCS GTS CKG TAC CAS CCR TC-3') (SEQ ID NO:44) using an annealing temperature of 64° C. This PCR reaction produces amplimers of 690 bp when using the *Streptomyces hygroscopicus* AM-3672 genome as a template. All PCR amplimers were gel-purified and cloned into pCR2.1-TOPO using TA cloning (Invitrogen). Two clones of each construct (CT and CoA-ligase) have been sequenced and analysed with Sequencher 4.1 (Gene Codes Corporation) and MacVector 6.5.3 software, and compared with sequences in the public databases using the CLUSTAL W and BLAST programs. CoA-ligase and CT amplimer sequences on DNA level were 97% identical with the corresponding sequences of the Geldanamycin producer *S. hygroscopicus* strain 3602, whereas the direct comparison between the two sequences of each gene turned out to give an identity of 98.5%. Given this degree of homology, both CoA-ligase sequences and also both CT sequences compared were considered to be identical and any differences probably caused by PCR errors. Therefore the analysis revealed one putative CoA-ligase (pKOS313-60-1) and one putative CT gene fragment (pKOS313-60-2) with very high homology of 97% to the Geldanamycin gene cluster. Both inserts of (pKOS313-60-1) and (pKOS313-60-2) have been used as probes to screen the genomic cosmid library for the herbinycin PKS and related genes. Analysis at this stage was done at the DNA level, only. Possible errors at the protein level have yet to be determined.

CoA-ligase ($AL_0$) Probe Screening. CoA-ligase gene fragments were amplified with degenerate forward primer LDDF1 (5'-GAY GAS CCS GCS TGG ATG YTS TA-3') (SEQ ID NO:43) and reverse primers LDDB2 (5'-CCR TCS GTS CKG TAC CAS CCR TC-3') (SEQ ID NO:44) using an annealing temperature of 64° C. This PCR reaction produces the $AL_0$ probe having 690 bp in length. Two separate clones (pKOS313-60-1 and pKOS313-60-2) were sequenced and analysed with Sequencher 4.1 (Gene Codes Corporation) and MacVector 6.5.3 (Accelrys), Each PCR insert (after removing sequence due to primers) was 644 bp (SEQ ID. NO: 22 and SEQ ID NO:23). Each was closely homologous (96%) to a 645 bp portion of the AL-ligase-homology domain region of the geldanamycin cluster. Each had a single deletion (at different locations) relative to the geldanamycin sequence. In each case where the two sequences varied, one matched the geldanamycin sequence. If a hypothetical sequence is created, using the common sequence where they match, and the one matching the geldanamycin sequence otherwise, then the insert of pKOS313-60-1 is 98.6% identical to this construct; pKOS313-60-5 is 98.3% identical; and the equivalent 945 bp portion of the geldanamycin cluster is 97.2% identical.

Carbamoyl Transferase (CT) Probe Screen. Carbamoyl transferase gene fragments were amplified with degenerate forward primer degCT2F (5'-AARGTSATGGGSYTSGC-SCCSTA-3') (SEQ ID NO:41) and reverse primers degCT3R (5' CCSARSGCSCKSGGSCCRAAYTC-3') (SEQ ID NO:42) using an annealing temperature of 55° C. This PCR reaction produces a CT probe of 650 bp in length. Two separate clones (pKOS313-60-3 and pKOS313-60-4) were sequenced and analysed. Each PCR insert (after removing sequence due to primers) was 599 bp (see SEQ ID NO:24 and SEQ ID NO:25). Each was closely homologous (96% identity) to a 600 bp portion of the AL-ligase-homology domain region of the geldanamycin cluster. Each had a single deletion (at different locations) relative to the geldanamycin sequence. If a hypothetical sequence is created as in the previous case (here there is one base-pair where all three vary), then the two inserts are each about 99% identical to this construct; and the equivalent 945 bp portion of the geldanamycin cluster is about 97% identical.

The inserts of pKOS313-60-1($AL_0$ probe) and pKOS313-60-4 (CT probe) were used to screen the genomic cosmid library for the herbimycin PKS and related genes (the two inserts were combined during screening, so that cosmids matching either would score as positive). Using the insert fragments of pKOS313-60-1 and pKOS313-60-4, the probes were prepared using colorimetric DIG-labelling reaction following the DIG nucleic acid detection Kit (Roche) The in-situ hybridization was done under standard conditions, hybridization temperature 65° C. following the DIG easy Hyb (Roche) protocol. Thirty six positive colonies were found, subjected to fragment analysis, and grouped by banding patterns. Seven cosmids representing two groups (pKOS279-78-14, -4, -11 from one group; pKOS279-78-17,-5,-19 from the other; as well as pKOS279-78-16 which appeared to be a possible member of the first group) were chosen for further analysis, in which BamHI fragments were end-sequenced. Seven independent fragments produced 13 legible end sequences, all closely homologous to regions of the geldanamycin cluster.

The seven legible end-sequenced regions of the four fragments from group one (see SEQ ID NO:26-SEQ ID NO:32) were all homologous to portions of the upstream portion of the geldanamycin cluster, with the most downstream sequence matching a portion of the CoA-ligase homology region near the upstream edge of the PKS genes and the most upstream match being over 20 kb away from the PKS genes. All seven regions appeared in fragments from pKOS279-784. All homologies found were in the range of 93%-96% DNA sequence identity. All were compatible with equivalent arrangements of genes between the geldanamycin and herbimycin clusters. The downstream edge of fragment4.group1 produced 405 bp of clear sequence with 96% identity to 405 bp within the 645 bp of the geldanamycin cluster homologous to the CoA-ligase-homolog probe; the 405 bp exactly matches the equivalent 405 bp from the theoretically constructed sequence described above (i.e., it matches both probe sequences when they are identical; if they differ, then it matches both the geldanamycin cluster and one of the two probes). Clone pKOS279-784 contains all or the bulk of the accessory genes on the upstream side of the cluster, extending into at least the initial polydomain PKS gene. The cosmids of group 1 were all recognized by the "CoA-ligase" probe.

The six legible end-sequenced regions of the three fragments from group two (see SEQ ID NO:33-SEQ ID NO:38) were all homologous to portions of the downstream portion of the geldanamycin cluster, with the most upstream sequence (from fragment1.group2) matching a portion of the module 7 region, the terminal module of the PKS genes, and the most downstream matching a region over 20 kb from the PKS genes. All three fragments appear to be present in pKOS279-78-17. It seems probable that pKOS279-78-17 contains all or the bulk of the accessory genes on the downstream side of the cluster, extending from at least the terminal polydomain PKS module region, and that the cosmids of group 2 were all recognized by the "CT" probe.

The herbimycin PKS gene cluster nucleotide sequence fragments are listed in SEQ ID NOS:22-38 below. [ASEQ ID NO:22 (insert of pkos313-60-1; CoA-ligase homology); SEQ ID NO:23. (Insert of pKOS313-60-2; CoA-ligase homology); SEQ ID NO:24 (Insert of pKOS313-60-3; carbamoyltransferase homology); SEQ ID NO:25 (Insert of pKOS313-60-4; carbamoyltransferase homology); SEQ ID NO:26 (Group 1, fragment 1a.Contig[4R/16J__20.L]); SEQ ID NO:27 (Group 1, fragment 1b.Contig[4R/16J__48.Rrev]); SEQ ID NO:28 (Group 1, fragment 2a.Contig[4T/U.L]); SEQ ID NO:29 (Group 1, fragment 3a.Contig[4V/14Q.L]); SEQ ID NO:30 (Group 1, fragment 3b.Contig[4V/14Q.Rrevc]); SEQ ID NO:31 (Group 1, fragment 4a.Contig[⁴U/11W/14P.L]); SEQ ID NO:32 (Group 1, fragment 4b.Contig[4U/11W/14P.Rrevc]); SEQ ID NO:33 (Group 2, fragment 1a.Contig [5F/19FI.L]); SEQ ID NO:34 (Group 2, fragment 1b.Contig [5F/19FI/17D.Rrevc]); SEQ ID NO:35 (Group 2, fragment 2a.Contig[5E/17C.L]); SEQ ID NO:36 (Group 2, fragment 2b.Contig[5E/17C.Rrevc]); SEQ ID NO:37 (Group 2, fragment 3a.17A-72-48.dna); SEQ ID NO:38 (Group 2, fragment 3b.17A-72-20.dna.revc).] Standard IUPAC ambiguity codes are used in the sequence.

The inserts of clones pKOS279-78-14 and pKOS279-78-4 were sequenced at Macrogen (Korea). To identify PKS genes that would connect the two cosmids, a new genomic DNA library was built. Sau3AI-partial-digested genomic DNA of Str. hygroscopicus AM3672 was cloned in the SuperKos plasmid to generate the new cosmid library. About 2000 colonies carrying cosmids were screened by in-situ hybridization against parts of gdmKS4 and gdmDH7, which were cloned in pKOS279-46A. [KOS279-46A was composed of two fragments from the gdm PKS cluster cloned into the EcoRI-HindIII sites of pKC1139 (Bierman et al., 1992, Gene 116: 43-49). The left fragment consisted of a 1.3 kb region upstream of AT4 amplified with the following primers: forward, 5'-TTGAATTCAGATCTAGTTCGCTGGAGGA-CAGCGACGTC [SEQ ID NO:45]; reverse, 5'-TTTCTA-GAGGATCCGCCGTCTGTTCC GGTCTGTCCGGTG [SEQ ID NO:46]. The right fragment consisted of a 1.3 kb region downstream of AT7 amplified with the following primers: forward, 5'-TTTCTAGACTGCAGCGCGGCGGTC-CGGGCG ACGTCCGT [SEQ ID NO:47]; reverse, 5'-TTAAGCTTATGCATCGGGTC GTGACCTCGGCGGT-GTC [SEQ ID NO:48]. Using this method, about a dozen cosmids were identified and ends of inserts in these cosmids were sequenced.

Two cosmids containing interesting sequences were chosen for further analysis. One of them, pKOS205-110-12, carrying sequences overlapping with the insert of pKOS279-78-17 was sequenced at Macrogen (Korea). Anther one, pKOS205-110.29, overlapping pKOS278-78-4 and pKOS205-110-12 was used as the template for sequencing by oligo walking combined with PCR to complete the approximately 2 kb gap between pKOS279-78.4 and pKOS205-110.12.

The sequence of the herbimycin PKS gene cluster and flanking genes is provided below (SEQ ID NO:2). In addition to the ORFs listed in TABLE 1 above, SEQ ID NO:2 includes additional open reading frames of genes encoding proteins that may be useful in the biosynthesis of progeldanamycin, herbimycin, and herbimycin analogs in certain host cells and/or have other uses. These include, for example and not limitation, the following ORFs (nucleotide boundaries): ORF11_hbm (complement of 12619-12999); ORF14_hbm (16346-17641) a putative permease; and ORF15_hbm (17750-18328). FIG. 3B shows the Herbimycin PKS gene cluster and upstream and downstream modifying genes and ORFs. Translations of selected ORFs in SEQ ID NO:2 are provided as SEQ ID NOS:85-114.

Example 4

AHBA Biosynthesis Gene Cluster Identification and Isolation

Figure 5:
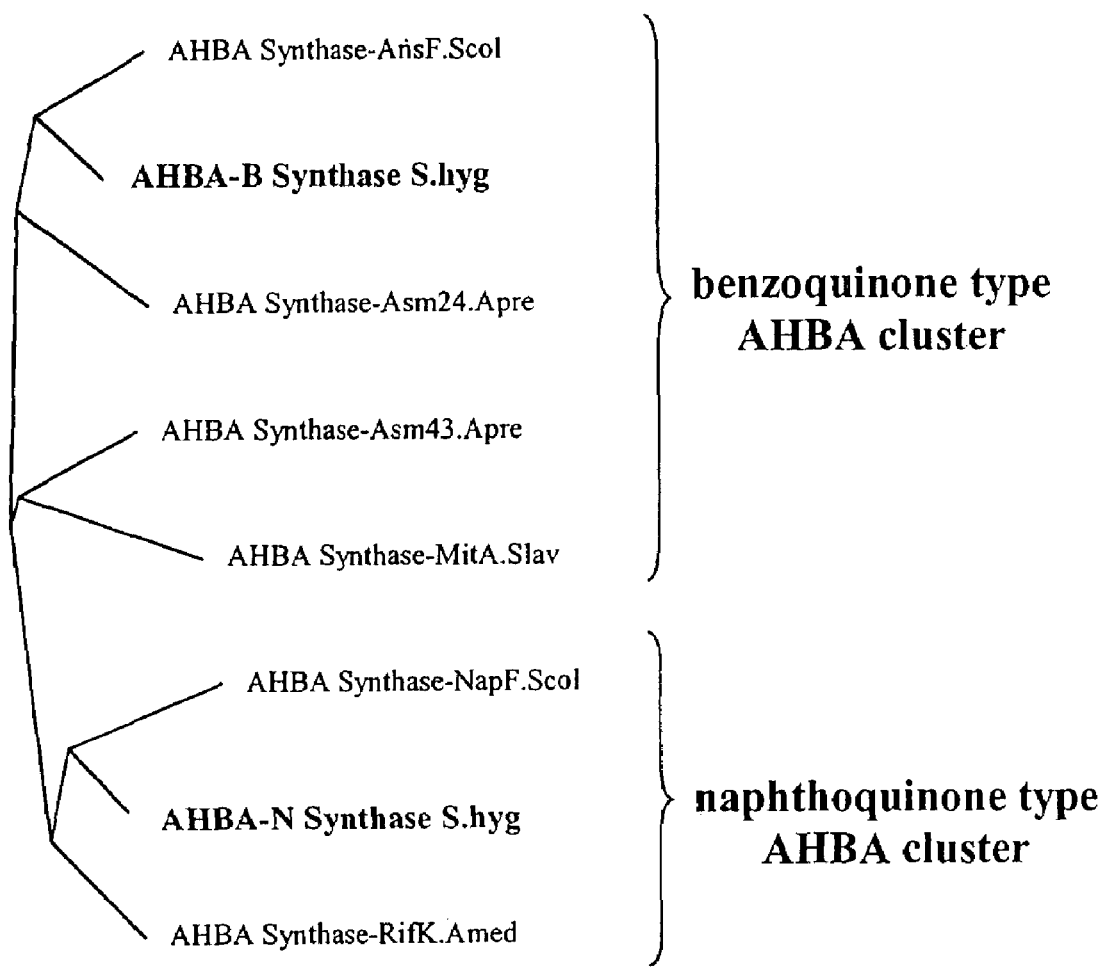
FIG. 5 is a phylogenetic tree showing the two groups of DNA sequences encoding AHBA-B type and AHBA-N type AHBA synthases.

Four homologs of the genes for AHBA biosynthesis were chosen to design a new set of PCR primers to screen the S. hygroscopicus NRRL 3602 genomic DNA for AHBA synthase and homologs (Yu et al., 2002, Proc Natl Acad Sci USA. 99:7968-73; August et al., 1998, Chem Biol 5:69-79; Leistner, 1999, Eur J Biochem 261, 98-107). Fifty-six AHBA amplimers were analyzed and their sequences compared resulting in two distinct DNA sequences encoding AHBA synthases being identified as AHBA-B and AHBA-N. FIG. 5 shows a phylogenetic tree of the two groups of AHBA-B and AHBA-N sequences having 75% homology. TABLE 2 below shows the homology data of AHBA cluster genes that strongly suggests that one AHBA synthase homolog belonged to the family associated with the biosynthesis of benzoquinone ansamycins (AHBA-B) and the other with naphthaquinone ansamycins (AHBA-N). Geldanamycin being a benzoquinone ansamycin, it was concluded that most likely the product of AHBA-B and not AHBA-N is involved in the biosynthesis of geldanamycin. Using the same PCR analysis method on the genomic DNA of the producer of herbimycin, S. hygroscopicus 3672, a closely related molecular analog of geldanamycin, 20 AHBA amplimers were analyzed and all of them were identified to be 100% identical with AHBA-B from the geldanamycin producer. Only one type of AHBA synthase was found in the producer of herbimycin, *S. hygroscopicus* 3672.

*latopsis mediterranei* S699." *Chem Biol* 5:69-79) the six ORFs were assigned to their deduced products and the functions found to be largely consistent with the postulated AHBA

TABLE 2

AHBA Biosynthesis Pathway Homologs in the Gdm and AHBA Clusters of *S. hygroscopicus* NRRL 3602 (SEQ ID NO: 3)

| AHBA biosynthesis pathway code | homology family | predicted function | ahba cluster (*S. hygroscopicus* NRRL 3026) | length (aa) | homolog | % identity |
|---|---|---|---|---|---|---|
| AHBA gene cluster ||||||||
| ahba1a | oxidoreductase | oxidoreductase homolog involved in aDAHP precursor biosynthesis | ORF6 | 360 | AnsG | 64%/360aa |
| ahba1b | phosphatase | phosphatase homolog involved in aDAHP precursor biosynthesis | ORF7 | 231 | AnsH | 73%/225aa |
| ahba1c | kinase | kinase homolog involved in aDAHP precursor biosynthesis | ORF3c | 265 | Asm22 | 63%/232aa |
| ahba3(#2) | aDHQ synthase | aminodehydroquinate synthase | ORF2 | 349 | MitP | 74%/335aa |
| ahba4 | aDHQ dehydratase | aminodehydroquinate dehydratase | ORF4c | 149 | Asm23 | 75%/139aa |
| ahba5 | AHBA synthase | 3-amino-5-hydroxybenzoic acid synthase | ORF5 | 388 | AnsF | 79%/387aa |
| Geldanamycin PKS gene cluster ||||||||
| ahba3(#1) | aDHQ synthase | aminodehydroquinate synthase | GdmO | 354 | Asm47 | 78%/340aa |

The AHBA-B synthase amplimer of 850 bp. was used as probe for screening of a genomic library made in a single copy BAC vector by The Institute for Genome Research (TIGR). 4,896 BACs with average insert sizes of 45 kb, equivalent to ca. 20× coverage of this genome, were screened and 36 AHBA synthase clones were identified. Given the gene coverage of this library, these numbers are consistent with the presence of the two AHBA synthase genes identified by PCR in this genome. AHBA-B and AHBA-N synthase containing BACs were distinguished by performing PCR with gene specific primers and it was found that about half of the AHBA synthase containing BACs belonged to each of the AHBA-B and AHBA-N types. Interestingly, when the AHBA synthase BACs were analyzed for the presence of PKS genes by performing PCR with degenerate KS primers, it was found that none of the 20 AHBA-B synthase containing BACs contained PKS genes, whereas 14 out of 17 AHBA-N synthase containing BACs also had PKS genes. As none of the putative geldanamycin AHBA-B synthase BACs apparently contained any KS genes, AHBA-B BAC clone pKOS-256-116-10 was fully sequenced by the shotgun method at TIGR and the resident genes of an 8 kb part of the pKOS-256-116-10 insert (approx. 50 kb total) was assigned to AHBA production on the basis of data base comparisons (FIG. 5). Six open reading frames (ORF) and the deduced functions of their products are listed in TABLE 2 as well as their homology to related genes. The ORFs corresponding to these genes are found in SEQ ID NO:3 as follows: ahba1a (basepairs 5263-6345); ahba1b (basepairs 6575-7270); ahba1c (basepairs 2427-3224 (complement); ahba3 (basepairs 1364-2413); ahba4 (basepairs 3397-3846 (complement); ahba5 (basepairs 4058-5224) and orf1 (possible regulatory protein) (basepairs 428-1252 (complement)). Translations of selected ORFs in SEQ ID NO:3 are provided as SEQ ID NOS:21, 39-40, and 147-153.

Key features of the AHBA biosynthesis genes and their deduced products. Based on the proposed AHBA biosynthetic pathway (August et al., 1998, "Biosynthesis of the ansamycin antibiotic rifamycin: deductions from the molecular analysis of the rif biosynthetic gene cluster of *Amyco-* pathway. With reference to FIG. 1 of the August et al. publication, the assignments were: E4P→aminoDAHP (ahba2); aminoDAHP→aminoDHQ (ahba3); aminoDHQ→aminoDHS (ahba4); aminoDHA→AHBA (ahba5). However no aminoDAHP gene was found in or near the AHBA cluster. Nor has one yet been found near the geldanamycin PKS cluster, while interestingly one pathway homolog, the aminodehydroquinate synthase gene, was found in both clusters. It was found that the genes for AHBA biosynthesis are not closely located to GdmO, the ahba3 homolog located downstream of the geldanamycin PKS gene, but instead are located more than 30 kilobases from the end of the BAC that contains GdmO. A similar situation holds true for the reported ansamitocin cluster (Yu et al.) and a distantly linked ahba cluster in the ansamitocin producer: here, three of the AHBA biosynthesis genes for ansamitocin production plus the remaining asm genes have recently been reported to be on a subcluster separated from all the other genes for AHBA biosynthesis by at least 30 kb. In this case also no ahba2-family homolog is present in either cluster, while a different pathway homolog, the ahba5 gene is found in both clusters.

Bacterial Strains and Culture Conditions. The geldanamycin producing strain, first described by DeBoer et al. (DeBoer et al., 1970, *J Antibiot* (*Tokyo*) 23:442-7; Leistner et al., 1999, *Eur J Biochem* 261:98-107) as *Streptomyces hygroscopicus* var. *geldanus* var. nova UC-5208, was obtained from the Northern Regional Research Laboratory of the Agricultural Research Service as *Streptomyces hygroscopicus* NRRL 3602. To confirm production of geldanamycin, spores from a single colony, stored as a suspension in 25% (v/v) glycerol at −80° C., were used to inoculate 5 ml of R2YE liquid media. The culture was incubated at 28° C. for 36 h, transferred into 100 ml geldanamycin production medium and the final culture incubated at 28° C. for another 5 days. Following low speed centrifugation, the cell pellet from the culture was extracted with methanol by stirring for 10 min. The methanol broth was clarified by centrifugation (17,500×g) and the supernatant was analyzed for the presence of geldanamycin using HPLC under the following conditions: column Inertsil C18 (4.6×150 mm, Ansys Technologies, Inc.), mobile phase 60% acetonitrile (isocratic), flow rate (2 ml/min), temperature (40° C.), detection (UV 315 nm), injection volume (10-20 microliters). Geldanamycin (Sigma-Aldrich) was quantified by comparing the peak area at 315 nm with that measured for a standard solution. The standard solution was prepared by dissolving pure geldanamycin at 0.2-0.5 mg/mL in HPLC-grade methanol. The titer of geldanamycin was approx. 250 mg/L.

Manipulation of DNA and organisms. For genomic DNA extraction, a spore stock was used to prepare a seed culture as described above. The entire seed culture was transferred into 50 ml of the same growth medium in a 250 ml baffled Erlenmeyer flask and incubated for 48 h at 28° C. A 20 ml portion of the cell suspension was centrifuged (10,000×g) and the resulting pellet was washed with 10 ml buffer 1 (Tris, 50 mM, pH7.5; 20 mM EDTA). The pellet was pulverized with mortar and pestle under liquid nitrogen and transferred into 3.5 ml of buffer containing 150 µg/ml RNase (Sigma-Aldrich). After incubation of the mixture at 30° C. for 20 min, the salt concentration was adjusted by adding 850 µl 5 M NaCl solution, then the mixture was extracted multiple times with phenol:chloroform:isoamylaclohol (25:24:1, vol/vol) with gentle agitation followed by centrifugation for 10 min at 3,500×g. After precipitation with 1 vol of isopropanol, the genomic DNA knot was spooled on a glass rod and redissolved in water (200 µl). This method yielded about 1 mg DNA with a protein factor of about 2, as determined by the ratio of the UV absorbances at 260 and 280 nm. Standard agarose gel electrophoresis using 0.7% Seakem® LE-Agarose (BioWhitaker Molecular Applications, Rockland, Me.) at a voltage of 50 mV over night revealed that the sample contained mainly high molecular weight DNA fragments of about 60 kb.

Genomic analysis of *S. hygroscopicus* NRRL 3602 for AHBA gene cluster. The following degenerate AHBA synthase primers were used to scan the genomic DNA of *S. hygroscopicus* for AHBA genes:

```
                                            [SEQ ID NO: 49]
degAH-F1  (5'-GTSATCGTSCCSGCSTTCACSTTC-3')

[SEQ ID NO: 50]
degAH-F2  (5'-ATC-ATGCCSGTSCAYATGGCSGG-3')

and two reverse primers

[SEQ ID NO: 51]
degAH-R1  (5'-GGSTBS-GKGAACATSGCCATGTA-3')

[SEQ ID NO: 52]
degAH-R2  (5'-CKRTGRTGSARCCASTKRCARTC-3')
```

Forward (F) and reverse (R) primers were tested in all possible combinations in standard PCR reactions with annealing temperatures between 50 and 60° C. The primers were also successfully used on genomic DNA of several other ansamycin producing strains at Tm 50° C. A typical 50 µl PCR reaction consisted of 200 ng genomic DNA, 200 pmol of each primer, 0.2 mM dNTP (containing 7-deaza-dGTP), 10% DMSO and 2.5 U Taq DNA polymerase (Roche Applied Science). Deg. PKS-KS primers were used to scan AHBA positive BAC clones (hybridization) for PKS genes (see also FIG. 3):

```
                                            [SEQ ID NO: 53]
degKS1F  (5'-TTCGAYSCSGVSTTCTTCGSAT-3')

[SEQ ID NO: 54]
degKS2F  (5'-GCSATGGAYCCSCARCARCGSVT-3'),

[SEQ ID NO: 55]
degKS3F  (5'-SSCTSGTSGCSMTSCAYCWSGC-3'),

[SEQ ID NO: 56]
degKS5R  (5'-GTSCCSGTSCCR-TGSSCYTCSAC-3'),

[SEQ ID NO: 57]
degKS6R  (5'-TGSGYRTGSCCSAKGTTSSWCTT-3') and

[SEQ ID NO: 58]
degKS7R  (5'-ASRTGSGCRTTSGTSCCSSWSA-3').
```

Figure 6:
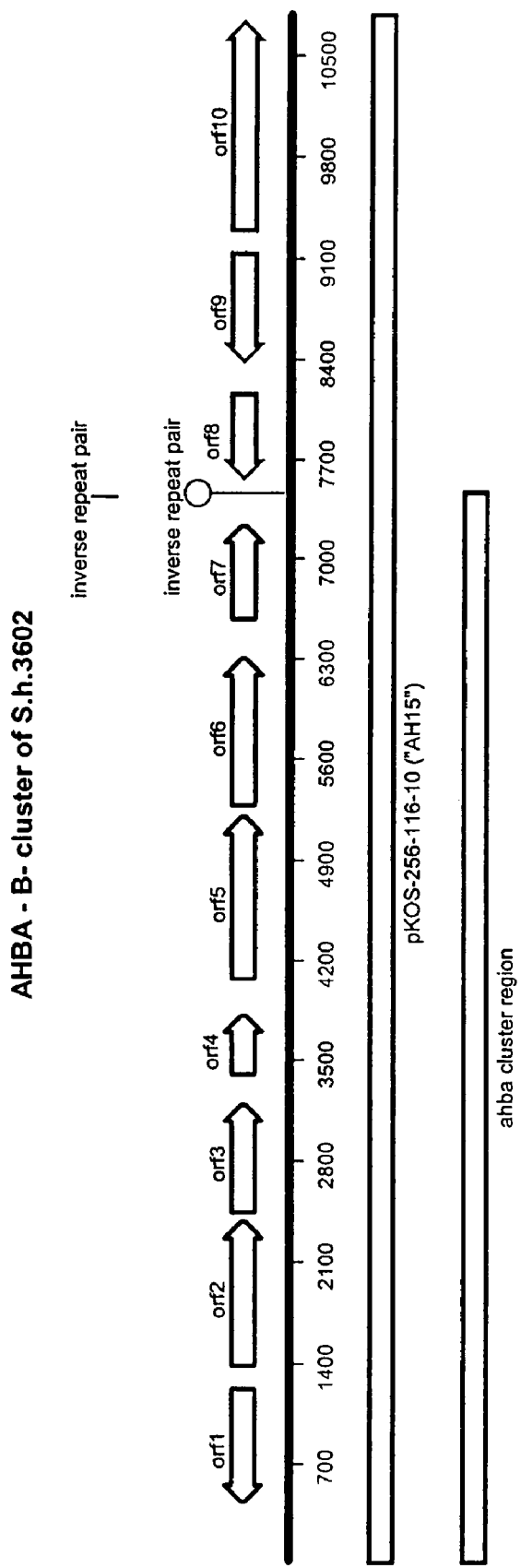
FIG. 6 is a schematic of pKOS-256-116-10 ("AH15") showing the open reading frames and other structural motifs of the AHBA-B gene cluster of *Streptomyces hygroscopicus* NRRL3602.

A set of four gene specific primers:
AH-B-spF   (5'-AGGACAGTGGCGCGGCAAGAA-3') [SEQ ID NO:59],
AH-B-spR   (5'-GGTCGACGATCTT-CGCGCGGCG-3') [SEQ ID NO:60]
AH-N-spF   (-5'-TCGACGTGGCTGCCGCGG-CTT-3') [SEQ ID NO:61], and
AH-N-spR   (5'-TGTCGA-CGAGGGCGTTGCGGG-3')
were used to distinguish between AHBA-B and AHBA-N synthase genes (FIG. 6). PCR amplimers were gel-purified and cloned into pCR2.1-TOPO using TA cloning (Invitrogen). For each primer pair, a representative set of cloned amplimers (600-800 bp) was sequenced using a Beckmann CEQ2000 with M13 forward and reverse primers.

Library construction and gene isolation. A genomic library of *S. hygroscopicus* NRRL3602 was constructed using the proprietary single copy BAC vector pHOS3 (TIGR). A total of 4,896 BAC clones were arrayed into 384 well microtiter plates and were spotted in high density onto nylon filters (Amplicon Express). A set of identical filters was created in order to probe the library simultaneously with different probes. Probes were labeled using $\alpha$-$^{32}$P-dCTP and a random prime labeling system (rediprime II, Amersham Pharmacia Biotech). Filters were hybridized at 68° C. for 12 h using ExpressHyb hybridization solution (Clontech). After removal of the probe and hybridization solution, the filter was washed twice for 30 minutes each time with 100 ml of buffer I (2×SSC: 300 mM NaCl, 30 mM sodium citrate pH 7.0, 0.05% SDS) at room temperature and then three times for 60 minutes each time at 50° C. with 100 ml of buffer II (0.1× SSC, 0.1% SDS) with continuous shaking. Finally, the filter was rinsed several times with 0.05×SSC and analyzed by autoradiography. BAC-DNA was prepared by alkaline lysis, starting with a 10 ml culture volume. The resulting DNA was first treated with RNase (Sigma-Aldrich) at 30° C. for 3 h and then with plasmid safe DNase (Epicentre Technoligies, Madison, Wis.) at 37° C. o/n. After heat inactivation at 70° C. for 10 min the DNA was precipitated with 1 volume isopropanol for 30 min on ice and recovered by centrifugation at 1,880×g for 45 minutes to separate the remaining smaller fragments from the large, intact BAC plasmids. The final pellet was washed with 70% EtOH and redissolved in 80 µl water. This method typically yielded about 100 µg of BAC DNA.

DNA Sequence and Analysis. The AHBA biosynthesis gene cluster DNA sequence is described in SEQ ID NO:3. The DNA and deduced protein sequences were analyzed with Sequencher 4.1 (gene Codes Corporation) and MacVector 6.5.3 (Accelrys) software, and compared with sequences in the public databases using the CLUSTAL W (Thomson et al.) and BLAST (Altschul et al.) computer programs. TABLE 2 above provides details of the open reading frames of the deduced protein sequences of SEQ ID NO:3. No aminoDAHP synthase (ahba2) is found in or near the ahba cluster; nor is one yet found near the gdm cluster; while one pathway homolog (ahba3; a DHQ synthase) is found in both clusters. A similar situation holds true for the reported ansamitocin cluster and a distantly linked ahba cluster in the ansamitocin producer. In this case also no ahba2-family homolog is present in either cluster, while a different pathway homolog (ahba5; AHBA synthase) is found in both clusters. FIG. 6 shows the AHBA biosynthesis gene cluster open reading frames, and secondary structure marking the end of the cluster. Open reading frames 8, 9 and 10 are shown to confirm that these sequences not forming part of the biosynthesis cluster mark the end of the cluster.

Example 5

Disruption of the gdmH Gene

This example demonstrates disruption of the gdmH gene involved in methoxymalonyl-ACP biosynthesis. The gdmH gene was disrupted by introducing pKOS279-37 into the *S. hygroscopicus* NRRL3602 strain by conjugation from its *E. coli* ET12567/pUB307 host according to a published method (Flett et al., 1997, *FEMS Microbiol. Lett.* 155: 223-29). Exconjugants resistant to apramycin (PKC1139 carries the accIV(3) gene) and kanamycin were isolated and one of them was grown at 30° C. in 6 ml of R5 liquid medium (Kieser et al., 2000, Practical *Streptomyces* Genetics: *A Laboratory Manual*. The John Innes Foundation, Norwich UK) supplemented with 100 µg ml$^{-1}$ of kanamycin for 2 days in 50-ml culture tubes at 200 rpm. Approximately 5% of this culture was transferred into 6 ml of fresh R5/apramycin liquid medium and the culture was grown at 37° C. for 3 days in order to force chromosomal integration of the gdmH gene disruption vector, pKOS279-37.

(pKOS279-37 was made as follows: The aphII neomycin/kanamycin resistance gene from Tn5 was excised as a StuI-SmaI fragment from SuperCos-1 (Stratagene), then inserted into the MscI site within gdmH carried in a 4-kb BstXI fragment, containing the gdmN, gdmH and gdmI genes, and cloned in pOJ260 (Bierman et al., 1992, *Gene* 116: 43-49) to give pKOS246-33. The XbaI-EcoRI fragment from pKOS246-33 was excised and cloned into the XbaI-EcoRI sites of pKC1139 (Bierman et al., 1992, *Gene* 116: 43-49) to give pKOS279-37.)

After recovery of the mycelia by centrifugation, cells were plated on tomato paste medium containing 100 µg ml$^{-1}$ kanamycin and grown at 30° C. for sporulation. Spores collected from these plates were diluted and replated on the same medium for single colonies. Among 100 colonies screened, 20 were apramycin sensitive and kanamycin resistant when assayed on plates containing apramycin or kanamycin, using 60 or 50 µg ml$^{-1}$ of antibiotic, respectively. Genomic DNA was isolated from 11 of these 20 colonies by an established method (Kieser et al., 2000, Practical *Streptomyces* Genetics: *A Laboratory Manual*. The John Innes Foundation, Norwich UK) and probed by Southern-blot hybridization (Kieser et al., 2000, Practical *Streptomyces* Genetics: *A Laboratory Manual*. The John Innes Foundation, Norwich UK) with the aphII gene to determine that all kanamycin resistant recombinant strains had the restriction fragment pattern upon digestion with PstI-EcoRV expected for integration of the aphII gene into the gdmH locus by a double crossover recombination (hybridizing bands at 2.9 and 3.2 kb that were absent in the NRRL3602 strain).

To determine geldanamycin production, each of the 11 strains was individually cultured in 35 ml of the geldanamycin production medium (DeBoer et al., 1970, *J. Antibiot.* 23:442-47) as described above. After 4 days, 500 µl of broth from each flask was mixed with 500 µl of methanol, the mixture was centrifuged at 12,000 rpm in a desktop microcentrifuge for 5 min to remove mycelia and other insoluble ingredients, then the supernatant fraction was analyzed by HPLC/MS. The results showed that geldanamycin was present (retention time and low-resolution MS data were identical to the reference standard) and that two new compounds were present with molecular masses and formulas of 518.2759 ($C_{28}H_{40}NO_8$[M-H]$^-$) and 520.2916 ($C_{28}H_{42}NO_8$ [M-H]$^-$), calculated on the basis of high-resolution MS data. These data are consistent with 4,5-dihydro-7-descarbamoyl-7-hydroxygeldanamycin and its hydroquinone form. Production of geldanamycin suggests that the gdmH is dispensible or that its mutation is compensated in trans by a paralog.

Example 6

Replacement of AT Domain in Module 7 of gdmA3 in *S. hygroscopicus* NRRL 3602

This example, and EXAMPLE 7, describe the substitution of AT domains in the geldanamycin PKS with heterologous domains. Plasmid and phage (not shown) delivery vectors were constructed by cloning DNA flanking the AT domains to be substituted in the gdmPKS. The heterologous AT domain used for the substitution was inserted between the flanking fragments and the vector was introduced into the geldanamycin producing organism. Replacement of the gdmAT domain occurs through stepwise double crossing over (homologous recombination). Analogous methods can be used for substitution of additional, or different, domains.

A DNA fragment (~1.3 kb) flanking the AT7 domain was PCR amplified from cosmid pKOS256-107-3 with the following oligonucleotides (EcoRI, BglII, XbaI, BamHI, PstI, HindIII, and NsiI restriction sites are underlined):

```
AT7 Left Flank
                                        [SEQ ID NO: 63]
for 5'-TTGAATTCAGATCTACGTCACTGCGCGGACAGGAGGTC

[SEQ ID NO: 64]
rev 5'-TTTCTAGAGGATCCGCCGTGGGTGGTGGCGTGGCCGGTG

AT7 Right Flank
                                        [SEQ ID NO: 65]
for 5'-TTTCTAGACTGCAGCGCGGCGGTCCGGGCGACGTCCGT

[SEQ ID NO: 66]
rev 5'-TTAAGCTTATGCATCGGGTCGGTGACCTCGGCGGTGTC
```

The PCR fragment for the targeted AT was cloned together using XbaI into pUCI9 using EcoRI and HindIII restriction sites. The resulting plasmid was pKOS309-8 (AT7 flanks). The rapAT2 cassette (McDaniel et al., 1999, *Proc. Natl. Acad. Sci. U.S.A.* 96, 1846-51) was inserted between the two flanking sequences of the plasmid with BamHI and PstI restriction sites. The AT and flanking fragments were moved into the delivery vector pKC1139 (Bierman et al., 1992, *Gene* 116: 43-49) with EcoRI and HindIII restriction sites. The delivery plasmid (pKOS309-23) contains the rapAT2 cassette flanked by 1.3 kb of gdm DNA for homologous recombination into the appropriate module.

The plasmid was introduced in *S. hygroscopicus* NRRL3602 by conjugation using *E. coli* ET12657/pUZ8002 (Kieser et al., Practical *Streptomyces* Genetics: *A Laboratory Manual* (The John Innes Foundation, Norwich, UK, 2000). Primary exconjugants were first grown in 5 ml liquid R5 containing 100 mg/l apramycin (apra) at 30° C. for 2 days. To generate the first crossover, 0.2 ml of these cells were used to inoculate 5 ml R5 with apra and grown at 37° C. for 36 hours. This step was repeated once and cells were plated on R5 agar with apra or Tomato agar with apra at 37° C. Single colonies from these plates were grown and their DNA analyzed by Southern blot for integration of the delivery plasmid by homologous recombination. Confirmed single crossovers were propagated in R5 without antibiotic selection at 37° C. for ~32 hours, plated on Tomato agar plates at 30° C. and allowed to sporulate (~10-14 days). Spores were harvested, plated on R5 and single colonies were screened for sensitivity to apra. To identify second crossovers (AT replacement), apra sensitive colonies were grown in geldanamycin production medium (DeBoer and Dietz, 1976, *J. Antibiot.* 29:1182-8) at 30° C. for 5 days. LC-MS was used to identify production of new geldanamycin compounds. Strain K309-1 containing the AT7→rapAT2 substitution was found to produce at least three new geldanamycin analogs that were purified and characterized by NMR spectroscopy. Those strains producing new metabolites were further analyzed by PCR and/or Southern blot to verify the expected replacement of the targeted AT domain in the gdm gene cluster.

Example 7

Replacement of AT Domain in Module 5 of gdmA2 in *S. hygroscopicus* NRRL 3602

A DNA fragment (~1.3 kb) flanking the AT5 domain was PCR amplified from cosmid pKOS256-107-3 with the following oligonucleotides (EcoRI, BglII, XbaI, BamHI, PstI, HindIII, and NsiI restriction sites are underlined):

```
AT5 Left Flank
                                        [SEQ ID NO: 67]
for 5'-TTGAATTCAGATCTGTGTTCGCCGGGGTCATCTACCAC

[SEQ ID NO: 68]
rev 5'-TTTCTAGAGGATCCGCCGTCGCTGCCCGTCTCCCCGGTG

AT5 Right Flank
                                        [SEQ ID NO: 69]
for 5'-TTTCTAGACTGCAGCCCGCCAGGACACCGACGCGGGCC

[SEQ ID NO: 70]
rev 5'-TTAAGCTTATGCATGGCGTTGCCCGCCGCGTACGGGGC
```

The PCR fragments for each targeted AT were cloned together using XbaI into pUC19 using EcoRI and HindIII restriction sites. The resulting plasmid was pKOS309-6a (AT5 flanks). The rapAT2 cassette (McDaniel et al., 1999, *Proc. Natl. Acad. Sci. U.S.A.* 96, 1846-51) was inserted between the two flanking sequences of the plasmid with BamHI and PstI restriction sites. The AT and flanking fragments were moved into the delivery vector pKC1139 (Bierman et al., 1992, *Gene* 116:43-49) with EcoRI and HindIII restriction sites. The resulting delivery plasmid (pKOS305-152) contains the rapAT2 cassette flanked by 1.3 kb of gdm DNA for homologous recombination into the appropriate module.

The plasmid was introduced in *S. hygroscopicus* NRRL3602 by conjugation using *E. coli* ET12657/pUZ8002 (Kieser et al., Practical *Streptomyces* Genetics: *A Laboratory Manual* (The John Innes Foundation, Norwich, UK, 2000). Primary exconjugants were first grown in 5 ml liquid R5 containing 100 mg/l apramycin (apra) at 30° C. for 2 days. To generate the first crossover, 0.2 ml of these cells were used to inoculate 5 ml R5 with apra and grown at 37° C. for 36 hours. This step was repeated once and cells were plated on R5 agar with apra or Tomato agar with apra at 37° C. Single colonies from these plates were grown and their DNA analyzed by Southern blot for integration of the delivery plasmid by homologous recombination. Confirmed single crossovers were propagated in R5 without antibiotic selection at 37° C. for ~32 hours, plated on Tomato agar plates at 30° C. and allowed to sporulate (~10-14 days). Spores were harvested, plated on R5 and single colonies were screened for sensitivity to apra. To identify second crossovers (AT replacement), apra sensitive colonies were grown in geldanamycin production medium (DeBoer and Dietz, 1976, *J. Antibiot.* 29:1182-8) at 30° C. for 5 days. LC-MS was used to identify production of new geldanamycin compounds. Strain K309-2 containing the AT5→rapAT2 substitution was found to produce at least two new geldanamycin analogs. Those strains producing new metabolites were further analyzed by PCR and/or Southern blot to verify the expected replacement of the targeted AT domain in the gdm gene cluster.

Analogs were not detected in experiments using constructs having substitutions of gdmAT2 with rapAT2, rapAT14, and eryAT2; gdmAT3 with rapAT2 or rapAT14; gdmAT4 with rapAT2; and gdmAT7 with rapAT14. This was likely due to the specific boundary junctions used for the domain substitutions in the constructs. Those of skill in the art will appreciate that by using constructs with different boundaries polyketide producing cells can be generated.

Example 8

Construction of Mutant Geldanamycin PKS Expression Plasmids Using the RED/ET Cloning Procedure This example describes the use of the RED/ET cloning procedure for replacement of the AT4 domain of geldanamycin module with a heterologous AT domain (rapAT2).

Plasmid pKOS331-178 is a derivative of pKOS279-69 in which the gdmAT5 domain is replaced with the rapamycin AT14 domain using the same boundaries for the gdmAT5 domain as above. Plasmid pKOS272-166 contains point mutations in the KR6 domain of gdmA3 that generate the same KR inactivating Tyr→Phe substitution used for inactivation of the KR6 domain in DEBS (Reid et al., 2003, *J. Am. Chem. Soc.* 42:72-79).

Figure 9:
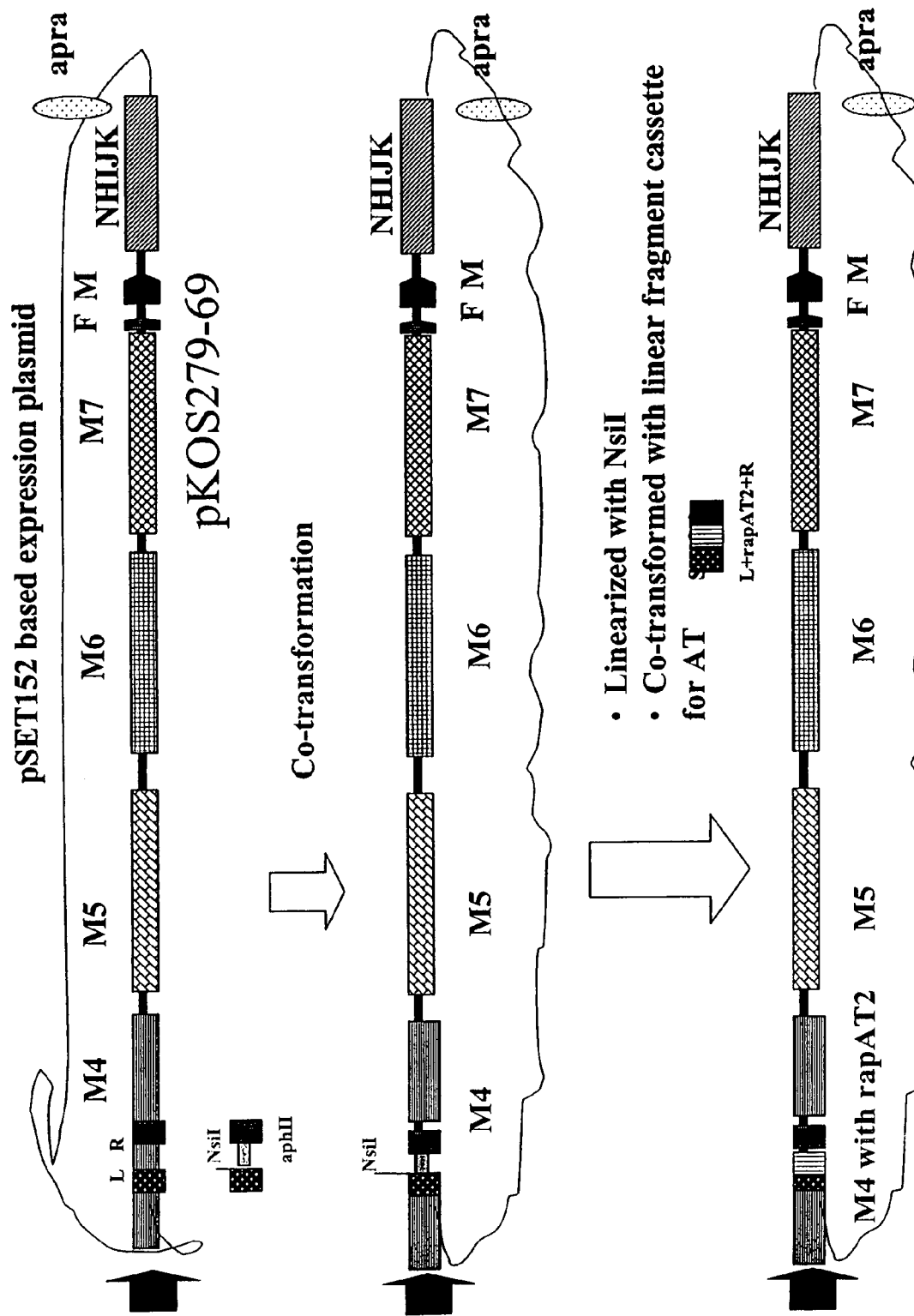
FIG. 9 illustrates a recombinational cloning strategy for domain replacement in PKS genes.

Plasmids pKOS331-178 and pKOS272-166 were constructed with a procedure based on RED/ET recombinational cloning (Datansko & Wanner, 2000, *Proc. Natl. Acad. Sci. U.S.A.* 97, 6640-45). The general strategy is outlined in FIG. 9. A unique restriction site is first introduced at the site of the targeted domain into the recipient PKS expression using an antibiotic (neo) resistance gene. The resulting plasmid is linearized using the unique site and co-transformation with the delivery DNA containing the modified cassette with flanking sequences homologous to the targeted plasmid. FIG. 9 shows the method for construction of PKS domain modifications in the gdmPKS expression plasmid pKOS279-69, using as an example the replacement of the AT domain of geldanamycin module 4 by a heterologous AT domain (rapAT2).

For plasmid pKOS331-178 (AT5→rapAT14) a neo marker was first cloned into the XbaI site of pKOS309-6a (described above) between the gdmAT5 flanking fragments to make pKOS331-74A. A linear fragment was obtained by digesting pKOS331-74a with HincII and isolating the fragment containing the neo marker and gdmAT5 flanks. The linear fragment was then co-transformed with pKOS279-69 into electrocompetent E. coli HS996/pSC101/BAD/γβαA cells (Gene Bridges). Eight apra/neo resistant colonies were screened and five were found to contain the neo marker recombined at the appropriate location of pKOS279-69. One clone was selected and designated pKOS331-124. The neo cassette introduced unique NsiI and AvrII restriction sites that were used to linearize the plasmid for the second co-transformation/recombination step. The delivery vector for this step, pKOS305-124A was constructed by inserting the rapAT14 cassette into the BamHI and PstI restriction sites of pKOS309-6a. A linear fragment was prepared by digesting with HindIII and EcoRI and isolating the fragment containing the rapAT14 cassette with the gdm flanks. This fragment was used with linearized pKOS331-124 to co-transform E. coli HS996/pSC101/BAD/γβαA cells. Eight apra resistant colonies were screened by restriction analysis and one clone was found to contain the correct gdm AT5→rap AT 14 substitution (pKOS331-178).

The same procedure was used to generate pKOS272-166 beginning with pKOS279-69. A neomycin marker was first introduced into gdmKR6 by RED/ET cloning to generate pKOS272-153. To construct the plasmid used in the second recombination step, pKOS272-122, two fragments were PCR amplified from gdmA3 with the following primer pairs and cloned into pKC1139:

generated by PCR with the primer M4F (5'-TCCTAGGACATATGGCGAATGACGAGC) [SEQ ID NO:75] and primer M4R (5'GCGTCGAAGAGGTTCTCCAG) [SEQ ID NO:76] (restriction sites AvrII and XmnI in M4F and M4R, respectively are underlined) was cloned into PCR4Blunt Topo (Invitrogen) and was further cut and used to replace the AvrII-XmnI fragment in pKOS313.57.1 to make pKOS279-68. The NdeI-PstI fragment from pKOS279-68 and an XbaI-NdeI fragment (carrying the ermE*p promoter) of pKOS159-8 (Rodriguez et al., Apr. 16, 2003, Rapid engineering of polyketide overproduction by gene transfer to industrially optimized strains. J. Ind. Microbiol. Biotech) were ligated together and inserted into XbaI-PstI sites of Litmus28 to give pKOS279-68B. The final plasmid, pKOS279-69, was made by ligating the EcoRI-PstI fragment from pKOS 179-68B, PstI-PstI fragment of 22.7 kb in size from pKOS256-107-3 with EcoRI-NsiI linearized pKOS159-8.

A gdmA2gdmA3::neo derivative (K279-48) of NRRL3602 was constructed using a protocol similar to above with the delivery plasmid pKOS27948. Plasmid pKOS279-48 was made by inserting the SpeI-XbaI fragment of pKOS27946B into the XbaI site of pKOS279-46A. pKOS27946A was composed of two fragments from the gdm PKS cluster cloned into the EcoRI-HindIII sites of pKC1139. The left fragment consisted of a 1.3 kb region upstream of AT4 amplified with the following primers: forward, 5'-TTGAATTCAGATCTAGTTCGCTGGAGGA-CAGCGACGTC; [SEQ ID NO:77] reverse, 5'-TTTCTA-GAGGATCCGCCGTCTGTTCC GGTCTGTCCGGTG

```
left half forward, 5'-CGGGATCCGAGCCCCAACTGGCGGTGCGCGGT;            [SEQ ID NO: 71]

left half reverse, 5'-GCGGAGAAGTTGCCCTGGCCGGGCCCGCCTAGGACTCCGG     [SEQ ID NO: 72]
CGGCGGACGAGTACA;

right half forward, 5'-CCGGAGTCCTAGGCGGGCCCGGCCAGGGCAACTTCT        [SEQ ID NO: 73]
CCGCCGCCAACGCCTATCTGGA;

right half reverse, 5'-GCTCTAGAGGGTCCGTTGGGCGCGGTGAGGCC.          [SEQ ID NO: 74]
```

Recombination between linearized pKOS272-153 and pKOS272-122 as above resulted in pKOS272-166.

Example 9

Production of Geldanamycin and Analogs By Gene Complementation in S. hygroscopicus NRRL3602.

This example describes construction and use of a host/vector system in which one or more gdm PKS genes are disrupted or deleted in the chromosome. Those same genes are then cloned into a plasmid or vector that can be used to deliver them back into the strain. They are under control of a native or heterologous promoter that results in expression of the genes and production of geldanamycin or an analog if they have been modified (gene complementation). It will be appreciated that this strategy is generally applicable to other domains.

Plasmid pKOS279-69 contains the gdmA2 and gdmA3 genes under control of the ermEp* promoter in the Streptomyces integration vector pSET152 (Bierman et al., 1992, Gene 116:43-49). A 7.8 kb NheI-PstI fragment (carrying module 4 and part of module 5) from pKOS256-107-3 was cloned into Litmus28 (New England Biolabs) to make pKOS313.57.1. At the same time, an AvrII-XmnI fragment

[SEQ ID NO:78]. The right fragment consisted of a 1.3 kb region downstream of AT7 amplified with the following primers: forward, 5'-TTTCTAGACTGCAGCGCGGCGGTC-CGGGCGACGTCCGT [SEQ ID NO:79]; reverse, 5'-TTAAGCTTATGCATCGGGTCGGTGAC-CTCGGCGGTGTC [SEQ ID NO:80]. Plamid pKOS279-46B was made by inserting the aphII (neo) gene containing StuI-SmaI fragment of SuperCos 1 (Stratagene) into the EcoRV site of pLitmus28 (New England Biolabs). Introduction of plasmid pKOS279-48 into S. hygroscopicus NRRL3602 followed by screening for double crossovers resulted in strain K279-48 in which the gdmA2 and gdm A3 genes have been disrupted by the neo resistance gene. This strain does not make modules 4-7 of the gdmPKS and therefore does not produce geldanamycin. Introduction of plasmid pKOS279-69 into K27948 restored geldanamycin production to levels comparable to the NRRL3602 strain.

The K279-48 and pKOS279-69 host/vector system was used to generate two engineered gdmPKSs that produced geldanamycin analogs. As described in Example 8, plasmid pKOS331-178 is a derivative of pKOS279-69 in which the gdmAT5 domain is replaced with the rapamycin AT14 domain using the same boundaries for the gdmAT5 domain as above. Plasmid pKOS272-166 contains point mutations in the KR6 domain of gdmA3 that generate the same KR inactivating Tyr→Phe substitution used for inactivation of the KR6 domain in DEBS (Reid et al., 2003, *J. Am. Chem. Soc.* 42:72-79). Both plasmids were constructed using a modified RED/ET cloning procedure described in Example 8. Introduction of pKOS331-178 into K279-48 resulted in production of the same 6-desmethoxy compounds as the gdmAT5→rapAT2 substitution described in Example 7. Introduction of pKOS272-166 into K279-48 resulted in production of at least two putative derivatives of geldanamycin as determined by mass spectrum and chromatographic retention.

Example 10

Inactivation and Heterologous Expression of Tailoring Genes

GdmL and GdmM are believed to encode mono-oxidases involved in post PKS oxidation steps (tailoring enzymes). Disruption of these genes in the geldanamycin PKS is expected to result in novel, geldanamycin-related, compounds due to loss of the oxygens at position 17 and/or position 21 of geldanamycin (resulting in a benzo-aromatic system instead of a p-chonoid system as in geldanamycin). See, for illustration FIG. 2. Homologous recombination was used to disrupt these genes.

a) Gdm M Disruption

For the Gdm M disruption, DNA fragments up- (fragment M1) and downstream (fragment M2) (FIG. 3) from GdmM were amplified by PCR introducing restriction sites, for M1 BamHI/XhoI and for M2 XbaI/NsiI, flanking the fragments M1 and M2. The aphII neomycin/kanamycin resistance gene from Tn5 was excised as a XhoI/XbaI fragment from plasmid pFdneoS [Denis & Brzezinski, 1991, *FEMS Microbiol. Lett.* 81: 261-64] and ligated between M1 and M2 in vector pLitmus 28 (Invitrogen) to give pKOS 313-148. The cassette was then excised by a BamHI/NsiI-restriction to be then cloned into the pKC 515 [Kieser et al., 2000, Practical *Streptomyces* Genetics: *A Laboratory Manual*. The John Innes Foundation, Norwich, UK] based phage vector KOS305-117A phage DNA linearized by restriction enzymes BamHI/PstI to give pKOS K313175-6.

For the disruption of the Gdm M gene, pKOS K313175-6 was introduced into *Streptomyces hygroscopicus* 3602 by transfection [Kieser et al.]. Lysogens resistant to neomycin (disruption cassette includes aphII gene) were isolated and grown at 30° C. in R5 liquid medium [Kieser et al.]. The mycelia was then grown on tomato paste agar for sporulation at 30° C. for 18 days. To select for second crossover events which result in loss of the prophage and it's outside marker accIV apramycin resistance gene spores were grown on R5 agar and isolated colonies were patched out in parallel on R5 agar with neomycin (100 µg/ml neomycin) and apramycin (60 mg/ml) selection. Apramycin sensitive but neomycin resistance colonies were then transferred in 5 ml YPD broth [Sigma] as seed culture and grown in 50 ml glass tubes at 30° C. for 48 h. 1 ml of the seed culture was then transferred into 50 ml Geldanamycin production media (pH7) [DeBoer & Dietz, 1976, *J Antibiot* 29:1182-8] and grown in 250 ml baffled flasks with continuos agitation for 6 days. The supernatant fraction of 1 ml crude extract/MeOH 1:1 mixture was then analyzed by LC/MS (analysis is ongoing). In 11 of the 12 analyzed mutants LC/MS data revealed two new compounds not present in *Streptomyces hygroscopicus* wildtype. Those compounds show fragmentation pattern similar to the geldanamycin sodium adduct and are detectable by UV at λ304 nm.

b) Gdm L Disruption

For the Gdm L disruption, DNA fragments up- (fragment M1) and downstream (fragment M2) from GdmL have been amplified by PCR introducing restriction sites, for M1 BamHI/XhoI and for M2 XbaI/NsiI, flanking the fragments M1 and M2. The aphII neomycin/kanamycin resistance gene from Tn5 was excised as a XhoI/XbaI fragment from plasmid pFdneoS and ligated between M1 and M2 in vector pLitmus 28 to give pKOS 390-6-1. The cassette was then excised by a HindIII/Stu1 restriction to be then cloned into the Hind3/EcoRV sites of pKC1139 [Kieser et al.] to give pKOS 390-7-1.

For the disruption of the Gdm M gene, pKOS 390-7-1 was introduced into *Streptomyces hygroscopicus* 3602 by conjugation from *E. coli* ET12567/pUz8006 according to a published method [Flett et al., 1997, *FEMS Microbiol Lett* 155: 223-9]. Exconjugants resistant to neomycin (disruption cassette includes aphII gene) were isolated. Isolated neomycin resistant exconjugants are grown in liquid R5 media [Kieser et al.] at 30° C. for 2 days with neomycin selection (100 µg/ml). Approximately 20% of the culture is then transferred into 50 ml liquid R5 media [Kieser et al., 2000] with neomycin selection (100 mg/ml) and grown for 2 days at 37° C. in order to force chromosomal integration of pKOS. After recovery of mycelia by centrifugation, cells are plated out on Tomato paste agar at 30° C. for sporulation. Spores from these plates are diluted and replated on R5 agar to obtain single colonies. To select for second crossover events which result in loss of the plasmid (and the accIV apramycin resistance gene marker), isolated colonies are patched out in parallel on R5 agar with neomycin (100 µg/ml neomycin) and Apramycin (60 mg/ml) selection. Apramycin sensitive but neomycin resistant colonies are transferred in 5 ml YPD broth (Sigma) as seed culture and grown in 50 ml glass tubes at 30° C. for 48 h. 1 ml of the seed culture is then transferred into 50 ml Geldanamycin production media (pH7) and grown in 250 ml baffled flasks with continuos agitation for 6 days. The supernatant fraction of 1 ml µl crude extract/MeOH 1:1 mixture is analyzed by LC/MS and novel geldanamycin-related compounds are identified.

SEQUENCE ID NOS: 1-3

GELDANAMYCIN CLUSTER (SEQ ID NO: 1)

```
  1 AGTCTAGGTC GGACTAGACC TTGTAAAACG ACGGCCAGTC CAGTGTGCTG GAAAGGCAAC
 61 GCGTCGTCCG GGGCCAGGAC TTCGATCACC CGGTCCGCCA CCCGCCCGCG CACGCCCTTG
121 CCCGGCAGTG CGACGAAGTC GGCCACGGCC GGGAGGGGGT CTGCGGGATC GGTGCGCCGG
```

-continued

SEQUENCE ID NOS: 1-3

```
 181  GCGTAGGCGG TGATGGCACG CCCCAGCGGG TGTTCCGATC CCTGTTCGAC CGCGCCCGCC
 241  AGCCGGACCA GTTCCTCCTC GCCGAGTCCG CCCGGTGCAG CCGTGACCCG GGCGACGCTC
 301  ATGTGCCCGG AGGTGAGGGT GCCGGTCTTG TCCAGGACGA CGGCGTCGAT GTGCCGCAGC
 361  CCCTCCAGCG CCTGCGGTCC GCTGACCAGG ACGCCCAGTT GGGCGCCCCG GCCGGTCGCC
 421  GCCATCAGCG CGGTGGGGGT CGCCAGGCCC AGCGCGCAGG GGCACGCCAC GACCAGGACG
 481  GCCACGCTCG CGGTGATCGC CGCCTGCGGC TCGGCACCGG CCCCGAGCCA GAATCCGAGG
 541  ACCGTGACGG CCAGGGTGAG CACGACCGGG ACGAAGACGC CCGCGGCCTT GTCCGCGAGC
 601  CGCTGCGCCC GTGCCTTGCC CGCCTGGGCC TCGGTCACCA GCCGGGTGAT CCGGGACAGT
 661  TGCGTATCGG CGCCCACCGC GGTGGCCCGT ACCAGGAGCA GGCCCCCTGC GTTGACGGCG
 721  CCGCCGATCA CGGGCGTACC GGGGCCGACT TCCACCGGCT CGCTCTCCCC GGTGACCAGG
 781  GAGAGATCGA CGGCCGAGCT GCCCTCCACC ACCGTGCCGT CGGTGGCCAG ACGCTCCCCG
 841  GGCCGGGCGA CGAAGACCTG GCCGACCCGC AGTTCCTCGA TCGGGACCAG GCGCTCGCCG
 901  TCGCCATCGC GTACCGACAC CTCCTTCGCC GCCAGCCGGG CCAGGGCGCG CAGTGCCACG
 961  CCGGTCCCCC GCCGGGCCCG TGTTTCCAGG AAGCGGCCGG CGAGGACGAA CAGCGGTACG
1021  CCGACGGCGG CTTCCAGATA GATATGGGCG ACGCCGTCCG AGGCGGTGGG CACCAGGCTG
1081  AAGGGCATCC GCATGCCGGG ATCACCGGCC CCGCCGAAGA ACAGCGCGTA GGAGGACCAG
1141  GCGAAGGAGG CCGCGACACC CAGCGAGACC AGGGTGTCCA TGGTGGCCGC CGAGTGTCGC
1201  AGGCCGCGCG CCGCCCGCAG GTGGAAGGGC CAGGCTCCCC AGACGGCGAC GGGCGCGGCG
1261  AGCACGAAGC ACAGCCACTG CCAGTTGCGG AACTGCAGAC CGGGGACCAT CGACAGGACC
1321  AGCACCGGGA CCGCGAGCAA GGCCGTGCTC AGCAGCCGGT CGCGTTCCTG CCGGGCGTCC
1381  CGCGCCTCGT CCCCGTCCTC GCGCCGTTCC TTCGCCGGCG GCTCGGGCAG CGCGGCGGTG
1441  TAGCCGGCCT GCTCGACGGT GGCGATGAGC TGGTCCGGGC CGACCTCGGG CGGGTGGTTC
1501  ACCCGGGCCC GGCCGGTGGC GAGGTTCACG CTGGCCGTGA CCCCGTCCAG CCTGGCCAGC
1561  TTCTTCTCGA CACGCTTCAC ACAGGCCGCG CATGTCATGC CGCCGATGGC GAGATCGGTC
1621  ACGACGGCCA CCGCTGCCGG TTCGCCGGCC ATCAGCGTCC ACTCCCCTGG TCCGTGTCCA
1681  TGCCACCCAT GTCCATGCCG CCACCGCCGT GGCCGTCTCC CGAGCCGCCG TCTCCCGAGC
1741  CGCCGTCTGT CGTGCTGGTG CCGTGCATGC CGGGGGCGAC GGGCCCGGCG CCCGCGCCGA
1801  CGGCGTAGGA AGCGGCGAAC GCCATCACCA GCAGCAGAAG GAATCCGCAC AGCGCCGGCG
1861  GGGGCAATGC CCTGGTAAGG AACGCACCCG GCGTCCGGCG GGCAGATGGG CGGGGCTGCG
1921  CCATATGAGG AAACTCCCGA TCGCTCCGTA CGGCTTCAGC GGATCCGGCC GTACCGGTAG
1981  AGGAGTCGGG ACGGCCGGCA CCCAGTTCC GACGCCTTGT CGTGACGCGC GTCACGACAC
2041  CAGGCTCGCC TGCCGAACGC GTGACCTGCT CAGCCCTGTT CATAGTGGCT CGGACTGCCG
2101  TCACGGTGGA CGAGACGGCC AAGCTGCTCC GCGCGGGCGC GGGGCATGAG AGTCCAGGTG
2161  CCGTCGGTGC GGTGCAGGGC GGCCGAGTGC CAGGGGTGG CCCAGACGTC GGCGGCGTCG
2221  AGGAGGCGGA TGCCGAATTT GGGGGCGCCG ATGGGCTGGG GGTGGATGGA CAGCCGTACG
2281  GAGCCAGGGT GGTGCTCGGC GATCAGGTCG CCCCAGGCTC GGCTGCGCTG GATGACGCCG
2341  TAGGCGCGTG TGCGGCATTC GCGTTGGAGG CGGAGCGGG TGCCGGTGAA GTCGGCGGTG
2401  TCGTCGACGA GGAACCGGAT GATGCCCCGG TAGAGGGCGA GGGTGTGGTC CCCGGAGCGG
2461  ACCTCGGCTC GCAGCGCCTC CAGGGTGGGG GCGTACCGCT CGTGCACCTG GACGCGTTTG
```

-continued

SEQUENCE ID NOS: 1-3

```
2521  GTGTGGTGGG GCAGGTCGCC CAGGACGTCG CGCAGGTCGA AGACGGAGAG GCGGTGCAGG

2581  CCCGACTCCC TTATGAGACG TCTGAGTCCG TCCGCGTAGG CGTCTATGTG GTCGTCCGGG

2641  ACGCGGATCA GGTCGCCGAA GACATGGCCG TCGGAGCAGA TGATCACGCG GGCGCCCGGC

2701  GGGTGGACCC GCTCGATCTC CTCGCACAGG GTGTTCAGGA AGCCGAGGGA GAGGCGTTCG

2761  CCCTGGTCGG GGAGGTGGCC GAGGACCTTG GCGGGGTTGG GGGACTTGCA GGGGAAGCCG

2821  GGCAGGGTGA AGACCACAGG TTCTCCGGCG CGTACGAACC CGGCGATCTG GCGCCGCTGC

2881  TGCGCGAACG CCTCCGCCGC CGCGGGCGAG GGTCGGTCG TGCGGTGGTA CGGCAGCAGC

2941  AGGTCCAGGA TGGCGGCGCT CATGCTGCTC GTGGAGCGGG TGTCCGGTGC GGTCGTCAGC

3001  GGCATGAGGT GGGTTCCTCC GTGAAGGTGT GCGCGACGCG GCATGCGGG CATGCGTCAG

3061  ACGCGTCGGT CGTAGCCGAC CGGCAGGTGG TTGGTCCCCC GGCCGAGGAC GGCCGGGATC

3121  CACTCGATGT CCCGGTCTTC GATGGCCAGG TGCGCTCCGG GGAGGCGGGA CAGGAGGGTG

3181  CCCAGCGCGA TCTGGAGTTC GGCGCGGGCC AGGGCCGCGC CGGGGCAGAA GTGGATGCCG

3241  TGACCGAAGG CCAGGTGGGG GTTGGGTGAG CGGTCCAGGT CGAGGGTGTC GGGGTCGGGG

3301  AAGCGGCGTG GGTCGCGGTT GGCGGCGCAC AGGGAGATGA TCACCGAGTC CCCGGCCGGG

3361  ACGTCCGTGC CGTGCAGGTC GCTGTCCTGG TCGAAGAAGC GCCAGGTGGT CAGCTCGAAG

3421  GCGCTGTCGT AGCGGAGGAG TTCGTCGACC GCGCGGGGCA TCAGCTCCGG GTCGTCGCGC

3481  AGCCGGGCGA GTTCGGCGGG GTGGCGGAAG AGGGCGATCA GGGCGGTGGT GATCTGGTTG

3541  GTGACCGGTT CCTGGCCCGC CACGAGGAGC TGGAAGATCA TCGAGTCCAG CTCCTCCTGG

3601  GAGAGTTCGC TGCGGTCGCG GGCCACGACC AGGCGGCTGA GCAGGTCGTC CTCCCCGTGT

3661  TCGCGCTTAT GGGCGACGAC CTCGGCTATG TAGCTCTGGA GCCCGTGCAG GCGGGCCTCG

3721  TACAGCGGGC GTCCGGGGTC GGTCGGTCCG ACCGGCTGGA CGACCTTGCC CCAGTCGCGG

3781  TCGAAGCGGG CCGCCGACTC CGGTGGCAGG CCGATGACTT CGGCGAGGAC CTGCAAGGGG

3841  AAGCGGGCGG CGAAGCCGGT GACCAGGTCC GCGGGGCCGG TTTCCGGGAG GGCGTCGACG

3901  AGGGTGTCGG CCAGCTCCTG GAAGCGGGGC CTCAGATGCT CGACGCGGCG CGGGGTGAAG

3961  GCGTCGGTGA CGAGGCGCCG CATGCGGGTG TGGTCCGGCG GGTCCTGGTG GAGGAGGTGG

4021  ACCTGGAGCT GGGAGTGCTG GGGCTCGGGC ATGATCGAGG CGCGGGCGCG CCAGCGGTCG

4081  TTGCCCCGGT CGTGGTTCTT GCCGAGGCGG TCGTCGCCCA GCGCGGAGTG CGCGGCGTCG

4141  TAGCCGGTGA CGAGCCAGGC GTGGACGCCG CTGGGAAAGC GGACGCGGTG CACCGGGCCG

4201  GTCTCGCGCA TCCGCTCGTA GAGGGGGTAC GGGTTGCTCT TGTAGGGGCA GCCCATCAGC

4261  GGCACGGGCT CGGGCAGGGC CTCGGGGGTC GTCCCGGATT CCTGGAGGGT CATGGAAGGT

4321  GCTCCTCAGA GGGCGAGTTC GGGCTGGTAG TGGTCCAGCC ACAGGGCGAG GTCGACGACG

4381  CGTTCGAGGC GGAGGCGGTG GCCCCACTCC AGTTGACCGG GCGGGGTGTC GAGGCAGGGT

4441  TTGACGCGGG TCTCGTCGGC GAGGGAGCGG ACGGTGTCGT CGGCGAGGGC GTCGCGGGCC

4501  ATGTTCTGCA GGCCGCGGTT GTAGTCGGGG TGATGGGTGG CCGGGTAGTG GTTCTTGGGG

4561  CGGTGCAGCA CCGAGTCGGG GGCCAGTCCG GTACCCGCGG CGCGCAGCAG GCTCTTCTCC

4621  CGGCCGTCGA AGTTCTTCAG GGTCCAGGGC GTGGTGAAGG CGTACTCGAC GAGCCGGTGA

4681  TCGCAGTAGG GGACGCGGAC CTCCAGGCCC TGCGCCATGC TCAACCGGTC CTTGCGGTGG

4741  AGGAGTTGAC GCAGCCAGCG GGTGAGCGAA AGGTGCTGCA TCTCGCGCTG CCGGTGCTCG
```

-continued

SEQUENCE ID NOS: 1-3

```
4801 GTGGGCGTCT CGCCGTCGAG GTGCGGTACG GCGGCCAGGG CGGTGCGATA GGTGTCGGCA
4861 CGGAACTCGC CGATGCGCAG GTCCAGTTCG GGGTTGAGCG CATCGCGGC CTCGTCGCCG
4921 GTCACCAGCA GCCAGGGGAA CGTGGACGCG GCGAGCGCCT TGGGGTTGTG GAACCACGGG
4981 TAGCCGCCGA AGACCTCGTC GGCCGCCTCG CCGGACAGGG CGACCGTGGA GTGCTTCCGG
5041 ATCTCCCCGA AGAGGAGGTA GAGCGAGGTG TCCATGTCGC CGACGCCGAT CGGCGAGTCG
5101 CGGGCCACGA CCACGGCCTT GCGGTGCTCG GGTCGAGCA GGGCACGCGG GTCCAGCACC
5161 ACCGTGCTGT GGTCGGTGCC GATGAACGCG CCCGCTTCCG TGGCGTACGG GGTGTCGTGG
5221 CCGGTGCGCA GAACATCATC GGTGAAGCTC TCGGCCTGGT CGCTGTAGTC GACGGCGTAG
5281 GAGCGGATAC GGGCGCCCGG GCCCTCGCGC AGCCGCAGTT CGTCGGCGAG CAGGGCGGTC
5341 AGGACGGTGG AGTCGATGCC GCCCGACAGC AGGGAGCACA GGGGACGTC GGCCTCCAGC
5401 TGAGCGCGGG CGGCGGCGCT CACCAGGTCG TGCACGCGGG CGACGGTCGC GTCCCGGTCG
5461 TCCGGGTGGG CGTCGGCCGC CAGCCGCCAG TAGCGGCGCT CGCGGATGCC GTCCCGGTCC
5521 AGGAGGAGCA GACCGCCGGG CTCGACCTCC CGCACGCCGG ACCACACCGT CGGACCGGTG
5581 TTGAACAGCA GGCCGTACGC CTCGCGCAGC CCGTCCGCGG CCACCCGGGG CCGTATCTCC
5641 GGGTGGGCGA AGAGCGCCTT GGGTTCGGAG GCGAAGGCCA GACCGCCGTC CACGGCCGCC
5701 CAGAAGAGGG GCTTGACGCC GAGCCTGTCG CGGACCAGGA GCAGCCGCTG TGCCCGCTCG
5761 TCCCAGACGG CGAACGCGAA CATGCCGTCC AGGTGGTCGG CCACCTCCTC GCCCCACTCG
5821 GCGTAGCCGC GCAGCACCAC CTCGGTGTCG CTGCGGGTGC GGAACTCATG TCCCCGGCCC
5881 TTCAGTTGTG AGCGGAGTTC GTGGTGGTTG TAGATCTCGC CGCTGTAGGT GAGCACGGTC
5941 GTCGGGGCAT CGGGCCGGTC GGTCATCGGC TGGACGCCAC CGGCGATATC GATGACGGCC
6001 AGGCGGCGGT GGCCGATCGC GGCACGCGGG CCGAGCCAGA CTCCGTCCGC GTCGGGGCCG
6061 CGCGGGGTCA GGGTGGCGGT CATGGCCTCG ATGACCGGGG CCTGGGTGCG GGGGTCCTGA
6121 TGGAAGGACA CCCAGCCGGT GATTCCGCAC ATGGGCACGA CTCCTCGGTG AGGGTGGGGC
6181 GGTGGCTCAG CGGGGTGCGG CGGGCGCCGC GTCGGTGGTC TTCTCGGTGA GGTTCGCGGG
6241 ATCGCGGGCG GCCGGGCGA GCAGCGGTAC GGCGAGGCAG GCGGCGAGGG CGGCGAGGGC
6301 CAGACCCGCC CGTACGCCGT CGTCCTGGCC GGCCGGCCCC CAGGCCGCCG TGGCCAGGGC
6361 CGGTCCGAGC GTGAAGCCGA GGCTGCGGGC GAGCTGGACG GTCGAGCCGA CCGTGGCGGC
6421 GCGGCCCGGC GGGGCGGCGC CCATGACCAG GGCCTGCACC GGGCCGCCGT TCAGGCCCAT
6481 GCCGAGTCCG GCCAGGGCGA GCCGCCAGGC CACGTCGGGA GGGGACCAGC CGTCGCCCAG
6541 CGGGACGAGC AGCAACAGGC CGCCGGCGGT GAGCGCGGCG CCGGTGACCG CGACGGGCCG
6601 GGCCCCGTAC CGGTCGGCGA GCCGTCCGCC GAGCGGGCCC GCCAGCCCCA TGCCGAGGGG
6661 GAAGGCGAGC ACCGTCAGGC CGGTGGTGGT GGCGCTGACG TCCTCGTCGC GCTGGAGGTG
6721 CAGGGCGACC ACGTAGTGCA TGGCGGCGAA ACCCACCGCC AGCGCCAGCA CCGCGCCGTG
6781 CGCCCGCAGC AGCCCCGCCG CCCGCAGCAC ACCGGCCACC GGACGGCCGC CCGGACCCCG
6841 CAGCCACCAC CACAGCGGCG GTGCGGCGAC GAGGGCGAGC GGCAGCCAGG CGGGTGTGTC
6901 GGAGGCCAGG GTCAGGGACA GCAGCAGGAT CGTTACTCCG GTGGCTATCA GGGCGGTGTC
6961 GCCGAGGAAG CGCCGGTCCG CGCCGCGCAG GCGGCCGTCC CGGGGCATCG CCCGCCACAC
7021 CACGCCAGCC GCCAGCAGAC AGAACGGGAT CTTGACCAGG AAGATCCAGC GCCAGCCGAG
7081 CTGGTCCAGG AGCAGACCGC CGACCGCCGG TCCGGTGACG GCGCCCAGGG GGCCGAGGGT
```

-continued

SEQUENCE ID NOS: 1-3

```
7141  CGCGGGCACG CTCATCGCCC GCCCGCGCGA CTCGGGCCGC ACCGAGCGGA TCGCCAGCAC

7201  CGGCATCGAC ACGAACAGCA CCGCACCGCA CGCGCCCTGC CCGATCCGGG CGGCGATCAG

7261  CCAGGCGGCC CAGGGGGACG CGGCGGCAAG CGCGCTGCAC AGCGCGAAGC CACCGGTGGC

7321  GGCCATCAGC GCGGGGCGGG TGCCCACGCC GTCGAGCCAG CGGCCGACGG CAACAGGAG

7381  TGCGACGACG GGAAGTTGGT AGCCCAGTAC CGCCCACTGG GCTGTCGCCG CCGGTACCCG

7441  CAGGCCCTGG GAGATGTCCG CGAGCGCCAC GTTGACGATA TTCATGTCGA GCATCGCCAC

7501  GAACGCCAGC GCGCCCGCCA CGGCCACCAG GAGCCAGCGG TCGTGGACTT CGGGTGGATC

7561  CGCCGGACGC TCGGTTACGT CCCCGGGCTG ATCCGCACCG GAAGCGTCGT CGGTCATACG

7621  CCCCTCCCTC TGGCCGGTCG GCCGCCGAGC GACGGCCTCG CTGTAGAAGT CGGGCGAACC

7681  GCGGAGTGAG TTCCCGGATG TATCAGGAAA AACGGCTGGA TTTCATAGTT CTCGGTGGTC

7741  GAAGGCGATC AGCGGGTCCC CGGTCAGCGG GTGCTCGACC ACGGCGGCGC GCACGCCGAA

7801  CACCTCGGCC AGCAGGGCCG GTCGCAGCAC CTCGCGGGGC GTTCCGGAGG CGACCACGCG

7861  GCCCTCGTGC AGGACATGCA GCCGGTCGCA CACGGAGGCG GCGGCGTTGA GGTCATGCAG

7921  CGACACCAGG GTCGTACGGC GTCGGCCGCG CAGCAGGGCG AGGAGTTCGA CCTGGTGGCG

7981  GACGTCGAGG TGGTTCGTCG GCTCGTCCAG GACCAGGACG TCCGTCCGCT GGGCGAACGC

8041  ACGGGCCAGC AGCACGCGTT GGCGCTCACC GCCGGACAGC TCGGTGAAGT GGCGGTCGGC

8101  GTGGTCCCCC ATGCCGACGT CCGCGAGAGA GCGCTCGACG ATGTCCCGGT CGGCGGCGTC

8161  CTCCCCGGCG AACGCCCGCT TGTAGGGCGT GCGGCCCATG GCGACGACCT CACGTACGGT

8221  CAGCTCGAAG TCCCCGCCCC GCTCCTGCGG GAGCGCGGCG ACGTGCCGGG CCGACCGCGC

8281  GGGGCTCAGC TCGCGGATGT CGGTGCCGTC GAGCAGGACA CGTCCGGCGG CGGGCTTCAG

8341  ATGCCGGTAC ACGGTCCGCA GAAGAGTGGA CTTGCCACTG CCGTTGGGCC CCACCAGGCC

8401  GGTGATCTCG CCTTCGGCCG CGATGAGGTG GGCATCGGCC ACGACCGTAC GTCCGGCATA

8461  CGCGACCCGC AGGTCCTCGA TGTCGATCCT CAACTCCCGC TCCCCAAGCG CCGGTCCAGC

8521  AGATACAGCA GCGCCGGAGC GCCGATCAGC GAGGTGACGA CCCCGACCGG CAGTTCCTGC

8581  GTGTCCATGG CCGTGCGGCA CACGATGTCG ACCACCACCA GCAGCAGCGC GCCGAAGAGC

8641  GCCGACACGG GCAACAGCCG ACGGTGGTCG CCGCCGACGA CCAGACGGCA GACGTGGGGG

8701  ACCATGAGGG CGACGAAGGC GATGGCCCCG GAGACCGCGA CGAGGACACC GGTGAGCAGG

8761  CTGGTGACCG CGAACAGCTC ACGGCGCAGC CGTACGACGT CGATGCCGAG CCCGGCCGCC

8821  GTCTCGTCGC CCATCAGCAG CGCGTTCAGG CCCCGGGCCC GGGCCTGGAG CAGCAGCAGG

8881  ACCGCCGGAA CCGCCACCGC CGGGGCGGCC AGCAGCGCCC AGCTCGCGCC GCTCAGGCTG

8941  CCCATCAGCC AGAACGCACA CTGTGGGTC TGCTGCTCGT CCCCGGCCTG GAGGACGAGG

9001  TAGCTGGTGA AGCCGGACAG GAACTGCCCG ATGGCCACCC CGGCGAGCAC CAGCCTGAGC

9061  GGTGCGAATC CCCCGCCACG TCGTGCCACC GCCCAGACGA GAGCGAAGGT GGCCAGGGCT

9121  CCCGCGAAAG CGGCACCGGA CAGGCCGAGG CCCAGCGCTC CCCCGGCGCC GAGGCCGAGG

9181  ACGATGGCGC CGACGGCACC GAGGGAGGCG CCGTTGGAGA CGCCCAGGAA GTACGGGTCG

9241  GCCAGCGGGT TGCGGACGAG GGCCTGCATG GCCGTACCGA CCAGGCCGAG CCCGGCACCC

9301  ACCAGAGCGG CCAACAGGGC GCGGGGCAGG CGTAGTTGCC ACACGATCAG GTCATTGGTG

9361  CCGGGCCGGG GGGCATCGCC GGTCAGTCTG CGCCAGACCA CGCTCCACAC CTCGCCCGGC
```

-continued

SEQUENCE ID NOS: 1-3

```
9421  GGGATCGACG TGGAACCCCA GGCGACCGCC GCTGTGAGGG CCGCGAGCAA CGCGACCGCC
9481  AGGAGCAGCG CCAGCGGCCC GGCGGGCACG GAACGCCGCG TGCGTGCACG GGCATCGGTG
9541  CCCTTCCCGC TCACCGTGGC GTCGAGCGCC ATCAGCCGAC CTTGCCCGGG TAGAGGGCCT
9601  TGGCGATCTC CTGGACGGCG TCGGCGTTCT CGACTCCGGC GATGGTGATC CGCTCGGAGC
9661  CGATGCGCAG GAAGTGGCCC TCCTCGACTG CCTTCAGGCC CTTGGTGGCG GGGTTCGACT
9721  CCAGCCACTT CCGCGCCTCG TCGAACGCCT TCTCGTTCGC CACCTCGCTG CCCCGATCAC
9781  GGACGCCCAA CTGGATCCAG TCCGGGTTCC TGGAAATGAC GTCCTCCCAG CCGACCTGCT
9841  TGTAGTCGCC GTCGCAGTCG GCGAAGACAT TGCGGGCACC GGCCAGAGTG ATCACCGCGT
9901  TGGCGACCTG GCGGTTGCAG ACGACGGTGG GCTGCTTGGT GCCGGCGTCG TAGTCGAAGA
9961  AGAAGTACGT CGGCCGCTCG CCCTCCGCCG TCCGGCCGAC GGCCTTGTGG ACGGCGTCCA
10021 CCTTCCCCTT CATTCCGTCG ACGAGTTCCT TCGCCTTCGC GCTGGTGCCG GTGACCGCGC
10081 CGAGGGAGGT GATGTCGGCC TCCACCGCGG ACAGGTCGGT CACCGCGCGT GTGTTCCGCG
10141 CCGCACAGGC GGTGGACTTG AGGTAGATGT GCTTGATCCC GGCCGCCTTG AACTCCTCCT
10201 CGGTCGGCGC GTCGCCCATG CCGCCGCCCA TGTTCATCGA GGCGAAGGTG TCGATGTACA
10261 GATCCGCGCC GGAGCCGAGG AGCTTCTCCT TCGGGATCAC CGATTGGCCG AGCACCTTCA
10321 CCTTCCGCGC CTGCGCGTCG AGTTCAGCGG GCAGTGAGCC CTTGCCGGGC GGGAAGCCGG
10381 TGCCGATGAC GTTGTCACCG GCGCCGAGGC GGAGCAGCAG CTCCAGGCTG GAGGCGTTAC
10441 TGGTGACGAT CTTCTTGGGG GCGTTGGAGA ATATGGTTTT GGCGCCCATG CAATCGGTGA
10501 CGGTGACCGG GTAGTCGCCG GTGGCCGACT TCTCGTCAGC GGGGCCCGCT TTGTCACCGT
10561 CGCCACTGCC GCCTCCGTCG CCGCAGCCCG CCACGAGGAG GCCGCCCAGC ACGGCGGCCG
10621 TCGTACCCCA CCACACACGA GAACGCATCG AAACTCTCCT GGATCCACTT GATACACGGG
10681 TTGCCCCGGA TCAGTAGTCG TGGCGGATGC GGCATCGGTT CCCGCTCGTC GGGAGCCGGC
10741 GAGAGCCATG GTCACCGCGC CGGCCCCTCG GCTCGGCCGG GGGTACAACC AGACCAGTAA
10801 GCGCGTACAG GCAGACTACG TACATGGCGT CGGTGACGCC CGGCTGATCG GGAGCGGCAG
10861 TTGATGGAGT CGACAGGAGA GATCGTGCAC CGCAATTTTC GCCTGGCTCT GGGGCGGCTG
10921 GCAGCCCTCG TCTGCGCGTC TGTCGTCGCC GTCACGGGCT GTGGCGGCGA CGACGAATCC
10981 GAGGCTCCGA AGCCGACCTC GAAGCCGACC GCCAACTCCG GGCTCGTACC TGTCGCCCAG
11041 GCCTGCGATG GCCTGTTCGA CGAGGCCATC GCGAAGGAGG CCCGGGGGCC GAACGGGCCC
11101 GGCAAGGTCT ATCCGGTCAA GACCGGGAGC ACCTCTCACG TGGCGAAGGC GCTGCGGGAG
11161 GAGTCGGCCA GGAGAAGCAC GCCCGAGGAC CTCTGCACCT TGACGGACCA GGCTGAGGGG
11221 AAGGAGCTGC TCGCCATCAC CGTGGCGTGG ACTCCCCACT CACCCCGTC GGGCCAGTCG
11281 GCGCGCTACA CGACCACCGT CGGTCCGGAA GACGCCGGCA GGCTCCTCGT CACATGTGAC
11341 ATCGGCAGCG GCGGCGGGAC GGAATCGGGA GGCGGGACGG AATCGGGAGG CGATCGTTCC
11401 CTGGAGTTCG CCATGCGCGA CTACTTCACC GTCAGCGACC ACTCCCACGC CAAGCTGCTC
11461 ATCGCCTCGG CGAAGAAGAT AACGTCGCAG TTGAAGTGCC GGGAAACTCC GAATACCCG
11521 GATCCGAAGG TTGTGGCACC GCCACCGAAG CGGGGGCTGC GGTAGCGCGG TCCTTTCACC
11581 TTGCGGCAGG TGATGGCGGT TTAATCGAGT CATGATCTAC CACGTCGTAC CGCTTGCCGA
11641 GTGGAACGCT GCTCCCGACC ACCCCTACAG CCCCGCATCC CTCACGGAGG ACGGTTTCAT
11701 CCACTGCTCT CCCGACGAGG AGACCACGCT GGCCGTCGTC AACGCCTTCT ACCGCGATGC
```

-continued

SEQUENCE ID NOS: 1-3

```
11761 GCCGAGGCCA CTGCTGGCGC TGCTCCTCGA CGAGGACCGG CTCACCGCGA GATGTGAATG

11821 GGAGGCCGCT GACCCCGCCC CGCCGCCCGG CGTCGCCGAG AACAGTCTGT TTCCCCATGT

11881 CTTCGGGCCG CTCAACCGCG ACGCGGTGGC GCGGATCCAG GAGGTCGCAT GGGACTCGGA

11941 AGGCCGGGCG GTGGGGCTGA CGGAGGTGAG CTGACGACGA GGGCCGTCAC AGTGGCGCGA

12001 GGCGGGCCTT GAGCAGGCAG AACTCGTTGC CTTCGGGATC GGCGAGGACG TGCCACTGCT

12061 CCTCCCCGGT CTGGCCGATG TCGGCCGGGC GCGCACCGAG CTTCAGGAGG CGTTCGAGCT

12121 CGGCGTCCTG ATCGCGGTCG GTGGCGTTGA CGTCGATGTG CAGCCGGGGT TTCCCGGGCT

12181 CCGGCTCGTC TCTGCGGCTG AGGATGATCG TCGGCTGCGG ACCGCCGAAC CCTTCACGCG

12241 GCCCGATCTC GAGGGTTCCG TCGTCCTCGC GATCGAGCAC CACGAAGTCC AGGACCTCGC

12301 ACCAGAACCG CGCCAGCACC TCGGGGTCGC GGCAACCGAG CACGAGTTCA CTGATACGAC

12361 ATGCCATTGA CGAAACCTAC TCTCGGCGTG GGAACTGCCG GGGGTGGCCG CACGCAGATC

12421 TCAGGGGCTC CCCGCAGTGA GGACTCTCGG GACCGTACCG GGCCAGGCGA GCAGTGGCGA

12481 ATGGATTTCA CGCCCTCGCC TGCCTGTGCG TCGTGGACGG CCGAGTACGG CCACCGCGGA

12541 GACACGCAGC CAACCCCAGC GCGCAGATCG GACTCGCCCT GCCCCTGACC GACTCGTTCA

12601 TCGCCTTGAG CGGGCCCCTG TGCGGACAGG ACTTCGTGGC GGCGGCCGCA CAGCGCAGAA

12661 GCTGGGCCTG CTCGGCTCCG ACGTCGGCGG CATCCGTGCC GCGTTCATCG ACGGCGTGGT

12721 GTAGACGTGC GCCACACGCC GTAATCGGCC GCGGTGGATC CCGGGTGTGG TGGTGGTACC

12781 GGTGACGTGA CCGAGCCTGC CCGCCGACCG GTCGCCGGAC CACCACTCCA AGGCAACTCG

12841 CCACCCAGTC GGCCCTGCTG GAACGCGGTC CGCTCCTCGA TCAGCTCGCG GACAGCGCCA

12901 CCAGGCTGAC CTCACCGGAG TCCCCTGCGT CGGCCTGGAT CGGCCTCGCC CTTTGCTTCG

12961 CGGGCGCCCT GCTCACGCCG TGCTCCAGCC GGTGGTCCGG ATCGGATGTC CTGGAATGCG

13021 AGAGGGCCCC CGGATGGTTC CGCGGGCCCT CGTGCGCCTA GGCATCGTCA GTGCGTGGCG

13081 GTCGCCACCG CCCGCCCCTC ATCGGCCGTC GCGGGCTTGG GGTTCAGCAA CCGCTCGGCA

13141 AGCTCACCGA ACAGGAGACC GAAACCACCC CACAGGACGA CCTGCATGGC CAGAGCGGAC

13201 AACCGGAACC GCCACAACAC GGTGGCGGGG AAGTCCCCCG GCACCTCGTT GACCACGGGA

13261 AGGAAGGCAT ACGCCAGCCC GACCACCACG GCGAACGCGG CCACCGCGGC CACGGTCGCG

13321 TACCAGGTGC CCAGCCTCGG GGCGAGCCGC TTGCCCACAA TGGTGACGCC CACCGCGAGG

13381 AGCACACTGA GCAGCATCAT CAGGAAATAC AGCGTCGTGC GCTTGCCGAT CGTGTCGCCG

13441 TTGCCGACCG CGGGCGGATT GGCCGGGTAC TTCAGGAACG CACCACGTA GACCGCCAGC

13501 AGCGCGCAGC CGGACAGCAG CAGCGCGGTG GCCCGCGGGG TGAAGCGGCC GACGCGGCCC

13561 AGGGCGACGC AGTACGCGAG GGCGGCGATA CCGCCGAAGG CGATCCCGTA GACCAGGACA

13621 CCGGTGGCCA GCCCGGCCGT GGACTGCACA CCACGCGAGA CCAGCTCGAC CTCGTGCTCA

13681 TGCGCGGGAG CGTGGGCCCC CTCGAAACCG ATCGCGCGGT CGACGCTCGG CTCACCGAGG

13741 AAGTAGGCGG CGACCAGGGC GAGCACGCCG GCCCCCAGAC CGGCGAGCAT GCCCCGGACG

13801 AGCAGATTTC TTACCATTGC GGAGTTCATG AGTGTGCGGC GTCCCTCGCG TCAGTGGCAG

13861 GGGAAACCGA GCAGATGACG GGCGTCATGC ACCCACTCAT GGACGTTCTC ACCGGAGACG

13921 ACCGCGGTGG CGCCCTGCTC GGCGCCGACG AAATACAGCA GGACCAGCAT CAGAATGCCG

13981 AAGAAAACCG CCCACGGAGC TATCGCCTTC AGCGGCAGCG TGGCAGGCAG TTCGGGCGTG
```

-continued

SEQUENCE ID NOS: 1-3

```
14041 GTGGCTGTGG GCTGCGCGAC ATGCTGCGCC ATGGCCAGGC CTCCTTAAGG GAGTTCGCGT
14101 CCCATCTCGG TGGAGCACAG GACGACGGCT ACGGGTCTGA CTCACGAGAG ACCCCGTCCG
14161 GGACCTCTCG CTCACAGTGG CGCGACCGTG CCGGATTCCC ACCGGCTTCC GTCTTACCGT
14221 CGTCGATATC GCACCGACCG TACCGCGTGT CGGGTTCATG GCCAAGACCA GCCACCTGGC
14281 GAGACGCTGC GCTGGGGTGC CTGAGGACGG TGCGGGAGCC GGGGCCTGCC CCCGGGCAGG
14341 CCCTAAAGTC GCGGCATGCG TCCGTCCGCC GAAAAGCGGC AGGCCCGCAC GGCGGACGCC
14401 CCCGCCGCTG CGTTGACCGG CGCATGAGCG GGTGCTCGAG ACTTCTTGCC TACGATGTGC
14461 TGATGCAGGT GATGCGCACC GGTCTTGGCT CCCTCCCGGA CGACACCCCG TGACGGACCT
14521 GATCCGCCGA GCCCTGACCG GCCGAGCCGC CCGGACCACG CCGCTGCTGG TCGTCTGCGC
14581 CCAGCTCCCG GTCACCCACT GGGCGGGCAA CCGGCTCGAT CTGCGCCGCT CGATGACCAT
14641 CGGGCTGCTT CTCATCGCCC CCGGTTTCGC GGTGGTGGCC GCCGCGCGCC CTGCCGCCTG
14701 GACGGGCACG GTCGGATCGC TGCCCGCCGC GGGCTACGTC GTGCTGCTCA CCCTCGGCCA
14761 GATGCTGGTC GTCCCGGCCG CCCGCGCCTG GGTGCCCGAC CTCGCCGAGA ACGGTCGGCT
14821 CGGCCTCTAC ACCGGCGCGC TGTCCTCCGT CTCCGGCCTG ATCGTCCTCA TCGGCAGCTC
14881 GGCCACCGGC GCCCTGCTCG ACCTGGGCCT CCCGCCCGCC GCCCCTGGC TCGTCCTCGC
14941 GGCCGTCCCG GCCCTCGCGG TGACACCGCT GCCCCGCCGT CCGAATCAGC CCAGGGTGAG
15001 CAGTTCCTCG TAGAAGCCGC CGAACTCCCG TTCCCGGTCG ACGAGGTGGA TCTCCTGGAT
15061 CCAGTGGCAG CGGCGTCCGG CCTTGTCGGT GCGCCGCAGC GGGGTGTCGT TGTCGGGCGT
15121 GATGTACGAC TCCACGCGCG CGCCGTCGAT CGTCTCGTGC GGGAACTCCC CGACCAGGTG
15181 GCCGGCGTGC CAGCCGCCCA GCTCCCATCC GGCCTCGGTG CCAGCCGCT CGACCTCGGC
15241 GTGCAACCGC TTCCCGGTGA TCTCCGGGTC GCTCTCGAAG AACCGCTTGC CTGCGTCGAA
15301 GACCTTGGGC AGATCGTCCC GCAGCCGGTG CTTGACCGGG TCATCGCCGA GGACGAAGGT
15361 CCGGCCGAAG TCGGCCTCGT ACTCTTCGAA GATCGGCCCG AGGTCGGCGA ATACGATGTC
15421 GTCCGTGCCG ATCACCCGGT CCGGCGGATT CTCCCGGTAC GGCAGGAGCG TGTTCGGCCC
15481 CGAGCGCACG ATCCGCTTGT GCCAGTGCCG GGTCGTACCG AACAGCTCGT TCGCCAGGTC
15541 CCGGATCCGG TCGCTGACCG CCCGCTCCCC CTCGCCCGGC GCCACCAGCC CGCGCCCCTC
15601 GATCTCCGCG AAGAGCCGTA CGGCCTTCGC CTGGGCATCC AGCAACCGTT CCGCGCGCGT
15661 GGGTTCGTCG TCCGCCATGG GCCCGACGGT AGGCTGCTAG ATCGTTTCCC GGCAACCGAA
15721 TTAGGCAGTC CTCAGTCGGC CCGGCCAGTC GCCGCCACCG TCACGCCCAG GCCGATCATC
15781 GCGAGGCCGC CCGCCCCGCC GACCATCGAA AGGCGGCGGT CCGAGCGGGC GAACCAGGAG
15841 CGGGCCGCCG AGGCGCCCAG GCCCCACAGG GTGTCCGTGA CCAGGCCGAT GGTGATCGGG
15901 ACCAGGCCCA ACACCATCAT CTGGACGGGA ACATGACCCA CCGAGTGGTC GACGAACTGC
15961 GGTAGCACCC CCGCGAAGAA GACGATGCCC TTCGGGTTGG TGACGCCCAC CAAAATGCCG
16021 TCCAGAATCG AACGCAGATC ACCACGCCGC TCATCGGCCG GAGCGTCCAT GTTCGCCACG
16081 CGCATCTCCC TGCGGTGCCG GAACGCCTGC ACACCCAGGT AGACGAGATA CGCCGCTCCC
16141 GCCAGCTTCA CGCCCATGAA CAGCGCCACC GAGCTCTCCA CCAGCGCGCC GAGGCCCAG
16201 GCCACGGCGA TCACCAGGGC GTAGCAGCCG ATCACATTGC CGAGGACCGT CGCGAGCGCC
16261 GTGCGGCGGC CGTGTGCGAG GGCCCTGCCG ACCACGAACA GCACACTCGG CCCCGGGATC
16321 ACGATCACCA AGAGCGACAT CGCCGCGAAC GTGAGAACAC TCTCCGTGGA CACCACGTGT
```

-continued

SEQUENCE ID NOS: 1-3

```
16381 CCGCCACCTC CTGAATCGCT CCGTCCAGGG GACATACAAG CAGATGGTGG GTTGTCCGCT

16441 CCAGACCCAG GCCCCCGGCC GGGGCTCGCA AGAAAGGGGC CCCGGCCGGC GAGCCGGCTG

16501 CTTACGACTG AGCGCTGGAC ACGGGCGCGT TGAGGTTCTC GTGGACCGCG CGGGCGATGC

16561 CCTCGATGTT GGCGATGCCG TCGTCCATCG TGGCGTTGTC CTGCGAGAGC ACCGTGATCG

16621 TGTAGTCGTG GTCGCCGCCG GTGAAGGCGC CGAGGCTGTG CACCCGCCAG CCGTTCGTGG

16681 CCCGCTCCAG CCAGCCGTTC TTCACATGCA CCTGGGCGTC GCTCGGCGCG CCGGCCGGGG

16741 TGCCCCAGCG CTGCGAGGGG ATGACCTCGG CCGTCAGCTT CAGGATGTAG GCGCGGGAGT

16801 CATCGCTGAG CACCGGGTTG GTGTGGGTCA CCAGTTGGAG GAGCTTTTCC TCATCGTTCG

16861 CGGTGATCTG GGTGAGCCCC CAGTGGCCCT CGCTGTCGAG GGTGGTGTTG GTCATTCCCG

16921 CGGCCTGCAG GAACCCGTTG ATCTTGTCCG CCCCGAGCTG CTTCCACAGC GCGGTGGTGG

16981 CGTCGTTGTC GGACTCTGTG ATCATGGCGG TGGCATGGTC CTTCTCCTCC TGTGTCAGGG

17041 CGCGATTGTC CTTCTGCGCG TCCCACAGCA GGGTGCTGAG CACGGTCACC TTGACCGTGC

17101 TCGCGGAGTC GAAGTGCCGG TCCGCATCCA GAGTGCAGGT GGTGTTCGTG GTGCGGTCGT

17161 GGAGGCTGAT CGCCGTGGTG GCGGCGGAGC CCTCCAGCGC CGAATTGATG TCCTCGGAGA

17221 GCTTGTCGGC GAGTTCCGGC CGGTCCGAGG TGCAGATCGC CGCCTGCGGG GTGGCCGCGT

17281 GAGCCGACCC CGCCGAGGCG ATCGTCGGCA CGAGCACCCC GGCGGCCAGC ACCGCTCTTG

17341 TCGCCAGGGT GGTACGGGGA GGCTGGGTTA TTCGTCGGTG TCGACCCATG GTGCGCTTGT

17401 CCATTCGTTC GTGGGGCAGT TGGACACGCG GTGCCTGCGC TCCGTTGCGA AGACATCCGG

17461 TGCTCCGACC CTGGATGACG AGCCGGAGGC GGGTGAGGTT CACGAACGCG TCCGAGTCTC

17521 ACAAGATCGC TCCACAATAG GCACCGCGCC CGGGCGGGCC GGGCGCGGTG CGGCGGACGA

17581 ACTGGGCGGC GACGGCCAGG ACGGCGAAGA ACATCGAGTG GCCCGGCTTC CACGGCCGAC

17641 CCCGGCCCGG CTTCCACGGC CGACCCGGGA CCCGGTCAGC TCTGAATGGC CGTGAGGAAG

17701 TCTCCGAGGG CTCGCGCGAC GGCGCCGGGG GCTTCCGCGG GGAGCAGGTG GCCGGCGTCC

17761 GGGACAGTCG TCAGGGTCGC GTGCGGGATG TGGGGCAAGA GGTGTTCGCG CAAGATGTGC

17821 GGCGGCTCAA CCACGTCGTT CTCCGCGGCC AGCACCGTCA CCGGGACCTC GATACGCCGT

17881 GCGGCATCGG TGATGTCCCG CGCGATTCCA CGCAGGGGCC ACTCCTGCCG GGCCTCGGCA

17941 CCGGCGGCGA GGCTGTCGCG CTCCGCGGTG GCCCGCACTG CCTCGGGCAG CGGTGTGGCG

18001 GTCAGGACGT GGTCGAGGGC GTGCCCCACC GTCTCGGCCG AGTCATAGGC GTGTGACAGG

18061 CCCTGCCGGT ATTCCTCGGT CACCATGGCG GGCGGCTGGG GCGGCGCGGG CGCGACGAGC

18121 ACCAGGCCGA CCAGGCCGGC CGGTCGGCGG GCCGCGACGA GCTGGCCCGC CTTGCCGCCC

18181 ATCGAGTGGC CGACGAGGAC GAACGCCCCC GACACGCGCT CCTCGATCAC ACGGACGAGA

18241 TCGTCGGCGA GCTGGTCGAG GTGATAGGGG CCGGGCAGCG CCCGCGAGGT GCCCCAGCCG

18301 CGCTGGTCGA AGCGGACCGT CGCCTGCCCG GCGGCAGGT GGCCGATCAC ACCGTTCCAG

18361 GTGTCGGCGG AGCCGCCCCA GTAGTGGGCG AACACCAGCG TCGGGCCCAT ATCGCCCCG

18421 ACTCGCACGT CGAGCGACCC GCCCGCCACG GGAACTCTCG TTGTCATTTC CATCATCTTC

18481 GCGCCTTCCC TGTCGGCCAC GGAAGGCGAC TCCGTCATCC TGCCGCAGCT CTGAACCAGT

18541 AACCTGACCT GCCGATCAGG CTCGGAATCG ACCGTAGGCG AGGGGGTGTC CACTCCTTGG

18601 CGGAAAGGAA CACGTTCATT GTGGAAAACG GACACAGTGC GGTGCGGCAA CTGCGCTACC
```

-continued

SEQUENCE ID NOS: 1-3

```
18661 TGCCTGCCGT GGGATCGGCG TACGGGGTGG AGGTCCTCGA TTTCGCGGCG CTGCGTTCGA
18721 TGGACACCCA GCGCCGTCGT ACCCAGCCGC AGCGCCCCGA CTTCCATGTG TTCGCGCTGG
18781 TCGGTTCCGG AACCGGCAGC CACGAAGCGG ACTTCCACAA CTACCGGCTG GGGGAAGGCG
18841 GCGCCGTGTG GATCCGGCCG GGCATGGTGC ACCGCTGGAG CGATATCGAC GCCTGCGACG
18901 GCCCGCTGAT CCTCTTCCGG CCCGGCTTCC TTTCCGGCTT CACAGCGTCG GAGGCCACCG
18961 CGCCGGCGTG CTGGCACCTG GACCGGCAGC GCCTGTCCCT CGCCCTGCTC GCGGCCGAAC
19021 ATCTCGGCCG CGAGCACAGC ACGGCAGTGC ACACACCACG CCTGGCATCC CCCGTCCTGC
19081 TGTCCCACCT GCTGGCGGCA CTGATCCTGC GCGCACTCCC CGGCACACCG CCCTCAGTCG
19141 GCCCGGCAAG CCCCGGCAGC CGACCTACCG AAGTGTTCCG CGCCTATCGG GCCGCCGTCG
19201 AAGAGCGCTT CACCGACTGG CACCATGTGG CCGACTACGC GCGGGCATTG GGCTACGACG
19261 TACGCACCCT CACCCGGACA ACGCGTGCCG CCACTGGCAC GGGCGCCAAG ACATTCCTCG
19321 ACCAGCGCAT CCTGCTGGAG GCGAAACGGC TGCTCGCCCA CACCGACCTG CCGGTCAGCG
19381 GCTGCGCCCG ACGCCTCGGC TTCCGGGACG TCGGCAACTT CACCACATTC TTCCGTCGCC
19441 AGGCCGGCCT GCCCCCCGCC GCGTGGCGCG CCGCATACAG CACCGCAGGC GCACAAGGCG
19501 GCTGACCCGC CCTCAGCGGC CGGGGGTCTG GCGAGTCACT GTCGCGGGGC AGGTTCACTG
19561 TCGCGGGGGC AGGTGCCGCA ATCCGTTCTC CAGCAGGGCG AAGGCGTGTT CCATGTCGGC
19621 CACCGCACCC GCATAGCGCT CGTCGGCCGG CTCCCCGTAC GCCAGGCGTT CGGCGTTGTC
19681 CTGCGCCAAC GCCCAGTGGA CCGCGACGAT TTGGACGGCG GCGAGCCGCG CGGTGAGTTC
19741 CGGAGTGTCC GCCGTTTCCC GCAGTGCCTC AGTCAGTGCG CGCTCGGCGC CGGTCTTGAA
19801 CCCTGCCATC CGGGCCACCA GCGAGGGCGC GTCGAGGATC ATGCGGTGGA GCCTGCGCAC
19861 TTCGGGCTGG TCGTTCAGCC CGGTGATCGG ATCCCGCTCG CGCAGCCCCT CGAGGAAGTG
19921 CTCGCGCAGT GCGGTCAGCG GGGCGGTACG GGGCGGGCGG GCCCGCACGA CGCGTGCGGA
19981 TTCGGTCTCG TGGTCGGCCA GCGGTGCAC CACGAGGTCT TCCTTCGTCG GAAGTAGGC
20041 GAAGAGGGTG CGCTTGGACA CCTCGGCCGC CTCGGCCACC TGGGCCACCG AGACCTGGTT
20101 GAAGCCGTAT TCGAGAAACA GCGAGATCGC CGCGTCGGAG ATCGCCGCGT GGGTCCGCTG
20161 CTTCTTTCGT TCCCGTAGCC CTGGCTTGCC GTCCACGGCG TCCACGGTAG CAGAAAACTG
20221 CCCCTGGTAA ATTTCTGCAC CGGGTATATA TTTACCCCGA GTGAGCCGAG TCGGAGCGTT
20281 GAGATGAGAT GGAGTGACGG TGTTGACGGA GAGCACGACC GAGGTCGTTG TCGCGGGTGC
20341 GGGCGCGACC GGACTGATGC TGGCGTACGA ACTGGCTCTG GCCGGGGTCG AGACCCTGGT
20401 GCTGGAGAAG CTGCCCCAGC GGATCCAGCA GGTGAAGGGC GGCACGATTC AGCCCCGTAC
20461 CGCCGAACTG CTGGAGTCCC GCGGCCTGCT GGAGCCGATG CTGCGGCGGG CCATTGCGCG
20521 TGATCCGGTG GGCGGCAGTT TCGGGCCCCT GCCCGTGCCC TTGGACTGCG CCCCCTGGCG
20581 GACCGAGCAC CCCTTCCCGA TCGGGATCCC TCAGTGGGAG ATCGAGGAGG TGCTCGAGGA
20641 GCGGGCGACC GCCGCCGGAG CGCGGGTGCT GCGCGGCACC GCCGTCTCAG GGGTCGCGCC
20701 GGACGACGAC GGTGTGGTCG TCACGGCGGA CGGCCTGCGG GCGCGGGCTC ACTATCTGGT
20761 GGCGTGCGAC GGCGGCCACA GTACGGTGCG CAAACTGCTC GGGCTGCCGT TTCCCGGCAG
20821 GGCCGGAACG CATCCGGCGG TGCTGGCCGA TATCCGTCTG TCCGCCGTAT CCTCACTGGT
20881 GCCGCGGCAG ATGGGACTTA TGAGCACCAT GACCCGTCAT GCGCGCGGCT ACTGGTCCAT
20941 GCTGGTCCCT CTCGGCGGCG ACCGGTACCG GTTCACCTTC GGGCACGCGG ACCAGGCGGA
```

-continued

SEQUENCE ID NOS: 1-3

```
21001 CACCGCCCGC GACACCCCCG TCACCCACGA GGAGATCGCG GCCGCGCTGC AGGCCGTGTA
21061 CGGCCCTGAG ACCACCCTCG GCGCCGTGGA CAACTCCTCG CGGTTCTCCG ACGCCACGCG
21121 ACAACTGGAG CACTACCGCA CGGGCCGTGT CCTGTTCGCC GGGGACGCCG CGCATATCCA
21181 CCCCCCGCTG GGCGCCCAGG GCCTCAACCT CGGCGTACAG GACGCGCTCA ACCTCGGGTG
21241 GAAACTGGCC GCGGTCCTCC AGGACCGGGC GCCGAACGGC TTGCTGGACA GCTACCACGC
21301 CGAACGGCAT CCGGTCGCGG CCCAGGTCCT GCATCACACC TCGGCGCAAC GCGTCCTGGC
21361 GATTTCGAAC CCGAGCGAGG ACGTGGCCGC CCTGCGCGAC ATCTTCACCG ACCTGCTGCG
21421 GCTGCCCGAC ACCAACCGCC ATCTCGCGGG GCTGATGTCC GGCCTCTCGC TGCGCTACGA
21481 CCTGCCCGGC GATCACCCGC TCACCGGAGA GCGCATCCCG GACGCCGATC TGGTGACCGA
21541 AACCGGCACC ACCCGGCTGT CGACGCTCTT CGGCTCCGGA CACGCCGTCC TGCTCGACCT
21601 GGCCGGAGCC GTCCCGGCCG ACCTCCCGCT CCCGCCACGA GTCGACCTCG TCCGCGCCAC
21661 ATGCGCCGAC GACATGGGCG CCGCCGCCCT GCTCATCCGT CCCGACGGCT ATGTCTGCTG
21721 GGCTACGGAC ACCTCCGCCG CCTGCGGCGA CACCCTGCTG GCCGCGCTCA CCGGCGACCT
21781 CGCGAGGGTG CCCTGAGCCA GGTGACAATG CGCTGAGCCG GGTGACAAAG AGGACGCCTA
21841 CGCGAAGGCC CTCAGGGTGT CCTCGCCGTC GGTCCACCAG ACGCCGAGCC GTTGGCGGAC
21901 CAGGAGCCAG CCGTCCGGGC CCCGGCGGAA TTCCCAGTCG TAGGGGCCGC CCATGGAGTA
21961 GGGAGAGGAG GTGCTCCCGG GTGCGGTGAC GGCCACGAAC CACATGTAGC CGATCCCCGT
22021 CGCCCGGTCG CCCTCCACGT CGACGTGCAT GTTGAGGATG TGATGCTGCA TGCTCGCGTA
22081 CGGTGATTCC ACCTCCTCCA CCTTGGCCCG GACCGCCTCT TTTCCGTGGA TCTTCTCCCA
22141 CGGCCCGAAC TCCAGCACCG CGTCCTCGGC CCAGCATTCG ATCCAGGTCT GCCAGTCCTT
22201 GCGGTCCAGC GCACGCCATC CGCGGATCAT GAGGGCGCGC AGGGCTTCCT TGTCCTCCAG
22261 GGCGCGCAGC CGGCGGGCCA GGCTGTCGTA GTCGGCTGTC GCTGTCATGA CGGGCCTCTT
22321 TCGTCCATGG GTGGGGATCT GTCCTGCCCG ACCGAGTCTG GACCGGTCGA AGACCGCCGA
22381 CCAGGCCGAA CGCCGCCTAG GAGCACCGCA CCCAGGCGGC ACACCGGCGG ACTCATGGAG
22441 GGCAGTTGGG CAACGGCCAG GGGTGAGCCG ACCCCGGCCA TGTCTCCAGC AGGTCGGGGG
22501 GAAGATCTCC TCGCTCGTCC AGCGGTGTGT GGTCAGGCCC TGCTCGTGGT GGTAGCGATC
22561 CCGGTGCGCC GGCCTGGGTC GTGTCGTACC GGAACCGTGT GCCCGATCCA CCGTAAATCC
22621 GCCGGACGAG GCGACGTGGC CGCCGCACGC CATCGGGCGG CCGGAGCGGC CGAAGACCCC
22681 TTGTTCCCGC TGTCAGCCGC TGCCGCCGCC GTGGTCAGGG GAATGAGGG GGATGTTTAG
22741 GGGACGGCCC GCTCGCTGCC GGAACAAGAA TCACAACAAC AGCAGCGAGC TTTCTCAAGC
22801 TCGTTCGAGC TTTCTCTCCC GGGCCTTCTT TCCCTTGGGC CGCGCAACCG GAGCGCGGCT
22861 GTCCCGCGCA AGGGCGATC CCGCGCGGGT CGGTCGCTCC TCCCGCGCGC CCTGCTTCGA
22921 ACCGAGAGGT GTGGCGGCAT GCTACGGACT GACCTGATCC GGCCGGTGCC CGAACTGCTC
22981 CGGGCCAACG CGGATCGCTT CGGTGACAAG CCGGCCTGTT CCGACGGACA CCGCACGGTC
23041 AGCCATGCCG AACTCGAACG CCGTACCCGG CGGCTGGCCG GTCATCTCGC CGGGCTGCGG
23101 CTGCACCCCG GCGACCGCGC CATGATCTGC CTGGGCAACC GCGTCGAGAT GGTGGAGAGT
23161 TACTTCGGCG TCCTGCGGGC GAACGGCGTG GCGGTGCCGG TCAACCCGCG TTCGACCGAT
23221 GCGGAACTCT CCTATCTGCT CGCCGACAGC GGCGCCCGGC TGGTGCTCAC CGATGTCGCC
```

-continued

SEQUENCE ID NOS: 1-3

```
23281 CACGCCGACC AGTTCGGCCG GCTGCGGGAA CAGTTCCCGG AGCTGAGGGT GGTGGTCAGC
23341 GGGGACGGCC CGCTGCCGAA GGGCTTCATC GCGTTCGAGC CGCTGCCGGA CACGGAGCCG
23401 CAGCTGGCAG CCCGCGACGA CCTGGGCCTG GACGAAATCA CCTGGATGCT CTACACCTCG
23461 GGCACCACGG GCCTGCCGAA AGGCGTGCTG TCCACACAGC GGAACTGCCT GTGGTCCCTG
23521 GCCGCCTGCT ACGTGCCGGT GACGGGGCTG ACCGCCGAGG ACCGCGTGCT GTGGCCGCTG
23581 CCGCTGTTCC ACAGCCTTTC GCACATCGTG TGTCTGCTGG CGGCCACCGC CGTCGGGGCC
23641 AGCACCCGGA TCGTGGACGG GGTGTCGACG GCCGATGTGC TGGACGCACT GCGCGAGGAG
23701 CGGTCGACCT TCATCGCCGG AGTGCCGACG CTCTACCACC ACCTGATCGA GGCGGCCCGC
23761 GAGCGCGACT TCGCCACGCC CGAGCTGCGG ATCGCGCTCG TGGGCGGGGC GGTGGCCACG
23821 GCGGACCTGG TCAGGTCGTT CGAGTCCGCC TTCGGAGTGC CACTCGTCGA CGCCTACGGC
23881 TCCACCGAGA CCTGTGGCGC GATCGCGGTG AACTGGCCAA CCGGCCCGCG GGTCGAGGGG
23941 TCGTGCGGGC TGCCGGTGCC GGGGCTGACG GTGCGGCTGG TGGACCCGGA CACCGGTGTC
24001 GACGTTCCGG CCGGGCGGGA AGGCGAGTTC TGGGTGTCCG GGCCGAACAT CATGGCCGGG
24061 TACCACAACC AGCCGGAGGC GACGGCCTCG GCGCTGCGCG ACGGCTGGTA CCGCACCGGG
24121 GACCTCGGCC GCCGCGACGA GGCCGGATTC TGCACGGTGA CCGGCCGGAT CAAGGAACTC
24181 GTCATCCGGG CCGGGGAGAA CATCCACCCC GGTGAGGTCG AGGCCGTGCT GCGCACCGTG
24241 CCCGGTGTGG CGGACGCGGC CGTGGTGGGC AAGCCGCATG CGGTGCTCGG CGAGGTTCCG
24301 GTGGCCTTCG TGGTGCCCGG CCCGGACGGC TTCGACCCGT CGGCGCTGCT GGCCACGTGT
24361 CGCGAGCGGC TGTCGTACTT CAAGGTCCCG GAGGAGATCT ACGAGATCGC GCGGGTGCCA
24421 CGCACCGCCT CGGGGAAGAT CACCCGGCAC GTACTGCTGG AGCTGCCCGC ACGGCTGCGG
24481 GCCGCCGGAG ACGGCCAGTA CGACTCGCTG CTGCGGCTGG ATTGGGTGCC GCAGTCCGCG
24541 CTGCCGGACG CCCCGGCCGG GACCGGTACC TGGGCACTGG CGGACGCCGA CGCGCTCGGG
24601 CTCGCGGTGG GGCTGCGGGC GGCCGGAGTG GACGCGCGGG TGGTGGGCGA GCCGGTGGGC
24661 GAGCCGGTGG CCGACTCCGT GGCCGGTCTT GTGGCAGGCT CCGTGGCCGA TCTCGCTGGA
24721 GATGACGGTG CGGCCCCGGA TGTGGTCGTG GTGACGCCTC CGGTGGCGGG CCTCCCGGAT
24781 GAGACCGGGG CCCCTGACGA GGCCGGGGTC ACGGTTGGCG AGCGCGCCGA CCGGCTGGCG
24841 GCCCGCCTTG GCGCCTGGCT GGCCGACGAC CGGCTGGCCG GACGACGTT CGTGGTGGCC
24901 ACCACGGGCG CGGTGGCCAC CGGCGCCGAG GAGGACGCAC CGGAGCCGCT GTCGGCCGCG
24961 CTGTGGGGTG TGGTGCGCTC GCTGCAGGCC GCCTACCCCG GCCGACTGAC GCTGGTGGAC
25021 GTGGACCTGG ACGGGGCCGG GGACAGGGCC GGGGACGGGG CCGGGGAGGA CGGTCGGGAG
25081 GCCGCGCTGT TGCGGGCCGT CCAGGGCGGG CACGACCAGG CGGCGATCCG TGGCGGAGTA
25141 CTGCTGGTCC CGCGCCTGAC CCGGATCTCG TTCCCCGCGG AGCCGGGGCC CGCCCCAACC
25201 CTGGACGCGG GCGGACTGGT CGTGATCACC GGTGGCGACA CCACCCGCGG CACCGCGCTG
25261 GCCCGCCATC TGGTGACCGT GTACGCGCCC CGTAACCTGC TGCTGCTCAG CGCGAATGGC
25321 CTGCCGGAAG AGGCGGCGGC CACGTTGCGG ACCGAGTTGG CGCGGACGG GGCCCAGGTC
25381 TCGATGGCCG TATGCGACCC GGCCGACCGG ACGGCGCTGG ACTCGGTGCT GGACGCACAG
25441 GCCCGGCCGG TGACCGCTGC CGTACACATC GAGGAGCCGA GCCCGGAACG GTCGCTCGAC
25501 ACGTCGCTGC GCGCCATGAC ACACCTGGAA GAACGGACCC GGGGGGCCGC CCCGGCACTG
25561 TTCGTCGTCG TCACCTCCGC CGCCGGGGTG CTGGGCTCGC CTGGCCGCCC GGACCGGGCG
```

-continued

SEQUENCE ID NOS: 1-3

```
25621 GCCGCCGACC AGTTCGGCGA AGCCCTGGTG CGGCGGCGCC GGGCGCTTGG CCTTGGCGGG
25681 CTGGCTCTGG CCTGGGGCCC GCTGCCGGGC GAGCATGGCA CGGCGCCGGT GGCCGGTGCC
25741 GTTCCCCTGC CCGAGGCGCT GGCCCTGTTC GACGCGGCGC TGACGGCTGG TCAGGGGCCG
25801 CTCGTGCTGC TCAGGCCGAG CACGACGGGG CTGCCGGGTG GCGAGCCGGT GCCCGCGGTG
25861 CTGCGTCATC TGGTGGACGC GCCGTCCGGC GTACCGGCGT CGGACGAACC CGCCGTCGCG
25921 GAGTTCCGGC GGCGGCTGGC CGCCGAGAGC GAGTCCGGCC GACAGCGCAT GGCGCTGGCG
25981 CTGGTGCGCG AGCACGCCGC GGCGACGTTG GGGCTGGCCT CGGCCGACCC GGTCGAGGCC
26041 GGCCAGGCAT TCAGCGCGTT CGGCTTCACC TCACTGACCG CGGTCGCGTT GAGGAACCGG
26101 CTGAACGCGG CCACCGGGGC ACGGCTCGCC GCCACGGTGG TCTTCGACCA TCCGACCCCT
26161 GCCGGGCTGG CGCGGCATCT GGTGCGGGAG ATCACCGGGA GGCGCGGCGT GCAGGCGCCG
26221 GTGCGAGCGC GCGGCGTGTC CGACGAGCCG GTGGCGATCG TGGCGATGGG CTGCCACCTG
26281 CCGGGCGAGG TCGCGACGCC CGAGGACCTG TGGCGGTTGG TGGCCGACGG GCGGGACGCG
26341 ATCGCCGGGT TCCCGGAGGA CCGGGCTGG GACCTGGCCG GGCTCTTCGA CTCCGACCCG
26401 GACGCCGTGG GCAAGTCCTA TGTGCGCGAG GGCGGTTTCC TCACCGACGC GGGCGGATTC
26461 GACGCCGCAT TCTTCGGCAT CTCGCCCCGT GAGGCGCTGG CGATGGACCC GCAGCAGCGG
26521 TTGCTGCTGG AGACCGCGTG GGAGACCTTC GAGAATGCCG GAATCGACCC GGGTTCGCTG
26581 CACGGCACCG ACGTCGGTGT GTTCAGCGGA GTGATGTACC ACGATTACGG GGCCGACGCC
26641 GGGACGGCGG CGGAGGGCCT GGAGGGGCAT CTCGGCGTGG GCAGCGCGGG GAGCGTCGTC
26701 TCCGGGCGGG TGGCCTACGC GCTGGGCCTG ACCGGGCCCG CGGTGACCGT GGACACCGCC
26761 TGCTCGTCCT CCCTGGTAGC GCTGCACCTG GCGGTTCAGG CGGTGCGCAC GGGCGAATGC
26821 TCGCTGGCGC TCGCCGGGGG TGTCGCGGTG ATGAGCAGGC CGACGTCGTT CATCGAGTTC
26881 TCCCGCCAGC GTGGCCTCGC CCCCGACGGC CGCTGCAAGT CCTTCGCGGA GGGCGCCGAC
26941 GGCACCAACT GGTCCGAGGG TGTCGGGTTG GTGTTGCTGG AGCGGCTGTC CGATGCCCGC
27001 CGCAATGGGC ATGAGGTGCT CGCCGTCGTC CGTGGCACCG CCGTGAACCA GGACGGCGCC
27061 AGCAACGGCC TGACCGCGCC CAACGGCCCC TCCCAGGAAC GGGTGATCCG GCAGGCGCTG
27121 GCGAACGCCG GGCTGACGGT GGCCGATGTG GACGCGGTCG AGGCCCACGG CACGGGCACG
27181 AGTCTCGGCG ACCCGATCGA GGCCCAGGCA CTCCTGGCCA CCTACGGGCA GGAGCGGCCG
27241 GAGGATCAGC CGCTGTGGCT GGGGTCGTTG AAGTCGAACA TCGGGCATGC GCAGGCGGCG
27301 GCGGGCGCGG CCGGTGTCAT CAAGATGGTC CAGGCCATGC GGCACGGCGT ACTGCCCAAA
27361 ACCCTCCACG CCGACGAGCC CACCAGCAAG GTCGACTGGA CGTCAGGTGC GGTGTCGCTA
27421 CTGTCCGAGG CCCGCCCTG GCCGGAGACG GGACACCCCC GCCGCGCCGG AATCTCCTCC
27481 TTCGGCGTCA GCGGGACGAA CGCACACGTG GTCCTGGAAC AGGCACCCCT GGAAGCGGCT
27541 GCACCCGAAA CACAGGCGAG CGACGCGGGC GCTCCTGGGC TCGTGGCCAC GGGCGGCGTA
27601 GTGCCGTGGG TGCTGTCCGC CAAGACTCCT GCGGCGCTGC GCGCTCAGGC AGAGCGTCTG
27661 GTCAGCCATC TGGAGTCCGG GAGCGACGCC AACCCGGTCG ATGTGGGCTG GTCGCTGGCC
27721 ACCACCCGGG CGGCGTTGGA GCACCGCGCG GTCATCCTGG CGACGGATGC CGAAGGAGGC
27781 ATGGCGACGG CGCGGGCTCT GGCGGAGGGG CGGCCTGACC CGCTCCTGGT CACCGGACAG
27841 ACCGGAACAG ACGGCAAAAC CGTGTTCATC TTCCCCGGCC AAGGCGCCCA ATGGGTGGGC
```

-continued

SEQUENCE ID NOS: 1-3

```
27901 ATGGGAGCCC AACTCCTCAA CACCTCACCC GTCTTCGCCG CCCGCCTGCG TGAGTGCGCC
27961 GATGCTCTAG CGCCGTATAC CGACTGGTCG CTCATCGACG TCATCACCGG CACGCCCGAC
28021 GCTCCCTCGC TTGAGCGTGT CGACGTCGTA CAGCCCGCCA CCTTCGCCGT CGTCGTCTCC
28081 CTCGCCGCAC TCTGGCAATC CGTGGGCATC CACCCCGACG CCGTCATCGG CCACTCCCAA
28141 GGCGAAATCG CCGCCGCCTG CGTCGCCGGA CACCTCACCC TCACCAACGC CGCCAAAATC
28201 GTCACCCTCC GCAGCCAGAC CATCGCCCAC CACCTCGCCG GACACGGCGG CATGATGTCC
28261 CTCGCCACCC CCGCCGACAC CATCGACCTC ACCAACTGGC ACGGCAAACT CTGGATCGCC
28321 GCACACAACA GCCCCAACGC CACCGTCATC GCAGGCGACA CCGACGCCCT GCACCAACTC
28381 CACACCCACT ACACCGACCA GGGCACCAGA GCCCGCATCA TCCCCGTCGA CTACGCCTCC
28441 CACACCGGAC ACGTCGACAC CATCAAAAAC CAGCTACAAG ACGTACTCGA CGGCATCACC
28501 CTCGAACCCG GCACCATCCC CTGGCTCTCC ACCGTCACCG GACAGTGGAT CGAACCCAAC
28561 ACCGTCGGCG ACAGCTACTG GTACCGCAAC CTCCGCCAAA CCGTGCAATT CGAGCACACC
28621 ATCCACACCC TCGCCGACCA GGGCTACCGC ACCTACATCG AAATCAGCCC CCACCCCGTC
28681 CTCACCACCG CCATCCAAGA AACCCTCGAA GCCAACGACA CCCCCAACAC CACCATCGTC
28741 ACCGGCACCC TCCGCCGCGA CGACGACACC CCCACCCGCC TCCTCACCAA CCTCGCCCAC
28801 CTCACCACCA ACGGAACACC AGTCAACTGG CCCACCCTCT TCACAGGCAC CCAACCCACC
28861 CGCATCCCCC TCCCCACCTA CCCCTTCCAA CACCACCACT ACTGGCTCCC CCGCAACACC
28921 AGCGCAGGCG ATGTGAGTGC CGTGGGCCTC CAGGGCACGG GCCACCCGCT GGCCGGGGCC
28981 GTGGTGAGCG TGCCCGACAC CGGGGGTGTG CTGCTCACCG GGCAGTTGTC GGTGGCCACC
29041 CACCCGTGGC TGGCCGACCA CGCCGTCTCC GGAACGGTGC TGCTGCCGGG CACCGCGATG
29101 GCCGAACTCG CCATCCGCGC CGGAGACGAG ACCGACACCC CCACCCTGGA AGAGCTGGTC
29161 ATCGGCCAGC CGATGACACT GCCCGAAGAC GGTGCACTAC ATGTCCAGGT ACTGGTCGGC
29221 GGCGTGGAGG ACGGGCGCCG AGGGGTGCGG ATCTACTCTC GCCCCGACGC GGCCCAGGAA
29281 CAGGAATGGC TGGAGCACGC CTCGGGCACA CTCGCCACGC AGCCGGACGG TTCGGCCGAG
29341 GGCGGCATGG AGAACGGCAT GCCCGAGTGG CCGCCGCCCG GTGTCGAGCC GATCGCTCTG
29401 GATGACTTCT ACGACGACCT CGCCCAGGCC GGGTATGAGT ACGGGCCCGC CTTCCGCGGG
29461 CTGAAGGCGG TCTGGAAGCG CGATGGCGAG GTGTTCGCGG AGGCCGCGCT GCCGGAGGAG
29521 CAGACGGACG TCGCCGGCCG GTTCGGTATC CATCCGGCGC TGCTGGACGC CGCGTTGCAC
29581 GCGAGCAACT TCTGTGTGCC CCCGGCCCCG GGCCAAACGC TCCTCCCCTT CGTGTGGAAC
29641 GGCGTACGGC TGCTGGCGGC GGGAGCCACG GCCGTCCGTG TGCGCGCCCG CGCCACCGGC
29701 ACGGACTCGT TCACGATCAG CCTGTTCGAC AGCACCGGCT CCCCCGTCGC CTCGGTGGAC
29761 TCCCTGGTGC TCCGGGCGAT CAGTCCCGAG CAGCTCGCTG CCGCCTCCGG CGGTGCCGGT
29821 CGGTCCGCTG ATGCGCTGTT CACGCTGGAC TGGACCGAGC ACCCCACCGC CCTGGGGACC
29881 GAGGTTTCCT GGGCCACCCT CGGCGATGCC CACACCGACG TGGACGCCCA CGTGGACGCG
29941 CTCATCGCGG GAGAGGACCG GCCCGGGGCC GTGGTCGCCG ACACCGCGGC CTGGGCCGCC
30001 GGGGACACCG GCCTGCCCGC GCGGGCCCGG GATCTGGCCG CCCGCGCGCT GGACCTGGTG
30061 CAGCGGTGGG TCGGCCGACC CGAACTCGCC GACGTCCGGC TCGTGTTGCT CACTCGTGGG
30121 GCGGTGTCCG TGCACGACAC CGCCGAGGTC ACCGACCCGG CCGCCGCCGC GATCTGGGGC
30181 CTGGTCCGCT CCGCCCAGTC CGAACACCCG GGCCGGATCG CCCTGGTGGA CACCGACGAC
```

-continued

SEQUENCE ID NOS: 1-3

```
30241 GTGTCGCGGG AGGCGCTGCC CGAGGCGGTG GCGGCCGGCG AGCCGCAAGT GGCGCTGCGC
30301 CGTGGGCTGC TGTGGGTGCC TCGTCTGGTG CGGTCGCCGC AGGGTCTCGC CGTACCCGCG
30361 CACGAGCACT GGTACCTCGA CGTCTCGGAG AAGGGCAGCC TGGAGAACCT GGTGCTGCGG
30421 CCGGATCCGG AGGCCACCGC GCCGCTGGCC ACCGGTCAGG TCCGGATCGA GGTCCGCGCC
30481 GCCGGTCAGA ACTTCCGGGA CGTACTCGTC GCGCTCGGCG GCGTGGCGGG TCAGGAGGGT
30541 CTGGGCGGCG AGGGTGCCGG GGTGGTGACC GAGGTCGGGC CGGGGTCGA GGGCCTGGCG
30601 GTGGGCGACC GGGTGATGGG CCTGTTCCCG CGCTCGTTCG GCCCGCTGGC CATCGCGGAC
30661 GCGCGCACGG TCGCGCCGAT CCCCGAGGGC TGGTCGTACG CCACGGCCGC CGGGGTGCCG
30721 GTGGCCTATC TGACGGCACT GTACGGGCTG CGGGACCTGG GCACCGTACA GCCGGGTGAG
30781 ACGGTGCTGG TGCACGCCGC CGCGGGCGGT GTGGGCATGG CCGCCGTCCA GTTGGCGCGG
30841 CACTTCGGCG CCACCGTGTA CGCCACCGCC CACCCGTCGA AGCACCATGT GCTGACCGCG
30901 CTGGGGGTGC CGGAGGGGCA TCTGGCGTCC AGCCGCGACC TCGGTTTCGC CTCGGCGTTT
30961 CCCGCGCTGG ATGTGGTGCT GAACTCCCTC ACCGGCGAGT ATGTGGACGC CTCGCTGGGG
31021 CTGCTCGGCA CGGGTGGCCG TTTCGTGGAG ATGGGCAAGA ACGACATCCG CGATCCCGCC
31081 TCGGTCGCCG CAGCACATCC CGGTGTGGGC TATCAGGCGT TCGACCTGGG AGGTGACGCG
31141 GGCCCTGACC GGATCCGGGA GCTGCTCGCG GAGCTGGTGG AACTGTTCGA GGCGGGCCGG
31201 ATCGAGCCGC TTCCGATACG GCACTGGGAC GTCACCCAGG CGCCGACGGC CTTCCGGTGG
31261 ATGAGCCAGG GGCGGCACAC CGGCAAGATC GTGCTCACCC TCCCCCGAGC CCTGGACCCG
31321 GACGGCACCG TCCTGATCAC CGGTGGCACC GGAACCCTCG GCGCCACCAT CGCCCGCCAC
31381 GTCGTCACCC ACCACGGCGC GCGCCAGTTG CTCCTCATCA GCCGTCAGGG TCCCGACGCC
31441 CCCGGCGCCA CCGATCTCAC CACCGAACTC ACCGAACTCG GCGCCACCGT CCGCATCACC
31501 GCCTGCGACA CCGCCGACCG CGACCAACTC GCCGCGCTCC TCGCCGACAT CCCCGCCGCC
31561 CACCCCCTCA CCGCCGTCAT CCACACCGCC GGCGCCCTGG ACGACGGTGT CCTGACCGCG
31621 CTCACCCCGG ACCGCCTCGA CACCGTCTTC CGCCCCAAGG TCGACGCCGT CACCCACCTC
31681 CACGACCTCA CCCGCGACCA GGACCTGGCC GCGTTCGTCA TCTACTCGTC CGCCGCCGGA
31741 ACGCTCGGCA ACGCGGGCA GGCCAACTAC GCCGCCGCCA ATGCCTTCCT CGACGCCTTC
31801 GCCCAGTGCC GGCACGCCCG CCACCGGCCC GCCACTTCGC TGGCGTGGGG GCTGTGGAGC
31861 GACACCAGCA CGCTCACCTC GACGATGGAC GCCACCGACG TACGCCGCAC ACGGCGGGCG
31921 GGGGTGCTGG GCATGGACAA CGCCGAGGCG CTGCGGGTGT CGACACCGG GTTGCGGTCC
31981 GGGCGGCCCG CGCTGGTGGC CGCGAAGATC GACCTCACCG CCCTGCGCGC GCCGGACGCC
32041 GAGTTGTCGC CGCTGCTGCG CGGACTGGCC CGTCCGGCGC GCCGCACCGC GCGCACCGCG
32101 GCCCCGGCGG CCGGTGGTCT GTCGGGGCAG CTGGCCGGGC TGTCCCCCGC CGGGCAGCGG
32161 GAGTTCCTGC TCAACCTGGT GCGGGCGGAG GCCGCGGTGG TCCTCGCCCA CGCCGGTCCT
32221 GAGGCGATCG AGCCGACCGT GGCGTTCAAG GAGATGGGTT TCGACTCGCT GACGGCGGTC
32281 GAACTGCGCA ACCGGCTGAA TGCGGCGACC GGGCTGCGGC TCCCCGCCAC GTTGCTCTTC
32341 GACCACCCGA CTCCGGCTCT TCTCACCGAG CTGTTCCATA CCGAGTTGGG CGGCGGCCCG
32401 GCACCCGCCG CGGCGGCCCC GGTGACCGTG CGTGCCGCCG CTGACGAGCC GATCGCCGTG
32461 GTGGCGATGA GCTGCCGTCT GCCGGGCGGG GTGACCGACC CGGACGGGCT GTGGAACCTG
```

-continued

SEQUENCE ID NOS: 1-3

```
32521 CTGCTCGAAG AGCGCGACGG CATCGCCGAC TTCCCCCGCG ACCGGGGCTG GGACTTGGAG
32581 GCGCTGTTCG ACGCCGACCC GGACCGGAGT GGCACCTCCT ATGTGCTGCG CGGCGGGTTC
32641 CTCGAGGACG CGGCCGGTTT CGACGCGGAC TTCTTCGGCA TCTCGCCACG TGAGGCGCTG
32701 GCGATGGACC CGCAGCAACG GCTGTTCCTG AAGCCTGCT GGGAGGTGTT CGAGCGGGCG
32761 GGCATGGACC CGACGACGGT GGGTGGCGGC GACATCGGCG TGTTCGCCGG CGTCATCAAC
32821 CAGGACTACG GCGTGCGGAG CGGGCCCGCT CCCGAGGACC TTGAGGGCTA TATGCTCACC
32881 GGCTCGGCGA CGAGTGTCGC CTCCGGCCGG GTGGCCTATG TGCTGGGCCT GGAGGGCCCG
32941 GCGGTGACGG TGGACACGGC GTGCTCCTCC TCACTGGTGG CCATGCACTG GGCCGTACAG
33001 GCGCTGCGCC AGGGCGAGTG CTCGATGGCA CTGGCCGGGG GTGCCACGGT GATGGGGCGG
33061 CCGTCGGCGT TCGTGGAGTT CTCGCGCCAG CGTGGCCTGG CGCCGGACGG CCTGTGCAAG
33121 GCGTTCGGCG CGGGTGCCGA CGGCACCACC TTCAGCGAGG GTGTCGGGGT ACTGCTGCTG
33181 GAACGGCTCT CCGACGCCCG CCGCAACGGC CACGAGGTGC TGGCCGTGAT CCGCGGTACG
33241 GCGGTCAACC AGGACGGCGC CAGCAACGGC CTCACCGCCC CAACGGCCC CTCCCAACAG
33301 CGGGTGATCC GGCAAGCACT CGCGAACGCC GGGCTGTCGG CCACCGACAT CGACGCCGTC
33361 GAAGCCCACG GCACCGGCAC CGCCCTCGGC GACCCCATCG AAGCCCAGGC ACTCCTGGCC
33421 ACCTACGGCC AGGACCGGCC GGGAGACGAG CCCGTATGGC TCGGCTCGCT GAAGTCGAAC
33481 ACCGGGCACA CGCTGGCCGC GGCAGGCGTG TCCAGCGTCA TCAAGATGGT GCTGGCGATG
33541 CGGCACGGCA CGCTTCCGCG CTCCCTGTAC GCCGACGAGC CCACGCCGGA AGTGGATTGG
33601 TCCCAGGGCG CGGTGTCCCT GCTCACGGAG GCCCGGCCCT GGCCGGAGAC GAGCCACCCA
33661 CGCCGCGCCG GGATCTCCTC CTTCGGCATC AGCGGCACCA ACGCCCACCT CATCCTGGAG
33721 CAGGCGCCCC AGTCCGAGAC CGAGCCCGAA GCCGCGCCGA AGGCGGACGG CGGCATGGAC
33781 ACCCCAGGGC TCGTGGCGAC CGGCGGGAGC GTGCCCTGGG TGCTGTCCGC CAAGACCCCC
33841 ACGGCCCTGC GGGCTCAGGC TCAACGACTC CTGGACCACC TGGAATCCGG GGTGACCGAC
33901 CGCCCCCTCG ACATCGGCTG GTCCCTGGCC ACCACCCGCA CCCTCCACGA CCACCGCGCC
33961 ATCATCCTCA CCGACACCGA GGGCGGTGAC GCCACAGCCG CCCTCACCGC CCTCGCGACC
34021 GGACAACCCC ACCCCCGCCT CACCACCGGC CACGCCACCA CCCACGGCAA GACCGTCTTC
34081 GTCTTCCCCG GCCAAGGCGC CCAATGGCAA GGCATGGGAG CCCAACTCCT CGACACCTCA
34141 CCCGTCTTCG CCACCCGCCT CCACGAATGC GCCGACGCCC TCGCCCCCTA CACCGACTGG
34201 AACCTCATCG ACGTCATCAC CGGCGCACCC CACGCCCCTT CGCTCGACCG CGTCGATGTC
34261 CTGCAGCCGA CCACCTTCGC CATCATGGTC TCCCTCGCCG CACTCTGGCA GGCCAACGGC
34321 ATCCACCCCG ACGCCGTCAT CGGCCACTCC CAAGGCGAAA TCGCCGCCGC CCACATCGCC
34381 GGACACCTCA CCCTCACCGA CGCCGCCAAA TCGTGGCCC TGCGCAGCCA GACCATCGCC
34441 CACCACCTCA CCGGACACGG CGCCATGATG TCCGTCCTCG CCTCCCACAC CTGGGTTCAA
34501 GAAGCACTGG CTCCCTGGCA CGGACACCTG TGGATCGCAG CCGTCAACGG CCCCGCCTCC
34561 GTATCCGTCT CCGGAGACCC CGACGCACTC GCCGAATTCG GTGTCACCCT CTCCAAGGCG
34621 AAGGTCTACC GCTGGCAGTT GCCGGGGGTG GACTTCGCCG ACACTCCGG ACACGTCGAC
34681 ACCATCAAAG ACCAGCTACA CCACGTACTC GACGGCGTCA CCGCCTCCCC CGGCACCGTG
34741 GCCTGGATGT CCACCGTCGA CGCCGACTGG GCCAACCCCA CACACATCGA CGCCCACTAC
34801 TGGTACCGCA ACCTCCGCGA CACCGTCCGC TTCGAAGAAG CCACCCGAGC CCTCCTCACC
```

-continued

SEQUENCE ID NOS: 1-3

```
34861 CACGGCCACC GCGTCTTCAT CGAAATCAGC ACCCACCCCG TCCTGACCAC CGCCATCCAG

34921 GACACCACCG AAACCCTCCC CGAGGTCCGG GCCACCATCA CCGGCACCCT CCGCCGCGAC

34981 GACGGTGGCC CCGACCGCGT CCTCACGAGC CTCGCGGAGC TCTCCACCGC CGGAATTCCG

35041 GTCCACTGGC CCACCGCGTA CGCCGGAACC ACACCCTCCC AAGTCCCCCT GCCCACCTAC

35101 CCCTTCCAGC ACCAGCACTA CTGGCTGGCC GCCACCGGCC ACCACGGGGA TGTCGGCTCC

35161 GTGGGACTGC GCGACGCGGC GCACCCGCTG CTGGGGCCG TGGTCAGCGT GCCGGACACC

35221 GGAGGGGTGC TGCTCACCGG GCGGCTGGCA CCGTCGGCGC AGTCCTGGCT GGCCGACCAC

35281 ATGCTGTCCG GCGTCGCCCT GGTGCCGGGT ACGGCGATCG TGGAACTGGC CGTACGGGCC

35341 GGGGACGAGA CGGGCACGCC GGTGCTGGAG GAGCTGGTCC TCGGCCAGCC GATGCTTCTC

35401 CCCGAGGACG GCTCGCTTCA GGTGCAGGTC CTGGTCGGCG CTGCCGAGGA CGACGAGCGC

35461 CGTGCGGTGC GTGTCTACTC CCCGCGGCGAC GAGTCCGAGC CGTGGGTCGA GCACGCGTCC

35521 GGCATCCTGT CCGCGCACGC GCTCGTTCCT GTCGAGGCAG AGCGGCAGTG GCCGCCCACC

35581 GGGGCGGAGC CCGTTGTCCT GGAGGGCTTC TACGACCGCC TGGCCCAGGC AGGCTATGAG

35641 TACGGTCCGG TGTTCCGCGG GCTCACCGCA GCGTGGACCC GCGGCGATGA TGTGTTCGCC

35701 GAGATCACCC TCGGCGAGGA CCAGCACGAC CTCGCGGGCC GCTTCGGGAT CCATCCGGCG

35761 TTGCTGGACG CGGCACTGCA CGCGAGCAAC TTCTGCCCGG GCAACGAGCC CGGCGGCGGG

35821 ACGTATCTGC CGTTCTCCTG GAACGGCGTG CAGTTGCACG CCGACGGCGC CACCGCCCTG

35881 CGGGTGCGGG TCACCTCCAC CGGGCCGGAC AATCTGTCCC TGCACGCGAC CGATCCGCAC

35941 GGGGTGCCCG TGGTGACCGT CGGCTCGCTG GTGCTCAGGG AGACCACCGC GGAGCAGCTC

36001 CGCACCACAT CGGCCACGTC CGCCGCGGAC TCCCAGTTCA CCGTGGAGTG GACCGAACAT

36061 CCCCTGGCCC GGGACGAGGT GGCGTGGGCG GCGCTGGAGG CCGTGCAGGA CGACGATACG

36121 TGGCCGCCGG TGGTCGTCGC CGACACCCGG GCGTTCGCCG CGCAGGGCGG CGGACTGCCG

36181 GACGAGGGCG GACTGCAGGA GGACGGCGAA CTACCGGAGC GCGCCCGTGA GCTGACCGGC

36241 CGGGCACTGG CCGCGATACA GCGTCTGATC AGCGACGACG CACTCGCCGA CAGCCGCCTG

36301 ACGCTGCTCA CCCGGGGTGG CATGGCGGTG CATGACGACA CCGAGGTCAC CGACCCGGCC

36361 GCCGCCGCGG TGTGGGCCT GGTGCGCGCC GCGCAGGCCG AGCACCCGGG CCGGGTGTGC

36421 GTGATCGACA TCGACGACCG GTCGGCCGAG GCCCTGACCG CCGCGCTGGC CACGGAGGAA

36481 CCCCAGCTCG CGCTGCGGGG CGGAACCGCG TGGGTGCCCC GCCTGGTGCG AGCGCGCCCG

36541 GGACTGGCGG TCCCGGCGGC CGTGGCGTGG CATCTGGACG TCACCGAACA CGGCACGCTG

36601 GAGAACCTCG CCCTGGTGCC CCATCCCCGG GCGGAGGCAC CGCTGGAGGC GGGCCAGGTG

36661 CGGATCGCGG TGCGCGCCGC CGGCCAGAAC TTCCGCGATG TGCTCATCGC CCTCGGCATG

36721 TACGAGGCGG AGATCGGCAC CGAGGGCGCC GGCGTGGTGA CCGAGGTCGG CCCGGGCGTG

36781 GCGGACCTGA CCGTGGGCGA CCGCGTGATG GGCATGTTGC CCGGTTCGTT CGGGCCGCTG

36841 GTGGTGGCGG ACCGGCGGAC GGTGGTGCGG ATGCCGCGCG GCTGGTCGTT CACGGCTGCG

36901 GCCGGGGTGC CGGTCGCCTA TCTCACCGCG TTGTACGCGT TGCGGGATCT GGGCGATGTC

36961 CAGCCGGGTG AGACGGTGCT GGTGCACGCC GCCGCCGGTG GTGTCGGCAT GGCCGCCGTA

37021 CACCTCGCCC ACCACTTCGG CGCCACCGTC CTCGCCACCG CCCACCCGGC CAAACACCAC

37081 AGCCTGGAAC AGCTCGGGGT GCCCACGGAA CGACGCGCCT CCAGCCGCGA CCTCGCCTAC
```

-continued

SEQUENCE ID NOS: 1-3

37141 GCCCGCACCT TCCCGACCGC CGACATCGTC CTCAACTCCC TCACCGGCGA ACACATCGAT
37201 GCCTCCCTCG GGCTCCTGGC CCCCGGCGGC CGTTTCATCG AGATGGGACG CACCGACATC
37261 CGGGACGTGG ACGAGGTGCG CGCGTCCCAT CCGGACCGGA CATATCGCGC GTTCGACCTG
37321 GGCGCGGACG CTGGGCCGGA CCGCATCCAG GAGCTGCTGG CCGAGCTGGT GGACCTGTTC
37381 GAGCAGGGCC TGATCCCTCC GTTGCCCACC CGGCCGTGGG AGATCACCCG CGCCCCCGAC
37441 GCATTCCGCT GGATGAGCCA GGGCCGCCAC ACCGGCAAGA TCGTGCTCAC CCTCCCCCGC
37501 ATCCCCGACC CCGAGGGCAC CGTACTGATC ACCGGCGGCA CCGGCACCCT CGGCACCGCC
37561 ATCACCCGCC ACCTCGTCAC CCACCACGGC GTACGCAACC TGGTCCTCGC CAGCCGCCAG
37621 GGGCCGAACG CCCTCGGCGC GGCCGACCTC CACGACGAAC TGACCGCACT GGGCGCACAG
37681 GTACGCATCA CCGCCTGCGA TATCGCCGAC CGCGGCCAAC TCGCCGCGCT CCTCGCCGAC
37741 ATCCCGTCCG ACCACCCCCT CACCGGCATC GTGCACACCG CCGGCGCCCT GGCCGACGGC
37801 ACCCTCACCA CACTCGACCC CGACCGCATC GACACCGTCT TCCGCCCCAA GGTCGACGCC
37861 GTCACCCACC TGCACGACCT CACCCGCGAC CAGGACCTGG CCCTCTTCGC CGTGTACTCC
37921 TCCGCCGCCG GAATCCTCGG GAACGCGGGT CAGGCCAACT ACGCCGCCGC CAATACCTTC
37981 CTCGACGCCT TCGTACAGCG GCGGCGCGCG GCGGGGCTCG CCGGGCTGTC ACTGGCCTGG
38041 GGCCTGTGGG CGGAGACCAG CGACCTGTCG GCCGCGCTGA TCACGGCCAA CCGGGATCGC
38101 ACCCAACACG GTGTCGTCCG CCCGATGGCC ACCGAGCACG CCCTGAGCCT CTTCGACTCC
38161 GCGCTCGGCC TGGGGTTGTC CCTGGTGGTA CCGGCGAAGC TGGACCCGGG CGCGCACGAG
38221 TCCGCCGCGG GCGCTGTGCC GCCGCTGCTC ACCGGCCTCC TCCGGCCGAC CCGGCGCACC
38281 TTGCGGTCCA CGGCGGGCCA ATCCGGCGAA GGCGGTCTCA CGGCCCGGCT GGCGGCGCTG
38341 TCCGAGGCCG ACCAGCACCG GCTGCTGCTG GACCTGGTAC GGGACCATAC TGCGACCGTA
38401 CTCGGGCACG CCGGGAAGGA CGCCGTGGAC GCCAGGCGCG CGTTCAGCGA GATCGGGGTC
38461 GACTCGCTCA TCGCGGTGGA ACTGCGCAAC CGGCTCGCCG GCGCGACCGG GCTGCGCCTG
38521 CCCGCGACGG TCGTGTTCGA CTACGCGACA CCGGAGGCGA TGGCCGGGCA TCTGCGGTCC
38581 GTGGTGGCCG GAGACACGGC CGCCCCTGCC TCCCCGTCGA CGTCGGCGGT GGCGCCCGCT
38641 TCCGCGGTGG CCCCGGCGGA CGACCCGGTG CCATCGTGT CGATGAACTG CCGGCTGCCC
38701 GGCAAGGTCA CCGGCCCCGG GGAGCTGTGG GATCTGGTGT CCCAGGGCCG GGACGCGATC
38761 GGCCCGTTCC CCACGGACCG CGGCTGGGAC GTGGAGACGC TGTTCGACCT CGATCCGGAC
38821 GCCGTGGGCA AGTCCTACGT ACGCGAGGGC GGTTTCCTCA CCGGCGCCGG CGACTTCGAC
38881 GCCGAGTTCT TCGGCATCTC GCCGCGTGAG GCGCTGGCGA TGGATCCGCA GCAGCGACTG
38941 CTCGCCGAGA CCTCATGGGA GCTGTTCGAG CGGGCGGGCA TCGACCCGGT GTCCGTGCGC
39001 GGACAGGCCA TCGGGGTGTT CGCCGGGGTC ATCGACCAGG GATACATCGC CCACTCCGAG
39061 GCCCCTCCGC CGGAGTTGGA GGGCTACCTG ATGACGGGCA GCACCACGAG TGTGGCCTCC
39121 GGCCGAGTGG CCTACCTGCT GGGCCTCGAA GGCCCCGCGG TGACGGTGGA CACGGCGTGC
39181 TCGTCGTCGC TGGTGGCGCT GCATCTGGCC GTGCAGGCGC TGCGGGCGGG CGAGTGCTCG
39241 ATGGCCATCA CCGGTGGCGT GACGGTGATC GCCAAGCCCG GCGGTTTCAT CAGCTTCTCC
39301 CGCCAGCGCG GGCTCGCGCC GGATGGCCGC AGCAAGTCCT TCAGCGAGGG CGCCGACGGC
39361 ACCAGCTTCA GCGAGGGCAT CGGTCTGGTG TTGCTGGAAC GGCTCTCCGA CGCCCGCCGC
39421 AACGGCCACG AGGTCCTGGC CGTGATCCGT GGCACGGCGG TGAACCAGGA CGGCGCGAGC

-continued

SEQUENCE ID NOS: 1-3

```
39481 AACGGCCTCA CCGCGCCCAA CGGACCCTCC CAGCAGCGAG TGATACGGCA GGCGCTGGCG
39541 AACGCCGGGC TGACGGTGGC CGACGTGGAC GCGGTCGAGG CCCACGGCAC CGGCACCGCC
39601 CTCGGCGACC CCATCGAGGC CCAGGCACTC CTGGCCACCT ACGGCCAGGA CCGGCCGGGG
39661 GACGAACCGC TGTGGCTCGG TTCGCTGAAG TCCAACATCG GCACACCCA GGCCGCCGCG
39721 GGCATCGCGG GCCTCATCAA GATGGTGCTG GCGATACGGC AGGGCACGCT TCCGCGGTCC
39781 CTGCACGCCG GCGAACCCAC CACCAAGGTC GACTGGACGT CGGGCGCGGT GTCGCTGCTG
39841 TCCGAGGCCC GGCCCTGGCC GGAGACGGGA CACCCCCGCC GCGCCGGAAT CTCCTCCTTC
39901 GGCATCAGCG GGACGAACGC ACACGTGATC CTCGAGCAGG GCCGGAGGT GGCTGTGCCC
39961 GCAACGGAGG CGCGCGACGC GGGCGCTCCT GGGCTGGTGG CCACGGGCGG CGTGGTGCCG
40021 TGGGCGCTGT CCGCCAAGAG CCCTGCGGCG CTGCGGGCCC AGGCCGAGCG TCTGGTCAGC
40081 CACCTGGAAT CCGGGGACGC TCCGCGTGCG GTGGACGTGG GCTGGACGCT GGCCACCACC
40141 CGAGCGGCGT TGGAACACCG CGCGGTCATC CTCGCCACCG ACACCGAAGA CGGCATCGCC
40201 ACCGCCCGCG CCCTGGCGGA GGGACGGCCT GACCCGCTCC TGGTCACCGG GCAGACCGGG
40261 ACGGACGGCA AGACCGTGTT CGTCTTCCCT GGTCAGGGGG CCCAGTGGGT GGGCATGGGA
40321 GCCCAACTCC TCAACACCTC ACCCGTCTTC GCGGCTCGCT TGAACGAATG TGCCGAGGCC
40381 CTGGCCCCGT ATACCGACTG GTCGCTGATG GACGTCATCA CCGGCGCTCC CGGCGCCCCT
40441 TCGCTCGAGC GTGTCGATGT CGTACAGCCC GCCACCTTCG CCGTCGTCGT CTCCCTCGCC
40501 GCACTCTGGC AATCCGTGGG CATCCACCCC GACGCCGTCA TCGCCCACTC CCAAGGCGAA
40561 ATCGCCGCCG CCTGCGTCGC CGGACACCTC ACCCTCACCA ACGCCGCCAA AATCGTCACC
40621 CTCCGCAGCC AGACCATCGC CCACCACCTC GCCGGACACG GCGGCATGAT GTCCGTCCTC
40681 GCCTCCCGGG AACAGGTCGA GGAAGCCCTC ACCCCGTGGC ACGGCAAACT CTGGATCGCC
40741 GCACACAACA GCCCCAACGC CACCGTCATC GCAGGCGACA CCGACGCCCT GCACCAACTC
40801 CACACCCACT ACACCGACCA GGGCATCAGG GCCCGCGTCA TCCCCGTCGA CTACGCCTCC
40861 CACACCGGAC ACGTCGACAC CATCAAAAAC CAACTCCACC AGACCCTGGC CGACACCACG
40921 ACCGAGCCCG GCACCATCCC CTGGCTCTCC ACCGTCACCG GACAGTGGAT CGAACCCGAC
40981 ACCGTCGACA GCGGCTACTG GTACCGCAAC CTCCGCCAAA CCGTGCAGTT CCACACCGCC
41041 ATCACCGCCC TCGCCCATGA GGGCTACCGC ACCTTCATCG AAATCAGCCC CCACCCCGTC
41101 CTCACCACCG CCATCCAAGA AACCCTCGAA GCCAACGACA CCCCCAACAC CACCATCACC
41161 GGCACCCTCC GCCGCGACGA CGACACCCCC ACCCGCTTCC TCACCCACCT CGCCCACCTC
41221 ACCACTCACG GCCACACCCC CGACTGGACC GCCCTCTACT CCGCCACCCA CCCCCGCCCC
41281 ACGCCCCTCC CCACCTACGC CTTCCAACAC CACCACTACT GGCTCACGCC GTCCGAGGTA
41341 CCGGAGGCGG TGGCCGACGG TGTGTTCTGG GACGCCGTGG AGCGGGGCGA CCTCGCCTCC
41401 CTGGCCGATT CACTCGGCGT CGAGGAGAAG ACGCTGGAGC CCGTGCTGCC GGGGTTGACG
41461 TCGTGGCGGC GCCGCAACCA GGACCAGTCC ACCGTGGACA CCTGGTCGTA TCGCATCGCC
41521 TGGGATCCGG TGGCGACCGG AGAGGCGCCC GTACTGCCGG GAGCGTGGCT GGTGGCCGTG
41581 GCCTCACCGC AGGCGAGCGA CGCCGCGGTG ACGGACGTGG TGGCCGCACT GGCCGCGCAC
41641 GGTGCCGATC CCGTGGTGGT CGAGGTCGAC ACGGTGGAAC AGGCGGAGGT GACCGCGCGC
41701 CTGCGGGAGC GGATATCCGA TTCCGATGAC GAGTACGCCG GAGTGGTGTC CCTGCTGGCG
```

-continued

SEQUENCE ID NOS: 1-3

```
41761 TGGGACGAGC GGAGCTACGA ACCCGGCACG CTCTCCCGGG GCGTGGCGGC CACGGTGGCG
41821 CTGATACAGG CCGTGGAGGA GATCGGGCTC GCCGCTCCCC TGTGGTGCCT GACGCGTGGC
41881 GCGGTCGCCG TGCGTGAGCC CTCCGAGGTG ACCAGCGAGT TCCAGCCGCT GGCCTGGGGA
41941 ATGGGCGTGG TGCAGGGGCT GGATCAGCCG TCCACCTGGG GCGGGATCGT GGATCTGCCG
42001 CGGACGCCGG ACGAGACGGC CCTTGTCCGG TTGTGCTCGG TGCTTGCCGG AGTGGACGCG
42061 GAGGACCAGG TCGCGGTGCG CGCGTCGGGG GTGTTCGCCC GGCGGATGCG GCGCGAACCG
42121 GTGACGTCGG CACCGGCGTG GCAGCCACGG GACACGGTGC TGATCACCGG TGGCACCGGC
42181 GGGCTCGGTT CGTACGTGGG CCGTTGGGCC GCGGGTCACG GCGCCCGGCG TGTGGTGCTG
42241 CTCAGCCGTC AGGGTGCGCA GGCGCCGGGC GCGGCGGAGC TGGAGGCCGA GCTGAGCGCA
42301 CTGGGCGCGG ATGTGACCAT CGCGGCGTGT GATGTGACCG ACCGGGACCA GCTAGCGGCC
42361 GTCCTGGCGG AGATCCCGGA TGACGCGCCA CTGTCGGCG TGGTCCACGC CGCGGGGCTG
42421 GCGCTGCCGG AGAAGCCGCT GTCGAAGATG ACACTCGCCG AGTTCGCCGA CATCGGCCAG
42481 GCGAAGATCG CCGGTGCGCG GCATCTCGAC GACCTGTTGG GGGAGCGGGA GTTGGACGCC
42541 TTCGTCCTGT TCTCGTCCGG AGCGGCGGCC TGGGGCAGCG GCGGCCAGAG CGCCTACGCC
42601 GCCGGCAACG CCTACCTCGA CGGGCTGGCG CAGCGCCGCC GCGCACGGGG GCTGGCGGCC
42661 ACGTCGGTGG CGTGGGCGC CTGGGCGGT GGCCTTGGCA CGATCGACGA GATGATGGGC
42721 GCGCAGTGGC GCCGTACAGG TCTGATGACC ATGGACCCGC GGCTGGCGGC GCTGGCGATG
42781 GCACACACCG TGGGCAGCGG CACCGCCCAC GGTGTGGTGG CCGACATCGA CTGGGAACGG
42841 TTCGCCCCCG GCTACACCAT GGCCCGGTTC CGGCCCCTGC TGCGGGGACT GCCCGATGTC
42901 ATCGACCTGC TGACCGAGGA CGCACCCGAG GACAGCGCGG GACAGACGGA GCTGATCGCA
42961 CGGCTGGCCG GACTGAGCCC CGAGGATCAG GAGCGGCTGC TCACCGAGCT GGTGCAGGCC
43021 GAGGCCGCGG CCGTACTCGG ACACGTGAGC GCCGACGCCA CCGGGGACCG TCCGTTCAGC
43081 GAGATCGGAT TCGACTCGCT GACGGCGGTG GAGCTGCGCA ACCGCCTCAA TGCCAGCACG
43141 GGGCTGAGGC TGCCCGCGAC GATGGTGTTC GACCACCCGC GGCCCAGTGT GCTGGCACGC
43201 CGTATCCGCA CCGAACTCGG CCATACCGAC ACCTCGTCGG TGGACTCGGT GCTGGCCGAG
43261 CTGGAGCGGC TGGAAGCACA TTTGCGGCG CTGCCGAAGG AGAAGATCGA ACGCGCCCGG
43321 ATCACCTCGC GGCTCCAGCG GATGACCACC AAGGTCGCCG AGATCGAGGC CGTCGGCACG
43381 GGCGGCGACA CCGTCACCGA ACGACTCGAC ACGGCGAACG CCGACGACGT GTTCGCCTTC
43441 ATCGACCAGG AGTTCGGCGT GGACTGATTC CCCGTCTCGT CTCCGCTCAC CGATTTCACC
43501 CACGAGGCTC TTGGCGAGGT CCAGATGGCG AATGACGAAA AGCTCCTCAA CTACCTCAAG
43561 CGGGTTACCG CCGACCTGCA CCAGACGCGG GAACGGTTGC GCAAGGCCGA GGCGGCGACG
43621 GAGGAGCCGA TCGCCATCGT CGGCATGGGC TGCCGCTTCC CGGGCGGCGT GACCACCCCG
43681 GACGGGCTGT GGGATCTGGT GGCCGACGGC CGGGACGCGA TCGCCGGGTT TCCGGAGGAC
43741 CGCGGCTGGA ACCTGGAGAA CCTCTTCGAC GCCGACCCCG ACTCCGTCGG CACCTCCTAT
43801 GTGCGCGAGG GCGGCTTCCT CACCGACGCG GCGGAGTTCG ACGCCGAGTT CTTCGGCATC
43861 TCCCCGCGTG AGGCGCTGGC CACCGATCCG CAGCAGCGGC TGCTGCTGGA GACCGCGTGG
43921 GAGACCCTCG AGCACGCGGG AATCGACCCG AGTTCGCTGG AGGACAGCGA CGTCGGCGTG
43981 TTCACCGGCC TGGCCAACGG CGACTACGCG CTGACCGTGG ACCAGGTGCC GGAAGGCTTC
44041 GAGGGGTATC TGGGCCTTGG TGGCGCGGGC AGCATCGCGT CCGGCCGTAT CTCGTACTCG
```

```
                         -continued
                     SEQUENCE ID NOS: 1-3

44101  CTCGGTCTGC TCGGCCCGGC GGTCACTCTG GACACCGGGT GCTCCTCGTC CCTCGTGGCG

44161  ATGCACTTGG CCAGTTATGC GCTCCGGTCC GGGGAGTGCT CCATGGCGCT CGCCGGTGGG

44221  GTGATGGTGA TGGCGACCCC TGGCGGCTTC GTCGGATTCT CCCGGCAGCG GGGGCTGGCG

44281  CGCGACGGGC GCTGCAAGTC CTTCGGTGAG GGCGCCGACG GCACCAACTG GTCCGAGGGC

44341  GTCGGTCTTG TGCTGCTGGA GCGGCTGTCC GAAGCCCACC GCAACGGCCA CCCGGTACTC

44401  GCGGTCATCC GTGGCACGGC CGTCAACCAG GACGGCGCCT CCAACGGCAT CACCGCGCCC

44461  AACGGGCCGT CCCAGGAACG GGTGATCCGG CAGGCGCTGG CGAACGCCGG ACTGTCGCTG

44521  GCCGATGTGG ACGCGGTCGA AGCCCACGGC ACCGGGACGA GTCTCGGCGA CCCGATCGAG

44581  GCCCAGGCAC TCCTGGCCAC CTACGGTCAG AACCGCCCGG AGGATCAGCC GCTGTGGCTG

44641  GGCTCCATCA AGTCCAACAT CGGCCATACC CAGGCCGCCG CGGGTGTCGC GGGCGTCATC

44701  AAAATGGTCC AGGCCATGCG GCACGGCGTA CTGCCCAAAA CCCTCCACGC CGACGAGCCC

44761  ACCAGCAAGG TCGACTGGAC GTCAGGTGCG GTGTCCCTGC TGTCCGAGGC CCGGCCCTGG

44821  CCGGAGACGG GACACCCCCG CCGCGCCGGA ATCTCCTCCT TCGGCGTCAG CGGGACGAAC

44881  GCACACGTGG TCCTGGAACA GGCACCCCTG GAAGCGGCTG CACCCGAAGT AGACGTAGAC

44941  GAGGCGGGCG CTCCTGGACT GGTGGCCACG GCGGCGTGG TGCCGTGGGT GCTCTCCGGT

45001  AAGACTCCTG CGGCGCTGCG GGCTCAGGCG GAGCGTCTGG TCAGCCACCT GGAATCCGGG

45061  GACGCTCCGA ATGCGGTGGA CGTGGGCTGG TCACTGGCCA CCACCCGGGC GGCGTTGGAG

45121  CACCGCGCGG TCATCCTGGC CACGGACACC GAAGGAGGCA TGGCGACGGC GCGGGCTCTG

45181  GCGGAGGGAC GGCCTGACCC GCTCCTGGTC ACCGGACAGA CCGGAACAGA CGGCAAAACC

45241  GTGTTCATCT TCCCCGGCCA AGGCGCCCAA TGGGTGGGCA TGGGAGCCCA ACTCCTCAAC

45301  ACCTCACCCG TCTTCGCCGC CCGCCTGCGC GAGTGCGCCG ATGCTCTAGC GCCGTATACC

45361  GACTGGTCGC TCATCGACGT CATCACCGGC ACGCCCGACG CCCCATCGCT CGACCGTGTC

45421  GACGTCGTAC AGCCCGCCAC CTTCGCCGTC GTCGTCTCCC TCGCCGCACT CTGGCAATCC

45481  GTGGGCATCC ACCCCGACGC CGTCATCGGC CACTCCCAAG GCGAAATCGC CGCCGCCTGC

45541  GTCGCCGGAC ACCTCACCCT CACCAACGCC GCCAAAATCG TCACCCTCCG CAGCCAGACC

45601  ATCGCCCACC ACCTCGCCGG ACACGGCGGC ATGATGTCCC TCGCCACCCC CGCCGACACC

45661  ATCGACCTCA CCAACTGGCA CGGCAAACTC TGGATCGCCG CACACAACAG CCCCAACGCC

45721  ACCGTCATCG CAGGCGACAC CGACGCCCTG CACCAACTCC ACACCCACTA CACCGACCAG

45781  GGCACCAGAG CCCGCATCAT CCCCGTCGAC TACGCCTCCC ACACCGGACA CGTCGACACC

45841  ATCAAAAACC AGCTACAAGA CGTACTCGAC GGCGTCACCC TCGAGCCCGG CACCATCCCC

45901  TGGCTCTCCA CGGTCGACGG ACAGTGGATC GAGCCCAGCA CGGTCGGCGA CAGCTACTGG

45961  TACCGCAACC TCCGCCAGAC CGTGCAATTC GAGCACACCA TCACCACCCT CGCCGACCAG

46021  GGCTACCGCA CCTTCATAGA AATCAGCCCC CATCCCGTCC TCACCACCTC CATCCAAGAA

46081  ACCCTCGAAG CCAACGACAC CTCCAGCACC ATCGTCACCG GCACCCTCCG CCGCGACGAC

46141  GACACCCCCA CCCGCCTCCT CACCAACCTC GCCCACCTCA CCACCAACGG AACACCAGTC

46201  AACTGGACCA CCCTCTTCAC AGGCACCCAA CCCACCCGCA TCCCCTCCC CACCTACCCC

46261  TTCCAACACC ACCACTACTG GCTCCCCCGC AACACCAACG CAGGCGACAT CGCCTCGGCC

46321  GGTCTCCACG ACCCCGGGCA CCCGCTGCTC ACCGCCGCCG TCCACCTCCC CGACACCGGT
```

-continued

SEQUENCE ID NOS: 1-3

```
46381 GGCACCGTTC TCACCGGGCG CCTCTCCCTG ACCACCCACC CCTGGCTGGC CGACCACACC
46441 GTGTCCGGCG CCGTCCTCCT CCCCGGCGCC GCGATGGCCG AACTCGCCAT CCGCGCCGGA
46501 GACGAGACCG ACACCCCCAC CCTGGAAGAG CTGGTCATCG AGCAGCCACT GGCGCTGCCG
46561 GACAGTGGCT TCCTGGACAT CCGGGTGGTC GTGGGCGGCC CTGACGAGTC CGGGCGTCGG
46621 GACGTACGCA TCTATTCCCG CGCCGAAGAA GAAACCGCGC AGTGGACGGA GCACGCCACC
46681 GGCACGCTGG CTCAGGACAC CACGGCTCCT CCGTCGCCCG CCGTCGCCGA ATGGCCACCC
46741 GCCGGTGCCG AGCCGGTGGC CGTCGAGGGG CTGTACGAGC AGATGGCCGA GGGGGGCTAC
46801 GACTACGGGC CGACCTTCCA GGGCCTGAAG GCGGTATGGA CCCGCGACGG CGAAGTGGGC
46861 GAGGTGTTCG CGGAGGCCGC GCTGCCGGAG GAGCAGACGG AGGCCGCCGG CCGGTTCGGC
46921 ATCCACCCGG CACTGCTGGA CGCCGCATTG CACGCGAGCA ACTACTGCCT GCCCGGGGAA
46981 CCCGGTAGCC GCATGCTGCT GCCGTTCGCG TGGAACGGCA TACGCCTGCA CGCCACCGGT
47041 GCCACGTCGG TGCGCGTGCA CGCCCGTTAC ACCGAGGACG GCGGGCTCTC CGTGGTCCTG
47101 GTCGACGCAG CCGGCGGGCT GGTCGCGTCG ATCGGTTCGC TGGTTCTGCG GGAGGTCGAC
47161 GCGGCGCAGC TCGAAGCGCT GACCTCCACG TCGGTGAACG ACTCACTCTG GACGGTCACT
47221 TGGACCGAAC ACACCGCCAC CACGGACGAG ATCCGGTGGG CACCGTCGG GGACGTCTCA
47281 CCCGTCCTCG CCGCCGCCGA AGCCCCGGCC TTCGCCGATG TCACAGAGAT CGCCACGGGG
47341 CCCGCCATCG GGATGGGCAC GGAGATCGCC GGGGCCGAGG AGCGGCCCGC GCTGGTCGTC
47401 GCCGACACCA CCGTATGGGA GTCCCGGGAC GCCGACCCCA TCACGCGGGC GCGGGAGCTG
47461 GCCACGCGGG CACTGGACCT GTTGCAGCGG TGGGTGACCC TGCCTGAGCT GTCGGAAACA
47521 CGGCTGGCGG TCCTCACGCG CGGTGCGATG GCCGTACACG ACTCGTCCGA GGTCACCGAC
47581 CCTGCCGCGG CGGCGATCTG GGGTCTGGTC CGCTCGGCCC AGTCCGAACA CCCCGGCCGC
47641 GTCCACCTCA TCGACACCGA CGGCCACTCG GACCACGCAC TGCGCAGCGC ACTGCCCACC
47701 GCACTCGCCA CCGACCAGCC CCAACTGGCC CTCCGCGACA ACACGCTCTG GGCGCCCCGG
47761 CTCACCGCCG CGGCACCCGT CGGCACACCG GCCCAGCCGC TCCCCCTCGA CCCCGAGGGC
47821 ACCGTTCTCA TCACCGGCGG CACCGGCACC CTGGGCGCCC TCACCGCCCG CCACCTCATC
47881 ACCCACCACG GCGCCCGGCA CCTGCTGCTC ACCAGCCGCC AGGGTCCCTA CGCCCCCGGC
47941 GCCACGGACC TCACCACCGA ACTCACCGAA CTCGGCGCCA CCGTCCACAT CACCGCCTGC
48001 GACACCGCCG ACCGCGACCA ACTCGCCGCC CTCCTCGCCA ACATCCCGGC CGCCCACCCC
48061 CTCACCGCCG TCGTCCACAC CGCCGGAACC CTCGACGACG CCCTGCTCAC CGACCTCACC
48121 CCGCAGCGCC TCGACACCGT CTTCCGCCCC AAGGTCGACG CCCTCACCCA CCTCCACGAC
48181 CTCACCCGCG ACCACGACCT GACCGCCTTC GTCATCTACT CCTCCGCCAC CGGCACCCTC
48241 GGCACCCCCG CCAGGCCAA CTACGCCGCC GCCAACACCT ACGCCGACGC CCTCGCCCAC
48301 CAGCGCCACG CCACCGGACT CCCCGCCACC TCCCTCGCCT GGGGCCTATG GGAAACCACC
48361 AGCGCCCTCA CCGCCACCAT GAACACCGAG GACCGCCGGC GCACCCACCG CGGCGGCGTG
48421 GCCCCCCTCA CCGACGACGA GGGGCTCGTC CTCCTCGACA CGGCCCTCAC CGCCACCCAC
48481 CACCCCCACC TCGTCCCGAT CAAGATCAGC CCGGCCTCCC TGCGAGCCGA TGACACGGCG
48541 CGGCCCGTTC CCCCGCTCCT CCGCCACCTC GTACGACGCC CCACGCGCCG CACGGCCCAC
48601 ACACCGGCCC CAGCGGACAC CCTGTCGCTC ACCCGACGGC TCGCCGCCCT CGACCACGGC
48661 GAACGGCTAC GGCACCTCAT CGAGCTCGTC CGCACCGAGG CGGCAGCCGT GCTCGGACAC
```

-continued

SEQUENCE ID NOS: 1-3

```
48721 CCGACGATCG ACAGCATCGG ACCGGACCAG CCCTTCCGGG ACGCCGGGTT CGACTCGCTG

48781 ACGGCGGTGG AACTGCGCAA CCGCCTCAAT ACGGCCACGG GACTGCGGCT CCCCGCGACC

48841 GTGGTGTTCG ACTACCCGAC CTCGGCGATC ACCGCCGGGT ATCTGCGGGA CGAGCTGTTC

48901 GGCTCGACGG AGGCGGCTCC GGCCGCCGTC GCCGGGCGGG GGGCCGACGC GGACGACCCC

48961 GTGGTCGTCG TCGGCATGGC CTGCCGACTC CCCGGACGGG TGACCGACCC GGACGGGCTG

49021 TGGCGGCTGG TGGCCGACGG GGAGGACGGC ATCGGGCGT TCCCCACCGA CCGCGGTTGG

49081 GATCTGGACA CGCTGTTCGA CCCCGACCCG GACCGGGTGG GCGCGACCTA CGTCCGCGAG

49141 GGCGGGTTCG TGGCGGGTGC CACCGAGTTC GACGCGGACT TCTTCGGCAT CTCCCCGCGT

49201 GAGGCCGTGG CGATGGACCC GCAGCAACGG CTGTTGCTGG AGACCGCGTG GGAGACCTTC

49261 GAGCAGGCCG GTATCGCCCC GCGGTCGGTG CAGGGCACCG ACACCGGCGT GTTCGCCGGG

49321 GTCATCTACC ACGACTACGG GACGAACGCC GGTGAGCTGC CCGAGGGCTC GGAGACCTAT

49381 CTGAGCACGG GCAAATCGGG GAGCGTGGTG TCCGGGCGGG TCGCCTACGC ACTGGGCCTG

49441 ACCGGTCCCG CGGTGACGGT CGACACGGCG TGCTCCTCCT CGCTGGTGGC CATCCACTGG

49501 GCGGCCAAGG CGGTGCGGGA GGGCGAGTGC TCGATGGCCC TGGCCGGGGG CGTGACGGTG

49561 ATGTCGACCC CGGAGGGGTT CGTGAGCTTC TCGCACCAGC GTGGGCTCGC CCCCGATGGC

49621 CGCAGCAAGT CCTTCGGCGA GGGCGCCGAC GGCACCACCT TCAGCGAGGG TGTCGGGCTC

49681 GTGCTGCTGG AACGGCTCTC CGAGGCCCGG CGCAACGGTC ACGAGGTGCT GGCCGTGATC

49741 GCCGGTACGG CGGTCAACCA GGACGGCGCC AGCAACGGCC TCACCGCCCC CAACGGACCC

49801 TCCCAGCAAC GGGTGATCCG GCAAGCACTC GCGAACGCCG GGCTGTCGGC CACCGACATC

49861 GACGCCGTCG AAGCCCACGG CACCGGCACC GCCCTCGGCG ACCCCATCGA AGCCCAGGCA

49921 CTCCTGGCCA CCTACGGCCA GAACCGCCCC GCCGACCAGC CCCTCTGGCT GGGCTCGCTG

49981 AAGTCCAACA TCGGCCACAC CCAGGCCGCC GCGGGCATCG CGGGCCTCAT CAAGATGATC

50041 CAGGCCATGC GGCACGGCAT GCTGCCCAGG ACACTCCACG CCGACGAGCC CACCACCAAG

50101 GTCGACTGGA CATCGGGCGC GGTGTCCCTG CTGACGGAGG CCCGCCCCTG GCCGGAGACC

50161 GGCCACCCAC GCCGTGCCGG GATCTCCTCC TTCGGCGTCA GCGGCACCAA CGCCCATCTC

50221 ATCCTCGAAC AGGCCCCGGA AGACGCGGCC ACCGCACCAG AAATCACGGA ACCGGAGGCT

50281 CCCGGGCTGG TGGCCACGGG CGGCGCGGTG CCGTGGGTGC TGTCCGCCAA GAGCCCCACG

50341 GCCCTGCGGG CGCAGGCCGA ACGCCTGATC GCCCACCTTC ACGCCCACCC CGAGATCGAC

50401 CCGGTGGACA TGGGCTGGTC ACTGGCCACC AGCCGCGCCG CCCTGGAACA CCGCGCGGTC

50461 GTCCTCGCCA CCGATCTCGA CCAGGCGACC GCCGCCCTCA CCGCTCTCAG CGAGGGGCAG

50521 CCGCACCCCG GCCTGGTCAC CGGGGAGACG GGCAGCGACG GCAAGACCGT CTTCGTCTTC

50581 CCCGGCCAGG GCGCCCAATG GCAAGGCATG GGAGCCCAAC TCCTCAACAC CTCACCCGTC

50641 TTCGCCACCC GCCTCCACGA ATGCGCCGAC GCCCTCGCCC CGTATACCGA CTGGTCGCTC

50701 ATCGACGTCA TCACCGGCGC ACCCGGCGCG CCCAGCCTCG ACCGTGTCGA TGTCCTGCAG

50761 CCCACCACCT TCGCCATCAT GGTCTCCCTC GCCGCACTCT GGCAGGCCAA CGGCATCCAC

50821 CCCGACGCCG TCATCGGCCA CTCCCAAGGC GAAATCGCCG CCGCCCACAT CGCCGGACAC

50881 CTCACCCTCA CCAACGCCGC CAAAATCGTC ACCCTCCGCA GCCAGACCAT CGCCCACCAC

50941 CTCACCGGAC ACGGCGCCAT GATGTCCGTC CTCGCCCCCC ACACCTGGGT CCAAGAAGCA
```

-continued

SEQUENCE ID NOS: 1-3

```
51001 CTCACCCCCT GGCACGAACA CCTGTGGATC GCCGCCGTCA ACGGCCCCGC CTCCGTATCC

51061 GTCTCCGGAG ACCCCGACGC ACTCGCCGAA TTCGGTGTCA CCCTCTCCAA GGCGAAGGTC

51121 TACCGCTGGC AGTTGCCCGG GGTGGACTTC GCCGGACACT CCGGACACGT CGACACCATC

51181 AAAGACCAGC TACACCACGT ACTCGACGGC GTCACCGCCT CCCCCGGCAA CATCGCCTGG

51241 ATGTCCACCG TCGACGCCAA CTGGACCAAC CCCACACACA TCGACGCCCA CTACTGGTAC

51301 CGCAACCTCC GCGACACCGT CCGCTTCGAA GAAGCCACCC GAGCCCTCCT CACCCACGGC

51361 CACCGCGTCT TCATCGAAAT CAGCACCCAC CCCGTCCTGA CCACCGCCAT CCAGGACACC

51421 ACCGAAACCC TCCCCGAGGT CCGGGCCACC ATCACCGGAA CGCTGCGCCG CGACGACGGC

51481 GGCCCCGACC GCGTTCTCGC GGGGCTGGGA GGGCTGTTCG CGGCCGGGGT GCCGGTGGAC

51541 TGGGGCGCCC TGTTCGCCAG TACCGGGGCC CGTCGGGTGC CGCTGCCCAC GTACGCCTTC

51601 CAGCACCGGC ACTACTGGCT GGAGCCCGCC AGGACACCGA CGCGGGCCGA GAGCGCCGAC

51661 GGCTCCCTGT GGGCGGCCAT CGAGGACGGA GACGCGCAGT CTCTCGCGCG GGATCTTGAT

51721 GTGGACGCGG CGGCCCTCGG CACGGTGCTG CCCGCGCTCG CCTCATGGCG TCGGCGCAGC

51781 CGGGAGGACT CCCTCACGGA CGCATGGCGG TACCGGATCG GCTGGACCCG GGTGGCCACG

51841 GCCGACCCGC AGTTGTCGGG CCGGTGGCTG GTGCTGGTCC GGCCGTGCG GGCGGGCTCG

51901 GCGCGGGTCC GTGCGGTGCT GGACGGGCTG GCCGCGCGGG GCGCCGAGGT GGTGGCCGCC

51961 GAGGTCTCCG AAACCGGCCG GGAGGCACTG GGCGACCAGG TCAAGTCGGC GGACGGCGGT

52021 GCCGGGGTGG TGTCCCTGCT CTCGTGGGAC GACCGCGCCG ACACCGAGTA CGGCACCGTG

52081 TCCACGGGCA CCGCCGCGAC GCTCGCGGTG GCACAGGCGT TGCGGGACCA CGGCGTCACC

52141 GCTCCGCTGT GGTGCGTCAC CAGTGGCGGG GTCGCGGTGG CCGGTGAGGC GGCCGACCCG

52201 GTGCAGTCCG CGGTGTGGGG ATTCGGCGCC GTACTCGGGC TCGACCACCC GGACACCTTC

52261 GGCGGCCTGA TCGATCTGCC GGCCGAAGGG GAGGGTGACG ACGAGGCGTT GCCGGACGGG

52321 CTGTTCGCGG CGCTGTCGTC CCCCGAGGGG GAGGACCAGC TCGCGGTGCG CGCCGACGGG

52381 CTGTTCGCAC GCCGGATGGT GCGCGACCGG GACGGCTCCG GCAGCCCCTG GAAGCCGCGC

52441 GGCACCGTGC TGGTCACGGG CGGCACCGGC GGGCTCGGTT CGCATGTGGC GCGCTGGCTC

52501 GCCACGAGCG GGGCGGACCA TGTGGTGCTG CTCAGCAGGC AGGGTGGTGA CGCGCCGGGC

52561 GCGGCCGAAC TGGTGGCGGA CCTGGCGGGG GTGGAGGTCA CGCTCGCCGC GTGTGATGTG

52621 ACCGACCGGG ACGCCGTGGC CGCGGTGCTG GCCGAAGCGG AGCGGACCCA TCCGCTGACC

52681 GCGGTGGTGC ACACCGCCGG TGCCGGGCTG CCCTCGGCTC CGGTCACCGA GGTGACCACC

52741 GAGGAGTTCG CCGCCGTCAC GGGGGCGAAG GTGCGCGGCG CGCTGGTGCT GGACGAGCTC

52801 GTCGGCGACC GGGAGCTCGA CGCGTTCGTG CTGTTCTCCT CCGGCGCCGG TGTCTGGGGC

52861 AGCGGCGGGC AGGCCCCGTA CGCGGCGGGC AACGCCTTCC TGGACGGGCT GGCGGCCCGG

52921 CGGCGGGCAC ACGGGCTCGC GGCCACGCGC GTGGCGTGGG GCGGCTGGGG CGGCGGGCTC

52981 GGCATGATCG ACGCCGACGG CGGCGACCAG TGGCGCCGTA TCGGCATCCT GCCGATGGAT

53041 CCGGCGCCCG CGCTGCGTGC GCTGGCGCGG GCCGTTGGGG GTGGTCTGCC GAATGTGATC

53101 GTCGCGGATG TCGACTGGGC GCGGTTCGTG CCGGGCTACA CGATGGCCCG GGAGCGGCCG

53161 CTGCTGCGGC AGTTGCCCGA GGTCGCCGAG ATCCTGGCGG CGGACACGCA GGGCGGGGC

53221 GCATCGCGGC GGGAGGTGCT CCTGGGCAGC CTGGCCGAGC TGACCGGCCC GGAGCAGGAG

53281 GTGTTCCTTA CCGACCTGGT GCGGCGTGAG GCGGCGGCCG TGCTCGGGCA TGCGGACGGG
```

-continued

SEQUENCE ID NOS: 1-3

```
53341 GACGCGGTGG AGCCGGAGCG TGCGTTCAAG GACACCGGGT TCGACTCGCT GACCGCGGTG

53401 GAGCTGCGCA ACCGGATCAA CACGGCCACC GGTCTCCAGC TCTCCCCCAC GGTGGTGTTC

53461 GACTATCCGA AGCCGACCAC GCTGGCGAGG AGGCTGCGTA CGGAGTTGGT CCCCACGGTG

53521 AACGGGGACG TGGACGGGGA CGGGACCGCG GACGGCGGGG CCGCCGGCGC GGACGGCCGC

53581 GAGCGGGAGA TCCGGCGGGT GCTGGCTTCG GTGCCACTGC GCCGCTTCCA CGAACTGGGG

53641 GTGCTGGACG CGCTGGTGCG CCTCGCGGAC TCCGCGGCCG GCGACCTGAG CGGTCTGCGC

53701 GACCTGGGCG ACCTGGGCGA CCTGGGCGAC CTGGGCACCG CCGCGGAGGC GGAGACCTCC

53761 GCGCTCGCGG AGCTGGATGC CGACGAGCTG GTGAGCCGGG CGATGCGCGG CACGACCTTC

53821 GGAAACGACT GACGCCGCGG TTGCGGAGAG GAGTACACAT GGCTGCGTCC CGGGAAGACC

53881 TGGTCAAGGC GCTGCGTACC TCGCTGATGG ACGCCGAGCG GCTGAAGCGG GAGAACGACC

53941 GGCTGATCGC CGAGTCCACC GAACCGGTGG CGATCGTGGC GATGGCGTGC CGGCTGCCGG

54001 GTGGGGTGAC CGACCCGGAG TCGCTGTGGG AGCTGGTGGA CGAGGGGCGG GACGCGATCG

54061 GGCCGTTCCC CACGGATCGC GGCTGGGACC TGGAGACCCT GTTCGACTCC GATCCGGACG

54121 CCGTGGGCAA GTCCTACGTA CGCGAGGCGG GGTTCCTGGA GGGGGCGGGC GGATTCGACG

54181 CCGCCTTCTT CGGCATCTCG CCGCGCGAGG CCCTGTCGCT GGACCCGCAG CAGCGGCTGC

54241 TGCTGGAGAC CGCGTGGGAG ACCTTCGAGC GGGCGGGGAT GGATCCGCGG TCGGTGGAGG

54301 GCCGGGACAT CGCGGTGTTC GCCGGGGGCA GCGGCCAGGG GTACGGCGGC GGTCCGGGTG

54361 AGGCGCCCAA GGGCCTGGAG GGCTATCTGG GGGTCGGCGC TTCCGGCAGT GTCATCTCCG

54421 GGCGCGTGTC GTACACGCTC GGGCTGACCG GTCCCGCCGT GACCGTGGAC ACCGCCTGCT

54481 CGTCCTCGCT GGTGGCCGCC CATCTCGCCG TGCAGGCGCT GCGGTCCGGC GAATGTTCCA

54541 TGGCGCTGGC CGGTGGTGTC GCCGTGATGG GCCAGCCCAC CGCCTTCGTC GAGTTCTCCC

54601 GGCAGCGTGG CCTGGCGCCC GACGGGCGCT GCAAGTCCTT CGGCGCGGGC GCCGACGGCA

54661 CCACCTGGTC CGAAGGTGTC GGGCTCGTTC TGCTGGAGCG GCTGTCGGAC GCCCGCCGCA

54721 ACGGCCACGA AGTGCTGGCC GTGATCCGGG GCACCGCGGT CAACCAGGAC GGCGCCTCCA

54781 ACGGACTCAC CGCGCCCAAC GGCCCCTCCC AGGAGCGGGT GATCCGCCAG GCCCTGTCCA

54841 ACGCCGGGCT GACGGTGGCC GACGTGGACG CCGTCGAGGC CCACGGCACC GGCACCGCCC

54901 TCGGCGACCC CATCGAAGCC CAGGCCGTTC TCGCCACCTA CGGCCAAAGC CGCCCGGAGG

54961 GCCGGCCGCT GTGGCTCGGC TCCCTCAAGT CCAACATCGG CCACGCGCAG GCCGCAGCGG

55021 GCATCGCCAG TGTCATCAAG ACCGTCATGG CCTTACGCCA CGGCCGGTTG CCGAAGACCC

55081 TCCACGCCGA ACAGCCCACC TCCCAGGTGA ACTGGACGTC GGGCGCGGTG TCCCTGCTCG

55141 CCGAGGCGCG GCGCGTGGCCG GAGACCGGAC ACGCCCGCCG CGCCGGGATC TCCTCCTTCG

55201 GCGTCAGCGG GACGAACGCA CACGTCATCC TGGAACAGGC CCCTGAGGAA GCCGAGGCGA

55261 CCGGGGAGAA CACCGCCGAT CAGGAACCGC CCGTACGCTC GGCGGAGTCC GCCGACCCCG

55321 GCCCGGTCGC CACCGGCCAC GTGGTGCCGT GGCTGCTCTC GGGCCATACG CAGGAGGCGC

55381 TGCGTGCCCA GGCCGCCCGG CTGCTGACCC AGGTGCGCGA GACGCCCTCC GACAGTCCGC

55441 GGGACGTGGG CTGGTCACTG GCCACCACCC GGACCCGGCT GGACCACCGC GCGGTCGTAC

55501 TGTGCGCCGA TGCCGAGCAG GCCGTCGCGG GGCTGGAGGC GGTGGCCTCG GCACGTCCGG

55561 CCCGGTCGGC GGTCACCGGG TCCGTGGCCT CCGGAAAGGT GGCGGTGCTG TTCACCGGGC
```

-continued

SEQUENCE ID NOS: 1-3

```
55621 AGGGCAGCCA GCGGGCCGGA ATGGGCCGCG AACTGCACGG CGCCCACCCG GTGTTCGCGC
55681 GGGCCTTCGA CGCCGTGTGC GCCCAGTTCG GCGACCTGCG CGACGGGGAC GACAAGGTCT
55741 CGCTGGCCGA GGTGATCTTC GCCGAGGAGG GGTCGGCGAC GGCAGCGCTG CTGGACCGGA
55801 CCGAGTTCAC CCAGCCCGCG CTGTTCGCGC TGGAGGTGGC GCTGTTCCGG CTCGTGGAGT
55861 CGTGGGGAGT GCGCCCCGCG TATGTGCTGG GCCACTCGAT CGGCGAAGTG GCGGCGGCCC
55921 ATGTGGCCGG GGTCCTGTCC CTGCCGGACG CCTGCACATT GGTGCGGGCG CGCGGGCGGC
55981 TGATGCAGCA ACTCACCGCG ACCGGGCGA TGGTCGCGGT GGAGGCGGCC GAGGACGAGG
56041 TGGCGCCGCT GCTCGCGGGG AAGGAGCACA AGGTCTCCAT CGCCGCGGTC AACGGCCCGG
56101 CCTCCGTGGT CGTCTCCGGT GACGAGGACG TGGTCACGGC GGTGGCGGAG ACGCTGGCGC
56161 GGCAGGGCCG CAAGACCAAG CGGCTCGTGG TCTCGCACGC CTTCCACTCC CCCCACATGG
56221 ACGGGATGCT GGACGCGTTC CGCGAGGTGG CGTCGCGGCT GGCCTACGCG CCACCCCGGA
56281 TACCCGTGGT GTCGAACCTC ACCGGCGCGG TCGCCGATCC CGAGGAGCTG TGCTCCCCCG
56341 AGTACTGGGT ACGGCATGCA CGTGGCGCGG TGCGGTTCCT CGACGGTGTC CGCACACTGG
56401 CCGACGAGGG CGTGCGCACC CATCTGGAAC TCGGCCCGGA TGGGGTGCTG ACCGCGATGG
56461 GGCAGGACTG TCTGCCCGAG GCGGACGCGG CGTTCGTGCC GTCCCTGCGT CCGGGCGTCC
56521 AGGAGCCGCA CGCGGTGCTG GCCGGGCTCG CCGGCCTGTA CGTACGGGGT GTGCGGGTGG
56581 ACTGGGACGC GATGTTCGCC GGGTCCGGCG CCCGGCCCGT CGCCCTTCCC ACGTACGCCT
56641 TCCAGCACGA GCACTACTGG CTGGAGCGGG CCGCCGGCTC CGGCGACGTG GGCGCGGTGG
56701 GGCTCGGCGA GGCGGGCCAT CCGCTGCTGG GCGCGGTGGT GCAGCTCCCG GAGACGGGCG
56761 GGGTGCAGCT CAGCGGGCGG CTGTCGGTAC GGGCCCAGCC CTGGCTGGGC GAACACGTCA
56821 TCTCCGGGGC GGTGCTGGTG CCCGGCACCG CCATGGTGGA ACTGGCCGTC CGCGCCGGGG
56881 ACGAGACCGG CACCCCGGTG CTGGAGGAGC TGGTGATCGG GCAGCCGATG GTGCTGCCCG
56941 GCGACACCGC CCTCAGTGTC CAGGTCGTCG TGGGCGCGGA CGAGGGCGGG CGGCGTACGG
57001 TGCGGATCTA CTCCCGTACC GACGGGGGCA CCGACTGGAC CGAGCACGCC ACCGGCACGC
57061 TCGCGGCGCA GGGCCCGGCA CCGCTGGACG GGGCCGCGGG CGGGGCCGCC GTCGAGTGGC
57121 CGCCCGCGGA AGCCGAGCCG ATCCCCGTGG AGGACTTCTA CCGCTCGCTC GTCGACGCCG
57181 GATACGCGTA CGGACCGGCG TTCCGCGGGC TCGTCGCCGC GTGGCGCCGG GACGGTGAGA
57241 TCTTCGGCGA TGTGGCGCTG CCGGAGGCGT CCGTCGCGGA GGCCGAGCGG TTCGGCATCC
57301 ACCCGGCGCT GCTGGACGCC GCACTGCACG CGGGCAGCTT CTGTCTGCCC TCCGACCCGG
57361 CGCGACAGGT GACCCTGCTG CCGTTCGCCT GGAACACCGT GCGTCTGCAC GCGGGCGGCG
57421 CGTCCGCGGT CCGGGTGCAT GTCCGCCCGG TCGGCGACGA CGCCTTCTCG GTACGCCTGA
57481 CCGACGGCTC GGGCCAGACG GTGGCCTCGG TGGACTCGCT CACCTTGCGG GCGGTGGACC
57541 CGGCCCAGCT CAAGATCGGC ACGGCCGACG ACGCGCTGTG GACGGTCCGC TGGAGCGAGA
57601 CCTCGCTGCC GGACGGCGCG GTCTCCTGGG CCCCGCTCGG CGAGTCGGCC ACCGGGGCAA
57661 CCGGGGGCTA CGGCGCCACA GGGGACGGCG GAGGCCCAGG GGGCGCGCTT CCCGACGTCC
57721 TCGTGGCCGA TACGCGCGCC TGGGCCGAAG ACCTCACCGG ACCGCCGACC GCGCGGGCCC
57781 GGGAGCTCAC CGGCCGCCTG CTGGAGGAGA TCCAGCGGTG GGTCGCCGAC GACGCCATGG
57841 CCGGGACGCG GCTCGCCGTG GTCACCCGCG GCGCGGTCGC GGTCCACGAC GACACCGAGG
57901 TCACCGACCC GGCCGCCACC GCGCTCTGGG GCCTGGTCCG CTCGGCCCAG GCCGAACACC
```

-continued

SEQUENCE ID NOS: 1-3

```
57961  CGGGGCGGGT GGCCCTGGTG GATGCCGACG GAGCGTGCGA GGAACTGCCC GCCGGGTGT
58021  GGTCCGGGGA CGAGCCCCAA CTGGCGGTGC GCGGTGGCGC CGTGTGGGTG CCACGCCTCA
58081  CCCGGGTCGA GCCCGGCCTG CGCGTGCCCG CGCAGGCGTC GTGGCATCTG GACTCGGCCG
58141  AGTACGGCAC CCTGGACAAT CTGGCGCTGC TGCCCGACGA GGCCGAGCCC GCACCGCCGG
58201  CGGCCGGTCA GGTGCGGATC GAGGTCCGCG CCGCCGGGCT CAACTTCCGG GATGTCCTGG
58261  TGGCTCTCGG CATGTATCCG GGCCGGTCGG TGATCGGCAC GGAGGGCGCC GGTGTGGTGA
58321  CCGAAGTCGG TCCGGGCGTC ACGGGCCTGG CCGTGGGCGA CCGGGTGATG GGCCTGTTCT
58381  CCGGCTCGTT CGGACCGCTG GCCACCGCCG ACGCGCGCAC GGTGATCCGG ATGCCGGAGG
58441  GCTGGTCGTT CGGCACGGCG GCCGGGGTGC CGGTGGCCTA TCTGACGGCG CTGTACGCGT
58501  TGCAGGACCT CGGGAGGGTC CAGCCGGGCG AGACGGTCCT GGTGCACGCC GCCGCGGGCG
58561  GTGTGGGCAT GGCCGCCGTC CAGCTCGCAC AGCACTTCGG CGCCACCGTC CTGGGCACCG
58621  CCCACCCCTC CAAGCACCAC GCACTCCACC GGCTGGGCGT TCCCGCCGAA CGGCTCGCCT
58681  CCAGCCGCGA CCTCGCCTAC GCCGACACCT TCCCCACCGC CGACGTCGTC CTCAACTCCC
58741  TCACCGGCGA GCACATCGAC GCCTCCCTCG GACTTCTCAA CCCCGGCGGC CGGTTCCTGG
58801  AGATGGGGAA GACCGACCTG CGGGAGCCCG GCGAGGTCGG GGCGCGGCAT CCGGAGGTCA
58861  CCTACCGGGC GTTCGATCTC GGTGGGGAGG CCCCCGCGGA GCGGGTGCGG GAGTTGCTGC
58921  ACCAGTTGGT GGAGCTGTTC GAGGCGGGCC GGATCGAGCC GCTGCCGGTA CGGCAGTGGG
58981  ACATCACCCG CGCCCCCGAG GCGTTCCGCT GGATGAGTCA GGGGCGGCAT ACCGGCAAGA
59041  TCGTGCTCAC CCTGCCACGC GCCCTGGACC CGGACGGCAC CGTCCTGGTC ACCGGTGGCA
59101  CGGGCACCCT CGGCGCCACG ATCGCCCGCC ACCTTCTCAC CCAGCACGGC GCACGCCATC
59161  TGCTGCTGGT CAGCCGCCGG GGACCGGACG CACCTGGCGC CACAGACCTG ACCACCGAAC
59221  TCACCGAACT CGGCGCCACC GTCCGCATCA CCGCCTGCGA CACCGCCGAC CGCGACCAAC
59281  TCGCCGCGCT CCTCGCCGAC ATCCCCGCCG ACCACCCCCT CACCGCCGTG GTCCACACGG
59341  CCGGGACCCT CGACGACGGT GTCCTGACCG CGCTCACCCC GGACCGCCTC GACACCGTCT
59401  TCCGCCCCAA GGTCGACGCC GTCACCCATC TCCACGACCT CACCCGCGAC CACGACCTGG
59461  CGGCGTTCGT GGTGTACTCG TCCGCCGCCG GAGTCCTCGG CGGGCCCGGC CAGGGCAACT
59521  ACTCCGCCGC CAACGCCTAT CTGGACGGAC TCGCACAGTG GCGGCGTGCG CACGGGCTCC
59581  CCGCCACCTC GCTGGCGTGG GGCATGTGGG CGCAGACCAG TGGCATGACG GCCGGGCTCG
59641  GCTCCGGCGA TCTGCACCGG GTGCGGCGTG GCGGCATCGT CGGGCTGTCC ACGGCGGAGG
59701  CCCTGGACCT GTTCGACCGG TCGGTGGCGT CCGGGCTGTC CCTGCTGGTG CCGTTGCGGT
59761  TGGACATCGC CGCCCTCGGT GCGGAGGCCG CGGAACCGCC GCCGCTGCTG CGGGGTCTGG
59821  TCCGGCCGGC CCGGCGTACG GCCCGGCCGG TGCCGAAGGC CGGTGAGGGC GGCCTCGCCG
59881  AACGGCTGGC CGGGCTGTCG GCGGCCGAAC AGGAGCGTCT GCTCATCGAG TTGATCCGCG
59941  AACAGGCCGC TTCGGTGCTC GGGTTCCCCA CGGTCGACCC GATCGGGCCG GAGCAGGCGT
60001  TCCGCGACAT GGGGTTCGAC TCGCTGACCG CGGTGGAGCT GCGCAACCGC CTCAACACGG
60061  CCACCGGGCT ACGGCTCCCC GCAACGCTGG TCTTCGACCA CCCGAGCCCC TTGGCCACCG
60121  CCGAGTTCCT GCGGGATCAA CTGGGCGGGC GCGCGGTCGA GGCGGCGCCC CGCCCGGCCC
60181  GGCGTGACCG GTCGGCTCCG GACGGGGCCG AGGATCCGGT CGTCGTGGTC GGCATGGGCT
```

-continued

SEQUENCE ID NOS: 1-3

```
60241 GCCGCCTGCC CGGCGACGTC CGCAGCCCCG AGGACCTGTG GCGGCTGATC GCCACCGGAA
60301 CCGACGCGAT CGGGCCGTTC CCGCAGGACC GGGGCTGGGA CCTGGCCGGG CTCTTCGACT
60361 CCGACCCGGA CGCACAGGGC AAGTCCTACG TACGCGAGGG CGGTTTCCTC ACCGACGCGG
60421 GCGGCTTCGA CGCCACGTTC TTCGGCATCT CCCCACGCGA GGCCCTGTCG ATGGACCCGC
60481 AACAGCGCGT CCTGCTGGAG ACCGCGTGGG AGACCCTGGA ACGCTCCGGA ATCGTTCCCA
60541 CGTCACTGCG CGGACAGGAG GTCGGGGTCT TCGTCGGGGC CAGTGGCCAG GGGTACGGCA
60601 CCGGCCCGGG CGCGGCGCCG GAAGGCTTGG AGGGCTATCT CGGGGTCGGC GGTGCGACGA
60661 GCGTGGCATC GGGCCGGGTG TCGTACACCT TCGGCCTGAC CGGTCCGGCG GTCACGGTGG
60721 ACACGGCGTG CTCCTCCTCG CTGGTGGCCC TCCACCTCGC CGCGCAAGCC CTGCGCTCCG
60781 GCGAATGCAC GATGGCACTC GCCGGCGGCG TCGCCGTCAT GGGCCAGCCC GGCGCCTTCG
60841 TCGAGTTCTC GCGCCAGCGC GGTCTCGCGT CCGACGGCCG CTGCAAGTCC TTCGGCGAGG
60901 GCGCCGACGG CACCAACTGG TCCGAGGGTG TTGGTCTGGT GCTGCTGGAA CGGCTCTCCG
60961 ACGCCCGCCG CAACGGCCAC GAGGTGCTGG CCGTGATCCG TGGCACGGCG GTGAACCAGG
61021 ACGGCGCGAG CAACGGCCTC ACCGCGCCCA ACGGACCCTC CCAGCAGCGA GTGATACGGC
61081 AGGCGCTGGC GAACGCCGGG CTGACGGTGG CCGACGTGGA CGCGGTCGAG GCCCACGGCA
61141 CCGGCACCGC CCTCGGCGAC CCCATCGAGG CCCAGGCACT CCTGGCCACC TACGGCCAGG
61201 ACCGGCCGGG GGACGAACCG CTGTGGCTCG GTTCGCTGAA GTCCAACATC GGGCATGCCC
61261 AAGCGGCCGC AGGCGTGGCC AGCGTCATCA AGATGGTGCT GGCGATACGG CAGGGCACGC
61321 TTCCGCGGTC CTTGCACATC AACGAACCCA CCACCCAGGT GGACTGGACG TCCGGTGCGG
61381 TGTGCCTGCT CACCGATGCC CGCCCTGGC CGGAGACCGG CCACCCCGC CGTGCCGGGA
61441 TCTCCTCCTT CGGAGTCAGC GGCACCAACG CCCATCTCAT CCTGGAGCAG GCACCTCAGC
61501 CCGAGCCCGA GCCCGCATCG AAGGCGGACG AGGGCACGGA CACCCCTGGG CTGGTCACCA
61561 CCGGCGGAAC CACCCCCTGG GTGCTGTCCG CCAAGACCCC GGCAGCTCTG CGGGCTCAGG
61621 CCCGACGCCT GCTGGACCAT CTGGAATCCG ACATGGACGC ACACCCAGTG GACATCGGCT
61681 GGTCACTCGC CACCACCCGC ACCCTCCACG ACCACCGCGC CGTCGTCATC ACCGACACCG
61741 AAGCCGATAG CGACGAAGCC GCAGCTGCTC TCACCGCCCT CGCGACCGGA CAACCCCACC
61801 CCCGCCTCAC CACCGGCCAC GCCACCACCC ACGGCAAAAC AGTGTTCGTG TTCCCTGGCC
61861 AAGGCGCCCA ATGGGTGGGC ATGGGAGCCC AACTCCTCAA GACTTCCCCC GTCTTCGCCG
61921 AACGTCTCCA CGAATGCGCC GCGGCCCTGG CCCCGTACAC CGACTGGTCG CTCATCGACG
61981 TCATCACCGG CACGCCCGAC GCTCCCTCGC TCGAGCGTGT CGACGTCGTA CAGCCCGCCA
62041 CCTTCGCCGT CGTCGTCTCC CTCGCCGCAC TCTGGCAATC CGTGGGCATC CACCCCGACG
62101 CCGTCATCGG CCACTCCCAA GGCGAAATCG CCGCCGCCTG CGTCGCCGGA CACCTCACCC
62161 TCACCAACGC CGCCAAAATC GTCACCCTCC GCAGCCAGAC CATCGCCCAC CACCTCGCCG
62221 GACACGGCGG CATGATGTCC GTCCTCACCT CCCGGGAACA GGTCGAGGAA GCCCTCACCC
62281 CGTGGCACGG CAAACTCTGG ATCGCCGCAC ACAACAGCCC CAACGCCACC GTCATCGCAG
62341 GCGACACCGA CGCCCTGCAC CAACTCCACA CCCACTACAC CGACCAGGGC ATCAGGGCCC
62401 GCATCATCCC CGTCGACTAC GCCTCCCACA CCGGACACGT CGACACCATC AAAAACCAAC
62461 TCCACCAGAC CCTGGCCGAC ACCACGACCG AGCCCGGCAC CATCCCCTGG CTCTCCACCG
62521 TCACCGGACA GTGGATCGAA CCCGACACCG TCGACAGCGG CTACTGGTAC CGCAACCTCC
```

-continued

SEQUENCE ID NOS: 1-3

```
62581 GCCAAACCGT GCAATTCGAG CACACCATCC ACACCCTCGC CAACGACGGC TACCGCACCT

62641 TCATCGAAAT CAGCCCCCAC CCCGTCCTCA CCACCGCCAT CCAAGAAACC CTCGAAGCCA

62701 ACGACACCCC CAACACCACC ATCACCGGCA CCCTCCGCCG CGACGACGAC ACCCCCACCC

62761 GCTTCCTCAC CCACCTCGCC GAACTGTCCA CCAGGGGAAC ACCAATGGAC TGGCCCACCG

62821 CGTACACCGG ATCACAACCC TCCCAAATCC CGCTCCCCAC CTACCCCTTC GAGCACGAGA

62881 CGTTCTGGCT GGACCGCGGC GGTCCGGGCG ACGTCCGTGC CGTGGGGCTG GAGGACACCG

62941 GCCATCCGCT GGTCGGGGCC GTGGTGAGCG TGCCCGACAC CGGAGGTGTG CTGCTCACCG

63001 GACGTCTCTC CCTGCGCAGC CACCCCTGGC TGGCCGACCA CGCCGTCTCC GGCACCGTCC

63061 TGCTCCCGGG TACGGCGATG GTCGAGCTGG CGGTGCGCGC CGGGGACGAG GCGGACACCT

63121 CCACCCTGGA AGAGCTGGTC ATCAGCCGGC CGATGACGGT GCCGGACGAG GGCACTCTGC

63181 ACGTCCAGGT GCTCGTCGGT GGCGAGGACC GCGGGCGCCG CAAGGTGGGG GTCTACTCGC

63241 GCCCGGAGGG CACACGGCAG TGGACCGAGC ACGCCACCGG CACCCTGACC GGACGGGCTA

63301 CCGGCACCCT GACCGCAGGG GCCACGGCCC CGCCGCCCGA GGCCGCTCAG CCGTGGCCGC

63361 CCGAGGGCTC GGAGCCCGTC GCCCTCGAGG GATTCTACGA GCATCTGGCC GAGGTCGGGT

63421 ACGAGTACGG CCCGGCTTTC CGCGGTCTGA GGGCGGTGTG GAAGCGGGAC GACGAGGTGT

63481 TCGCCGAAGT GTCCGTGCCG GAGGAGCAGA CCGGGGTCGC CGGGCGGTTC GGCATCCACC

63541 CGGCGCTGCT GGACGCCACC CTGCACGCCG GGAACTTCTG CTTCCAGTCC GATGGTGAGC

63601 GGCCCACGAT GCTGCCGTTC GCATGGACCG ATGTGCGGCC CCACGCCGTG GGCGCAACCA

63661 CCGTGCGGGT GCGGGCGACG GTGTCCGACG GGACGGGCT GTGCGTACGG ATCTCCGATC

63721 CGCAGGGCGT ACCGGTCGCC ACGATCGGCT CCCTCCAGCT CCGGGAGACC ACACCCGACC

63781 AGTTGCGCGC CCTGTCCGCC GCATCGGGCG GCAATGCGCT GTGGGCGGTC GACTGGGCCG

63841 AGTGCGGGCT CGATGCCACG GAAGCGCGGT GGGCCACGCT CGGGGAGAGT CGGCTCCCGG

63901 ATTCCCCGCC GAGCTACCCC GATCTCTCCA CGGCTGTGGA GGCCGTGGAA AGCGCGGAGG

63961 CCGGAGAGCG GCCCGCCGTG CTCGTCGCCG ACGTGTCCGC CTGGGTTCCG GAGAAGACCG

64021 GACCCATCGA CCGTACGCAC GCGCTCTGTG CCCGGGTCCT GGATCTGCTG CGGCAATGGG

64081 TGGACCGGCG CGAACTCGCG GACACCCACC TGGTCGTCCT CACCCACGGC GCCATGGCCG

64141 CCCACGACAC CGCCGAGGTC ACCGACCCGG CCGCGGCCGC CGTCTGGGGC TTGGTCCGCT

64201 CGGCCCAGTC CGAGCACCCC GGCCGTATCC GGCTCATCGA CATCGACGAC CACTCCCACC

64261 AGGCCCTGCC CACCGCACTC GCCACCACCG AGGCCCAACT CGCCCTCCGC GACGCCACCG

64321 CCTACACCCC CCATCTGACG CCCGCACCCG CCACCACGCC CGAGCCCCTC ACCCTCGACC

64381 CCGAGGGCAC CGTCCTCATC ACCGGCGGCA CCGGCACCCT CGGCGCCCTC ACCGCCCGCC

64441 ACCTCATCAC CCACCATCAC GCACGCCATC TCCTCCTGGT CAGCCGCCAG GGCCCCGACG

64501 CGCCCGGCGC CACGGACCTC ACCACCGAAC TCACCGAACT CGGCGCCACC GTCCACATCA

64561 CCGCCTGCGA CACCGCCGAC CGCGACCAAC TCGCCGCCCT CCTCGCCGAC ATCCCGGCCG

64621 CCCACCCCCT CACCGCCGTC GTCCACACCG CCGGAACCCT CGACGACGCC CTGCTCACCG

64681 ACCTCACCCC GCAGCGCCTC GACACCGTCT CCGCCCCAA GGTCGACGCC CTCACCCACC

64741 TCCACGACCT CACCCGCGAC CACGACCTGA CCGCCTTCGT CATCTACTCC TCCGCCACCG

64801 GCACCCTCGG CACCCCCGGC CAGGCCAACT ACGCCGCCGC CAACACCTAC GCCGACGCCC
```

```
-continued
                   SEQUENCE ID NOS: 1-3
64861  TCGCCCACCA GCGCCACGCC ACCGGACTCC CCGCCACCTC CCTCGCCTGG GGCCTATGGG
64921  AAACCACCAG CAGCCTCACC GCCGGCATGA CCGCCACCCA GCAGCAACGC ACCCGCGACA
64981  GCGGCGTCGT TCCCCTGACC GACGCCGACG GCATGCGCCT CCTCGACACC GCGCTCGCCA
65041  CCCGCCACCC TCATCTCGTC CCCCTCGAAC TCGACCTCGC CGCCCTCCAG AACAACACCG
65101  GCCCGCACAC CCTCCCGCCC CTGCTGCGCA CCCTCATACG CGGCCACCAC CGCCCCACCG
65161  CCCACACCAC AGCCCAGCCC GAGGACGACG CCCCGTCCCT GGCCGAGCAG CTGGCCGCCC
65221  TCGACCCGAC CCAGCGGCAC CAGCGCCTCA CCGCGCTTGT CCGCGCCGAA GCCGCGGCCG
65281  TCCTCGGACA CCCCACCCCG GACGCGGTGG GGCCGGACGA CGCCCTCTTC GAGATCGGGT
65341  TCGACTCGCT GACCGCGGTG GAACTGCGCA ACCGCCTCAA CGCGGCCACC GGCCTCCAGC
65401  TCGCCGCGGC GATGCTGTTC GACTACCCAA CCCCGTCGAT GGCCGCCGAG CACCTCCAGG
65461  AACAGCTCGC GCTGGACGCG GCCACCACGG AAACACACGT GGCGGCCCGG GAAGCGGCGG
65521  AAGACGACGA CCAGAGCACG GAGAGGTGAG ACAAAGCATG TTCGACGTGG CGAAGTATCT
65581  GCGGCGCATC GGGGTGGAGG GGACGCCCCC ACCGACCCTC GACACCCTCC GTCATCTGCA
65641  CAAACGGCAT CTCATGGCGG TCCCGTACGA CAACTCCACA GCCCCCGACC GGCTCCCGGC
65701  CTCGCGGCAT CTGACGAACG TCCCGCTGGA CCTGGTGTTC GGGCATGTGG TGACCGAGGG
65761  CCATGGCGGA GTGTGCTACG AGCTCAACCG GTTGTTCCAC ACGCTGCTGG CGGAGCTCGG
65821  CTACGACGTG CGCATGGTGG CGGCGGCGGT GCGGCAGGCG AACGGGACCT TCGGCCCGGA
65881  GCGGGAGCAC ACCTTCGACC TGGTCCACCT CGATGGCCGG ACCCACCTCG TGGACGTGGG
65941  CTTCCCCGGG CCGTCCTATT CGGAGCCGTT GTACCTGTCC GAAGAAGAGC AGCACCAGTA
66001  CGGCTGCTCG TACCGCGTGA CCGAACACGA CGGCTACCGG GTGGTGGAAC GGCGGCCCAA
66061  GGGGAGCGAC TGGCAGCCGG TGTACCGGTT CCGGCCGGAG CTGGCCGATC CGTCCGGCTG
66121  GGACGCGGTG CGGCTGGACA GCCTGGACGA CTACGCACAG GACTCGGTGC TCGCCGGGAC
66181  CACCTTCCGC AGCCGGGCCA CGGACAACGG GAAGATCGTG CTGATCGGCA GGCGCTACTT
66241  CACCGTCGAG GACGGGGTGG AGCGCACCAA GGTGCTGGTG AAGGCGGACG AATTCCAAGA
66301  CGTGGTCGAC CTGATCCTGG CGGGCGCATG ACCGGGAAGG AGGCGGCAGT GGACACCGCG
66361  CGGGAAACGG ACAGCCTCGA GGCCGAGGTG CTGATCGTCG GCTACGGACC GGTGGGCCAG
66421  CTACTGTCGG TGCTACTGGC CCAGCGCGGG CGGCGCGTGA CGGTCGTGGA GCGCTGGCCG
66481  GAGCCGTACC GGCACCCCCG GGCGGTCGGG TTCGACAGTG AGGCCGCGCG CCTTCTGGCC
66541  TCGGCCGGGA TCGGCGACTC GCTCGACAAG TTCACCGAAC CCGCGCGGGA CCACGCCTGG
66601  CAGAACACGA AGGGCGAGAC GCTGATCGAC CACGAGGTGG CCGACCGGGG GCACTGCACC
66661  TGGCCGGAGG CTTTGTCGGC GTATCAGCCC GCCCTGGAGT CCGCGCTGAT CGAGCACGGG
66721  GAGACGCTGC CGCCGCTGCG GATCCTGCGC GGATACGAGG CGGTGGGACT CGCGGACGAC
66781  GGCGACCATG TGACCTTGAC CGTGGTCGGC CCGGACGGGG AGAAGACGGA CCTCACCGCG
66841  CTGTGGGTGG TCGGCTGCGA CGGCGCGAAC AGCCTGGTAA GGACGGGCGT CGGCACCACC
66901  ATGACGGACC TCGACTTCTC GTACGACTGG CTGATCTGCG ATGTGCGGTT GCACGAGCAC
66961  CGCGAGTTCC GGCCGAACAA CCTGGAGATC TGCGATCCGG CGCGCCCCG GACGGCGGTG
67021  TCCGCGGGTC CTGGCCACCG GCGGTACGAG TTCATGCGGG TGCCCGCGGA CGACCCCGAA
67081  CACTTCGGCA CCGTGGAGAG CGCCTGGGAG CTGCTGCGGC TGTTCGATGT GACGCCCGAG
67141  AACGGCGTTC TGGACCGGCA CGCGGTCTAC ACCTTCCAGG CCCGCTGGGC GGAGCGCTGG
```

SEQUENCE ID NOS: 1-3

```
67201 CGGACCGGAC GGATGGTGCT GGCCGGGGAC TCGGCACACC TCATGCCGCC GTTCGCGGGG

67261 CAGGGCATGT GCTCCGGATT CCGTGACGCG GCCAATCTGG CCTGGAAACT GGACCTGGTC

67321 CTGGGCGGAC ACGCGGCGCC GACGCTGCTG GACACCTACA CCACCGAGCG GCGGGCACAC

67381 GTGCGGCACG CGGTGGAGAT GTCGGTGGGC CTGGGCCGGG TGGTGTGCAT GGCGGACCCG

67441 GCCGCGGCGG CGGACCGTGA CGCGGCGATG CTGGCCGCGC GCAAACGCAA CATCGGCCCG

67501 AGTGCCGCCC GCCGTTCCGT GGTGAGGCCG CTCGTGGACG GGCTGCTACG GCAGGACGGT

67561 CAGGGCCGCC CGGCACCGTA CGCCGGCCAG GCGGGCCCCC AGTGGCGAGT GTGCCGCGCG

67621 GGAACCACCG GCCTGTTCGA CGACGTGGTG GGCACCGGTT TCGTCCTCCT CTACGCCGAG

67681 GACGTGTTCC CCGCGCTGGA CGCGCGGCGG CTGACATTCC TCGACAGCAT CGGCACCCGA

67741 CTGGTGCGCA TGGTCCCCGC GGACACGCCC CCGGCCGCCC TGGGCCACG GGACGCGCTG

67801 GACGTGGAGG ACCGGTACCT GTCCTATCTG TCGGAGATGG ACGCGCTGGC GGTACTGGTA

67861 CGCCCGGACT TCTACCTGTT CGGCATCGCG GAGGACGAGG GCGAACTCCT CTCTCTCGTA

67921 GACGACTTGG CCACCCAGCT GAGCCCGTCA CCCACTCCTT CGTAAGGCTC CCCTGCCTGG

67981 GCATGGCTGG TCCCTTCCCC CAAGTTCCCT GAGGGAAGGG ACCAGTTGCT TTCACGGCCC

68041 TGCGGCCGTC GAAGCCTCAA GGAGCCCCGC GCGGCTTCCG GCATGCGGCG CACGGCCTCC

68101 GGGCTGATGG CGCCGGCCGC CGTACGAGCG CTGCGGAGGC TCGTCGACGA GATGGAGGCG

68161 CTTCAGGTCG ACCGGGCGCG TGAACTCGGC TGGTCCTGGG GCGACATCGC CGGGTCGCTC

68221 GGCGTTTCGC GGCAGCTCGG CGCACCAGAA GCACACGCGG TGGCGTGCGA AGACCCCGCA

68281 TCCGGCTTCG CGGCCGGGGG CGGGGTCTGA TGGCACCTCG GGTGAGGCGC CAGCAAGGGG

68341 CGCGGGGCTG TGTCGATGTG CGGCTCCGCC GGGTGGGCGC GACCAGCCAC GACGGCGCCG

68401 CGGAAGATCG ACGGCAGGTC AGGTCATATC CACCGGAGCG ATTAGGTGTC CGAAGTGACG

68461 CTCTCCCCCG TCCCCGCCGC GCGGCGGCGT TCGTCGCCCG CCTTGACCAG GGCGTATCTG

68521 ATGGCCAGGG CCGCCGCGTT GACCGCGTGC AACGCTTCCT GCGCGCCGGT GTCAGGGTGT

68581 ATCTGGCCGG TGACGGCGGC CGAGGTGCAC TGGGCGGCCT CCAGGCAGGC GACGCACGCC

68641 TCCACGAGGG CGTCCGGGCG TGTGCCGGAG GATCGGCCCA GTTTCGTCAG CAGCCGGGTG

68701 ATATCCCGGT GCGCTTCGGT GATCGGGTCC GCCGCCATCG GGTCAGTGCC CCCGCGTACC

68761 GTCGTCGGCC AACGGCCCTA TGTCCCCGGC CGGGGCCAGG GTGAGGAACC GCTGCTCCCA

68821 CAGGGCGAAC ACCTCGGTGG CCAGTGCGTC CGACAGCCCG CCCACGGTCT TGGCCAGATC

68881 CCCGAGGGTG GTGGTGCCGT CGACCGCGCC GAGCAGTTCG TACAGCTCGG GCGACACCTT

68941 CGCGGACGGG CCGCCGTCGT AGTCGAGGTG GATCTCGTGG GTCTTGGCTC CCGCCGAGGC

69001 GTCCGGACCG GCCGTCCTGC GCTCGACCAG CCGGGTCACC GGGCGGAACC GCGGCACCAG

69061 AACGCCCAGG TCGGGCGAGG CTTTGCCGCG TACCAGGCAG TCCTCCACCA CCAGAACGTC

69121 CAGGTCGGTG GTCAGGAAGC TGGTGACCAC GTCGTCGAGG CTCTGCACGA TGGGTTCGGC

69181 GTTGTTGTTG AAGGAGGTGT TGAGGAGCAC GGGGGTGCCG GTCAGTTCGC CGAATCGCCG

69241 CACCAGGCGG TGGAACCGCT CGCCGGACTC GGCGGAGACG ACCTGTACCC GGGCGGTGCC

69301 GTCCACGTGG GTGACCGCGC CGAGTTCCGT ACGCCGCTCC GGCAGCACCG GCACCACGAA

69361 GGACATGAAC TCGTGGTTGC CATCCGCGCC GGAGAGGTCG AAGTAGTCGC GGGCGGCTTC

69421 GGCGGTGACC ACCGGGGCGA ACGGCCGGAA GCCCTCGCGC TTCTTCACCA TCGCGTTGAT
```

-continued

SEQUENCE ID NOS: 1-3

```
69481 GCGGGTCCGG TTCTCCTCGG GGCGTGCGTC CGCGACGATG CTGCGGTGGC CCAGGGCGCG
69541 GGGGCCGAAC TCGGAGCGGC CGTACGCCCA GCCGAGCACC TGTCCCTCGG CGAGGAGTCC
69601 GGCCGCGGTC TCCACGGCGT CGTCCGGGAA CTCCACATCG ATCAGCGGCG CCCAGTCGGC
69661 CAACCGTGCC CTGATCTGCT CCCGGCCGCC CAGTGCCGGG CCGAGGCTCG CGCTGAGCAG
69721 CCGCTTCCCC GGGCGCTCCA GCGTGCCAAG GCTCGCCGCC GCGGCGTAGG CGGCGCCCTC
69781 GCCCGCGCCC GCGTCGTGCG AGGCGGGGTG CACGAACACC TCGTCGAAGA GTCCGGACTT
69841 GAGGATCAGC CCGTTGAGGC TGGAGTTGTG GGCGACGCCA CCGCCGAAGC ACAGGCGGGA
69901 GTGGCCGCTG GTCTTCGCCC AGTATTCGAG GATGTGCAGC ACGATCTTCT CGACCGTCTC
69961 CTGGAGCGCG GCGGCGAAGT CGCGGTGCGC TTGGGTGAAC GGCTCGCCCT GCGGCGCGG
70021 CCGGAAGCCC TCGGCGTAGA CAGCGGGCT GACCAGGTTC GGCACCATGA TGTTGCCGTG
70081 CAGCTCGTAC TCGCCGTTGT CCTGGAGGGT GTAGAGCTTG GCGAAGGTGT CGCGGTAGGT
70141 CTCCGGGTTG CCCCAGGGGG CCAGACCCAT CACCTTGTAC TCGTCGCCGA AGCCGTAGCC
70201 GAGCAGATAG GTGGCGTTCA GGTAGAGCCC GCCGAGCGAC TTGGGCACCG GGTAGTCGGC
70261 CAGCTTCTCC AGCCGCGTGC CCTCGGCGCG GTAGACGGTG CCGGAGTGCA GTTCGCCACG
70321 GCCGTCCAGC ACCAGGACCA GTGCGGAGTC CATGCCGGAG TGCAGATACG AGGAGTACGC
70381 GTGCGCCTCG TGGTGCGGCA CGTACACCAG CTTCTCGTCC GGCAGGTCCC AGCCCAGGCC
70441 CTCCTTCAGC CGCTGCCGGA TCAGCTCCCG GGAGTAGCGC AGGGGCGCCC TCGGATATTC
70501 GGTGTAGAGG TGGTTGAGGA CGGTGTCGAT GTGGTTCTCG GGAAAGTAGT AGCCCACCGC
70561 GTCGACGTCC TCGGGCCGCG CACCGCCAG GGCCAGGCAC TCACGGACCG CGTTGAGGGG
70621 AAATTTGGTT GTCTTCTTGA TCCGGTTGAG CCGCTCCTCC TCCACGGCGG CCACGAGTTC
70681 GCCGTCGCGG ATCAAGGAAG CCGCCGAGTC ATGAAAGAAC ACCTCTCCGA GCTGCGGCAC
70741 CACATCGGTG TCCGCGGCGG AGAAGTTGCC GTTGAGCCCG AGCACAAGCA CAGTGATCAC
70801 CCAAACCAGT CGGAGGCGAA CGCGAGGATG CGGGGCGGAA GACGCCCGCC GGTCACCGGG
70861 AGCGCGGCAG CGCCGCGTCG GCGAGCTCAG GCGCCGTCAG CCGCAGCGTC GTCGGAGCCG
70921 GCTGGCACGC GGGGGTGAGG TGGAGGCGTT CGACCCCCTC CTCGTCGGGG ACCGCGAGGG
70981 CGACGGTGCA GGCGCAGGTG GTGTCGGCGA ACCCGGCGAA GCGGTAGGCG ACCTCCATCA
71041 TCCGGTTGCG ATCGGTGCGC CGGAAGTCGG CGGCCAGGTG CACCCCGGCC TGCGCCGCCT
71101 GATCGGCCAG CCAGCTCAGC AGGGTGGACC CGGCGCCGTA GGAGACCACG CGGCACGAGG
71161 TGGCCAGCAG TTTCAGATGC CACACCGCGG GGTGCCGTTC CAGCAGCACG ATGCCGACGG
71221 CCCCGTGCGG ACCGAACCGG TCGGCCATCG TGATGACCAG CACCTCGTGT GCGGGGTCGG
71281 TGAGCAGTCC GCGCAGTGCG GAGTCGGGGT AATGCACACC GGTGGCGTTC ATCTGGCTGG
71341 TGCGCAGGGT CAGTTCCTCG ACCCGGGACA GCTCCCGCTC CGTGGCGCGG GAGATGCCCA
71401 TGCGTATGTC CAGGGTGCGC AGAAAGTCCT CGTCGGGCC GCTGAACTCG GCCCGCTCGG
71461 CGTCACGGCG GAACCCGGAC TGGTACATGT TCCGGCGCTG CCGCGAGTCC ACGGTGACCA
71521 CGGCGGGGCT GAACTCGGGC AGCCGGGTGA GCCCGGCCAG GTCCTCGGCC GCGTAGCAGC
71581 GCACTTCGGG GAGCCGGTAG GTGACCTCGG CCCGTTCGGC GGGCTGGTCG TCGACGAACG
71641 CCATGGCGCG GTCGGCGAAG TTCAGCCGAT CGGCGATGGC GCGCAGCGAT GCGGACTTGG
71701 GGCCCCAGCC GATGTGCGGC AGTACGAAGT ACTCGGCCAG GCCCAGCGCT TCCAGGCGCT
71761 CCCAGGCGTG GTCGTGGTCG TTCTTGCTGG CGATCGACTG GAGAATGCCG CGTTCGTCGA
```

-continued

SEQUENCE ID NOS: 1-3

```
71821 GGGTGGTGAT GACATCGCGC ACCCACTCGA ACGGCAGCAC CTCGCCGTCT TCGAGCAGGG

71881 TGCCGCGCCA CAGTGTGTTG TCCAGGTCCC AGACGAGACA TTTGACGGCC GTCGGCGGCT

71941 CGCTCACGGG CTTCCCCTCC GTCATGCTTG CACCTTCTTC CGCGTGTGCT GGGCGAGGAC

72001 GAGCTGGCAG ATCTCGCTGG TGCCCTCGAT GACTTCCATC AGCTTCGCGT CGCGGTAGGC

72061 CCGGGCCACC ACATGGCCGT CGGATGCCGC GGCCGACGCC AGGAGCTGTA CGGCGCGTGC

72121 CGCGCCCTCG GCGGCCTCGC GGGACGCGAC GTACTTGGCG TGCACCGCGT CGACCGCCAT

72181 GTCGGGCGAG CCGGTGTCCC AGGAGGCGCT GGCGTGTTCG CAGGCCCGGG TGGCGTGCCG

72241 CTCCGCGACG TACAGTTCGG CCAGGTGCCG GGCCACCAGC TGGTGCTCGG CGAGTTTGCG

72301 GCCGGACTGT TCCCGGCTGG CGGTGTGCGT GGCGGCGGCG TCCAGGCAGG CGCGCAGGAT

72361 GCCGACGCAC CCCCACGCCA CGGACATGCG CCCGTAGGTG AGCGCCGCGG TGGTCGCCAG

72421 GGGCAGCGGC AGTCCGGTGC CACCGAGTAC GTGGCCGGCG GTACCCGGA CCGCGTCCAG

72481 GGTGATGTCC GCGTGGCCGG CGGCGCGGCA GCCCAGCGGG TCCGGCACCC GCGTGATGCG

72541 GACGCCGGGG GCCTGGGCGG GCACGACCAC GGCCGCGGCG CCGCCGCGGT ACTTCCCGAA

72601 CACCACCAGC AGGTCGGCGT AGTGGGCGGC GGTGATCCAC ACCTTGCGCC CGGTGACGAC

72661 CACGTGTGTG CCGTCGTCGG CGATCTCGGT CTCCATCGCC GCCAGGTCGC TGCCCGCCCC

72721 GGGCTCGCTG AATCCGACCG CCGCCAGGTC ACCGGAGGTC AGCCGGGGCA GAAAGGTGCC

72781 CCACTGCTCC GCACCGCCCA GCCGCCGTAC GGTCCATGCC GCCATGCCCT GGGACGTCAT

72841 CACGCTGCGC AGCGAGCTGC ACCGGGCGCC GACCGCCGCG GTGAGCTCCC CGTTGGCATG

72901 GCTGTCCAGT CCGGTGCCGC CGTGCTCGGC GCCGACCTGC GCGCACAGCA CACCGGAGGC

72961 GCCGAGTTTG ACCAGGAGGT CGCGGGGCAG CTCCCCGGCC AGGTCCCAGG CGTCCGCCCG

73021 GTCCCCGATC AACCCGCTGA CCAGCTCCGT ATGGCTGGTG GCGGCGTCGG TCACGGCTGT

73081 GCCCCGCGCA GCCGCAGGAC CATCGTGGTC ATCGCGTTGA CCGTGCGGAA GTTGTCCAGC

73141 GCCAGGTCGG GGCCGGTGAT CACCACGTCG AAGGTCGACT CCAGGTGCAC GACCAGCTCC

73201 ATGGCGAACA TCGAGGACAC GGCGCCGGTG CCGAACAGGT CGGTGTCCGG GTCCCAGGTC

73261 TGCTTGGTGC GCTGTTCGAG GAACTGCTGC ACCTCCTGCG CCACCGTCTC GGCGGTGTGG

73321 CTGCCCGGCT CGGATGAGAT GGTCACGCCA GTTCCTTCCC GTATGCGTAG AACCCGCGGC

73381 CCGACTTGCG GCCCAGGTGG CCGTCGCGGA CCTTCTTCAG CAGCAGTTCG CACGGCGCGC

73441 ACCGGGCGTC GCCGGTACGT AGCTGCAGCA CGCGCAGCGA GTCGGCGAGG TTGTCCAGGC

73501 CGATCAGGTC CGCGGTGCGC AGCGGCCCGG TGCGGTGGCC CAGGCAGTCC CGCATGAGTA

73561 CGTCCACGGC CTCCACCGTC GCCGTGCCCT CCTGCACCAC CCGGATCGCG TCGTTGATCA

73621 TCGGGTGCAG CACCCGGCTG GTGACGAACC CCGGCCCGTC GCCGACGACG ACCGGCTTGC

73681 GCTCCAGCGC ACGCAGCAGA TCCGTCACGG CGGTCATCAC CGCTTCCCCG GTACGGGGC

73741 CGCGGATCAC CTCCACCGTC GGGATCAGAT AGGGCGGGTT CATGAAGTGG GTGCCGACCA

73801 GCCGTGCCGG ATCGGCGATA TGACCGGCCA GTTCGTCGAT CGGGATGGAG GAGGTGTTCG

73861 AGATCAGCGG CACCCGCGCT CCGGTGAGCC CGGCGACCGC TTCGAGCACC TTGGCCTTGG

73921 TGGGGGTGTC CTCGGTGACG GCCTCCACCA CGGCGGTGGC GTTCCGGCCG TCGGCCAGGG

73981 ACGCGGTGAC CGTCAGCTCG CCCTGCGGGC GACCGGCCGG CAGGGCTCCC ATGAGCTGCG

74041 CCATGCGGAG CCGTTCGGTG ACCGCGGCCC GTGTTCGGCC GGCCTTGGCC TCGTCCACCT
```

-continued

SEQUENCE ID NOS: 1-3

```
74101 CGACGACCGT CACCGGGATT CCGTGCCCGA CGACGAGAGA GGTGATTCCC AGTCCCATCG
74161 TTCCTGCGCC CAGCACCGTG AGCCGCGGCG CTTCCGCATC TCCGCTCATC AATCGCCTCC
74221 GCAGCGCGTT GTGAACAACG TGCCGACCAT GACACGCGCT TCCGCGTTCA CGGTATTCTC
74281 CGGGCGGTCA CCCAAATCCC CTAAGGATCC CCCCTATACC CCCCTCAGCC GGAATATGAG
74341 TTCCAGCATT CTGGAAGACG CCATTGCGCG GCGCATCGAC GGATTCTTAG CATGGGCCGC
74401 ATTGCCTTTC CCTGAACCTT CCCTTTTCAG CTTTGCGGGG TGCGGAAATC CAATGGCTCA
74461 GCAAGTCGAT GTGACCGAAG AAATTCTCGG ATATGTCCGG GAACTGTCCC TGCGCGATGA
74521 CGAGATTCTG GCCGGGCTGC GGGCACAGAC CGCGGGTCTG CCCGCCGCGC AGGCCATGCA
74581 GGTGATGCCC GAGGAGGGCC AGCTCCTCGG GCTGCTGGTC AGGCTCGTCG GCGCCCGTTC
74641 GGTGTTGGAG ATCGGCACCT TCACCGGATA CAGCACGCTG TGCATGGCGC GGGCCCTGCC
74701 GGCCGACGGC ACGCTGGTGA CCTGCGACAT CACGGCGAAG TGGCCGGGGC TCGGCCGCCC
74761 GTTCTGGGAG CGCGCCGACG TGGCGGACCG CATCGACGTG CGCATCGGCG ACGCCAAGGA
74821 GACACTGGCC GGACTGCGGC GGGAGGGCCG GGAGTTCGAC CTGGTCTTCA TCGACGCGGA
74881 CAAGACCGGA TACGCGCACT ATTACGAGGA GTCGCTGGCG ATGCTGCGGC GTGGCGGGCT
74941 CATCGTCCTG GACAACACCC TCTTCTTCGG CCGGGTGACC GACCCAGCCG CGCAGGACGC
75001 CGACACCGCC GCCCTGCGCG AGGTGAACAA GCTGCTCCGG GAGGATGGCC GCGTCGAGAT
75061 CAGCATGCTC ACCGTGGGGG ACGGCATCAC GCTCGCGGTC AAACGCTGAG TCCGCGGCTG
75121 AGCGTCTGCG CGGCTGAGCG TCTGAACGTC TGAACGTCTG ACGGCCATGT TCCGGGGGTC
75181 TCCCGGGACA TGGCCGTCCG CGCGGCTCCG CTGTCAGGCG CGCCGCGCCG CGGTCACGCC
75241 AACTCCGGCC GGTCGACGTA CAGTTCGGTG GGCAGTTGCT CCCGGTGCTT GATGTCCAGC
75301 TTGCGGAACA CCCCGGGTCA GATGCTGCTCC ACCGTGCTGG CCGTGACGTA CAGCTTCCCG
75361 GCGATCTCCC GGTTGGTGTA GCCCATCGCG GCCAGCGACG CGACACGCCG TTCGGAGTGC
75421 GTCAGCCGCT CGATCGCGGT GTCCGACTTC GGCGTTGGTG CGGTGGCATG GTGCTGGTCG
75481 TCGGCCGGCA GCCACTCCTC GTACAGCGAC GCCGCGTCGC ACATCTTCGC CACATGCCAG
75541 GCCCGGCGCA TGGTCCGGCG GGCCTGCTTC TTCTCACCGA GCGCGTGGTA CGCCTGGCTG
75601 AGGTCCCACA GCGTGCGGGC CAGCTCGTAC TTGTCCTCCT GCTCGGTGAA CAGGCCCACC
75661 GCCTCGTTGA GCAACTGCGG CCGCCGCTTC GCCGAACTGG TGGCCGCCAG AAGACGCAAC
75721 GACTGCCCGC GGGCCCGGGC GCCGTCCGTG TGCGGACGGC TGAGCTGCTG GTACACCAGG
75781 ATCCGGGCCT GGTCGTGGTT GCCCTGCGCC AGCCATGCCT CCGCCGCCCC GATCCGCCAC
75841 GGCACCGGGT CGCAGCCGCT GCTCAGCCCC CAGTCGGTGA GCAGTTCACC GCACAGCAGG
75901 AAGTCCGCGA GCGCGGCCTG GTGCCGGCCG GCCGCCAGGA AGTAGTGGCC GCGCGCGTAC
75961 AGGTAGTGCA GCCCGTAGGA GCTTTTGAAC ATGGCGTTGG CACGGTCTG CGCGACATGG
76021 AACCCCGCCT CCTCGTGCCG CCCCATCCGC GTACACGCCA GGATGAGGGC GCCGAGCGGC
76081 AGCCCGATCG CGACACCCCA GGCGCCGGGG GAGGCGTGGG TGAGGGCGGC GCGGGACTGC
76141 TCCGCGGCCT CGGCGAGGTC ACCGCGGCGC AGTGCGATCT CGGACCTGGC CGCCGACAGC
76201 ACCGCCTGCC GCATCGGGAC GTGCGGTCCC CCACCGGTCT CGCCGAGCGC ACCCTCGCAC
76261 CAGGCGGACG CCAGGTCGTT CCGGCCGCCG TAGACCAGGG CGAGCAGGGC GAACAGCCCC
76321 GCCTGCTCGT GGCATGCCGG GTCGTGCCCG AGCTGCAGTT CGCGCAGCAC CTCCTCGGCC
76381 CGCCGGACGG TGTCATGGGT CTGCCCGCCG GTGAGCACGT CGGCCAGGAC GGTGCCGGCC
```

-continued

SEQUENCE ID NOS: 1-3

```
76441 CGGGGCCACA CCGCCGCCCG TGTCGCCGCG GAGCCACCGT GGTGTGCCGG GGCCGCCCGC

76501 CGCTCCGCCA GCCAGGGATA GGTGCAGGTG AGTGCCGCCT CGATGGCATG GAGCTGGTCC

76561 GTGGCCGCGG GGTCCTCGCG CAGGTGGGCG AGCAGCCCCT CCACCTCGCT CAGTCCCCCC

76621 TTCCACAGGA GCTGCATGAG CAGGGTGACG CTGTCGGGGA GGCCGAGCCG GCCGGCGCGG

76681 ACGGCGGCGT ACAGCGGTGC GTGGTGCCGC GTGGCGGTGG ACGGATTGAT CTTCCATTCC

76741 GCCCCGGCGA GCTTCGCCTG CAGGGCTGCA CGGCGCTCTT CGTGCGGGCA TTGCTCGAAG

76801 GACTGCTCCA GTAAGTCGAC GGCGATGGAC GCCTCTTCGC CCACCGCCAC CTGCTCGGCC

76861 ACTTCCAGAA GCACCTCGGC CGACCACGAG TCGGGGATCT GCCCGGCCCG CACCAGATGA

76921 CGGGCGATCG CGGTGGCGGG CCTGCCCTGG TCGTGCAGCA GCCGCGCGGC CCGCTGGTGC

76981 AGGGTCCTGC GGGCCTGTGC CGGCATGTCG TTGAGCACGC TCAACCGCGC CGCCTCCTGC

77041 CGGAACTCGC CCTCGTCCAT CAGTCCGGCC CCGGTCAGCG CCGCGAGCAC CTGGCTGATG

77101 GGCTCGGGCT CGTGTCCGGT CATCCAGGCG AGGTCGGCGG CGGGCAGGGC GGATCCCACC

77161 ACGGCCAGTG CGCGCACCAC GTCCAGGAAG ATCGGCTCAT TGCGGTGCAG GCAGCTCAGG

77221 AAGGACTGGC CGTAGCCGGC CTGGCTGGCC TCGCCGTGTT CGCGATAGTC GGACAGCAGA

77281 GTGTGCAGCA GCAGCCGGTT GCCACCGGTG GCGGCGCAGA TGTCGCCGAC GTGGCGGCGC

77341 GCGGTCTCCC CCAGCTCCGC CACGACCACT TCGGCCACCT GGCCGGGGGA GAGCGGGCCC

77401 AGGCCGATGC GGCGCAGGTG CTGGGCGCGC AGCAGTTCGT AGCGGAGCGG CAGGGACGAC

77461 GGCAGGCTCA AGTCGTCGGT GAATACGGCC GCGATGCGCG CCGAGTCCAG GCGCCGCACC

77521 AGTTGCAGGA GGAAGTGTGC GGAGGCCGCG TCGCTGTGCC GGACATCGTC CACGGCGACG

77581 AGCAGCGGCG TGTGTTCCGC GTGGTCGATC AGCGAGGTGC ACAGCCGGTG GCACAGCCGG

77641 GCGATCCCGG CCTGGTCCAG CGGATCGCCG GCCGCGCGGA GGATGTCCGG CAGCCCCGGT

77701 ACCTCGGGCA GCCCGCCCGG TGATTTCCAG GCGCCGCGGG CCAATTGTGA GACGACCCCG

77761 AAGGGAAGGT CCCGCTCGCT GGGGGAACAC GTCGCTGTGA CGGTGAGATA GCCGGCCTCG

77821 GAGGCTCGCT CGGCGAACGA CCGGAGCAGG GTCGTCTTCC CGCATGCCAG CGGTCCGTCC

77881 ACGAGAAGAG CCTGCCCGGG CCGCACCAAA GAGTCACCGA ATGGATGTCC GAGGTACGCC

77941 GCGGTATGCA ATACCCCGCC CATCGGACGG GAATTCGACT CGGTATTCAA CGGCATGGCA

78001 TAGCTGTAGG GCATGGTGAT GGTCCCCGAT CGAGGTCGAC GGAATACGGA CTCGCGGCCC

78061 TTGAGTCAGA CCAAATTGTT GATCGGGACA CGATTCCATC AGCACGCCCC CGCCCGCCTC

78121 AACCCCTACC GGAACCTCCG CCCCCTAACC GGCGCCACCA CATCTCGTTC TCTTCATCGC

78181 GCCGTCAGTT ATCCGTGGCG GGCGCCGCAC GGTCAACCCC CTATCGAGTC CGTGCGCCCC

78241 TAAAACGTAT GCGGAGAAAC GTCCAGGCGG CTCGGATACC GTGACGCGTC ACCATGCGGG

78301 CGCGCGGGGC ATCGCCGCGA GGGTGGCGCC GACGGTGTCC TCGGCGATCC CGCGCACCAG

78361 TCCGGGCCCC GCGGGGCTAT CCAGGACGAA CGTCAGCCCG TCGGTGGCCT TCTTGTCCAG

78421 GCGCATCAGC TCCACCAGCT CGGACACGGA GACATGCGGG GGCAGCGCGG TCGGCAGGCC

78481 GTAGCGGGCG ACCACGTCAT GATGCTCGGC CACGCGCTCC GGGCCGATGC GCCCCAGCGC

78541 GCCGGCGAGC CGGCCGGCGA AAACCGTGCC GATGGCCACT CCCTCCCCGT GCCGCAGCGC

78601 GAACCCGGTG GCACGTTCCA GCGCATGCCC CAACGTGTGT CCGTAGTTGA GGAGGTGGCG

78661 CAGGCCCGAG TCGCGCTCGT CCGCGGCGAC GATGCCCGCC TTGAGCGTCA CACTGGCCGA
```

-continued

SEQUENCE ID NOS: 1-3

```
78721  GATCTGGTCG AGCAGCGGCA GCCCGTCGAG ATCGGGCGCG CCGATGAAGT GGCAGCGGGC
78781  GATCTCACCG AGGCCGTTGC GCCATTCCCG TTCGGGCAGG GTCTTCAGAT GTTCGAGGTC
78841  GCAGAGCACG GCCGCGGGCT GCCAGTAGGC GCCGACCAGA TTCTTGCCCT CGGGCAGATT
78901  CACCGCGGTC TTCCCGCCGA CGCTCGCGTC CACCTGGGCG AGCAGCGAGG TCGGCACGTG
78961  TACGACCGGG GTGCCCCGGT GGTAGAGGGC GGCGGCCAGG CCCACCGTGT CGGTCGTGGT
79021  GCCGCCGCCA CAGGACACCA CCACATCCGA GCGGGTCAGT CCGAATCCGA CGAACCGGCG
79081  GCACAGATCG GTCACGGCGG CCAGGTCCTT GGCCGCCTCC CCGTCGCGGG CGGGTACGAC
79141  GAGCGAGGGC ACTCCTGGGT CGGGGGTCTG CTCGGCGGGC CGCGCGGTGA CCACCACCGC
79201  CCTGCGCGCG CCCAGGGCG CCACCACCTG TGGGAGCAGC CGCTGCACAC CGTGTCCGAT
79261  GTGCACGGTG TAGGAGCGTT CGGCCAGCCC GACGACGACC TGTCGGGCGG GGGAAGCGGA
79321  ACTGGCGGCC GGACTGGAAG TCGACGTGGT CAAGACTGCT TTCCCATCGC TGGCGCGGCC
79381  CCGGCGAGAA GCCGTCTCGC CGGGGCCGGA ATCGGGTGCG TGCGGAGCCC TTTTCAGTCC
79441  TCGACCGCGA TCGCGGCGGC CGGGCACAGG AACGAGGCCT CGGCGACGCT GTCGCGCAGC
79501  GCGAGCGGCG GCCGCGGGTC CAGCAGGACC ACTGTCCCGT CCTCCTCCCG CTGGTCGAAA
79561  ACCTCCGGCG CCGCCAGCGC GCAATGCCCG GCCGCGCAGC ACTTCTCCTG ATCCACCGAG
79621  ACCTTCACCA TCGTGTTCCC CTCATCATCC TTTCTGTCATC CGTTCCGCGG TCACCAGGCG
79681  ACGGGCACAC GGGCGACGCC GAAGTTCATC GACTCGTACA AAAACGCCAG GTCGTCGAAC
79741  GGGACCTCCA GGCGGAGCGT CGGCAGCCGG CGCAGCAGGG TCTCCAGGGC GATCTGGAGC
79801  TCGACCCGGG CGAGGGTCTG CCCCAGGCAC TGGTGCACTC CAAAGCCGAA CGCGACATGT
79861  TCGCGGGCGT TCGGCCGGCT CAGGTCCAGT TCGTGGGCGT CCGCGAAGTG GGGGTCGCGG
79921  TTGGCGCTGG GCAGATTGAT GATCACCCCT TCACCGCCCG GGATGAGCAC CCCGCCGACC
79981  TCGACGTCCT CGGTGGCCAC CCGTCCCGTG CCTTCCTGGA CGATCGTGAT GTACCGGAGC
80041  AGTTCGTCCA CCGCGTTGCC CATCAGCCCG GCGTCCGCCC GCAGCCGGGC GAGCTGTTCG
80101  GGGTGGCTCA GCAACAGGAC GGTGGACAGG GCGATCATGT TGGCGGTGGT CTCGTGCCCG
80161  GCCAGCAGCA GCACCAGGGC GGTGGCGACC ACCTGCTGCT GGGTGAGCCC GCCCGTCAGC
80221  TCCTGGTCGA CGATGAGCCG GCTGAGGAGA TCGTCTCCCG GGTCGGCGCG CTTGGCCGCG
80281  CACATCCGGG CGACGTAGTC CACCATGACG CCGAGCGCGG CGCCCATCTC CTCGGCCGAC
80341  GCGGTGAAGT CCATGACGCC CTGCGACGCC TGCTGGAACT CCGCGAAGTC GGCGTCCGAG
80401  ACCCCCAGCA TCACACCGAT CACCTGGGAC GGCAGGGGGA AGGCGAAGTC GGCCACCAGG
80461  TCGGCCGGCG GCCCCTGGGC GATCAGCCGG TCCAGGAGGC CGTCCACGAT GCCCTGGATC
80521  ATCGGCCGCA TCGCCTCGGT GCGCCGGATG GTGAAGTTCG CGGTGAGCAT GCGGCGGATC
80581  CGGGCGTGCT CCGGATCGTC CATCCTCCCG AGGTTGAACA CCTCGGCCGG CACCTCGAAC
80641  TTCACGAAGC GCGGCATCGC CTTGTGCGTG CCGTCGGCGC TGAACCTGCT GTCGCCGAGC
80701  GCGGCCCGCG CCTCGTGATA GCCGGTGACG AGAAACGGGG TGCTGCCATC CCACATCCGC
80761  ACCCGCGTGA CGGCGGACCG CTCGCGCAAC TCCTCGTATC CAGCGGGGG TGAGAACGGG
80821  CATGCAGCAG CCCGCGATTC GGGGTAGTCG CGTATCTCGT CCATGCCTGT CCGTCCTGTC
80881  CGTCGCTTCG TCGCCACCAC TGCGCCGCCC TACGGATGGA CAAGTCTGGT CCGCGCACCC
80941  GCTCCCCACT CCCCTAACCA CTCCCCTATG CCCCCTTGGC TTGAGGGCAG GTATCCCCCC
81001  TTGCCTCGGC GGCAGGACAC TCAGCAGGAG GACGATCCGG TGGCTCCGAT GAGCAGCCAC
```

| SEQUENCE ID NOS: 1-3 |
|---|

```
81061 AGACGACGCG ACAGCTCCTG CCGATTTCCC ACGGAGAGCT TGCGGTAGAT GCGCGTCAGA

81121 TGCTGCTCCA CGGTGCTGAC CGTGATGTAG AGGCTCTTGG CGATCTGCCG GTTGGACATC

81181 CCCGACGCGG CCAGGGTCGC CACGCGCCAC TCGGCCTCCG AGATAACGGG CTGCTCTGCG

81241 CCTTCGGCCG ATGCGCCGGG CTCTCTCTCC TCGGACTCCC CGGCGGCTTC CGACAGTCGA

81301 GCGTCCACGG AGCTCTCGGC GCCGTCCACG ACCAGGTCCC TGCGGCTCTC GTGCTGGGCG

81361 CTGATCCCGC ACTCGTCCAT CAGCTTCTGC GCCTCATGCC AGGTGGTGCG AGCCTGTTGG

81421 GTCTCTCCGG TGCTGAGGAA GTCCTGGCTG AGCTCGGCGA GCGTACGGGC GAGTTCGAAA

81481 CGGTCGCCGT GCTCGCGCAG ACACTTGGCG GACTGATAGA GGAGCAGCCT GCGCTTGTCC

81541 GGGTCCTCGG CCATGGCCAG AACGCGCAGC GCTCGGCCAC GGGTGCTCAA GGGGCGGTCG

81601 GGCGAGAGCT TGAGCTCTTC CAGGGCGAGT CTTTTGGCCT CCGCCGGCTC CTGGACATGC

81661 AGATACGCCT CGGCGGCGTC GATGCGCCAG GGCGCCAGGT CGCCGAAGTC CACGGGCCAC

81721 TGGTCCATCA GCATCCCGCT CACCATGAAA TCGCTCAGCC CGGCATAGGA GCGGTTGGTG

81781 GCCAGACAGT ACTGTCCGCG AGCCCGGAGG TACTCCAATC CCACAACGCT GTCGAACATT

81841 TCCTTCGGCA CCCAGTAACG CAGATATCGC TCGGCCTCAT CGAGTCTGCC GATGGCGGTG

81901 TGGGCCGCCA CCAGAACGGA GAGCGGCAAT CCGATGGCGA CGCCCCATCC GCGCGGGGGG

81961 ATGGAATTCA GTGCGGTGCC GGCGAAATCG ATGGCCGAGG TGAAGTCCCC ACGGCGGCAT

82021 CTGATGTAGG CGCGCATGGA CAGGGCGACG GCGCCGGGCG TCTTCATGTT CAGCTTGTCG

82081 GCCGCGGTGA AAAGCGCGCC GCACAGCCGG TCCGCCGTTT CCGCTTCTCC TCTCGCGGCT

82141 AATGCCCAGA CCATCCGGCA GGCGTATGCG TACGCGAACC AGAAGTGATT GGAGGGCGAC

82201 AACAGATGCA TGGCATCGGG AGAGAAGTCC GCCACCTGCC GGGGATCCTG GAAATGCCCG

82261 ATCTCCATGC CCAGTTCGCC GACGGACAGC TGCAGACCGT GCTCCAGGTT GGCCGCCCAC

82321 AGCCCGTCGA CTTCCCCGTC CGAGAGAGGC TGGTCGGGGA AGTCATGGAT CAGGGTCGGT

82381 TTAAGGAAGG TGGCCCACTG CCGGGTCACC CGCAGAGCGG CCATGCTGGA CGCGTTATCG

82441 GTGTCACCAC CGCCCGACAG CCACTTGAAG GCTTCTTCCC CATCGCTGAA CCGGCCGAAC

82501 CACAGCACCA TGAAGAGCAG GAAGCACAGA TACCGCTCGG GGATGTCGGC GGGGAATTCC

82561 TCCCGTATCG CGGCCAACAG GCGGTCCAGT TCGGGTTCGG CGGTCGCCGG ATTGCTGGAC

82621 CATAACGCCC CGACCAGCGC CATGAGAATG TCCATGTGCT CCCGCCGGCC GAGGTCCGCG

82681 CGGGCGGCGA GCCGCAGGCC GGCGATCGCT TCCTCCGTAC GGCCGTGGTC GAGATTCTTC

82741 TGGGCCGCGT GCCAGAGCAC TGTGACGCCT TTTTGGTCGG GCGTTTTATC GGCGGTGACC

82801 AGAAGTTCCG CCACCGCGAT CGGGTCGGCC CCGTCGGCAT ACAGAAGTTC GGCCGCTTTC

82861 GCGCTGAGGC GGGCCCGGTC CTCCGCGGGC AGCGTCTCCA GCGTGGCGTA TCGCGCCGCG

82921 GGGTGCCGGA AACGTCCGTC CTCCAGCAGT CCCGCGGAGT TCATGATGGT GATGGCCCGG

82981 GCCGCGCGTT CCTGGCCGCA TTCGAGCAGA TTGGCCACCC GCCACGGGCT GCCGTACCGG

83041 TCCAGCACCG CGAGGGCCTG TGCCACCTGG AGCAACGCCG GATGGGATAA CAGACACCCG

83101 CGATAGGCCT CCTGGAACTC CGCACCGACA GTGACAGCAG TCTCCGGCCC GCCCGGAGCG

83161 GCTTGGAGAT GGTCGCGCAG CAGGGCCTTG ACCAGTCTGG GATTGCCACC GCTGACGGCG

83221 TGGCAGGAGG CGCGGATCCG GTCGGCCAGG TCGGCGTCGC TGTGCCGCTC CAGCAGGTAT

83281 CCGACCCCGG ATTCCGGGAG TGTATCGATC TTGATCTTGT AGAACTCGTG GAAGCCGTGA
```

-continued

SEQUENCE ID NOS: 1-3

```
83341 GTCGGGGCGC ACAACGGATG TGTCTGCCCG CCGGTCATCA CGACGAGTGT GCGAGTGCCG
83401 GACGCATGCC TGGCGATATA CAGAAGGCAC ATGAGGGAGG GGTAGTCGGC ATGCTCGGCA
83461 TCGTCAATCG CGATGATCAG CTGCTTGCCG CCCGCGATAC GGTGCAGCAC ATCGGATATT
83521 TCACGGACCA GGCTTCTCAG CATGCCGGGT TCGGCCTCCG AATACCGCTC TCCGGCAGTC
83581 CTCCAGCGCG CCACGACGTC CAATTCGCCC ATGAACGCGG AGGACCAGAT CAGCCGTTCC
83641 ACTATGTTGA ACGGGATGGC GGTGTCGTCC GCGAATCCGG ACGCCGTAAG ACAGACCGCA
83701 CCCGACTCGG CCGCCTGTTC CTTCAGACAG CCCAATAAGG AGGTCTTTCC GACACCGGGC
83761 CCCCCGGTCA CTTGGAGAAG CCCGCCGTTG CCTCGTGCTG CCGCGTCGAG GACGTCGCGA
83821 AGCTCGAATT GATAATCTGT CAGTCCCATA CTCATCAGTC CTCGCTGTGG GGGTGTGCGT
83881 CTGAGCGATG AGTTGATCTC CGCAGTCATC CCACCCTGCG GAAGAAGGCT TCTCTGACGA
83941 GACAGATAAC CGCTGCGCCG ACGGCGGCCG ATTCCCTGAT CTGGATCACC TCCGGTGGGA
84001 GCCCATGTCC TTGACGTTCA TACAAGCAGA GTCACAACCG GAGCGAAACC TTCCACCGAT
84061 CATGATGAAC CACGGTTTCC GACCCCCGTG TGAACGTGCC TGCCCGAGCG GGCGGCCCCC
84121 TTCCTCGCAC CCCCGAGAAG GGCGGGGCGC CACCGGTGCC GACGCGCAGG AGAAATGCGA
84181 TGTGCGGCAT GCCGACGCGA ATGCACCTCG GACTCTGAAC CGGTTATGGA CCCGGCAGCA
84241 TTCCTTGCCC TGTGCAAAGC TGGCGGTTTA CCAGCAGCCG CCCCGGCCGG TCGCCGCTCC
84301 ACGCCCGTCC CAGCGGGCTC CGGAGCGGCA AGTGCCCCAC CTGCGGTCAT CCCCCGGTTG
84361 CCTCAAAGTC ATGTCGCGTA CCATTCCCGG CAACCTCCTC GCCCCTCAGC AGATATGTCT
84421 GCCCCCGACT CGCGACGGAG ATACGGGGAT TGACCCCTAT ATGATCACCG CGACAGCGCG
84481 ACCATAAACG GCCGCCGCCC CATGATTCCC CTAAACTCTT CGCCGTGATT TGGCCGGGAT
84541 TTATCTGCCT GCAAAACGGC CGAAACGGGT GCGCCGTGGA CCGAGCCCGG GGCCGGACCC
84601 GCGGCATACG ACGCCGGAAG TCCTGGCTCC TGGCCACTTC AGAGACGAGG GAGCGTGAAC
84661 TGTGACCGTC AAGGGCGCGT TGTTCGACTT CTCCGGGACG CTGTTCCGAA TCGAGTCCGC
84721 CGAGTCCTGG CTCCGCACCG TGCTGGAGCG GAGCGGGACC GCGGTCCCGG ACGAGGATGT
84781 CCTACGGTAC GCGCGGAACC TGGAGGAGGC CGGTGCGCTG CCCGGCGGCG CCCCGCCGCT
84841 CGCGGTGCCG CCGCACCTGG AGGAGGTGTG GGCCGTACGG GACCGCGGCG CCGAGCCGCA
84901 CCGGGCCGCC TTCACCGGTA TGGCCCGCGA GGTGCCGCTG CCCCGCCCCG AGCTCTACGA
84961 CGCCCTCTAT GACCGCCATA TGGAGCCCGC CGCCTGGCGG CCCTACCCCG ACGCCCGCGA
85021 GGTGCTGGGC GAGCTGCGCC GGCGCGGGGT GCGGATCGCG GTGGTCAGCA ACATCGGCTG
85081 GGATCTGCGC CCGGTCTTCC GCGCCCACGG CCTGGACCCG CTGGTGGACG CCTATGCGCT
85141 CTCGTACGAG CACGGGGTGC AGAAGCCGGA CCCGAGGCTG TTCCAGGCCG CGTGCGACGC
85201 GCTGGGCGTG GCCCCGGGCA CGCGGTGATT GGTGGGCGAC GACCGCCGGG CGGACGCGGG
85261 AGCGGCGGCC CTGGGCTGCC GGGTCCACCT GGTGGACCAT CTCCCGGTGG ACCGGCGTCC
85321 GGACGCCCTG CGCGCGGTTC TCGGCCTGCC GCCGGACGCC GCCACGGCCC CCTAGGCCCC
85381 GCGGAACGAA GCCCGAAAGG GATCTCACGG GGCGAACCCA CCGGTTCGGG CGATCCCCCC
85441 ATGCCGCCCG AACCGGCGGA GACATACGGC GGCCCTCGAA GGATCGGCGG ACAACCGAAC
85501 GTCGCCTGAG TATATTGGCT GACAGCCAGC CAACGCAGGA GTTACAGCAT GGTCCCCCGA
85561 AGCCCGTCGG TCAATGAGGA GTTGCGCCGC CGATCCCAGG CCCGTCTGCT GGAGGCGACG
85621 GTCGAGCTGA TCGACGAGCA CGGCTACGAG GCGACCACCC TCGCCCATAT CGCCGACCGG
```

-continued

SEQUENCE ID NOS: 1-3

85681 GCCGGGGCGG CC

HERBIMYCIN CLUSTER (SEQ ID NO: 2)

```
   1 CGGGCGGATC TCCACCTCGG TGTCGGGTCG CTGCTGCGGG CGGGTCGCCC AGCGGCGGCG
  61 TACAGGGGCG TCACAGTGGC TTCCGCGCGG CAGGTGCGGC GGGCCGGGAA GGGCGGTGGC
 121 CGGCCGGCGA CGGCTGCCAG GCGCGTAGCC GCAGGCTGTT GCCGACCACC AGCAGCGAGC
 181 TGACCGACAT CGCGGCCGCC GCGAGCATGG GGTTGAGCAG GCCGACCATG GCCAGCGGTA
 241 CGGTCACGGC GTTGTAGCCG AACGCCCAGA GCAGATTGAC GCGGATCGTG GCGAGCGCAC
 301 TGCGGGCGAG GCGGACCGCG TCCGCCAGGG TCTCGATGTC ACCGCGTACC AGGGTCACAT
 361 CGGCCGCCCC GATCGCCACA TCCGTGCCCG TGCCCATGGC GATGCCGAGG TCGGCGCCGG
 421 CCAGGGCGGC CGCGTCGTTG ACCCCGTCAC CGACGACGGC GACCCGGTAG CCCTGCTCCC
 481 GCAGCTCCCG GACGAGGGCG GCCTTGTCCT CCGGGGTGCA CCGGGCGTGC ACCTCCTCGA
 541 TGCGGAGGTC GGTGGCGACG GCGCGGGCGG GCGCCTCGCG GTCGCCGGTG GCGAGCACCG
 601 GTCGCACGCC CAGGCGGCGG AGCCGCTCCA CGGCCCGGTA GCTTCCCGGG CGCAGCACAT
 661 CACCGACCTC GATCAGTGCC TCGGTCTCGC CGTCGACGCG GACCACGACC GGTGTACGGG
 721 CGGCGGTCTC GGAGGCCGAC AGCGCCTGAG CCAATACCGG GGGCAACGCG TCGTCCGGGG
 781 CCAGGACTTC GACCAGCCGG TCCGCCACCC GCCCGCGCAC GCCCTTGCCC GGCAGCGCGA
 841 CGAAGTCGGC CACGGCCGGG AGGGACTTTC CGGGAACGGT GCGCCGGGCA TGGGCGGTGA
 901 TGGCACGCCC CAGCGGGTGT TCCGATCCCT GTTCGACCGC GCCCGCCAGC CGGACCAGTT
 961 CCTCCTCGCC GAGCCCGCCC GGTACGGCGG TGACCCGGGC GACACTCATC TGCCCGGAAG
1021 TGAGGGTGCC GGTCTTGTCC AGTACGACGG CGTCCAGGTG CCGCAGCCCC TCCAGCGCCT
1081 GCGGTCCGCT GACCAGGACG CCCAGTTGGG CGCCCCGGCC GGTCGCCGCC ATCAGCGCGG
1141 TGGGGTCGC CAGGCCCAGC GCGCAGGGGC ACGCCACGAC CAGGACGGCC ACGCTCGCGG
1201 TGATCGCGGC CTGTGGCTCG GCACCGGCCC CGAGCCAGAA TCCGAGGACG GTGACGGCCA
1261 GGGTGAGCAC GACCGGGACG AAGACGCCCG CGGCCTTGTC GGCGAGCCGC TGCGCCCGTG
1321 CCTTGCCCGC CTGGGCCTCG GTCACCAGCC GGGTGATCCG GGACAGTTGG GTATCGGCGC
1381 CGACCGCGGT GGCCCGTACC AGGAGCAGGC CCCCCGCGTT GACGGCACCG CCGGTCACGG
1441 GCGTGCCGGG GCCGACTTCC ACCGGCTCGC TCTCCCCGGT GACCAGGGAC AGATCGACGG
1501 CCGAGCTGCC CTCCACCACC GTGCCATCGG TGGCCAGGCG CTCGCCGGGC CGGGCGACGA
1561 AGACCTGGCC GACCCGCAGT CCTCGATCG GGACCAGGCG CTCGCCGTCG CCGTCGCGTA
1621 CCGATACCTC CTTGCCGGCC AGCCGGGCCA GGGCGCGCAG TGCCGCGCCG GTCCCCAGCC
1681 GGGCCCGCGT TTCCAGGAAG CGGCCGGCGA GGACGAACAG CGGTACGCCG ACGGCGGCTT
1741 CCAGATAGAC ATGGCCACG CCGTCCGAGG CGGTGGGCAC CAGGCTGAAG GCATCCGCA
1801 TCCCGGGTTC GCCGGCCCCG CCGAAGAACA GCGCGTAGGA GGACCAGGCG AAGGAGGCCA
1861 CGACACCCAG CGACACCAGA GTGTCCATGG TCGCCGCCGA GTGGCGCAGG CCGCGCGCCG
1921 CCCGCAGGTG GAAGGGCCAG GCTCCCCAGA CGACGACGGG GGCGGCGAGC ACGAAGCACA
1981 GCCACTGCCA GTTGCGGAAC TGGAGACCGG GAACCATCGA CACGACCAGC ACCGGGACCG
2041 CGAGCAACGC CGTGACCACC AGCCGGTCGC GCTCCCGCCG GGCGTCCTGC GCCGCGTCCC
2101 TGTCCTCGCT CCGTTCCTTC CTGGGCGGCT CGGGCAGCGC GGCGGTGTAG CCGGCCTGCT
```

-continued

SEQUENCE ID NOS: 1-3

```
2161  CGACGGTGGC GATGAGCTGG TCCGGGCCGA CCTCGGGCGG GTGGTTCACC CGGGCCCGGC
2221  CGGTGGCGAG GTTCACGGTG GCCGTGACCC CGTCCAGCCT GGCCAGCTTC TTCTCGACAC
2281  GCTTCACACA GGCCGCGCAG GTCATGCCGC CGATGGAGAG GTCGGTCATG GCGGCCAAGG
2341  CCGTCGGTTC GTCGGCCATC AGCGTCCACT CCCCTGGTCC GTGTCCATGC CGCCCATGTC
2401  CATGCCGCCA CCGCCGTGGC CGTCTCCCGA GCCGCCGTCT GTCGTGCTGC TGCCGTGCAT
2461  GCCGGGGCG ACGGGCCCGG CGCCCGCGCC GACGGCGTAG GAGGCGGCGA ACACCATCAC
2521  CAGCAGCAGC AGGAATCCGC ACAGCGCCGG CGGGGGCAAT GCCCTGGACA GGAACGCACC
2581  CGGTGTCCGG CGGGCAGATG GGCGGGGCTG CGCCATATGA GGAAACTTCC AATCACTCCG
2641  TACGGCTTCA GCGGATCCGG CCGTACCGGT AGAGGAGTCG GGACGACCGG CAGCCGAGTT
2701  CCGGCGCCGT GCTGTGATGC GCGTCATGAC ACCGGGCTCG TCCGGCGAGC GCGTGACCTG
2761  CTCAGCCCTG TTCATAGTGG CTCGGTCTGC CGTCACGGTG GACGAGACGG CCGAGCCGCT
2821  CCGCGCGGGC GCGGGCATG AGCGTCCAGG TGCCGTCGGT GCGGTGCAGG GCGGCCGAAT
2881  GCCAGGGGGT GGTCCAGACA TCGGCGGCGT CCAGGAGGCG GATGCCGAAT TTGGCGGCGC
2941  CGATGGGCTG GGGGTGGATG GACAGCCGTA CGGAGCCGGG GTGGTGTTCG GCGATCAGGT
3001  CGCCCCAGGC CCGGCTGCGC TGGATGACGC CGTAGGCACG GGTGCGGCAT GCGCGTTGGA
3061  GGGCGGAGCG GGTGCCGGTG AAGTCGGCGG TGTCGTCGAC GAGGAACCGG GTGATGCCCC
3121  GGTACAGGGC GAGGGTGTGG TCCTCGGAGC GGACCTCGGC TCGCAGCGCC TCCAGGGTGG
3181  GGGCGTACCG CTCGTGCACC TGGGCGCGCT TGGTGTGGTG GGGCAGGTCG CCCAGGATGT
3241  CGCGCAGGTC GAAGACGGAG AGGCGGTGCA GTGCCAACTC CCGTATGAGG CGTCTGAGTT
3301  CGTTTGCGTA GGCGTCTATG TGGTCATCCG GGACGCGGAT CAGGTCGCCG AAGACATGGC
3361  CGTCGGAGCA GATGATCACG CGGGCGCCCG GCGGGTGGAC CCGCTCGATC TCCTCGCACA
3421  GGGTGTTCAG AAAGCCGAGG GAGAGGCGTT CGCCCTGGTC GGGGAGGTGG CCGAGAACCT
3481  TGGCGGGGTT GGGCGACTTG CAGGGGAAGC CGGGCAGGGT GAGGACCACG GGTTCTCCGG
3541  CGCGGACGAA CCCGCCGATC TGGCGCAACT GGTGCGCGAA CGACTCCGCC GCCGTGGGCG
3601  TGGGGTCGGT CGTGCGGTGG TACGGCAGCA GCAGGTCCAG GATGGCGGCG CTCATGCCGC
3661  TCGTGGAGCG GGTGTCCGGT GCGGTCGTCA GCGGCATGAG GTGGGTTCCT CCGTGAGGGT
3721  ATGCGCGACG CGGGCATGGG GGCATGCGGG CATGCGTCAG ACGCGTCGGT CGTAGCCGAC
3781  GGGCAGGTGG TTGGTCCCCC GGCCGAGGAC GGCCGGGATC CACTCGATGT CTCCGTCGTC
3841  GATGGCCAGA TGCGCTCCGA GGAGGCGGGT CAGGAGGGTG CCCAGCGCGA TCTGGAGTTC
3901  GGCGCGGGCC AGGGCCGCGC CGGGGCAGAA GTGGATGCCG TGGCCGAAGG CGAGGTGGGG
3961  GTTGGGCGAG CGGTCGAGGT CGAGGGTGTC GGGGTCGGGG AAGCGGCGCG GGTCGCGGTT
4021  GGCGGCGCAC AGGGAGATGA TCACCGAGTC GCCGGCCGGG ACCTCGGTGC CGTGCAGGTC
4081  GCTGTCCTGG TCGAAGAAGC GCCAGGTGGT CAGCTCGAAG GCGCTGTCGT AGCGGAGGAG
4141  TTCGTCGACC GCGCGGGGCA TCAGCTCCGG GTTGTCGCGC AGCGGGCGA GTTCGGCGGG
4201  GTGGCGGAAG AGGGCGATCA GGGCGGTGGT GATCTGGTTG GTGACCGGTT CCTGGCCCGC
4261  CACGAGGAGC TGGAAGATCA TCGAGTCCAG CTCCTCCTGG GAGAGTTCGC GGCGGTCATG
4321  GGCCACGACC AGGCGGCTGA GCAGGTCGTC CGCCCAGTGT TCGCGCTTAT GGGCGACGAC
4381  CTCGGCTATG TAGCTCTGGA GTCCGTGCAG ACGGGCCTCG TACAGCGGGC GTCCGGGGTC
4441  GGCCGGTCCG ACCGGCTGGA CGACCTTGCC CCAGTCGCGG TCGAAGCGGG CCGCCAACTC
```

-continued

SEQUENCE ID NOS: 1-3

```
4501  ATCTGGCAGG CCGATGACTT CGGCGAGGAC CTGGAAGGGG AAGCGGGCGG CGAAGCCGGT
4561  GACCAGGTCC GCGGGGCCGG TTTCCGGGAG GGCGTCCACG AGGGTGTCGG CCAGCTTCTG
4621  GAAGCGCGGC CTCAGTTGCT CGATGCGGCG CGGGGTGAAG GCGTCGGTGA CGAAGCGCCG
4681  CATGCGGGTG TGGGTCGGTG GGTCCTGGTG GAGGAGGTGC ACCTGGAGCT GGGAGTGCTG
4741  GGGCTCGGGC ATGATCGAGG CGCGGGCGCG CCAGCGGTCG TTGCCCCGGT CGTGGTTCTT
4801  GCCGAGGCGC TCGTCGCCCA GTGCGGAGTG CGCGGCGTCG TAGCCGGTGA CGAGCCAGGC
4861  GAGTACGCCG CTGGGAAAGC GGACGCGGTG CACCGGGCCG GTCTCGCGCA TCCGCTCGTA
4921  GAGGGGGTAC GGGTTGCTCT TGTAGGGGCA GCCCATCAGC GGCACGGGCT CGGGCAGGGC
4981  CTCGGGGGCC GTCCCGGATT CCTGGAGGGT CATGGAAGGT GCTCCTCAGA GGGCGAGTTC
5041  GGGCTGGTAG TGGTCCAGCC ACAGGGCGAG GTCGACGACG CGTTCGAGGC GGAGGCGGTG
5101  GCCCCACTCC AGTTGGCCGG GCGGGGTGTC GAGGCAGGGT TTGAGGCGGG TCTCGTCGGC
5161  GAGGGAGCGG ACGGTGTCGT CGGCGAGGGC GTCGCGGGCC ATGTTCTGCA GGCCGCGGTT
5221  GTAGTCGGGG TGGTGGGTGG CCGGGTAGTG GTTCTTGGGG CGGTGCAGCA CCGAGTCGGG
5281  GGCCAGTCCG GTGCCCGCCG CACGCAGCAG GCTCTTCTCC CGGCCGTCGA AGTTCTTCAG
5341  GGCCCAGGGG GTGGTGAAGG CGTACTCGAC AAGCCGGTGA TCGCAGTAGG GGACGCGCAC
5401  CTCCAGGCCC TGGGCCATGC TCAACCGGTC CTTGCGGTGG AGGAGTTGAC GCAGCCAGCG
5461  GGTGAGCGAG AGGTGCTGCA TCTCGCGCTG CCGGTGCTCG GTGGGCGTCT CGCCGTCGAG
5521  GTGCGGTACG GCGGCCAGGG CGGTGCGATA GGTGTCGTCC CGGAACTCGC CGATGCGCAG
5581  GTCCAGTTCG GGGTTGAGCG GCATCGCGGC CTCGTCTCCG GTCACCAGCA GCCAGGGAAA
5641  GGTGGCGGTG GCGAGCGCCT TGGGGTTGTG AACCAGGGG TAGCCGCCGA AGACCTCGTC
5701  GGCCGCCTCG CCGGACAGGG CGACCGTGGA GTGCTTCCGG ATCTCCCCGA AGAGGAGGTG
5761  GAGCGAGGTG TCCATGTCGC CGACGCCGAT CGGCGAGTCG CGGGCCACGA CCACGGCCCT
5821  GCGGTGCTCG GGGTCGAGCA GGGCACGCGG GTCCAGTACC ACCGTGCTGT GGTCGGTGCC
5881  GAGGAACGCG CCCGCTTCGG TGGCGTACGG GGTGTCGTGG CCGGTGCGCA GCACATCACC
5941  GGTGAAGCTC TCGGCCTGGT CGCTGTAGTC GACGGCGTAG GAGCGGATAC GCGCGCCCGG
6001  GCCCTCGCGC AGCCGCAGTT CGTCGGCGAG CAGGGCGGTC AGGACGGTGG AGTCGATGCC
6061  GCCCGACAGC AGGGAGCACA GGGGGACGTC GGCCTCGAGC TGGGCGCGGG CGGCGGTGCT
6121  CACCAGGTCG TGCACCCGGG CGATGGTCGC GTCCCGGTCG TCCGGGTGGG CGTCGGCCTC
6181  CAACTGCCAG TAGCGGCGCT CGCGGATGCC GTCCGGTCC AGGAGGAGCA GACCGCCGGG
6241  CTCGACCTCC CGCACGCCGG ACCACACCGT CGGACCGGTG TTGAACAGCA GGCTGTACGC
6301  CTCGCGCAGC CCGTCCGCGT CCACCCGTGG CCGTATCTCC GGATGGGCGA AGAGCGCCTT
6361  GGGTTCGGAG GCGAAGGCCA GACCGCCGTC CACCTCCGCC AGAAGAGGG GCTTGACGCC
6421  GAGCCGGTCG CGGACCAGGA GCAGCCGCTG GCCCGCTCG TCCCAGACGG CGAACGCGAA
6481  CATGCCGTCC AGGTGGTCGG CCACCTTCTC GCCCCACTCG GCGTAGCCGC GCAGCACCAC
6541  CTCGGTGTCG CTGCGGGTGC GGAACTCGTG TCCCAGGCCG CTCAGTTGTG AGCGGAGTTC
6601  ATGGTGGTTG TAGATCTCGC CGCTGTAGGT GAGCACGGTG GTCGGGCGT CGGGCCGGTC
6661  GGTCATCGGC TGGACGCCAC CGGCGAGGTC GATGACGGCC AGGCGGCGGT GGCCGATCGC
6721  GGCGCGCGGG CCGAGCCAGA CTCCGGCCGC GTCGGGGCCG CGCGGGGCCA GGGTGGCGGT
```

-continued

SEQUENCE ID NOS: 1-3

```
6781  CATGGCCTCG ATGACCGGGG CCTGGGTGCG GGGGTCCTGG TGAAAGGACA CCCAGCCGGT

6841  GATTCCGCAC ATGGGTGCGA CTCCTCGGTG AGGGTGGGGC GGTGGCTCAG CGGGGTGCGG

6901  CGGGCGCCGC GTCGGTGGTC TTCTCGGTGC GGTTCGCGGG ACCGCGGGCG GGCCGGGCGA

6961  GCAGCGGTAC GGCGAGGCAG GCGGCGAGGG CGGCGAGGGC GAGCCCCGCC CGTACGCCGT

7021  CGTCCTGGCC CGCCATCCCC CAGGCCGCCG TGGCCAGGGC CGGTCCGAGG GTGAAGCCGA

7081  GGCTGCGGGC GAGCTGGACG GTCGAGCCGA CGGTGGCGGC GCGGTCCGGC GGGGCGGCCC

7141  CCATGACCAG GGCCTGGGCC GGGCCGCCGG CCAGGCCCAT GCCGAGTCCG GCCAGGGCGA

7201  GCCGCCAGGC CACGTCGGGA GGGGACCAGC CGTCGCCCAG CGGGACGAGC AGCAGCAGGC

7261  CGACGGTGGT GAGCGCGGCG CCGGTGACCG CGACGGGCCG GGCCCCGTAC CGGTCGGCGA

7321  GCCGTCCGCC GAGCGGGCCC GCCAGCCCCA TGCCGAGGGG GAAGGCGAGC ACCGTCAGGC

7381  CGGTGGTGGT CGCGCTGACG TCCTCGTCAC GCTGGAGGTG GAGGGCGACC ACGTAGTGCA

7441  TGGCGGCGAA ACCCACCGCC AGCGCCAGCA CCGCGCCATG CGCCCGCAGC AGCCCCGCCG

7501  CCCGCAGCAC ACCGGCCACC GGACGGCCGC CCGGACCCCG CAGCCACCAC CACAGCGGCG

7561  GTGCGGCGAC GAGGGCGAGC GGCAGCCAGG CGGGGGTATC GGAGGCCAGG GTCAGGGAGA

7621  GCAGGAGGAT CGTTACACCG GTGGCTATCA GGGCGGTGTC GGCGAGGAAG CGCCGGTCCG

7681  CGCCGCGCAG GCGGCCGTCC CGGGGCATCG CCCGCCACAC CACGGCCAGC GCCAGCAGAC

7741  AGAACGGGAT CTTGACCAGG AAGATCCAGC GCCAGCCCAG GTGGTCCAGG AGCAGACCGC

7801  CGACCGCCGG TCCGGCGACG GCGCCCAGGG GGCCGAGGGT CGCGGGCACG CTCATCGCCC

7861  GCCCGCGCAG CTCGGGCCGC ACCGAGCGGA GCGCCAGCAC CGGCATCAGC ACGAACAGCA

7921  CCGCGCCGCA CGCGCCCTGT CCGATCCGGG CGGCGATCAG CCAGGCCGCC CAGGGGGACG

7981  CGGCGGCAAG CGCGCTGCAC AGCGCGAAGC CACCGGTGGC GACCAGCAGC GCGGGGCGGG

8041  TGCCCACGTC GTCGAGCCAG CGGCCGACAG GCAACAGGAG GGCGACGACG GGGAGTTGGT

8101  AGCCGAGTAC CGCCCACTGG GCGGTCGCCG CCGGTACCCG CAGGCCCTGG GAGATGTCCG

8161  CGAGCGCCAC GTTGACGATG TTCATGTCGA GCATCGCCAC GAACGCCAGC GCGCCCGCCA

8221  CGGCCACCAG GAGCCAGCGG TCATGGACTT CGGGTGGATC CGCCGGCCGC TCGGGTACGT

8281  CCCCGGCCTG ATCCGCACCG GACGCGTCGT CGGTCATGCA CCCCTCCCTC TGGCAGGTCG

8341  GCCGCCGGGC GACGGCCTCG CTCTAGAAGT CGGGCGAACC GCGGAGTGAG TTCCCGGATG

8401  TATCAGGAAA AACGGCTGGA TTTCATGGTT CCCATTTCAT AGTTCCCGGT GGTCGAAGGC

8461  GATCAGCGGG TCCCCGGTCA GCGGATGCTC GACCACGGCC GCACGTACGC CGAACACCTC

8521  GGCCAGCAGG GGCGGTCGCA GCACCTCGCG GGGTGTACCG GAGGCGACCA CGCGACCCTC

8581  GTGCAGGACA TGCAGCCGGT CGCACACGGA GGCGGCGGCC TTGAGGTCAT GCAGCGACAC

8641  CAGGGTCGTA CGGCGTCGGC CGCGCAGCAG GGCGAGGAGT TCGACCTGGT GGCGTACGTC

8701  GAGGTGGTTC GTCGGCTCGT CCAGGACCAG GACGTCCGTC TGCTGGGCGA ACGCACGGGC

8761  CAGCAACACA CGTTGCCGCT CGCCGCCGGA CAGCTCGCTG AAGTGGCGGT CGGTGTGGTC

8821  CCCCATGCCG ACGTCCGCGA GAGCACCCGC GACGATGTCC CGGTCGGCGG CGTCCTCCCC

8881  GGCGAACGCC CGCTTGTAGG GGGTGCGGCC CATGGCGACC ACCTCACGTA CGGTCAGCTC

8941  GAAGTCCCCG CCCCGCTCCT GTGGGAGCGC GGCGATGTGC CGGGCCGACC GCGCGGGGCT

9001  CAGCTCGCGG ATGTCGGAGC CGTCGAGCAG CACACGTCCG GCGGCGGGCT TCAGATGCCG

9061  GTACACGGTC CGCAGAAGAG TGGACTTGCC ACTGCCGTTG GGCCCCACCA GACCGGTGAT
```

-continued

SEQUENCE ID NOS: 1-3

```
9121  CTCGCCTTCG GCCGCGATGA GGTGGGCATC GGCCACGACC GTACGTCCGG CGTACGCGAC
9181  CCGCAGGTCC TCGATATCGA TCCTCAACTC CCGCTCCCCA AGCGCCGGTC CAGCAGATAC
9241  AGCAGAGCCG GAGCGCCGAT GAGCGAGGTG ACGACCCCGA CCGGCAGTTC CTGCGTGTCC
9301  ATGGCCGTGC GGCACACGAT GTCGACCACC ACCAGCAGCA GCGCGCCGAA GAGCGCCGAC
9361  ACGGGCAGCA GTCGGCGGTG GTCGCCGCCG ACGACAAGGC GGCAGACGTG GGGGACCATG
9421  AGGGCGACGA AGGCGATGGC CCCGGAGACC GCGACGAGGA CGCCGGTGAG CAGGCTGGTG
9481  ACCGCGAACA GCTCACGGCG CAGCCGTACG ACGTCGATGC CGAGCCCGGC CGCCGTCTCA
9541  TCGCCCATCA GCAGCGCGTT CAGGCCCCGG GCCCGGGCCT GCAACAGCAG CAGGACCGCC
9601  GGAACCGCCA CCGCAGGGGC GGCCAGCAGC GGCCAGCTCG CCCCGCTCAG GCTGCCCATC
9661  AGCCAGAACA GCACACTGTG GGTCTGCTGC TCGTCCCCGG CCTGGAGAAC GAGGTAGCTG
9721  GTGAAGCCGG ACAGGAACTG CCCGATGGCC ACCCCGGCGA GCACCAGCCT GAGCGGCGCG
9781  AATCCGCCAC CGCGCCGCGC CACCGCCCAG ACGAGAGCGA AGGTGGCCAG GGCTCCCGCG
9841  AAAGCGGCAC CGGACAGACC GAGGCCCAGC GCTCCCCCGC TGCCGAGGCC GAGGACGATG
9901  GCGGCGACGG CACCGAGGGA GGCGCCGTTG GAGACACCCA GGAAGTACGG GTCGGCCAGC
9961  GGGTTGCGGA CGAGCGCCTG CATCGCCGTA CCGACCAGGC CGAGCCCGGC ACCCACCAGG
10021 GCCGCCAACA GGGCGCGGGG CAGGCGCAGT TGCCACACGA TCAGGTCGTT CGTGCCGGGC
10081 CGGGGCGCGT CGCCGCTCAG TCTGCGCCAG ACCACGCTCC ACACCTCACC GGGCGGTATC
10141 GACGTGGAAC CCCAGGCGAC CGCCGCTGTG AGGGCCGCGA GCAACGCGAC CGCCAGGAGC
10201 AGCGCCAGCG GCCCGGCGGG CATGGAGCGC CGGGTGCGCA CACGGGCATC GGTGCCCTTC
10261 CGGCTCACCG TGGTGTCGAG CGCCATCAGC CGATCTTGCC CGGGTGGAGG GCCTTGGCGA
10321 TCTCCTTGAC GGTGTCGGCG TTCTCGACTC CGCCGATGGT GGTCCGCTCG GAGCCGATGC
10381 GCAGGAAGTG GCCCTCCTTG ACGGCCTTCA GGCCCTTGGT GGCGGGGTTC GACTCCAGCC
10441 ACTTCCGCGC CTCGTCGAAC GCCTTCTGGT TCGCCGCCTC GCTGCCCCGA TCGCGGACGC
10501 CCAACTGGAT CCAGTCCGGG TTCCGGGAAA TGACGTCCTC CCAGCCGACC TGCTTGTAGT
10561 CGCCGTCGCA GTCGGCGAAG ACATTGCGGG CACCGGCCAG AGTGATCACC GCGTTGGCGA
10621 CCTGGCGGTT GCAGACGACG GTGGGCTGCT TGGTGCCGGC GTCGTAGTCG AAGAAGAAGT
10681 ACGTCGGCCG CTCGCCCTCC GCCGTCCGGC CGACCGCCTT CCGGACGGCG TCCAGCTTCC
10741 CCTTCATGCC GTCGACGAGT TCCTTCGCCT TCGCGCTGGT GCCAGTGACC GCGCCGAGGG
10801 AGGTGATGTC GGCCTCCACC GCGGACAGGT CGGTCACCGC GCCCTTGTTC CGCGCCGCAC
10861 AGGCGGTGGA CTTGAGGTAG ATGTGCTTGA TTCCGGCCGC CTTGAACTCC TCCTCGGTCG
10921 GCGCGTCGCC CATGCCGCCG CCCATGTTCA TCGAGGCGAA GGTGTCGATG TACAGATCCG
10981 CGCCGGAGCC GAGGAGCTTC TCCTTCGGGA TCACGGACTG CCCGAGCGCC TTCACCTTCC
11041 GCGCCTGCGC GTCGAGTTCA CCGGGCAGCG TTCCCTTGCC GGGCGGGAAG CCGGTGCCGA
11101 TGACGTTGTC ACCGGCGCCG AGGCGCAGCA GCAGTTCCAG GCTGGAGGCG TTGCTGGTGA
11161 CGATCTTCTC GGGGGCCTTG GAGAACGTGG TCTTGGCGTC CATGCAATCG GTGACGGTGA
11221 CCGGGTAGTG GCCGGTGGCC GACTTCTCGT CGGCGGGGCC CGCCTTGTCA CCGCCGCCAC
11281 TGCCGCCTCC GTCACCACAG CCCGCCACGA GGAGGCCACC CAGCACCGCG GCCGTCGTAC
11341 CCCACCACAC ACGAGAACGC ATCGAAACTC TCCTGGATCC ACTTGATACC CGGGTTGCCC
```

-continued

SEQUENCE ID NOS: 1-3

```
11401 CGGATCAGTA GTCGTGGCGG ATACGGCATC GGTTCCCGCT CAGTGGGAGC CGGTGAGAGT
11461 CTCTGAACTT GAAGGGCAGA CTAGGTACGT GGCGTCGGTG ACGCATGGAG TCGACAGGAG
11521 AGAACGTGCA CCGCAAACTC CGCCTGCCTC TGGGGCGGCT GGCAGCCCTC GTCTGCACAT
11581 CTGTCATCGC CGTCACGGGC TGTGGCGGCG GTGACGGCGA ATCGGGGCT CCGGAGCCGA
11641 CCTCGAAGCC GACCGCCGGC GCCGGGCTCA TACCTGTCGC CCAAGCCTGC GGCGGCCTGT
11701 TCGACGAGGC CATCGCGAAA GAGGCCCGGG AGCCGAACGG GCCCAGCGAG GTCTATCCGG
11761 TCGAGACCGA GAGCACCGGC CACGTGGCGA AGACGCTGCG GAAGGAGTCG GCCAGGAGGA
11821 GCACGCCCGA GGACCTCTGT ACCTTGACGG ACAAGGCCGA GGGGAAGGAG CTGCTCGCCC
11881 TCACCGTGGC CTGGACTCCC CACTCACTCC CGTCGGGCCG GTCGGTGCGC TACACGACCA
11941 CCGTCGGTCC GGAGGACGCC GGCAGGCTCC TGGTCGCGTG TGACATCGAC AGCGGAAGGG
12001 GGACGGAGTC GGGCGGGGGT CGTTCCCTGG AGTTCGCCCT GCGCGACCAC TTCACCGTCA
12061 GCGACCACTC CCACGCCAAA CTGCTCATCG CCTCGGCGAA GAGGACAACG TCGCAGCTCG
12121 ACTGCCGGGA AGCGCCCGAA TACCCGGACC CGAAGGTTGT GGCACCGCCA CCGAAGCCCG
12181 GGCTGCGGTA GCGCGGTCCT TCCACCCTGC CGCAGATGAT GGCGGTTTAA TCGAGTCATG
12241 ATCTACCACG TCGTACCGCT TGCCGAGTGG AACACCGCTC CCGACCGCCC CTACAGCCCC
12301 GCATCCCTCA CGGAGGACGG TTTCATCCAC TGCTCCCCCG ACGAGGCGAC CACGCTGGCC
12361 GTCGTCAACG CCTTCTACCG CGATGCGCCG AGGCCGCTGC TGGCGCTGCT CCTCGACGAG
12421 GACCGGCTCA CCGCGAAATG CGAATGGGAG GCCGCGAACC CCGCCCCGCC GCCCGGCGTC
12481 GCCGAGAACT GCCTGTTTCC CCATGTCTTC GGGCCGCTCA ACCGCGAGGC GGTGGCGCGG
12541 ATCCAGGAGA TCGTATGGGA CTCGGAGAGC CGGGCGGTGG GGTTGACGGA TGTGCGCCCA
12601 CGCTGACGAC GAGGGCCGTC AGAGTGGAGC GAGGCGGGCC TTGAGCAGGC AGAACTCATT
12661 GCCTTCGGGA TCGGCGAGGA CGTGCCACTG CTCCTCCCCG GTCTGGCCGA TGTCGGCCCG
12721 CCGTGCACCG AGCTTCAGGA GGCGTTCGAG CTCGGCGTCC TGATCGCGGT CGGTGGCGTT
12781 GACATCGATG TGCAGCCGGG ATTTCCCGGG CTCCGGCTCG TCCCTGCGGC TGAGGATGAT
12841 CGTCGGCTGC GGACCGCCGA ACCCTTCGCG CGGCCCGATC TCGAGGGTTC CGTCGTCCTC
12901 GCGATCGAGC ACCACGAAGT CCAGGACCTC GCACCAGAAT CGCGCCAGCA CCTCGGGGTC
12961 GCGGCAACCG AGCACGAGTT CACTGATACG ACATGCCATT GACGAAACCT ACTCTCAGCG
13021 TGGGTACTGC CGGGGTGGCC GCGCGCAGAT CTCAGAGGCT TCCCGCAGTG AGGACTCTCG
13081 GGACCGTACC GGGCGAGGCG AGCAGTGGCG AATGGATTTC AGGCCCTCGC CTGCCTGTCT
13141 CCCTCGGGAC GCTCGCCGGG GCCGGAGCCG GAGCTGGGAC TGAGGCTGGG ACTGACGGCC
13201 TCCGCAGCCG AGTGGGCGCC TTCGGCCCCG TATCGGCGCA GCAGCCACAG GCCATACGCG
13261 GCCTGGAAGA CGAACACGCT CACCTGCCAC CAGTCCGGGG CCGAGCCCGG CGAGCGGATC
13321 TGGAAGAAGT CGTCGAGCCC ATGGACGACG ACCATCGGCC AGACCGAGCC GATCGCGTAA
13381 CGCAGACCCG CACAGGTGAA GCCGAAGAGA CCGGCGGACA GCATCTGCCA CAGCGTGTCG
13441 TCGAGCGGAT CGCCGAAGAA CAGGAAGTTC TGGAGGTGTC CTGCTCCGAA TAAGACGGCG
13501 ACGCCGACGG TCGCGCGGAT CGGACCGAGC GGGTTGAGTG CCTGCTGGAC GAGGCCCCTG
13561 CTGTAGATCT CCTCGTTGAT GCCGACCCAC AGCAGCGAAA CCAGGCCGCT GACGATGACC
13621 GTCGCACTGC CGTCGAGACC CGCCACGGTG TACGAACAGG CAATGAGCAG CATCGGCGCG
13681 GCCGGCCACC AGCGTCGTGG ACGGCCGAGT ACGGCCACCG CGGAGCGGCG CAGCCAGCCC
```

```
13741  CACCGCCACA GGACGAGCCA CACCCCCGCG GCACAGATCG CGTTGACCAG GGTGGCGCCG

13801  AGATCCGGAT ACCACGAGGG CGCCAGCGGA GGCAGGATCA CCTCGGCGAA CAGCAGCAGC

13861  ACCGCATGCC ATGCGAAGGT CAACTCCACC GCGCCCCAGA GCGGATGACG GATGACGTGG

13921  CCTTTCCACC GCTTCATCAC GAGACCGAGC GTAGCCGCGG ACAGGACTTC GTGGCAGGCG

13981  GCCGCACAGC CCAGAAGCTG GCCTGCTCG GTCGGCGTCA GTTCGTGGCG GTTGCCACCG

14041  TCCGGCTCTC ATCGGCCGTC GCGGGCCTGG GATTCAGCAA CCGCTCGGCA AGCTCACCGA

14101  AGAGAAGACC GAACCCACCC CACAGAATCA CCTGCATGGC CAGCGCGGAC AACCGGAACC

14161  GCCACAACAC CGTGGCGGGA AAGTCCCCCG GCACCTCATT GACCACAGGC AGGAAGGCAA

14221  ACGCCACCCC GATCACCACG GCGAACGCCG CCACCGCCAC CACGGTCGCA TACCAGGTAC

14281  CCAACCTCGG CACGAGCCGC TTGCCCACCA TCGTGGCCCC CACCGCCAGG AGCACACTGA

14341  GCACCATCAT CAGGAAGTAC AGCGCCGTAC GCTTACCGAT CGTGTCGGCG TTACCGACCG

14401  CGGGCGGATT GGCCGGATAC TTCAGGAACG GCACCACATA CACCGCCAGC AGCGCACACC

14461  CCGACAGCAA CAGCGCGGTG GCCCGCGGCG TGAAACGGCC GACACGGCCC AGGGCCACGC

14521  AATACGCCAG AGCGGCGATA CCACCGAAGG CGATCCCATA GACCAGGACA CCGGTGGCCA

14581  GCCCGGCCGT GGACTGCACA CCACGCGAAA CCAGCTCGAC CTCATGCTCA TGCGCGGGAG

14641  CGTGAGCCCC CTCGAAGCTG ATCGCACGGT CCACGTTCGG CTCACCGAGG AAATAGGCGG

14701  CGACCAGGGC CGGCACACCG GCCCCCAGAC CCGCGAGCAT GCCCCGGATC AGCAGATTTC

14761  TCACCATTGC GGAGTTCATG ACTATGCGGC GTCCCTCACA TCAGTGGCAG GGGAAACCGA

14821  GCAGATGACG GGCGTCATGC ACCCACTCAT GAACGTTCTC ACCGGAGACA ACGGCGGTGG

14881  CGCCCTGCTC GGCGCCGACG AAATACAGCA GGACCAGCAT CAGGATGCCG AAGAAGACCG

14941  CCCAGGGAGC TATCGCCTTC AGCGGCAGCG TGGCGGGCAG TTCGGGGGTG GTGGCAGTGG

15001  GCTGCGCGAC ATGCTGCGCC ATGACCAGGC CCTCCTTAAG GGAGTTCGCG TCCCATCTCG

15061  GTGGTGCACA GGACGACGGC TACGGGTCTG ACTCACCACA GATCCCGTCC GGGACCCCTG

15121  GTTCACAGTG GCGCGACCGT GCCGGATTCC CACCGGCTTC CGTCTTACCG TCGTCGATAT

15181  CGCACCGACC GTACCGCGTG TCGGGTTCAT GGCCAAGACC GCCCACCTGG CGAGACGCTG

15241  CGCCGGGACG TCCTGAGGAC GGTGCGGGAG CCGGGGCCTG CCTCGGGCAG GCCCTAAGGT

15301  CGCGGCATGC GCATCGTCTC CCTGCTGCCC GCCGCGACCG ACATCGTCAC CGAACTCGGA

15361  CTCGCCGAGC ACCTGGTCGG CCGGACGCAC GAATGCGACT GGCCACCGCG GACCGTGGCG

15421  TCCGTTCCCG TGGTCACCGG AGCCGACCTC GACCAGAACA CCCTCACCAG CCGGGAGATC

15481  TCCGACGCGG TCGGCGGATC GACGCACTCC GGGTCGTCCC TCTACACCCT CGACACCGAA

15541  GCGCTCGCGG CCCTGGGCCC CGACGTGGTG CTCACCCAGG ATCTGTGCGA GGTGTGCGCC

15601  GTCTCGTACG AGAGGGTCAG CCGGGCCGTC CGGCTGCTCG ACGCCGACAC CCGCGTCCTC

15661  AGCCTGGAGC CACGCACGCT CGACGATGTA CTGGACTGCC TGGTCACCGT GGGTGAGCTG

15721  CTCGGCGTGC GCGAGCGCGC CGAGCAGCGC CGGGCCGAGC TGCACGACCG CCTCGAGCGG

15781  ATCCGCCGGT CGGTCGCGGG CCGCGCCCGG CCCCGGGTCG TGGCGATCGA ATGGCTCGAC

15841  CCGCTGTGGC CCGCCGGACA CTGGGTACCC GACCAGATCA GCGCCGCGGG CGGCGCACCG

15901  CTGCTCGCCG TGTCCGGCGA GCACACCAAG CCGATGACCT GGGAATCGGT GCGCGCCGCC

15961  CGCCCGGAGG TGGTGCTGGT CCTGCCGTGT GGCTTCCCGC CGGAACGGAC CCTGCGCGAG
```

-continued

SEQUENCE ID NOS: 1-3

```
16021 ACGGAACTCC TCACCCGCCT CCCGGGCTGG ACGGAACTGC CCGCCGTACG GGCCGGGCGG
16081 GTCTGGGTGC TGGACGGGCC GGCCTACTTC AACCGCCCGG GCCCTCGTGT GGTGCGCGGA
16141 GCGGAAGTAC TCGCCCACGT CCTGCACGGT GTACGGGCCG GGACCGCGGT GACGGCGGAC
16201 GAGGCACACC CGTTCCCGGG CGCCCCCGGC CGGTGACGCG GTTCCGTCCG CCCAAAAGCC
16261 ACGGCAAGTG CTCGGCGCTT CTTGCATACG ATGCGCTGAT GCATAAGATG CGCACCAGTC
16321 TTGGCTCCCT CTCGGACGAC ACCCCATGAC GGACCTGATC CGCCGCGCCC TGACCGGCCG
16381 AGCCGCCCGG ACGGCGCCGA CCCCGAAGTC CCCGCGTGAG CGCACCTGGA GGCATCTGTC
16441 TCCGCTTCTG CGGCTGCTGA TCCTGACCCA ACTCGCCTTC AACGTCGGCT TCTTCGCGGT
16501 CCTGCCCTTC CTCGCCGAGC ACCTGGGCAC CGCGATCGGC ATGGCGGGAT GGATGGTCGG
16561 ATTCGTCCTC GGTCTGCGGA CCTTCAGCCA GCAGGGGCTG TTCGTGGTCG GCGGCTGGCT
16621 GGTGGACCGC TACGGCGTGC GCCCCGTCGT GCTGACCGGC TGTGCCGCGC GGATCGCGGG
16681 CTTCGTCTGG CTCGGCTACG CGGAGCGGAC CTGGGCGGTG ATCGGCGCGG TGCTGCTGAT
16741 CGGCTTCGCC GCCGCGCTGT TCTCCCCCGC GGTGGAATCC GAAGTGGCCC GGCAGGCGGT
16801 GGCCTGGGAG GGGGAGGGCC ACGGTTCGCG CACCCGGGTC CTGGCCCTGT TCACCGTCTC
16861 CGGCCAGGCC GGTACCTTCG TCGGTCCCCT CCTCGGCGGT TTGCTGCTCG GCGTGGAGTT
16921 CCGCGCCGCG TGCCTCGCCG GAGCCGGGGT CTTCGTCCTC GTCCTCGCCG GCACGCCTG
16981 GCTGATGCCG CGGCACATCC CGGGCCGGGT CCGTAACCGG GAGCAGGGCG GCGTCCGCGC
17041 GATGGTGCGC AACCGGCGAT TCCTCGCCCT GTGCTGCGCA TACGGCACCT ATCTGCTCGC
17101 CTACAACCAG CTCTACCTGG CCCTCCCGGC CGAAGTGGAG CGCGCGGCGG GCTCCCAGGT
17161 GCCGCTGTCG TGGCTGTTCG CCCTGTCTTC CCTGCTGGTC GTCTTCGCCC AGCTCCCGGT
17221 CACCCACTGG GCGGGCAACC GGCTCGATCT GCGCCGCTCG ATGACCATCG GCTGCTCCT
17281 CATCGCCGCC GGTTTCGCGG TCGTGGCCGC CGCGCGCCCG GCCGCCTGGA CGGGCGCCGT
17341 CGGATTGCTG CCCGCCGCGG GCTACGTCGT GCTGCTCACC CTCGGCCAGA TGCTGGTCGT
17401 CCCGGCCGCC CGCGCCTGGG TGCCCGACCT CGCCGAGGAC GGTCGGCTCG GCCTCTACAC
17461 CGGGGCGCTG TCGTCCGTCT CGGGCCTGAT CGTCCTCATC GGCAGCTCGG CCACCGGCTC
17521 CCTGCTCGAC CTGGGCCTTC CGCCCGCCGC CGCTGGCTC GTCCTCGCCG CCGTCCCGGC
17581 CCTCGCGGTG ACACTGCTGC CCCGCCGCCC GGATCAGCCC AGGGTGAGCA GCTCCTCGTA
17641 GAAGCCGCCG AACTCGCGTT CCCGGTCGAC GAGGTGGATC TCCAGGATCC AGTGGCAGCG
17701 GCGTCCGGCC TTGTCGGTGT GCCGCAGCGG GGTGTCGTTG TCGGGCGTGA TGTACGACTC
17761 CACGCGCGCG CCGTCGATCG TCTCGTGCGG GAACTCCCCG ACCAGGTGGC CGGCGTGCCA
17821 GCCGCCCAGC TCCCAGCCGG CCCCGGCGGC CAGCCGGTCC ACCTCGGCGT GCCGCCGCTT
17881 CCCGGTGATC TCCGGGTCGC TTTCGAAGAA CCGCTTGCCC GCGTCGAAGA CCTTGGGCAG
17941 ATCGTCCCGC AGCCGCCGCT TGACCGGGTC GTCGCCGAGG ACGAAGGTCC GGCCGAAGTC
18001 GGCCTCGTAC TCTTCGAAGA TCGGTCCGAG GTCGGCGAGC ACGATGTCGT CCGTGCCGAT
18061 CACCCGGTCC GGCGGATTCT CCCGGTACGG CAGGAGCGTG TTCGGCCCCG AGCGCACGAT
18121 CCGCTTGTGC CAGTGCCGGG TCGTGCCGAA CATCTCGTTC GCCAGGTCCC GGATCCGGTC
18181 GCTGACCGCC CGCTCCCCCT CGCCCGGCGC CACCAGCCCG CGCCCCTGGA TCTCCGCGAA
18241 GAGCCGTACG GCCTTCGCCT GGGCATCCAG CAACCGTGCC GCGCGCGCGG GTTCGTCGTC
18301 CGCCATGGGC CCGACGGTAG GCCGCTAGAT CGTTTCCCGG CAACCGGATG AGGCAGTCCT
```

-continued

SEQUENCE ID NOS: 1-3

```
18361 CAGTCGGCGC GGCCGGTCGC CGCCACCGTC ACACCCAGGC CGATCATCGC GAGGCCGCCC

18421 GCCCCGCCGA CCATCGAGAG GCGGCGGTCC GAGCGGGCGA ACCAGGAGCG GGCCGCCGAG

18481 GCGCCCAGGC CCCACAAGGT GTCCGTGACC AGGCCGATGG TGACCGGGAC CAGGCCCAGC

18541 ACCATCATCT GGACGGGAAC ATGACCCGCC GAGTGGTCGA CGAACTGCGG CAGCACCGCC

18601 GCGAAGAAGA CGATGCCCTT CGGGTTGGTG ACCCCCACCA AAATGCCGTC CAGGATCGAA

18661 CGCAGATCAC CACGCCGCTC ATCGGCCGGA GCGTCCATGT TCGCCACGCG CATCTCCCTG

18721 CGGTGCCGGA ACGCCTGCAC ACCCAGGTAG ACGAGATACG CCGCTCCTGC CAGCTTCACG

18781 CCCATGAACA GCGCCACCGA GCTCTCCACC AGCGCGCCGA GGCCCCACGC CACGGCGACC

18841 ACCAGGGCGT AGCAGCCGAT CACATTGCCG AGGACCGTCG CGAGCGCCGT GCGGCGGCCG

18901 TGGGCGAGGG CCCTGCCGAC CACGAACAGC ACACTCGGCC CCGGGATCAC GATCACCAAG

18961 AGCGACATCG CCGCGAACGT GAGAACACTC TCCGTGGACA CCACGTGTCC GCCACCTCCT

19021 GAATCGCTCC GTCCAGGGGA CATACAAACA GATGACGAA CGCCCGCTCC AGCCTCAGGC

19081 ACCCGCGGAC AGTGGCCGCT CCCCTACTTG GTCACGGAAT AGGAGTGCGC TCCGGTTCCG

19141 GCGAGTGCTC CCCCGTCCAC GATCAGGTAC TCGTCGCGGA TGGGCCGCCC CATGGGCCAG

19201 GACTCCAGGA TCTCGCGGGT GCCCGCCGCG TAACGGGCCT GCGCGGACAG GGTGGAGCCG

19261 GAGATGTGCG GGGTCATCCC GTGGTGCGGC ATGGTGCGCC AGGGGTGGTC GGCGGGGGCG

19321 GGCTGCGGGT ACCAGACGTC GCCCGCGTAG CCCGCCAACT GGCCGCTGCG CAGGGCACGG

19381 TCGACGGCGT CCCGGTCCAC GATCCGGGCC CGGGCCGTGT TGATCAGGTA CGCGCCGCGC

19441 TTCATCGTGG CGAGCAGTTC GTCCCCGAAC AGGCCCTCGG TCTCGGGGTG CAGCGGCGCG

19501 TTGATGGCCG GGCCACGCAG TCCGCGATGT TCCAGCCGCC GTCGAGAACG ACCTGGTGGG

19561 AGGGCAGATA GTTCCGCACC AGGGACAGGG TCATCATCAC CACGTGCTCG GCGACGCTGA

19621 TGCTGTTGGA GTACCTCACC TCGGCGACCG TCACCCCGTG TGCGATCGCC GCGTCGAGGT

19681 CGACGTGGTC GGAGCCGATG CCCGCGGTGA TGGCGAGCTT CAGGTTCTTG GCGACGGCGA

19741 TGCGCTCGGA CGTCAGGTAC GCGGGCCAGA ACGGCTGCGA GATCACGACA TCGGCATCGG

19801 GCGGCTCTCG GTCGAACACC GAGCCGTCGC CGTCCTTGTC GGAGGTGACG TGGGCAGGTG

19861 CGGTTCACCA TCCTCGCCGC TGAACGGCCT GGTCAAAGCG AATCTCGCTA TGCTCGTATA

19921 GTCGGCGGCT ATCGCCCGTG TCCGTTGAGG CAGGTGTGCA GGCGCTCGTC CAGCGCCTGC

19981 CGTACGTCGG CCTCCCGGGC CACCGTGAGC AGCGCCCCGG CGAGGACGGA GGGCGGGTCG

20041 TCGGGGCCGG TGACCAGCCC GACCCGCGGC CCGTGCACGG GCCCCTCCAG GGGCACCACC

20101 CGCATGCCCT CCGGTACGCC GAACATATGC AGCCAGGCGT GCGAGATCAC GCTGGACCAG

20161 CGGCCGCCGG GCAGGTGGGC GTACAGCCCG GCGACGCTGT CCGACTCGAT GGCGGGCGTG

20221 ACGGTGGCGC CGTCGGCGGC GAAGCACTCG TCCATGATGC GGCGGTTGCG CATCCGCGGG

20281 CCGAGCAGGC ACAGGGGGAG GTCGGCCGCC TGCGCCCAGC GGGCCGTGGC CGCGGTGGCG

20341 AGCGAGCCGT CGACGGGTGT GACGTATCGC TCCTCGTACA GCGGGAGCCG GCGCAGGCCG

20401 CCCAGGGAGT CGTCGTCGAG GTAGGTCATC GCCGCGTCCA GTTCGAACTC GGCCAGCCCG

20461 TGGGTGATGT CGATCGAGGA CAGTGACTCG ATGCTCACCC GGGCCCTCGG GTGGCTTTCG

20521 CAGAAGGGGC TGGTGAGGAG GGACGCGGCG GGCATCGCGG TGGGGATCAC TCCCAGGCGG

20581 AGGGTACCGG TCAGGCCGTC GCCCAACGCC GACAGCTCCT GCCGCAGCCC GTCCCGCTCG
```

-continued

SEQUENCE ID NOS: 1-3

```
20641 GCGAGGATGC GGTGTGCCCA CGCCAGCACC ACCTCGCCCT CCGGGGTGAG CCCCTCGTAC
20701 CGTCGTCCCC TGCGCACGAT CGGCACACCG AGTTCGTGTT CAAGGCGGCG GATGGCGGCG
20761 GCCAGCGACG GCTGGGACAC ATAGCAGGCG GCCGCCGCGC GGACGAAGTG GCGCTCGCGG
20821 GCGAGGGCGA CCAGGTATTC CAACTGGCGC AGTTGCATGC GTGACCTCCA CGACGCGTCC
20881 CGTCCCGAGG GCGCGGCGTA CAGCATCGTG CAGGCTGCGG CTGTCCGCGA GGTGGTCGAC
20941 GGGTGGGGAG TTCGGTGTCG CTCACCAGCA CACGGCCGGG ACCCGCATAA AGGGCCCCGG
21001 CCGGTGAATC GGACGACCTT CGAGACGGGT CCGGCCAGTG ACGGTGACCC GAACGAAGCT
21061 GCTTACGACT GAGCGCCGGA CGCGGGCGCG TTGAGGTTCT CGTGGACCGC GCGGGCGATG
21121 CCCTCGATGT TGGCGATGCC GTCGTCCATC GTGGCGTTGT CCTGCGAGAG CACCGTGATC
21181 GTGTAGTCGT GGTCGCCGCC GGTGAAGGCG CCGAGGCTGT GCACCCGCCA GCCGTTGGTG
21241 GCCCGCTCCA GCCACCCGTT CTTCACATGC ACCTGGGCGT CGCTCGGCGC ACCGGCCGGG
21301 GTGCCCCAGC GCTGCGAGGG GATGACCTCG CCCGTCAGCT TGAGGATGTA GGCGCGGGAG
21361 TCATCGCTGA GCACCGGGTT GCTGTGGGTC ACCAGTTGGA GGAGCTTTTC CTCGTCGTTC
21421 GCGGTGATCT GGGTGAGCCC CCAGTGGCCC TCGCTGTCGA GGGTGGTGTT GGTCATCCCC
21481 GCGGCGTGCA GGAACCCGTT GATCTTGTCG GCCCCGAGCT GCTTCCACAG CGCGGTGGTG
21541 GCGTCGTTGT CCGACTTCGT GATCATGGCG GTGGCATGGT CCTTCTCCTC CTGCGTCAGG
21601 GCGCGATCGT CCTTCTGCGC GTCCCACAGC AGGGTGCCGA GCACGGTCAC CTTGACCGTG
21661 CTCGCGGAGT CGAAGTGCCG GTCCGCGTCC AGAGTGCAGG TGGTGTTCGT GGTGCGGTCG
21721 TGGAGGCTGA TCGCCGTGGT GGCGGCGGAG CCCTCCAGTC CGAGTTGAT GTCCTCGGAG
21781 AGCTTGTCGG CGAGTTCCGG CCGGTCCGAG GTGCAGATCG CCGCCTGCGG GGTGGCCGCG
21841 TGTGCCGACC CCACCGAGGC GATCGTCGGC ACGAGCACCC CTGCGGCCAG CGCCGCCTTT
21901 GTCGCCAGGG TGCTACGGGG AGCCTGGGTT ATTCGTCGGT GTCGACCCAT GGTGGGCTTG
21961 TCCATTCGTT CGTGGGGCAG TTGGACACGC GGTGCCTTCG CTCCGTCGCG AAGCCATCCG
22021 GGTGCTCCGA CCCTGGATGA CGAGCCGGAG GCAGGTGAGG TTCACGAACG CGTCCAAGTC
22081 TCACAAGATC GCTCCACAAT AGGCACCGCG CCCGGGCGGA CCGGGCGCGG TGCGGCGGAC
22141 GAGCCGGGAC CCGGTCAGCG CCGAATGGCC CTGAGGAAGT CTCCGAGGGC TCGGGCTACG
22201 GCGCCGGGGG CTTCCGCGGG GAGCAGGTGG CCGGCGTCAG GGACGGTCGT CAGGGTCGCG
22261 TGCGGGATGT GGGGCAAGAG GTGTTCGCGC AGGATGTGCG GCGGCTCCAC CATGTCGTTC
22321 TCCGCGGCAA GCACCGTCAC CGGGACCTCG ATACGCCGTG TGGCATCGGT GATGTCCCGC
22381 GCGATTCCGT GCAGGGGCCA CTCCTGCCGG GCCTCGGCGC CGGAGGCGAG GCTGTCGCGC
22441 TCCGCGGTGG CCCGCACCGT CTCGGGCAGC GGTGTGGCGG TCAGGACATG GTCGAGGGCG
22501 TGCGCCACCG TCTCGGCCGA GTCGTAGGCG TGTGACAGGC CCTGTCGGTA CTCCTCGGTC
22561 ACCATGGCGG GTGGCTGGGG CGGTGCGGGC GCGACGAGCA CCAGACCGGC CAGACCGGCC
22621 GGTCGGCGGG CCGCGACGAG CTGGCTCGCC TTGCCACCCA TCGAGTGGCC GACGAGGACG
22681 AACGGCCCCG ATACCCGCTC CTCGACCACA CGGACGAGAT CGTCGGCGAG CTGGTCGAGG
22741 TGATAGGGCC CGGGCAGCGC CCGCGAGGTG CCCCAGCCGC GCTGGTCGAA GCGGACCGTC
22801 GCCTGCCCGG GCGGCAGGTG GCCGAGCACA CCGTTCCAGG TGTCGGCGGA GCCGCCCAG
22861 TAGTGGGCGA ACACCAGCGT CGGACCGGTA TCGCCCCGA CTCGCACATC GAGCGATCCG
22921 CCCGCCACGG GAACTCTCAT TGTCATTTCC ATCATCTTCG CGCCTTCCCT CTCGGCCGCG
```

-continued

SEQUENCE ID NOS: 1-3

```
22981 GAAGGCGACT CCGTCGTCCT GCCGCAGCTC GGAACCAGTA ACCTGACCTG CCGATCAGGC

23041 GCGGAATCGA CCGTAGGCGA GCGAGTGTCC ACTCCTTGGC GGAAAGGAAC ACGTTCATTG

23101 TGGAAAACGG ACACAGTGCG GTGCGGCAAC TGCGCTATCT GCCTGCCGTG GGATCGGCGT

23161 ACGGGGTGGA GGTCCTGGAT TTCGCCGCGC TGCGTTCGAT GGACACCCAG CGCCGTCGTA

23221 CCCAGCCGCA GCGCCCCGAC TTCCATGTGT TCGCGCTGGT CGGCTCCGGA ACCGGCAGCC

23281 ATGAAGCGGA CTTCCACAAC TACCGGCTGG GGGAAGGCGG CGCCGTGTGG ATCCGGCCGG

23341 GCATGGTGCA CCGCTGGAGC GATATCGACG CCTGCGACGG CCCGCTGATC CTGTTCCGGC

23401 CCGGTTTCCT TTCCGGCTTC ACGGCGGCAG AGGCCACCAC ACCGGCGTGC TGGCATCTGG

23461 ACCGGCAGCG GCTGCCCCTC GCCCTGCTCG CGGCCGAACA TCTCGGCCGC GAGCACAGCA

23521 CGGCAGTGCA CACACCACGC CTGGCATCCC CCGCCCTGCT CTCCCACCTG CTGGCGGCGC

23581 TGATCCTGCG CGCACTCCCG GGCACACCGC CCTCGGCCGA GGCGGCAAGA CCCGGCAGCC

23641 GGCCAACCGA AGTGTTCCGG GTCTATCGGG CCACCGTCGA AGAGCGCTTC GCCGAATGGC

23701 ACCAGGTGGC CGACTACGCA CGGGCGTTGG GCTACGACGT ACGCACCCTC ACCCGGGCAA

23761 CGCGCGCCGC CACCGGCACG GGCGCCAAGA CCTTTCTCGA CCAGCGCATC CTGCTGGAGG

23821 CGAAACGGCT GCTCGCCCAC ACCGATCTGC CGGTCAGCGG CTGCGGCCGA CGCCTCGGCT

23881 TCCGGGACGT CGGCAACTTC ACCACGTTCT TCCGGCGCCA GACCGGCCTG CCCCCCGCCG

23941 CGTGGCGCGC CGCGTACAGC ACCGGCGGCA CACGCGGCGT CTGACTCGCC CTCGGCGGCC

24001 GGGGTCCGGA GAGTCACTGA TGTGCGGGGG CAGGTTCACT GTTGCGGGGG CAGGTGCCGC

24061 AATCCGTTCT CCAGCAGGGC GAAGGCGTGC TCCATGTCGG CCACGGCACC CGCGTAGCGC

24121 TCGTCGGCCG GCTCCCCGTA CGCCACACGT TCGGCGTTGT CGTCTGCCAA CGCCCAGTGG

24181 ACCGCGACGA TTTGGACGGC GGCGAGCCGC GCGGTGAGTT CCGGAATGTC CGCCGTTTCC

24241 CGCAGTGCCT CGGTCAGGGC GTGCTCGGCG CCGGTCTTGA ACCGTGCCAT CCGGGCCACC

24301 AGCGAGGGCG CGTCGAGGAT CATGCGGTGC AGCCTGCGCA CCGCGGGATG GTCATTGAGC

24361 CCGGTGATCG GATCCCGCTC GCGCAGCCCC TTGAGAAAGT GCTCGCGCAG TGCGGTCAGT

24421 GGGTCGGTGC CCGGCGGGCG GGCCCGTACG ACGCGTGCGG ATTCGGTCTC GTGGTCGGCC

24481 AGGCGGTGCA CCACGAGGTC TTCCTTGGTC GGGAAGTAGG CGAAGAGGGT GCGCTTGGAC

24541 ACCTCGGCCG CCTCGGCCAC CTGGGCCACC GAGACCTGGT TGAAGCCGTG TTCGAGAAAC

24601 AGCGAGATCG CCGCGTCGGA GATCGCCGCG TGGGTCCGCT GCTTCTTTCG TTCCCGTAGT

24661 CCTGGCTTGC CGTCCACGGC GTCCACGGTA ACAGAAAACT GCCCCTGGTA AATTTCTGCA

24721 CCGGGTATAT ATTTACCCTC GGTGAGCTGA TCCGGAGCGT TGAGATGAGA TGGAGTGACG

24781 GTGTTGACGG AGAGCACGAC CGAGGTCGTT GTCGCGGGCG CGGGCCCGAC CGGGCTGATG

24841 CTGGCGTACG AACTGGCTCT GGCCGGGGTC GAGACCCTGG TGCTGGAGAA GCTGCCAGAG

24901 CGGATCCAGC AGGTGAAGGG CGGCACGATT CAGCCCCGCA CCGCCGAACT GCTGGAATCC

24961 CGCGGCCTGC TGGAGCCGCT GCTGCGGCGG GCCATCGCGC GTGGTCCGAT GGGCGGCCAT

25021 TTCGCGGCCC TGCCCGTGCC CCTGGACTGC ACCCCTGGC GGACCGAGCA CCCCTTTCCG

25081 ATCGGGATCC CTCAGTGGGA GATCGAGGAG GTGCTCGAAG AGCGGGCGAC CGCCGCCGGC

25141 GCGCGGGTAC TGCGCGGCGC CGCCGTCTCA GGGGTCGCGC CGGATGACGA TGGTGTGGTC

25201 GTCACGGCGG ACGGTCTGCG GGCGCGGGCT CACTACCTGG TGGCGTGCGA CGGCGGCCAC
```

-continued

SEQUENCE ID NOS: 1-3

```
25261 AGTACGGTGC GGAAACTGCT CGGGCTGCCG TTTCCCGGCC GGGCCGGAAC GCATCAGGCG
25321 GTGCTGGCCG ATATCCGGCT GTCCGCCGTT TCCTCGCTGG TGCCGCGGCA GGCGGGGCAT
25381 ATGAGCACCC TGACCCGTCA GGCGCGGGGC TACTGGTCCA TGCTGGTCCC TGTCGGCGGC
25441 GACCGGTACC GGTTCACCTT CGGGCATGCG GACCAGGCGG ACACCGCCCG CGACACCGCC
25501 GTCACCCACG AGGAGATCGC GGCCGCGCTG GAGGCCGTGT ACGGCCCCGA GACCACCCTC
25561 GGCGGCGTGG ACAACTCCTC GCGGTTCTCC GATGCCACAC GGCAACTGGA GCACTACCGC
25621 ACGGGCCGTG TCCTGTTCGC CGGGGACGCC GCGCATATCC ACCCCCCGCT GGGCGCCCAG
25681 GGCCTCAACC TCGGCGTACA GGACGCGCTC AACCTCGGGT GGAAACTGGC CGCGGTCCTC
25741 CAGGACCGGG CGCCGAGCGG GTTGCTGGAC AGCTACCACG CCGAACGGCA TCCGGTCGCG
25801 GCCCAGGTCC TGCATCACAC CTCGGCGCAG CGCGTCCTGA CGAGTCCGAA CCCGAGCGAG
25861 GACGTGGCCG CCCTGCGCGA CATCATCACC GACCTGCTGC GCCTGCCCGA CACCAACCGC
25921 CATCTCGCGG GGCTGATGTC CGGTCTCTCG CTGCGCTACG ACCTGCCAGG CGATCACCCG
25981 CTCACCGGGC AGCGCATGCC GGACGCCGAT CTGGTGACCG AGACCGGCAC CACCCGGCTG
26041 TCGACACTGT TCGGCTCCGG GCACGCCGTC CTGCTCGACC TGGCCGGAGC CGTCCCGGCC
26101 GACCTCCCGC TCCCGCCACG AGTCGACCTC GTCCGCGCCA CATGCGCCGA CGATCTGGGC
26161 GCCGCCGCCC TGCTCATCCG CCCCGACGGC TATGTCTGCT GGGCTACGGA CACCACCGCC
26221 GCCTGCGCGA CACCCTGCT GGCCGCGCTC ACCGGCGACC TCGCGAGGGT GCGCTGAGCC
26281 GGGTGACAAG GCCGAGTGAC AAGGCCGAGT GACACGGAGG ACGCCTACGC GAAGGCCCTC
26341 AAGGTGTCCT CGCCGTCGGT CCACCAGACA CCGAGCCGCT GGCGGACCAG GAGCCAGCCG
26401 TCCGGGCCCC GGCGGAATTC CCAGTCGTAG GGGCCGCCCA TGGAGTAGGG GGAGGAGGTG
26461 CTCCCGGGCT CGGTGACGGC GACGAACCAC ATGTAGCCGA TCCCCGTCGC CCGGTCGCCC
26521 GCCACGTCGA CGTGCATGTT GAGGATGTGA TGCTGCATGC TCGCGTAGGG TGATTCCACC
26581 TCCTCCACCT TGGCCCGGAC CGCCTCTTTT CCGTGGATCT TCTCCCACGG CCCGAACTCC
26641 AGCACCGCGT CCTCGGCCCA GCATTCGATC CAGGTCTGCC AGTCCTTGCG GTCCAGCGCC
26701 CGCCATCCGC GGATCATGAG GGCGCGCAGG GCTTCCTTGT CCTCCAGTGC CTGGAGTCTG
26761 CGGGCCAGGC TGTCGTAGTC GGCGGTCGCT GTCATGACGG GCCTCTTTCG TCCATGGGTG
26821 CTGGTCGGTC CTGCCCGATC GAGTCTGGAC CGGTCGAGCA CCGCCGACCA GGCCGAACGC
26881 CGCCTAGGAG CACCGCACCC AGGCGGCACA CCGGCGGGCT CATGGAGGGC AGTTGGGCCA
26941 CGGCCAGGGG TGACCGACCC CGGGCGGTCA GGTCTCCAGC AGGTCAGGTC TCCAGCAGGT
27001 CGGCGGGAAG ATCTCCTCGA TCGTCCACCG GTGTGCGGTC AGGCCCTGCT CGTGGTGGTA
27061 GCGCAGCAGT GTGTCGAGGG CCGCGCGGTT GGCGGCCACG CCATAGGGCC ACCAGTCCTC
27121 GGTCATCAGC TCGGCGTTCT CCTCGTACAG CGCGTTCAGC CAGGGCACCA TGAACGGGGC
27181 CTCGTACAGT CGCCGTCCCT GCCGGTACCG CCGGGCTCCT GCCTCCTTCG CCGCCACAAA
27241 GCCCTCGTAG ACGGCGCGGG CCGGCCAGGG ACACCGGCCC TGTACAGCGC CGGTTCCCGT
27301 GCCGGTGCGA GCGGGTCGCC CCACACCGGG ACCGTGCCCC GAACCACCG TAAGTCCGCA
27361 GGACGGGGCG GCGCGGCCAC CGCACACCAT CGGGGCGGCC GGAGCGGCCG AAGCCCCCTC
27421 ATTCCCCCTG ACGGCCACTG CCGCCACCGT GGTCAGGGGG AATGAGGGGG ATGTTTAGGG
27481 GACGGCCCGC TCGCCGCCGG AACAAGAATC ACAACAACAG CAGCGAGCTT CCTCAAGCTC
27541 GTTGGAGCTT TCTCTCCCGG GCCTTCTTTC CCTTGGGCCG CGCAACCGGA GCGCGGCTGT
```

-continued

SEQUENCE ID NOS: 1-3

```
27601 CCCGCGCAAG GGGCGATCCC GCGCGGGCCG GTCGCTCCTC CCGCGCGCCC TGCTTCGAAC
27661 CGAGAGGTGT GGCGGCATGC TACGGACTGA CCTGATCCGG CCGGTGCCCG AACTGCTCCG
27721 GGCCAACGCG GATCGCTTCG GTGACAAGCC GGCCTGTTCC GACGGACACC GCACGGTCAG
27781 CCATGCCGAA CTCGAACGCC GTACCCGGCG GCTGGCCGGT CATCTCGCCG GACTGCGGCT
27841 GCACCCCGGC GACCGCGCCA TGATCTGCCT GGGCAACCGC GTCGAGACGG TGGAGAGCTA
27901 CTTCGGCGTT CTGCGGGCGA ACGGCGTGGC GGTGCCGGTC AACCCGCGTT CGACCGATGC
27961 GGAACTCTCC TATCTGCTCG CCGACAGCGG CGCCCGGCTG GTGCTCACCG ATGTCGCCCA
28021 CGCCGAGCAG TTCGACCGGC TGCGGGAACA GTTCCCGGAG CTGAGGGTGG TGGTCAGCGG
28081 GGACGGGCCG CTGCCGAAGG GCTTCATCGC GTTCGAGCCG CTGCCGGACA CGGAGCCGGA
28141 CCTGGCGGCC CGCGACGACC TGGGCCTGGA CGAAGTCGCC TGGATGCTCT ACACCTCGGG
28201 CACCACGGGC CTGCCGAAAG GCGTGCTGTC CACCCAGCGG AACTGCCTGT GGTCCCTGGC
28261 CGCCTGCTAC GTACCGGTGA CGGGGCTGAC CGCCGAGGAC CGTGTGCTGT GGCCGCTGCC
28321 GCTGTTCCAC AGCCTCTCGC ACATCGTGTG TCTGCTGGCG GCCACCGCCG TCGGGGCCGG
28381 CACCCGGATC GTGGACGGGG TGTCGACCTC CGATGTGCTG GACGCGCTGC GCGAGGAGCG
28441 GTCGACCTTC ATCGCCGGAG TGCCGACGCT CTACCACCAT CTGATCGAGG CTGCCCGCGA
28501 GCGCGACTTC GCCACGCCCG AGCTGCGGAT CGCGCTCGTG GGCGGGGCGG TGGCCACGGC
28561 CGACCTGGTC AGGTCGTTCG AGGCCACCTT CGGAGTGCCA CTCGTCGACG CCTACGGATC
28621 CACCGAGACC TGTGGCGCGA TCGCGGTGAA CTGGCCCACC GGCCCACGGG TCGAGGGGTC
28681 GTGCGGGCTG CCGGTGCCGG GGCTGACGGT GCGGCTGGTG ACCCCGACA CCGGTGTCGA
28741 CGTTCCGGCC GGGCGGGAAG GCGAGTTCTG GGTGTCCGGG CCGAACATCA TGGCCGGGTA
28801 CCACAACCAG CCGGAGGCGA CGGCCGCGGC GCTGCGCGAC GGCTGGTACC GCACCGGGGA
28861 CCTCGGCCGC CGTGACGAGG CCGGATTCTG CACGGTGACC GGCCGGATCA AGGAACTCGT
28921 CATCCGGGCC GGGGAGAACA TCCACCCCGG TGAGGTCGAG GCCGTGCTGC GCACCGTGCC
28981 GGGTGTGGCG GACGCGGCCG TGGTGGGCAA GCCGCACGCG GTGCTCGGCG AGGTCCCGGT
29041 GGCCTTCGTG GTGCCCGGCC CGGACGGCTT CGACCCGTCG GCGCTGCTGG CCACGTGTCG
29101 TGAGCGGCTG TCGTACTTCA AGGTCCCGGA GGAGATCTAC GAGATCGCGC GGGTGCCGCG
29161 CACCGCCTCG GGAAGATCA CCCGGCACGT ACTGCTGGAG CTGCCCGCAC GGCTGCGGGC
29221 CGCCGGGGAC GGCCAGTACG ACTCGCTGCT GCGGCTGGAC TGGGTGCCGC ATCCCGCGCT
29281 GCCGGACGCC CCGGCCGGGA CCGGAACCTG GGCGCTGGTG GACGCGGACG CGCTCGGGGC
29341 CGGGCTCGCG GAGGGGCTGC GGGCGGCGGG GGTGGACGTG GCCGATCCGG TGGCCGATTA
29401 CGTGGCCGAT CCGGTGGCCG ATGTCGCTGG AGATGACGGT GCGGCTCCGG ACGTGGTCGT
29461 GGTTGCGCCT CAGGTGGTGG GCCTCCCCGA AGAAGCGGGG GTCCCCGACG AGGCCGGGGT
29521 CACGGCTGGC GAGGCGGCCG ACCGGCTGGC GGCCCGGCTG GGCACCTGGC TGGCCGACGA
29581 CCGGCTGGCC GGGACGACGT TCGTGGTGGC CACCACTGGC GCGGTGGCCA CCGGCTCCGA
29641 GGAGAACGCA CCGGAGCCGC TGTCGGCCGC GCTGTGGGGT GTGGTGCGCT CGCTCCAGGC
29701 CGCCTACCCC GGCCGACTGA CGCTGGTGGA CGTGGACGAC GAAGGGGGCG GGGCCGGGGA
29761 GGACGGTCGG GTGGCCGCGC TGTTGCGGGC CGTACAGGAC GGGCACGACC AGGCGGCGAT
29821 CCGTGGCGGA GTGCTGCTGG TCCCGCGCCT GACGCGGATC TCGGTCCCGG CGGAGCCGGG
```

-continued

SEQUENCE ID NOS: 1-3

```
29881 GCCCGCCCCG GCCCTGGACC CGGACGGACT GGTCGTGATC ACCGGTGGCG ACACCGCCCG
29941 CGGCACCGCG CTGGCCCGCC ATCTGGTGAC CGCGTACGGC GCCCGTAACC TGCTGCTGCT
30001 CAGCGCGAAT GGCCTGCCGG AAGAGGCGGC GGCCGCGTTG CGGACCGAGT TGGCGCGGGA
30061 CGGGGCCCAG GTCTCGATGG CCGTGTGCGA CCCGGCCGAG CGGGCGGCGC TGGACTCGGT
30121 GCTGGACGCA CAGGACCGGC CGGTGACCGC TGCCGTACAC ATCGAGGAGC CGGGTCCGGA
30181 ACGGTCGCTC GCCACCTCGC TGCGCGGCAT GACGCACCTG GAGGAACGGA CGCGGACGGC
30241 CGGGCCCGCG CTGTTCGTCG TCGTCACCTC CGCCGCGGGG GTGCTGGGCT CGCCGGGTCG
30301 CCCGGACCTG GCGGCCGTCG ACCAGTTCGG CGAAGCCCTG GTGCGGCGGC GCCGGGCGCT
30361 CGGCCTGAGC GGGCTGGCGC TGGCTTGGGG GCCGCTGCCG GGCGAGCAGG GCACGGCACC
30421 GGTGGCCGGT GCCGTTCCCC TGCCCGAGGC GCTGGCCCTG TTCGACGCGG CGCTGACGGC
30481 TGGTCAGGGC CCACTGGTGC TGCTCAGGCC GAGTACGACG GGGCTGGCGG GTGGCGAGCC
30541 GGTGCCCGCG GTGCTGCGTC ACCTGGTGGA CGCGCCGTCC GGCGTACCGG CGTCGGACGA
30601 ACCCGCCGCC GCGGAGTTCC GGCGGCGGCT GGCCGCCGAG AGCGAGTCCG GCCGCCGGCA
30661 CATGGCACTG GCGCTGGTGC GCGAGCACGC CGCGGCGGCG CTGGGGCTGG CCTCGGCCGA
30721 CCCGGTCGAG GCCGACCAGG CGTTCAGCGC GTTCGGCTTC ACCTCACTGA CCGCGGTCGC
30781 GCTGAGGAAC CGGCTGAACG CGGCCACCGG GGCACGGCTC GCCGCCACGG TGGTCTTCGA
30841 CCATCCGACC CCCGCCGGGC TGGCACGCCA TCTGGTGCGG GAGATCACCG GGAAGCGAAG
30901 CGTGCGGGCG CCGGTGCGGG CGCGCGGGGT GTCCGACGAG CCGGTGGCGA TCGTGGCGAT
30961 GGGCTGCCAC CTGCCCGGCG AGGTCGCGAC GCCCGAGGAC CTGTGGCGGC TGGTGGCCGA
31021 CGGGCGGGAC GCGATCGCCG GGTTCCCGGA GGACCGGGGC TGGGACCTGG CCGGGCTCTT
31081 CGACTCCGAC CCGGATGCCG TGGGCAAGTC CTACGTCCGC GAGGGCGGTT TCCTCACCGG
31141 CGCGGGCGGA TTCGACGCCG CCTTCTTCGG CATCTCGCCC CGCGAGGCGC TGGCCATGGA
31201 CCCGCAGCAG CGGCTGCTGC TGGAGACCGC GTGGGAGACC TTCGAGAACG CCGGAATCGA
31261 CCCGGGTTCG CTGCACGGCA CCGACGTCGG TGTGTTCAGC GGAGTGATGT ACCACGATTA
31321 CGGGGCCGAC GCCGGGACGG CGGCGGAGGG CCTGGAGGGG CATCTCGGCG TGGGCAGCGC
31381 GGGGAGCGTC GTCTCCGGAC GCGTGGCCTA CGCGATGGGC CTGACCGGGC CGCGCGGTGAC
31441 GGTGGACACC GCCTGCTCGT CCTCCCTGGT GGCGCTGCAC CTGGCGGTTC AGGCGGTGCG
31501 TACGGGCGAA TGCTCGCTGG CGCTCGCCGG GGGTGTCGCG GTGATGAGCA GGCCGACGTC
31561 GTTCATCGAG TTCTCCCGCC AGCGCGGCCT CGCCCCCGAT GGCCGCTGCA AGTCGTTCGC
31621 GGAGGGCGCC GACGGCACCA ACTGGTCCGA GGGTGTCGGG TTGGTGTTGC TGGAGCGGCT
31681 GTCCGATGCC CGCCGCAATG GCATGAGGT GCTCGCCGTG GTCCGTGGCA CGGCGGTGAA
31741 CCAGGACGGG GCGAGCAACG GCCTGACCGC GCCCAACCGC CCTTCCCAGG AACGGGTGAT
31801 CCGGCAGGCG CTGGCGAACG CCGGGCTGAC GGTGGCCGAT GTGGACGCGG TCGAGGCGCA
31861 CGGCACCGGC ACGAGTCTCG GCGACCCCAT CGAGGCCCAG GCGCTCCTGG CCACCTACGG
31921 GCAGGAGCGG CCGGAGGGTC AGCCGCTGTG GCTGGGGTCG TTGAAGTCGA ACATCGGGCA
31981 TGCGCAGGCG GCGGCGGGCG TGGCCGGTGT CATCAAGATG GTGCTGGCCA TGCGGCACAA
32041 CACGCTGCCG AAAACGCTGC ACGCGGAGCG GCCCACTACG CAGGTGGACT GGTCGCAGGG
32101 TGCGGTGTCG CTGCTGTCCG AGGCCCGGCC CTGGCCGGAG ACCGGACACC CCCGCCGCGC
32161 CGGAATCTCC TCCTTCGGCG TCAGCGGGAC GAATGCCCAT GTGGTCCTGG AGCAGGCGCC
```

-continued

SEQUENCE ID NOS: 1-3

```
32221 GCCTGAGGTG GCCGTGCCCG AAGCAGAGGC CAGCGAGGCG GGCACTCCTG GGCTGGTGGC

32281 CACGGGCGGC GTGGTGCCGT GGATGCTGTC GGGTAAGACT CCTGCGGCGC TGCGCGCCCA

32341 GGCCGAGCGT CTGGTCAGCC ACCTGGAATC CGGGGACGCT CCGCGTGCGG TGGACGTGGG

32401 CTGGTCACTG GCCACCACGC GCGCCGCCCT CGATCATCGC GCGGTCATCC TCGCCACGGA

32461 TACCGAGGAC GGCATCGCCA CCGCCCGCGC TTTGGCGGAG GGACGGCCCG ACCCGCTCCT

32521 GGTCACCGGG CAGACCGGGA CAGACGGCAA GACCGTGTTC GTCTTCCCCG GCCAGGGAGC

32581 CCAGTGGGTG GGCATGGGGG CACAACTCCT CAACACCTCG CCCGTCTTCG CCACCCGGCT

32641 ACACGAGTGC GCCGACGCGC TGGCCCCGTA TACCGACTGG TCGCTCATCG ACGTCATCAC

32701 CGGCGCACCC GATGCCCCTT CGCTCGACCG TGTCGACGTC GTACAGCCCG CCACCTTCGC

32761 CGTCGTCGTC TCCCTCGCCA CCCTCTGGCA ATCCATGGGT ATCCACCCCG ACGCCGTCAC

32821 CGGCCACTCC CAAGGCGAAA TCGCCGCAGC CTGCGTCGCC GGACACCTCA CCCTCACCAA

32881 CGCCGCCAAA ATCGTCGCCC TGCGCAGCCA GATCATCGCC GACCACCTCG CCGGACACGG

32941 CGGCATGATG TCCCTCGCCA CCCCCGCCGA CACCATCGAC CTCACCAACT GGCACGGCAA

33001 ACTCTGGATC GCCGCACACA ACGGCCCCAA CGCCACCGTC ATCGCAGGCG ACGCCGAAGC

33061 CCTGCACCAA CTCCACGCCC ACTACACCGA CCAAGGCACC CGAGCCCGCA TCATCCCCGT

33121 CGACTACGCC TCCCACACCG GACACGTCGA CACCATCAAG AACGAACTCC ACCAAACCCT

33181 GGCCGACACC ACCACCGAGC CCGGCACCCT CCCCTGGCTC TCCACCGTCG ACGGGGAGTG

33241 GATCGAACCC GACACGCTCG ACAGCGGCTA CTGGTACCGG AACCTGCGCC AAACGGTGCA

33301 GTTCCACACC GCCATCACCA CCCTCGCCGA CCAGGGCTAC CGCACCTACA TCGAAATCAG

33361 CCCCCACCCC GTCCTCACCA CCGCCATCCA AGAAACCCTC GAAACACACA ACACCCCCAA

33421 CGCGATCGTC ACCGGAACCC TCCGCCGCGA CGACGACACC CCCACCCGCC TCCTCACCAA

33481 CCTCGCCCAC CTCACCACCC ACGGAACACC CGTCAACTGG CCCACCCTCT TCACCGGCAC

33541 ACACCCCACC CGCATCACCC TCCCCACCTA CCCCTTCCAA CACCACCACT ACTGGCTCCC

33601 CCGCAACACC ACCACAGGCG ATGTGAGTGC CGTGGGCCTC AGGGCACGG GCCACCCGCT

33661 GGCCGGGGCC GTGGTGAGCG TGCCCGACAC CGGTGGTGTG CTGCTCACCG GCAACTGTC

33721 GGTGGCCACC CACCCCTGGC TGGCCGACCA CGCCGTCTCC GGAACCGTCC TGCTGCCCGG

33781 CGCCGCGATG GCCGAACTCG CCATCCGCGC CGGAGACGAG ACCGCCACCC CCACCCTGGA

33841 AGAACTGGTC ATCGGCCAGC CGATGACACT GCCCGAAGAC GGTGCGCTGC ACGTCCAGGC

33901 ACTGGTCGGC GGCGAGGAGG ACGGGCGCCG AGGGGTACGG ATCTACTCCC GCCCCGACGC

33961 GGCCCAGGAA CAGGAATGGC TGGAGCACGC CTCGGGCACG CTCGCCACGC AGCCGGACGG

34021 TTCGGCCGAG GGTGGCAGGG AAGACGGCAT GGCCGAGTGG CCGCCGCCCG GTGTCGAACC

34081 GATCGCTCTG GATCACTTCT ACGACGACCT CGCCCAGGCC GGGTACGAGT ACGGCCCCGC

34141 GTTCCGCGGG CTGAAGGCGG TCTGGAAGCG CGATGGCGAA GTGGGCGAGG TGTTCGCGGA

34201 GGCCGCGCTG CCGGAGGAGC AGACGGAGGC CGCCGGCCGG TTCGGCATCC ACCCGGCACT

34261 GCTGGACGCC GCGTTGCACG CGAGCAACTT CTGTGTGCCC CCGGTCCCGG GCCAGACGCT

34321 GCTCCCCTTC GTGTGGAACG ACGTACGGCT GCTGGCGGCG GGAGCCACGG CCGTCCGTGT

34381 GCGCGCCCGT GCCACCGGCC CGGATTCGTT CACGATCAGC CTGTACGACA GTACCGGCTC

34441 CCCCGTCGCC TCGGTGGACT CCCTGGTGCT CCGGGCGATC AGTCCCGAGC AGCTCGCCGC
```

-continued

SEQUENCE ID NOS: 1-3

```
34501 CGCGTCCGGC GGCGCCGATC GGTCCGCTGA TGCGCTGTTC ACGGTGGACT GGACCGAGCA
34561 CCCCACCGCC CTGGGGACCG AGGTCTCCTG GACCACCCTC GGCGACACCC ACACCCACGC
34621 CGACGTGGAC GCAGCCATGG ACGCGCTCAT CGCGGAGAG GACCGCCCCG GGGCCGTGGT
34681 CGCCGACACC ACGGCCTGGG CCGCCGGGGA CACCGAGCTG CCCACGCGGG CCAGGGACCT
34741 GGCCGCCCGC GCGCTGGACC TGGTGCAGCG ATGGCTAGCC CAACCCGAAC TCGACGACGT
34801 CCGGCTGGTG TTGCTCACCC GTGGGGCGGT GTCCGTACAC GACACCGCCG AGGTCACCGA
34861 TCCGGCCGCC GCCGCGATCT GGGGCCTGGT CCGCTCCGCC CAGTCCGAAC ACCCGGGCCG
34921 GATCGCCCTG GTGGACACCG ACGACGCGTC GCGGGAGGCG CTGCCCGAGG CGGTGGCGTC
34981 CGGCGAACCG CAGGTGGCGC TGCGCCGTGG GCTGCTGTGG GTGCCGCGTC TGGTGCGGTC
35041 GTCGCAGGGT CTCGCCGTAC CCGCCCACGA GCACTGGTAC CTCGACGTCT CGGAGAAGGG
35101 CAGCCTGGAG AACCTGGTGC TGCGGCCGGA TCCGGAGGCC ACCGCGCCGC TGGCCACCGG
35161 TCAGGTCCGG ATCGAGGTCC GCGCCGCCGG TCAGAACTTC CGGGACGTGC TCGTCGCGCT
35221 CGGCGGCGTG GCGGGTCAGG AGGGTCTGGG CGGCGAGGGC GCCGGTGTGG TGACCGAGGT
35281 CGGGCCGGGG GTCGAGGGCC TGGCCGTGGG CGACCGGGTG ATGGGTCTGT CCCGCGCTC
35341 GTTCGGCCCG CTGGCCACCG CGGACGCGCG AACGGTCGCG CCGATCCCCG AGGGGTGGTC
35401 GTACGCCACG GCCGCCGGAG TGCCGGTGGC CTATCTGACG GCGCTGTACG GACTGCGGGA
35461 CCTGGGCAAT GTGCAGCCGG GTGAGACGGT GCTGGTGCAC GCCGCCGCGG GCGGTGTGGG
35521 CATGGCCGCC GTCCAGTTGG CGCGGCACTT CGGCGCCCTC GTGTATGCCA CCGCCCATCC
35581 GTCGAAGCAC CATGTGCTGA CCGCGTTGGG GGTGCCGAG GGGCATCTGG CGTCCAGCCG
35641 CGACCTCGGC TTCGCCTCGG CGTTTCCCGC GCTGGACGTG GTGCTGAACT CCCTCACCGG
35701 CGAGTATGTG GACGCCTCAC TGGGGCTGCT CGGCACCGGT GGCCGCTTCG TGGAGATGGG
35761 CAAGAACGAC ATCCGCGATC CCGCCGTGGT CGCCGCGGCA CATCCCGGTG TGGGCTATCA
35821 GGCGTTCGAC CTGGAGGTG ACGCGGGGCC GGACCGGATC CGGGAGTTGC TCACTGAGCT
35881 GGTGGAGCTG TTCGAGGCGG GCCGGATAGA GCCGCTTCCG GTGCGGCAGT GGGACATCAC
35941 CCGCGCCCCC GAGGCGTTCC GCTGGATGAG CCAGGGGCGG CACACCGGCA AGATCGTGCT
36001 CACCCTCCCC CGCGCCCTGG ACCCGGACGG CACCGTCCTG ATCACCGGCG GCACCGGAAC
36061 CCTCGGCGCC ACCGTCGCCC GCCACCTCGT CACCCAGCAC GGCACACGCC GACTACTGCT
36121 GGTCAGCCGC CGGGGACCGG ACGCACCCGG CGCCACCGAC CTCACCACCG AACTCACCGA
36181 ACTCGGCGCC ACCGTCCACA TCACCGCATG CGACACCGCC GACCGCGACC AACTCGCCAC
36241 CACCCTCGCC GACATCCCGG CCGACCACCC CCTCACCGCC GTCATCCACA CGGCCGGGAC
36301 GCTCGACGAC GGCACCCTCA CCGCACTCAC CCCGGACCGC CTCGACACCG TCTTCCGCCC
36361 CAAGGTCGAC GCCATCACCC ACCTCCACCA CCTCACCCAC GACCACGACC TGGCCGCCTT
36421 CGTCATCTAC TCCTCCGCCG CCGGAACGCT CGGCAACGCG GCCAGGCCA ACTACGCCGC
36481 CGCCAACGCC TTCCTCGACG CCTTCGCCCA GTGGCGGCAC GCCCGCCATC GGCCCGCCAC
36541 CTCGCTGGCG TGGGGGCTGT GGAGCGACAC CAGCACGCTC ACCGCGACGA TGGACGCCAC
36601 CGACGTGCGC CGCACACGGC GGGCGGGGGT GCTGGGCATG ACAACGCCG AGGCGCTGCG
36661 GGTGTTCGAC ACCGGGTTGC GGTCCGGGCG GCCCGCGCTG GTGGCAGCGA AGATCGACCT
36721 CACCGCCCTG CGCGCGCCGG ACGCCGAGTT GTCGCCGCTG CTGCGCGGTC TTGCCCGCCC
36781 GGCGCGCCGC ACCGCGCGGA CCGCGGCCCC GGCGGCCGGT GGTCTGTCGG GGCAGTTGGC
```

-continued

SEQUENCE ID NOS: 1-3

```
36841 CGGGCTGTCC CCCGCCGGGC AGCGGGAGTT CCTGCTCAAC CTGGTGCGGG CGGAGGCCGC
36901 GGTGGTCCTC GGCCATACCG GGCCTGAGGC GATCGAGCCG ACGGTGGCGT TCAAGGAGAT
36961 GGGCTTCGAC TCGCTGACGG CGGTCGAACT GCGCAACCGG CTGAATGCGG CGACCGGGCT
37021 GCGGCTCCCC GCCACGTTGC TCTTCGACCA CCCGACCCCG GCTCTTCTCA CCGAGCTGTT
37081 CCACACCGAG CTGGGCGGCG GCCCGGCACC CGCCGCGGCG GCCCCGGTGA CCGTGCGCGC
37141 CGCCGCTGAC GAGCCGATCG CCGTGGTGGC GATGAGCTGC CGTCTGCCGG GCGGAGTGAC
37201 CGACCCGGAC GGGCTGTGGA ACCTGCTGCT CGGAGAGCGC GACGGCATCA CCGACTTCCC
37261 CCGTGACCGG GGCTGGGACC TGGAGGCGCT GTTCGACGCC GACCCGGACC GGAGTGGCAC
37321 CTCCTATGTG CTGCGTGGCG GGTTCCTCGA GGACGCGGCC GGTTTCGACG CGGACTTCTT
37381 CGGCATCTCG CCGCGTGAGG CGCTGGCGAT GGACCCGCAG CAACGGCTGT TCCTGGAAGC
37441 CTGCTGGGAG GTGTTCGAGC GGGCGGGCAT GGACCCGACC GCGGTGGGAG GCGGCGACAT
37501 CGGCGTGTTC GCCGGCGTCA TCAACCAGGA CTACGGCGTG CGGAGCGGTC CCGCTCCCGA
37561 GGACCTCGAG GGCTATATGC TCACCGGCTC GGCGACGAGT GTCGCCTCCG GCCGGGTGGC
37621 CTATGTGCTG GGCCTGGAGG GCCCGGCGGT CACGGTGGAC ACGGCGTGCT CCTCCTCACT
37681 GGTGGCCATG CACTGGGCCG TACAGGCATT GCGGCAGGGC GAGTGCTCGA TGGCGCTGGC
37741 CGGGGGCGCC ACGGTGATGG GGCGGCCGTC GGCGTTCGTG GAGTTCTCAC GCCAGCGCGG
37801 CCTGGCGCCG GACGGCCTGT GCAAGGCGTT CGGGGCGGGT GCGGACGGCA CCACCTTCAG
37861 CGAGGGTGTC GGGGTACTGC TGCTGGAACG GCTCTCGGAC GCCCGCCGCA ACGGCCACGA
37921 GGTGCTGGCC GTGGTCCGCG GTACGGCGGT GAACCAGGAC GGCGCCAGCA ACGGCCTCAC
37981 CGCCCCCAAC GGCCCCTCCC AGCAGCGCGT GATCCGACAG GCACTGGCGA ACGCCGGACT
38041 GTCGGCCACC GACATCGACG CCGTCGAAGC ACACGGCACC GGCACCGCCC TCGGCGACCC
38101 CATAGAAGCC CAGGCACTCC TGGCCACCTA TGGCCAGGAC CGTCCTGGGG ACGAGCCCGT
38161 ATGGCTCGGC TCGCTGAAGT CGAACACCGG GCACACGCTG GCCGCGGCAG GCGTGTCCAG
38221 CGTCATCAAG ATGGTGCTGG CGATGCGGAA CGGCACGCTT CCGCGCTCCC TGTACGCCGA
38281 CGAGCCCACA CCGGAAGTGG ATTGGTCCCA GGGCGCGGTG TCCCTGCTCA CCGAGGCCCG
38341 GCCCTGGCCG GAGACCGGAC ACCCCCGCCG CGCCGGAATC TCCTCCTTCG GCATCAGCGG
38401 CACCAACGCC CACCTCATCC TGGAGCAGGC CCCTCAGCCC GAACCCAGG CCGAGACCGA
38461 CCCCGAGCCC GAAGCCGCGC CGAAGGCGGA CGACGGCATG GCCACTCCCG GGCTCGTGGC
38521 GACCGGCGGG AGCGTGCCCT GGGTGCTGTC CGCCAAGACC GCCACGGCCC TGCGGGCTCA
38581 GGCTCAACGG CTCCTGGACC ACCTGGAGTC CGGGGTGACC GACCGCCCCC TCGACATCGG
38641 CTGGTCCCTG GCCACCACCC GCACCCTCCA CGACCACCGC GCGGTCATCC TCACCGACAC
38701 CGAGGGCGCT GACGCCACGG CCGCCCTCAC CGCCCTCGCG ACCGAACAAC CCCACCCCCG
38761 CCTCACCACC GGCCACGCCA CCACCCACGG CAAGACCGTG TTCGTGTTCC CCGGCCAGGG
38821 CGCCCAATGG GCAGGCATGG GAGCCCAACT CCTCGACACC TCACCCGTCT TCGCCACCCG
38881 CCTCCACGAA TGCGCCAAAG CTCTCGCCCC CTACACCGAC TGGTCACTCA TCGACGTCAT
38941 CACCGGCGCG CCTGATGCCC CTTCGCTCGA CCGCGTCGAC GTCCTCCAGC CCACCACCTT
39001 CGCCATCATG GTCTCCCTCG CCGCACTCTG GCAGGCCAAC GGCATCCACC CCGACGCCGT
39061 CATCGGCCAC TCCCAAGGCG AAATCGCCGC AGCCTGCGTC GCCGGACACC TCACCCTCAC
```

-continued

SEQUENCE ID NOS: 1-3

```
39121 CAACGCCGCC AAAATCGTCA CCCTCCGCAG CCAGACCATC GCCCACCACC TCACCGGACA
39181 CGGCGCCATG ATGTCCGTCC TCGCATCCCC CACCTGGGTC CAGGAAACAC TCGCACCCTG
39241 GCACGGACAC CTATGGATCG CCGCCGTCAA CGGCCCCGCA TCCGTCTCCG TATCCGGAGA
39301 CCCCGACGCA CTCGCCGAAT TCGGCACCAC CCTCTCCAAA GCCAAGGTCT ACCGCTGGCA
39361 ACTCCCCGGC GTCGACTTCG CCGGACACTC CGGACACGTC GACACCATCA AGACCAGTT
39421 GCACAACGTA CTCGACGGCA TCACCGCCAC ACCCGGCCAC ACCGCCTGGA TGTCCACCGT
39481 CGACGCCGAC TGGGCCAACC CCACACACAT CGACCCCGAC TACTGGTACC GCAACCTCCG
39541 CGACACCGTC CGCTTCGAAG AAGCCACCCG AGCCCTCCTC ACCCAGGGCT ACCGCGTCTT
39601 CATCGAGGTC AGCACCCACC CGGTGCTGAC CACCGCCATC CAGGACACCA CCGAATCCCT
39661 CCCCGATACC CCCACCACCA TCACCGGCAC CCTCCGCCGC GACGACGGCG GCCCCGACCG
39721 CGTCCTCACC AGCCTCGCGG AGCTCTCCGC CGCCGGAATT CCGGTCCACT GGCCCACCGC
39781 GTACGCCGGA ACCACACCCT CCCAAGTTCC GCTGCCCACC TACCCCTTCC AGCACCAGCA
39841 CTACTGGCTG GCCGCCACCG GCCACCACGG GGATGTCGGC TCCGTGGGAC TGCGCGACGC
39901 GGCGCACCCG CTGCTGGGGG CCGTGGTCAG CGTGCCGGAC ACCGGAGGGG TGCTGCTCAC
39961 CGGGCGGCTG GCACCGTCGG CGCAGTCCTG GCTGGCCGAC CATATGCTGT CCGGCGTCGC
40021 CCTGGTGCCG GGTACGGCGA TCGTGGAACT GGCCGTACGG GCCGGGGACG AGACCGGCAC
40081 ACCGGTGTTG GAGGAGCTGG TCCTCGGCCA GCCGATGCTT CTCCCCGAGG ACGGCTCGCT
40141 TCAGGTGCAG GTCCTGGTCG GCGCGGCCGA GGACGATGAG CGCCGTACGG TGCGGGTCTA
40201 CTCCCGCGGC GACGAGTCCG AGCCCTGGGT CGAGCACGCC TCCGGCATCC TGTCCGCGCA
40261 GGCGCTCATA CCTGTCGAGG CGGAGCGGCA GTGGCCGCCC GCCGGGCGG AACCCGTTGC
40321 CCTGGAGGGC TTCTACGACC GCTTGGCCGA GGCAGGCTAT GAGTACGGTC CGGTGTTCCG
40381 CGGTCTCACC GCGGCGTGGA CGCGCGACGG TGATGTGTTC GCCGAGGTCA CCCTCGGCGA
40441 GGAGCAGCAT GACCTCGCGC GCCGCTTCGG CATCCATCCG GCGTTGCTGG ACGCGGCGCT
40501 GCACGCGAGC AACTTCTGCC CGGGCAACGA GCCCGGCGGC GGGACGTATC TGCCGTTCTC
40561 CTGGAACGGT GTGCAGTTGC ACGCCGACGG CGCCACCGCC CTACGAGTGC GGGTCACCTC
40621 CACCGGGCCG GACAACCTGT CCCTGTACGC GACCGATCCG CACGGGGTGC CCGTGGTGAC
40681 CGTCGGGTCG CTGGTGCTCA GGGAGACCAC CGCGGAGCAG CTCCGCACCA CATCGGCCTC
40741 GTCCACCGCG GATTCCCAGT TCACCGTGGA GTGGACCGAA CATGCCCTGG CCCGGGACGA
40801 GGTGGCGTGG GCGGCGCTGG ACGCCGTGCC CGACCAGGAC ACGTGGCCGC CGGTGGTCGT
40861 CGCCGACACC CGGGCATACA CCGCGGAGGG CGGCGAACTA CCGGAGCGCG CCCGTGCGCT
40921 GACCTGCCGG GCACTGGCCG CGATACGGCG TCTGATCAGC GACGACGCAC TCGCCGACAG
40981 CCGTCTGGTG CTGCTCACCC GGGGTGGCAT GGCGGTGCAT GACGACACCG AGGTCACCGA
41041 CCCGGCCGCC GCCGCGGTGT GGGGCCTGGT GCGCGCCGCG CAGGCCGAGC ACCCGGGCCG
41101 GGTGTGCGTG ATCGACACCG ACGACCGGTC GGCCGAGGCC CTGCCCGCCG CGCTGGCCAC
41161 GGAGGAACCC CAGCTCGCGC TGCGTGGCGG AATCGCGTGG GTGCCCCGCC TGGTGCGAGC
41221 GCGCCCGGGC CTGGCGGTCC CGGCCACCGC GGCGTGGCAT CTGGACGTCA CCGAACACGG
41281 CACACTGGAG AACCTCGCCC TGGTGCCCCA CCCTCGGGCG GAGGCGCCGC TGGAGGCGGG
41341 CCAGGTGCGG ATCGCGGTAC GCGCCGCCGG TCAGAACTTC GCGGATGTGC TCATCGCCCT
41401 CGGCATGTAC GAGGCGGAGA TCGGCACCGA GGGCGCGGGC GTGGTGACCG AGGTCGGCCC
```

-continued

SEQUENCE ID NOS: 1-3

```
41461 GGGCGTGGCG GATCTGGCCG TGGGCGACCG TGTGATGGGC ATGCTGCCCG GTTCGTTCGG
41521 GCCGCTGGTG GTGGCGGACC GGCGGACGGT GGTGCGGATG CCGCGCGGCT GGTCGTTCAC
41581 GGCGGCGGCC GGGGTGCCGG TCGCCTATCT CACCGCGCTG TACGCGTTGC GGGATCTGGG
41641 CGATGTCCAG CCGGGCGAGA CGGTGCTGGT GCACGCCGCA GCCGGTGGAG TCGGCATGGC
41701 CGCCGTACAC CTCGCCCACC ACTTCGGCGC CACCGTCCTC GCCACCGCCC ACCCGGCCAA
41761 ACACCACAGC CTGGAACAGC TCGGGGTGGC CACGGAACGG CGCGCCTCCA GCCGCGACCT
41821 CGCCTACGCC CACACCTTCC CGACCACCGA TATCGTCCTC AACTCCCTCA CCGGCGAACA
41881 CATCGACGCC TCGCTGCGGT TGCTCAACCC CGGTGGCCGT TTCATCGAGA TGGGACGTAC
41941 CGACATCCGG GACGTGGACG AGGTGGCCGC GACGCACCCG GACCGCACCT ATCGCGCGTT
42001 CGACCTGGGC GCGGACGCGG GGCCGGATCG CATCCAGGAA CTGCTGGTCG AGCTGGTGGA
42061 CCTGTTCGAG CAGGGCCTGA TCCCTCCGTT GCCCACCCGG CCGTGGGAGA TCACCCGCGC
42121 CCCCGACGCG TTCCGCTGGA TGAGCCAGGG CCGCCACACC GGCAAGATCG TGCTCACTCT
42181 CCCGCGCACC CCCGACCCCG ACGGCACCGT ACTGATCACC GGCGGCACCG GCACCCTCGG
42241 CACTGCCATC GCCCGTCACC TCGTCACCCA CCACGGTGTA CGCAACCTGG TCCTCACCGG
42301 CCGCCAGGGG CCGAACGCCC CCGGCGCGGC CGACCTTCAC GACGAACTGA CCGCACTGGG
42361 CGCACAAGTA CGGATCACCG CCTGCGACAG CGCCGACCGC GGCCAACTCG CCGCACTCCT
42421 CGCCGGCATC CCGTCCGACC ACCCCCTCAC CGGCATCGTG CACACCGCCG GCACCCTCGC
42481 CGACGGCACC CTCACCACAC TCGACCCCGA CCGCATCGAC ACCGTCTTCC GCCCCAAGGT
42541 CGACGCGGTC ACCCACCTGC ACGACCTCAC CCGCGACCAG GACCTGGCCC TCTTCGCCGT
42601 GTACTCCTCC GCCGCCGGAA TCCTCGGGAA CGCGGGCCAG GCCAACTACG CCGCCGCCAA
42661 CACCTTCCTC GACGCCTTCG TACAGCAGCG GCGCGCGGCG GGGCTGGCCG GGCTGTCGCT
42721 GGCCTGGGGC CTGTGGGCGG AGACCAGCGA GCTGTCGGCC GCGCTGATCA CGGCCAACCG
42781 GGATCGCACC CGACACGGTG TCGTCCGCCC GATGACCACC GAGCACGCCC TGAGCCTCTT
42841 CGACTCCGCC CTCGGCCTGG GGCTGCCCCT GGTGGTACCG GCGAAGCTGG ACCCCGGCGC
42901 ACACGAGTCC GCCGCGGGCG CTGTGTCGCC GCTGCTCACC GGGCTCGTCC GGCCGACCCG
42961 ACGCACCCTG CGGTCCACGT CGGGCCAATC CGGCGAAGGC GGTCTGACGG CCCGGCTGGC
43021 GGCGCTGTCC GAGGCCGATC AGCACCGGCT ACTGCTGGAC CTGGTACGGG ACCATACGGC
43081 GACCGTGCTC GGGCACACCG GGAAGGACGC CGTGGACGCC AGGCGCGCGT TCAGCGACAT
43141 CGGGGTCGAC TCGCTCATCG CGGTGGAACT GCGCAACCGG CTCGCCGGCG CGACCGGGCT
43201 GCGGCTGCCC GCGACGGTCG TGTTCGACTA CGCGACACCG GAGGCGATGG CCGGACATCT
43261 GCGGTCCGTG GTGGCCGGAG ACACGGCCGC CCCCGCCTCC CCGTCGACGT CGGCGCCCGC
43321 TTCGGCGGTG GCCCCGGCGG ACGACCCGGT GGCCATCGTG TCGATGAACT GCCGACTGCC
43381 CGGCAAGGTC ACCGGCCCAG GGGAACTGTG GGATCTGGTG TCCCAGGGCC GGGACGCGAT
43441 CGGCCCCTTC CCCACGGACC GCGGCTGGGA CGTGGAGACG CTGTTCGACC TCGACCCGGA
43501 CGCCGTGGGC AAGTCCTACG TACGCGAGGG CGGTTTCCTC ACCGGCGCCG GTGACTTCGA
43561 CGCCGAGTTC TTCGGCATCT CGCCACGCGA GGCGCTGGCG ATGGATCCGC AGCAGCGACT
43621 GCTCGCCGAG ACCTCATGGG AGCTGTTCGA GCAGGCGGGC ATCGACCCGA TGTCCGTGCG
43681 CGGACAGGCC ATCGGGGTGT CGCCGGGGT CATCGACCAG GGATACATCG CCCACTCCGA
```

-continued

| SEQUENCE ID NOS: 1-3 |
|---|

```
43741  GGCGCCCCCG CCGGAGTTGG AGGGCTACCT GATGACCGGC AGCACCACAA GTGTGGCCTC
43801  CGGCCGAGTG GCCTATCTGC TGGGCCTCGA AGGCCCCGCG GTGACGGTGG ACACGGCGTG
43861  CTCGTCGTCG CTGGTGGCGC TGCATCTGGC CGTACAGGCG CTGCGGGCGG GCGAGTGCTC
43921  GATGGCCATC ACCGGTGGCG TGACGGTGAT CGCCAAGCCC GGCGGTTTCA TCAGCTTCTC
43981  CCGCCAGCGC GGGCTCGCGC CGGACGGCCG TAGCAAGTCC TTCAGCGAGG CGCCGACGG
44041  CACCACCTTC AGCGAGGGCA TCGGTCTGGT GCTGCTGGAA CGGCTCTCGG ACGCCCGCCG
44101  CAACGGCCAT GAGGTACTGG CCGTGATCCG TGGCACCGCG GTGAACCAGG ACGGGGCGAG
44161  CAACGGCCTC ACCGCTCCGA ACGGGCCCTC CCAGCAGCGA GTGATCCGGC AGGCCCTGTC
44221  CAACGCCGGG CTCACAGTGG CCGACGTGGA CGCGATCGAG GCACACGGCA CCGGCACCGC
44281  CCTCGGCGAC CCCATCGAGG CACAGGCACT GCTCGCCACC TACGGCCAGG ACCGCCCGGG
44341  GGACGAACCC GTGTGGCTCG GCTCGCTGAA GTCCAACATC GGCCACACGC AGGCCGCCGC
44401  GGGCATCGCG GGCCTCATCA AGATGGTGCT GGCGATGCGG CATGGCATGC TTCCGCCCTC
44461  ACTGCACGCC GGCGAGCCCA CCACCAAGGT CGACTGGGCG TCGGGGCGG TGTCCCTGCT
44521  GTCCGAGGCC CGACCCTGGC CGGAGACGGG ACACCCTCGC CGCGCCGGAA TCTCGTCCTT
44581  CGGCATCAGC GGGACGAACG CACACGTGAT CCTGGAGCAG GGGCCGGAGG TGGCTGTGCC
44641  CGAGGCGGAG ACGGGCGCTC CTGGGTTGGT GGCCACAGGC GGTGTGGTGC CGTGGGTGCT
44701  GTCCGCCAAG AGCCCTGCGG GGCTGCGGGC TCAGGCCGAG CGTCTGGTCA GCCACCTGGA
44761  ATCCGGGGAC GCTCCGCGTG CGGTGGACGT GGGCTGGTCA CTGGCCACCA CGCGCGCTGC
44821  CCTCGATCAT CGCGCGGTCA TCCTCGCCAC GGATACCGAG CAGGGCACGG CGACCGTCCG
44881  TGCCCTGGCG GAGGGACGGC CCGACCCGCT CCTGGTCACC GGGCAGACCG GGACGGATGG
44941  CAAGACCGTG TTCGTCTTCC CCGGCCAGGG AGCCCAGTGG GTGGGCATGG GGGCACAACT
45001  CCTCAGCACC TCTCCCGCCT TCGCCACCCG GCTACGCGAG TGTGCCGACG CGCTGGCCCC
45061  GTATACCGAC TGGTCGCTCA TCGACGTCAT CACCGGCGCA CCCGATGCCC CTTCGCTCGA
45121  CCGTGTCGAC GTCGTACAGC CCGCCACCTT CGCCGTCGTC GTCTCCCTCG CCACCCTCTG
45181  GCAATCCATG GGTATCCACC CCGACGCCGT CACCGGCCAC TCCCAAGGCG AAATCGCCGC
45241  AGCCTGCGTC GCCGGACACC TCACCCTCGA CGCCGCCGCC AAAATCGTCG CCCTGCGCAG
45301  CCAGATCATC GCCGACCACC TCGCCGGACA CGGCGGCATG ATGTCCGTCC TCGCCTCGCG
45361  GGAACAGGTC GAGGAAGCCC TCACCCCGTG GCAGGGCAAG CTCTGGATCG CCGCGCACAA
45421  CAGCCCCCAG GCGACCGTCG TCGCAGGCGA CATCGACGCT CTGCACGAAC TCCACGCCCA
45481  CTACACCGAC CAGGACATCC GAGCCCGCAT CATCCCCGTC GACTACGCCT CCCACACCGG
45541  ACACGTCGAC ACCATCAAGA ACGAACTCCA CCAAACCCTG GCCGACACCA CCACCGAGCC
45601  CGGCACCCTC CCCTGGCTCT CCACCGTCGA CGGGGAGTGG ATCGAACCCG ACACGCTCGA
45661  CAGCGGCTAC TGGTACCGGA ACCTGCGCCA AACGGTGCAG TTCCACACCG CCATCACCAC
45721  CCTCGCCGAC CAGGGCTACC GCACCTACAT CGAAATCAGC CCCCACCCCG TCCTCACCAC
45781  CGCCATCCAA GAAACCCTCG AAGCCAACGA CACCTCCAAC ACCACCATCA CCGGAACCCT
45841  CCGCCGCGAC GACGACACCC CCACCGCCT CCTCACCAAC CTCGCCCACC TCACCACCAA
45901  CGGCCACACC CCCGACTGGA CAGCCCTCTA CTCCGCCACC CACCCCCACC CCACGCCCCT
45961  CCCCACCTAC CCCTTCCAAC ACCACCACTA CTGGCTCACA CCGTCCGAGG TGCCGGAGGC
46021  GGTGGCCGAC GGTGTGTTCT GGGAGACCGT GGAGCGGGGC GACCTCGCCT CCCTGGCCGA
```

-continued

SEQUENCE ID NOS: 1-3

```
46081 TTCCCTCGGC GTCGAGGAGA AGGCGCTGGA GCCCGTCCTG CCGGGGCTGA CGTCGTGGCG

46141 GCGCCGCAAC CAGGACCAGT CCACCGTGGA CGCCTGGTCG TATCGCATCG CCTGGGATCC

46201 GGTGGCCAGC GGGGAGGCGC CCGTACTGCC AGGAGCGTGG CTGGTGGCCG TGGCCTCACC

46261 GCAGACGAGC GACACCGCGG TGACGGGCGT GATCGCCGCG CTGGCCGCGC ACGGCGCCGA

46321 TCCCGTGGTG GTCGAGGTGG ACACGGTGGA GCGGGCGGAG GTGACCGCCC TCCTGCGGGA

46381 GCGGATGTCG GGTTCCGATG ACGAGTACGC CGGGGTGCTG TCCCTGCTGG CATGGGACGA

46441 GCGGACCTGC GAACCCGGCA CGCTCTCCCG GGGCGTGGCG GCCACCGTGG CGCTGATGCA

46501 GGCCGTGGAG GAGATCGGGC TCACCGCTCC CCTGTGGTGC CTGACGCGTG GCGCGGTCGC

46561 CGTGCGTGAA CCCTCCGAGG TGACCAGCGA GTTCCAGCCG CTGGCCTGGG GAATGGGCGT

46621 GGTGCAGGGG CTGGATCAGC CGTCCACCTG GGGTGGGATC GTGGATCTGC CGCGGACGCC

46681 GGATGATACG GCCCTTGCCC GGTTGTGCTC GGTGCTTGCC GGAGTGGACG CGGAGGACCA

46741 GGTCGCGGTG CGCGCGTCGG GGGTGTTCGC CCGGCGGATG CGGCGCGAAC CGGTGACGTC

46801 GGCACCGGCG TGGCAGCCAC GCGACACGGT GCTGATCACC GGCGGCACCG GCGGACTCGG

46861 CTCGTACGTG GCCCGTTGGG CCGCGCGTCA CGGCGCCCGG CGTGTGGTGC TGCTCAGCCG

46921 TCAGGGTGCG CAGGCGGCGG GCGCGGCGGA GCTGGAGGCC GAGCTGACCG CGCTGGGCGC

46981 GGACGTGACC ATCGCGGCGT GTGATGTGAC CGACCGGGAC CAGCTCGCGG CCGTCCTGGC

47041 GGAGATTCCG GATGACGTGC CGTTGTCGGC CGTGGTCCAC GCCGCGGGGC TGGCGCTGCC

47101 GGAGAAGCCG CTGTCGAAGA TGACACTCGC CGAGTTCGCC GATATCGGCC GGGCGAAGAT

47161 CGCCGGTGCG CGGCACCTCG ACGATCTGCT GGGGGAACGG GAGTTGGACG CCTTCGTCCT

47221 GTTCTCGTCC GGAGCGGCGG CCTGGGGCAG CGGCGGCCAG AGCGCCTACG CCGCCGGCAA

47281 CGCCTATCTC GACGGGCTGG CGCAGCGCCG CCGCGCACGG GGCTGGCGG CCACGTCGGT

47341 GGCGTGGGGC GCCTGGGGTG GCGGCCTTGG CACGATCGAC GAGGCGATGG GCGCGCAGTG

47401 GCGCCGTACG GGTCTGATGA CCATGGACCC GCGGCTGGCG GCGCTGGCGA TGGCGCACAC

47461 CGTGGGCAGC GGCACCGCCC ACGGGGTGGT GGCCGACATC GACTGGGAAC GGTTCGCCCC

47521 CGGCTACACC CTGGCCCGGT TCCGGCCGCT GCTGCGGGGA CTGCCCGATG TCATCGACCT

47581 GCTGACCGAG GACACACACG AGGACGGCGC GGGACAGACG GAGCTGATCG CACGGCTGGC

47641 CGGGCTGAGC CCCGGGACC AGGAGCGGCT GCTCACCGAG CTGGTGCAGG CCGAGGCCGC

47701 GGCCGTACTC GGACACGCGA GCGCCGATGC CACCGGGGAC CGTCCGTTCA GCGAGATCGG

47761 ATTCGACTCG CTGACGCGCG TGGAGCTGCG CAATCGCCTC AATGCCGGCA CGGGGCTGAA

47821 GCTGCCCGCG ACGATGGTGT TCGACCACCC GCGGCCCAGT GCGCTGGCGC GCCGTATCCG

47881 CACCGAACTC GGCCAGACCG ACACCTCGTC GGTGGACTCG GTGCTGGCCG AGCTGGAGCG

47941 GCTGGAAGCA CATTTGGCGG CGCTGCCGAA GGAGAAGATC GAACGCGCCC GGATCACCTC

48001 GCGGCTACAG CGGATGACCA CCAAGGTCGC CGAGATCGAG GCCAACGGCG CGGGCGGCGA

48061 AACCGTCACC GAACGACTCG ACACGGCGAA CGCCGACGAC GTGTTCGCCT TCATCGACCA

48121 GGAGTTCGGC GTGGACTGAT TCCCCGTCTC GTCTCCGCTC ACCGATTTCA CCCACGAGGC

48181 TCTTGGCGAG GTCCAGATGG CGAATGACGA AAAGCTCCTC AACTACCTCA GCGGGTTAC

48241 CGCCGACCTG CACCAGACGC GGGAACGGTT GCGCAAGGCC GAGGCGGCGA CGGAGGAGCC

48301 GATCGCCATC GTCGGCATGG GCTGCCGCTT CCCGGGCGCC GTGACCACCC CAAACGGGCT
```

-continued

| SEQUENCE ID NOS: 1-3 |
| --- |

```
48361  GTGGGATCTG GTGGCCGACG GCCGGGACGC GATCGCCGGG TTTCCGGAGG ACCGCGGCTG

48421  GAACCTGGAG AACCTCTTCC ACGCCGACCC TGACTCCGTC GGCACCTCCT ATGTGCGCGA

48481  GGGCGGTTTC CTCGCCGACG CGGCGGAGTT CGACGCCGAG TTCTTCGGCA TCTCCCCGCG

48541  TGAGGCGCTG GCCACCGACC CGCAGCAGCG GCTGCTGCTG GAGACCGCGT GGGAGACCCT

48601  CGAGCACGCG GGAATCGACC CGAGTTCGCT GGCGGACAGC GACGTCGGCG TGTTCACCGG

48661  CCTGGCCAAC GGTGACTACG CGCTGACCGT GGACCAGGTG CCGGAGGGGT TCGAGGGATA

48721  TCTGGGTCTC GGTGGCGCGG GCAGCATCGC GTCCGGCCGC ATCTCGTACT CGCTCGGTCT

48781  GCTCGGCCCG GCGGTCACTC TGGACACCGG GTGCTCCTCG TCCCTCGTGG CGATGCACTT

48841  GGCCAGTTAT GCGCTCCGGT CCGGGGAGTG CTCCATGGCC CTCGCCGGTG GCGTGATGGT

48901  GATGGCCACC CCCGGCGGCT TCGTCGGATT CTCCCGGCAG CGGGGGCTGG CGCGCGACGG

48961  GCGCTGCAAG TCCTTCGGTG AGGGCGCGGA TGGCACCAAC TGGTCCGAGG GCGCCGGTCT

49021  TGTGCTGCTG GAACGACTGT CCGATGCCCG CCGCCATGGG CATGAGGTGC TCGCGGTCAT

49081  CCGTGGCACC GCCGTCAATC AGGACGGCGC TTCCAACGGC ATCACCGCGC CAACGGCCC

49141  GTCCCAGGAA CGGGTGATCC GCCAGGCACT GGCGAACGCC GGGCTGACGG TGGCCGATGT

49201  GGACGCGGTC GAGGCGCACG GCACCGGCAC GAGTCTCGGC GACCCCATCG AGGCCCAGGC

49261  GCTCCTGGCC ACCTACGGCC AGAACCGCCC GGAGGATCAG CCGCTGTGGC TGGGCTCCAT

49321  CAAGTCCAAC ATCGGCCATA CCCAGGCCGC CGCGGGTGTC GCGGGCGTCA TCAAGATGGT

49381  GCAGGCCATG CGGCATGGCG TACTGCCCAA GACACTCCAC GCCGACGAGC CCACCACCAA

49441  GGTGGACTGG TCGCAGGGTG CGGTGTCGCT GCTGTCCGAG GCCCGGCCCT GGCCGGAGAC

49501  CGGACACCCC CGCCGCGCCG GAATCTCCTC CTTCGGCGTC AGCGGGACGA ATGCCCATGT

49561  GATCCTGGAG CAGGCGCCGC CTGAGGTGGC CGTGCCCGAA GCAGAGGCCA GCGAGACGGG

49621  CACTCCTGGG CTGGTGGCCA CGGGCGGCGT GGTGCCGTGG ATGCTGTCGG GTAAGACTCC

49681  TGCGGCGCTG CGGGCTCAGG CCGAGCGTCT GGTCAGCCAC CTGGAGTCCG GGAGCGACGC

49741  CAACCCGGTC GATGTGGGCT GGTCGCTGGC CACCACCCGG GCGGCTCTGG ATCACCGCGC

49801  GGTCATCCTC GCCACGGATA CCGAGGACGG CATCGCCACC GCCCGCGCTT TGGCGGAGGG

49861  ACGGCCCGAC CCGCTCCTGG TCACCGGGCA GACCGGAACA GACGGCAAGA CCGTGTTCGT

49921  CTTCCCCGGC CAGGGAGCCC AGTGGGTGGG CATGGGGGCA CAACTCCTCA ACACCTCCCC

49981  CGCCTTCGCC ACCCGGCTAC GCGAGTGTGC CGACGCGCTG GCCCCGTATA CCGACTGGTC

50041  GCTCATCGAC GTCATCACCG GCGCACCCGA TGCCCCTTCG CTCGACCGTG TCGACGTCGT

50101  ACAGCCCGCC ACCTTCGCCG TCGTCGTCTC CCTCGCCACC CTCTGGCAAT CCATGGGTAT

50161  CCACCCCGAC GCCGTCACCG GCCACTCCCA AGGCGAAATC GCCGCAGCCT GCGTCGCCGG

50221  ACACCTCACC CTCACCAACG CCGCCAAAAT CGTCGCCCTG CGCAGCCAGA TCATCGCCGA

50281  CCACCTCGCC GGACACGGCG GCATGATGTC CGTCCTCGCC TCGCGGGAAC AGGTCGAGGA

50341  AGCCCTCACC CCGTGGCAGG GCAAGCTCTG GATCGCCGCG CACAACAGCC CCCAGGCGAC

50401  CGTCGTCGCA GGCGACATCG ACGCTCTGCA CGAACTCCAC GCCCACTACA CCGACCAGGA

50461  CATCCGAGCC CGCATCATCC CCGTCGACTA CGCCTCCCAC ACCGGACACG TCGACACCAT

50521  CAAGAACGAA CTCCACCAAA CCCTGGCCGA CACCACCACC GAGCCCGGCA CCCTCCCCTG

50581  GCTCTCCACC GTCGACGGGG AGTGGATCGA ACCCGACACG CTCGACAGCG GCTACTGGTA

50641  CCGGAACCTG CGCCAAACGG TGCAGTTCCA CACCGCCATC ACCACCCTCG CCGACCAGGG
```

-continued

SEQUENCE ID NOS: 1-3

```
50701 CTACCGCACC TACATCGAAA TCAGCCCCCA CCCCGTCCTC ACCACCGCCA TCCAAGAAAC

50761 CCTCGAAGCC AACGACACCT CCAACACCAC CATCACCGGA ACCCTCCGCC GCGACGACGA

50821 CACCCCCACC CGCCTCCTCA CCAACCTCGC CCACCTCACC ACCCACGGAA CACCCGTCAA

50881 CTGGCCCACC CTCTTCACCG GCACACACCC CACCCGCATC ACCCTCCCCA CCTACCCCTT

50941 CCAACACCAC CACTACTGGC TCCCCCGCAA CACCAGCACA GGCGACATCG CCTCAGCCGG

51001 TCTCCACGAC CCCGCGCACC CGCTTCTCAC CGCCGCCGTC CACCTCCCCG ACACCGGTGG

51061 CACCGTCCTC ACCGGGCGGC TCTCCCTGAC CACCCACCCC TGGCTGGCCG ACCACACCGT

51121 GTCCGGTGCC GTCCTCCTCC CCGGCGCCGC GATGGCCGAA CTCGCCATCC GGGCCGGAGA

51181 CGAGACCGCC ACCCCCACCC TGGATGAGCT GGTCATCGAG CAGCCACTGG CGCTACCGGA

51241 CAGTGGCTTC CTGGACATCC GGGTGGTCGT GGGCGGCCCT GACGAGGCCG GGCGTCGGGA

51301 CGTACGCATC TACTCCCGCG CCGCAGAAGA ATCAGCGCAG TGGACGGTGC ACGCCACCGG

51361 CACGCTGGCC CAGGACACCA CGGCTCCTCC GTCGCCCACC GCCGCCGAAT GGCCACCCGC

51421 CGGTGCCGAG CCGGTGGCCG TCGAGGGCCT GTACGAGCAG ATGGCCGAGG GGGGCTACGA

51481 CTACGGACCG ACGTTCCAGG GCCTGAAGGC GGTATGGACC CGCGACGGCG ACGTGGGCGA

51541 GGTGTTCGCG GAGGCCGCGC TGCCGGAGGA GCAGACGGAG GCCGCCGGCC GGTTCGGCAT

51601 CCACCCGGCA CTGCTGGACG CCGCGTTGCA CGCGAGCAAC TACTGCCTGC CGGGGAGCC

51661 CGGCGGCCGT ATGCTGCTGC CGTTCGCGTG GAACGACATA CGCCTGCACG CCACCGGTGC

51721 CACTTCGGTG CGCGTACACG CCCGTTACAC CGAGGACGAC GGCCTCTCCG AGGTCCTGGT

51781 CGACACGGCC GGAGGGCTGG TCGCGTCGAT CGGTTCGCTG GTTCTGCGGG AGGTCGACGC

51841 GGCGCAGCTC GAAGCGCTGG CCTCCACCTC GGTGAACGAC GCGCTGTGGA CGGTCACTTG

51901 GACCGAACAC ACCGCCACCA CGGACGAGAT CCGGTGGGGC ACCCTAGGGG ACGTCTCACC

51961 CGTCCTCGCC GCCGCCGAAG CCCCGGCCTT CGCCGATGTC ACAGAGATCG CCACCGCGCC

52021 CGCCACGGAG ATCGCCGGGA CCGAGGACCG GCCCGCGCTG ATCGTCGCCG ACACGACAGC

52081 ATGGCAGTCG CGGGACGCCG ACCCCATCAC GCGGGCGCGC GAACTGGCCA CGCGGGCGCT

52141 GGACCTGTTG CAGCGGTGGG TGACGCTGCC TGAGCTGTCG GAAACACGGC TGGCGGTCCT

52201 CACCCGCGGT GCGATGGCCG TACACGACTC GGCCGAGGTC ACCGACTCCG CCGCGGCGGC

52261 GATCTGGGGT CTGGTCCGCT CGGCCCAGTC CGAACACCCC GGCCGCATCC AGCTCATCGA

52321 CGCCGACGGC CACTCGGACC ACACACTGCG CAGCGCACTG TCCACCGCAC TCACCACCGA

52381 CCAGCCCCAA CTGGCCCTCC GCGACAACAC GCTCTGGGCG CCCCGGCTCA CCCCGACAAC

52441 ACCCGCCGAC ACACCCGCCC AGCCGCTCCC TCTCAACCCC GAGGGCACCG TTCTCGTCAC

52501 CGGCGGCACC GGCACCCTCG GCGCTCTCAC CGCCCGCCAT CTCATCACCC ACCACGGCGC

52561 CCGGCACCTG CTCCTGATCA GCCGCCAGGG GCCCGACGCC CCCGGCGCCA CCGACCTCAC

52621 CACCGAACTC ACCGAACTCG GCGCCACCGT CCACATCACC GCATGCGACA CCGCCGACCG

52681 CGACCAACTC GCCACCACCC TCGCCGACAT CCCGGCCGAC CACCCCCTCA CCGCCGTCAT

52741 CCACACCGCC GGAACCCTCG ACGACGGCAC CCTCACCGCA CTCACCCCGA ACCGCCTCGA

52801 CACCGTCTTC CGCCCCAAGG TCGACGCCAT CACCCACCTC CACCACCTCA CCCACGACCA

52861 CGACCTGGCC GCCTTCGTCA TCTACTCCTC CGCCACCGGC ACCCTCGGCA CCCCCGGTCA

52921 GGCCAACTAC GCCGCCGCCA ACACCTACGC CGACGCCCTC GTCCACCAAC GCCACGCCGC
```

-continued

SEQUENCE ID NOS: 1-3

```
52981 CGGGCTCCCC GCCACCTCCC TCGCCTGGGG GCTATGGGAA ACCACCAGCG CCCTCACCGC
53041 CACCATGAAC ACCGAGGACC GCCGACGCAC CCACCGTGGC GGTGTGGCCG CCCTGACCGA
53101 CGACGAGGGG CTCGCCCTCC TCGATAGGGC CCTCACCGCC ACCCACCACC CCCACCTCGT
53161 CCCGATCAAG ATCAGCCCGG CCTCCCTTCG GGCCGATGAC ACGGCGCAGC CCGTTCCGCC
53221 GCTGCTCCGC CACCTCGTAC GGCGCCCCAC GCGCCGTACG GCCCACACAC CGGCCCCCGC
53281 CGACACCCTG TCGCTCGCCC AACGGCTCGC CGCCCTCGAC CAGGGCGAAC GGCTACGGCA
53341 CCTCACGGAG CTCGTCCGCA CCGAGGCGGC GGCCGTACTC GGACATACGA CGATCGACAG
53401 CATCGGGCCG GACCAGCCCT TCCGCGACGT CGGGTTCGAC TCCCTCACGG CGGTGGAACT
53461 GCGCAACCGC CTCAATGCGG CCACGGGACT GCGGCTCCCC GCGACCGTGG TGTTCGACTA
53521 CCCGACCCCG GCGATCACGG CCGGGTATCT GCGGGACGAG CTGTTCGGCC CGGCGGAGGC
53581 GGCCCCGGCC GCCGTCGCCG GGCCGGGGGC CGACGCGGAC GATCCCGTGG TCGTCGTCGG
53641 CATGGCCTGC CGGCTCCCCG GACGGGTGAC CGACCCGGAC GGGCTGTGGC GGCTGGTGGC
53701 CGACGGGGAG GACGGCATCG GGGCGTTCCC CACCGACCGC GGTTGGGATC TGGACACGCT
53761 CTTCGACCCC GACCCGGACC GGGTGGGCGC GACCTACGTC CGCGAGGGCG GGTTCGTGGC
53821 GGGGGCCACC GAGTTCGACG CGGACTTCTT CGGCATCTCC CCGCGTGAGG CCGTGGCGAT
53881 GGACCCGCAG CAACGGCTGC TGCTGGAGAC CGCGTGGGAG ACCTTCGAGC AGGCCGGTAT
53941 CGCCCCACGG TCGGTGCAGG GCAGCGACAC CGGTGTGTTC GCCGGGGTCA TCTACCACGA
54001 CTACGGGACG AACGCCGGTG AGCTGCCCGA GGGCTCGGAG ACCTATCTGA GCACGGGCAA
54061 ATCGGGGAGC GTGGTGTCCG GGCGGGTGGC CTACGCGCTG GGCCTGACCG GTCCCGCGGT
54121 GACGGTCGAC ACGGCGTGCT CCTCCTCGCT GGTGGCCATC CACTGGGCGG CCAAGGCGGT
54181 GCGGGAGGGC GAGTGCTCGA TGGCCCTGGC CGGGGGCGTG ACGGTGATGT CGACCCCGGA
54241 TGGGTTCGTG AGCTTCTCGC ACCAGCGCGG GCTCGCCCCC GACGGCCGCA GCAAGTCCTT
54301 CGGCGAGGGC GCCGACGGCA CCACCTTCAG CGAGGGCGTC GGGCTCGTGC TGCTGGAGCG
54361 GCTCTCCGAG GCGCGGCGCA ACGGTCACGA GGTGCTGGCC GTGGTCCGCG GTACGGCGGT
54421 CAACCAGGAC GGCGCCAGCA ACGGCCTCAC CGCCCCCAAC GGCCCCTCCC AGCAACGGGT
54481 GATCCGCCAG GCCCTGTCCA GTGCCGGACT GTCGGCGACC GACATCGACG CCGTCGAAGC
54541 CCACGGCACC GGCACCGCCC TCGGCGACCC CATAGAAGCA CAAGCGCTGC TGGCCACCTA
54601 CGGCCAGGAC CGCCCCGCCG ACCAGCCCCT CTGGCTGGGC TCACTGAAGT CCAACATCGG
54661 CCACACCCAG GCCGCCGCGG GCATCGCGGG CGTCATCAAG ATGATCCAGG CCATGCGGCA
54721 CGGCATGCTG CCCAGGACAC TCCACGCCGA CGAGCCCACC ACCAAGGTCG ACTGGACGTC
54781 GGGCGCGGTG TCCCTGCTCA CCGAGGCCAG GCCCTGGCCG GAGACCGGAC ACCCCCGCCG
54841 CGCCGGAATC TCCTCCTTCG GCGTCAGCGG CACCAACGCC ATCTCATCC TCGAACAGGC
54901 CCCGGAGGAG GCGGCCACCG CACCAGAGAC CACGGAGCCG GAGGCTCCCG GCTGGTGGC
54961 CACGGCCGGC GCGGTGCCGT GGGTGCTGTC CGCCAAGAGC CCAACGGCCC TGCGGGCGCA
55021 GGCCGAACGC CTGATCGCCC ACCTTCACGC CCACCCCGAG ACCGACCCGG TGGACATGGG
55081 CTGGTCGCTG GCCACCAGCC GCGCCGCCCT GGAACACCGG GCGGTCGTCC TCGCCACCGA
55141 TCTCGACCAG GCGACCGCCG CCCTCACCGC CCTCAGCGAA GGGCAGCCGC ACCCCAGCCT
55201 GATCACCGGG GAGACCGGCA GTGATGGCAA GACCGTGTTC GTGTTCCCCG GCCAGGGCGC
55261 CCAATGGGCA GGCATGGGAG CCCAACTCCT CGACACCTCA CCCGTCTTCG CCACCCGCCT
```

-continued

SEQUENCE ID NOS: 1-3

```
55321 CCACGAATGC GCCGAAGCTC TCGCCCCCTA CACCGACTGG TCACTCATCG ACGTCATCAC
55381 CGGCGCGCCT GATGCCCCTT CGCTCGACCG CGTCGACGTC CTCCAGCCCA CCACCTTCGC
55441 CATCATGGTC TCCCTCGCCG CACTCTGGCA GGCCAACGGC ATCCACCCCG ACGCCGTCAT
55501 CGGCCACTCC CAAGGCGAAA TCGCCGCAGC CTGCGTCGCC GGACACCTCA CCCTCACCAA
55561 CGCCGCCAAA ATCGTCACCC TCCGCAGCCA GACCATCGCC CACCACCTCA CCGGACACGG
55621 CGCCATGATG TCCGTCCTCG CATCCCCCAC CTGGGTCCAG GAAACACTCG CACCCTGGCA
55681 CGGACACCTA TGGATCGCCG CCGTCAACGG CCCCGCATCC GTCTCCGTAT CCGGAGACCC
55741 CGACGCACTC GCCGAATTCG GCACCACCCT CTCCAAAGCC AAGGTCTACC GCTGGCAACT
55801 CCCCGGCGTC GACTTCGCCG GACACTCCGG ACACGTCGAC ACCATCAAAG ACCAGTTGCA
55861 CAACGTACTC GACGGCATCA CCGCCACACC CGGCCACACC GCCTGGATGT CCACCGTCGA
55921 CGCCGACTGG GCCAACCCCA CACACATCGA CCCCGACTAC TGGTACCGCA ACCTCCGCGA
55981 CACCGTCCGC TTCGAAGAAG CCACCCGAGC CCTCCTCACC CACGGCACC GCGTCTTCAT
56041 CGAAGTCAGC ACCCACCCCG TCCTGACCAC CGCCATCCAA GAGACCACCG AAACCCTCCC
56101 CGAAGTCCGG GCCACCATCA CCGGGACGCT GCGCCGCGAC GACGGCGCCG CGGACCGCGT
56161 TCTCGCGGGG CTGGGCGGGC TGTTCGCGGC CGGGGTGCCG GTGGACTGGG GCGCTCTGTT
56221 CGCCGGTACC GGGGCCCGCC GGGTGCCGCT GCCCACGTAC GCCTTCCAGC ACCGGCACTA
56281 CTGGCTGGAG CCCGCCAGGA CCCCGACGCG GGCCGAGACC GCCGACGGCT CCCTGTGGGC
56341 GGCCATCGAG ACGGCGACA CGCAGTCCCT CGCACGGGAT CTCGAGGTGG ACGCGGCGGC
56401 CCTCGGCACG GTGCTGCCCG CGCTGGCCTC ATGGCGTCGG CGCAGCCGGG AGGATTCCCT
56461 CACGGACGCA TGGCGGTACC GGATCGGCTG GACCCGGGTG CCGCGGCCG ATCCACAGAT
56521 GTCGGGCCGG TGGCTGGTGC TGGTCCCGGC CGTGCGGGCG GGCTCGGCGC GGGTCCGAGC
56581 GGTGCTGGAC GGGCTGGCCG CGCGGGGCGC CGAGGTGGTG CCGCCGAGG TCTCCGAGAC
56641 CGGCCGGGAG GCGCTGGGCG ACCAGGTCAA GTCGGCGGAC GGCGGTGCCG GGGTGGTGTC
56701 CCTGCTCTCG TGGGACGACC GCGCCGACAC CGAGTACGGC ACCGTGTCCA CGGGCACCGC
56761 GGCCACGCTC GCGGCGGCGC AGGCGTTGCG GGACCACGGC ATCACCGCCC CGCTGTGGTG
56821 CGTCACCAGT GGCGGGGTCG CGGTGGCCGG TGAGACGGCC GACCCGGTGC AGTCGGCGGT
56881 GTGGGGATTC GGCGCCGTGC TCGGGCTCGA CCACCCGGAC ACCTTCGGCG GCCTGATCGA
56941 CCTGCCGGCC GAAAGGGAGG GTGACGGCGA GGCGCTGCCG GACGGGCTGT TCGCGGCGCT
57001 GTCGTCTCCG GAGGGGGAGG ACCAGCTCGC GGTGCGCGCC GACGGGCTGT TCGACGCCG
57061 GATGGTGCGC GACCGGGACG GCTCCGGCAG CCTCTGGAAG CCACGCGGCA CCGTGCTGGT
57121 CACGGGCGGC ACCGGCGGGC TCGGCTCGCA TGTGGCGCGC TGGCTCGCCA CGAGCGGGGC
57181 GGACCATGTG GTGCTGCTCA GCAGGCAGGG CGGTGACGCG CCGGGCGCGG CCGAACTGGT
57241 GGCGGACCTG GCGGGGGTGC AGGTCACGCT CGCCGCCTGT GATGTGACCG ACCGGGAGGC
57301 CGTGGCCGCG GTGCTGGCGG AGGCGGAGCG GACCCATCCG CTGACCGCGG TGGTGCACAC
57361 CGCCGGTGCC GGGCTGCCCT CGGCTCCGGT CACCGAGGTG ACCGCCGAGG AGTTCGCCGC
57421 CGTGACGGGG GCGAAGGTGC GCGGGGCGCT GGTGCTGGAC CAGCTCGTCG GCGATCGGCA
57481 GCTCGACGCG TTCGTGCTGT TCTCCTCCGG CGCCGGTGTC TGGGGCAGTG GCGGGCAGGC
57541 CCCGTACGCG GCGGGCAACG CCTTCCTGGA CGGGCTGGCG GCCCGGCGGC GGGCCCACGG
```

```
57601  GCTGGCGGCC ACATCGGTGG CGTGGGGCGG CTGGGGCGGC GGGCTCGGCA TGATCGACGC
57661  CGACGGCGGC GATCAGTGGC GCCGTATCGG CATCCTGCCG ATGGATCCGG CGCCCGCGTT
57721  GCGTGCGATG GCGCGGGCAG TGGGCAGTGG TCTGCCGAAT GCGATTGTCG CGGACGTCGA
57781  CTGGGCGCGG TTCGTGCCGG GATACACGAT GGCCCGGGAG CGGCCGCTGC TGCGGCAGTT
57841  GCCCGAGGTC GCCGAGATCC TGGCGGCGGA CGCGCGGGGC GGGGGCGCAT CGCGGCGGGA
57901  GGTGCTTCTG GGCAGCCTGG CCGAGCTGAC CGGCCCGGAG CAGGAGGTGT TCCTGACCGA
57961  TCTGGTGCGG CGTGAGGCGG CGGCCGTGCT CGGGCATGCG GACGGGACG  CGGTGGAGCC
58021  GGAGCGTGCG TTCAAGGACA CCGGGTTCGA CTCGCTGACC GCGGTGGAGC TGCGCAACCG
58081  GATCAACGCG GCCACCGGGC TCCAGCTCTC CCCCACGGTG GTGTTCGACT ATCCGAAGCC
58141  GACCACGCTG GCGAGGAGGC TGCGTACGGA GCTGGTCCCC GCCGTGAATG GGGACGCGAA
58201  CGGGGGCATG ACGGGGACG  GGACCGCGGA TGGCGGGGCC GTCGGCGCGG AGGGCCGCGA
58261  GCGGCAGATC CGGCGGGTGC TGGCCTCGGT GCCGTTACGC CGCTTCCACG AGCTGGGGGT
58321  GCTGGACGCG CTGGTGCGCC TCGCGGACTC CGCGGCCGGT GACCCGAGCG GTCTGCGCGA
58381  CCTGGGCGAC CTGGACACCG CCGCGGAGGC GGAGACCTCC GCGCTCGCGG AGCTGGATGC
58441  CGACGAGCTG GTGAGCCGGG CGATGCGCGG CACGACCTTC GGAAACCACT GACGCCGCGG
58501  TTGCGGAGAG GAGTACATAT GGCTGCGTCC CGGGAAGACC TGGTCAAGGC GCTGCGTACC
58561  TCGCTGATGG ACGCCGAGCG GCTGAGGCGG GAGAACGACC GGCTGATCGC CGAGTCCACC
58621  GAACCGGTGG CGATCGTGGC GATGGCGTGC CGGCTGCCGG GCGGGGTGAC CGACCCGGAG
58681  TCGCTGTGGA AGCTGGTGGA CGAGGGGCGG GACGCGATCG GGCCGTTCCC CACGGATCGC
58741  GGCTGGGACC TGGAGACGCT GTTCGACGCC GATCCGGACG CCGTGGGCAA GTCCTACGTA
58801  CGCGAGGCGG GATTTCTGGA GGGGGCGGGC GGGTTCGACG CCGCGTTCTT CGGCATCTCG
58861  CCGCGCGAGG CCCTGTCGCT GGACCCGCAG CAGCGGCTGC TGCTGGAGAC CGCGTGGGAG
58921  ACCTTCGAGC GGGCGGGGAT GGATCCGCGG TCGGTGGAGG CCGGGACAT  CGCGGTGTTC
58981  GCCGGGGGCA GCGGCCAGGG GTACGGCGGC GGTCCGGGTG ACGCGCCCAA GGGCCTGGAG
59041  GGTTATCTGG GGTCGGGGC  TTCCGGCAGT GTCATCTCCG GGCGTGTGTC GTACACGCTC
59101  GGGCTGACCG GGCCCGCCGT CACCGTGGAC ACCGCCTGCT CGTCCTCGCT GGTGGCCGCC
59161  CATCTCGCCG TACAGGCCCT GCGGTCGGGC GAATGCTCCA TGGCGCTGGC CGGTGGTGTC
59221  GCCGTGATGG GCCAGCCCAC CGCCTTCGTC GAGTTCTCCC GGCAGCGTGG CCTGGCGCCC
59281  GACGGGCGCT GCAAGTCCTT CGGCGAGGGC GCCGACGGCA CCACCTGGTC CGAAGGTGTC
59341  GGGCTCGTGT TGCTGGAGCG CTGTCCGAC  GCCCGCCGCA ACGGCCACGA CGTGCTGGCC
59401  GTGATCCGGG GCACCGCGGT CAACCAGGAC GGCGCCTCCA ATGGCCTCAC CGCGCCCAAC
59461  GGCCCCTCCC AGGAGCGGGT GATCCGGCAG GCCCTGTCCA ACGCCGGGCT GACGGTGGCC
59521  GACGTGGACG CGGTCGAGGC TCACGGCACC GGCACCGCCC TCGGCGACCC CATCGAAGCC
59581  CAGGCCGTTC TCGCCACCTA CGGCCGGAAA CGCCCCGCCG ACCAGCCCCT CTGGCTCGGC
59641  TCCCTCAAGT CCAACATCGG CCACGCACAG GCCGCCGCGG GCATCGCCAG TGTCATCAAG
59701  ACCGTCATGG CCTTACGCCA CGGCCGGCTG CCGAAGACCC TCCACGCCGA ACAGCCCACC
59761  TCCCAGGTGA ACTGGACGTC GGGCGCGGTG TCCCTGCTCA CCGAGGCGCG GGCGTGGCCG
59821  GAGACCGGAC ACGCCCGCCG CGCCGGGATC TCCTCCTTCG GCGTCAGCGG AACGAACGCC
59881  CACGTCATCC TGGAACAGGC CCCCGAGGAA GCCGAGGCGA CCGGGGAGAA CACGGCCGGT
```

-continued

SEQUENCE ID NOS: 1-3

```
59941 CAGGAACCGT CCGTACGCTC GGCGGAGTCC GCCGACCCCG GTCCGGTGGC CACCGGCCAG

60001 GTGGTGCCGT GGGTGCTCTC GGGCCATACG CGGGAGGCGC TGCGTGCCCA GGCCGCCCGG

60061 CTGCTGACCC AGGTACGGGA GACGCCCGCC GACGGCCTCC GGGACGTGGG CTGGTCACTG

60121 GCCACCACCC GGACCCGGCT GGACCACCGC GCGGTCGTGC TGTGCGCCGA TGCCGAGCAG

60181 GCCGTCGCGG GGCTGGAGGC GGTGGCCTCG GGCGCGTCCG CCCGGTCGGC GGTCAGCGGG

60241 TCCGTGGCCG CCGGAAAGGT GGCGGTGCTG TTCACCGGGC AGGGCAGCCA GCGAGCCGGA

60301 ATGGGCCGTG AACTGCACGG CGGCTACCCG GTGTTCGCGC GGGCCTTCGA CGCCGTGTGC

60361 GCCCAGTTCG GCGACCTGCC CGACGGGGAC GACAAGGTCT CGCTCGCCGA AGTGGTCTTC

60421 GCCGAGGAGG GGTCGGCGAG GGCAGCGCTG CTGGACCGGA CCGAGTTCAC CCAGCCCGCG

60481 CTGTTCGCGC TGGAAGTGGC GCTGTTCCGG CTCGTGGAGT CGTGGGGAGT GCGCCCCGCG

60541 TATGTGCTGG GCCACTCGAT CGGCGAAGTG GCCGCGGCCC ATGTGGCCGG GGTCCTGTCC

60601 CTGCCGGACG CCTGCACATT GGTACGGGCG CGCGGGCGGC TGATGCAGCG ACTCACCGCG

60661 ACCGGGGCGA TGGTCGCGGT GGAGGCGGCC GAGGACGAGG TGGCGCCGCT GCTCGCGGGG

60721 AAGGAGCACA AGGTCTCCAT CGCCGCGGTC AACGCCCGA CCTCCGTGGT CGTCTCCGGT

60781 GACGAGGACG TGGTCACGGC GGTGGCGGAG ACGCTGGCGC GGCAGGGCCG CAAGACCAAG

60841 CGGCTCGTGG TCTCGCACGC CTTCCACTCC CCGCACATGG ACGGGATGCT GGACGCGTTC

60901 CGCGAGGTGG CGTCCCGGCT GACCTACGCG CCGCCACGGA TACCCGTGGT GTCGAACCTC

60961 ACCGGCACGG TCGCCGAACC CGGGGAGCTG TGCTCCCCCG AGTACTGGGT ACGGCATGCG

61021 CGGGGCGCGG TGCGGTTCCT CGACGGTGTC CGCACACTGG CCGATCAGGG CGTGCGCACC

61081 CATCTGGAAC TCGGCCCGGA CGGGGTGCTG ACCGCGATGG GGCAGGACTG TCTGCCCGAG

61141 GCGGACGCGG CGTTCGTGCC GTCCCTGCGT CCGGGTGTCC AGGAGCCCCA CGCGGTGCTG

61201 GCCGGGCTCG CCGGGCTGTA CGTACGGGGT GTACGGGTGG ACTGGGACGC GATGTTCGCC

61261 GGGTCCGGCG CCCGGCGCGT CGCCCTTCCC ACGTACGCCT TCCAGCACGA GCACTACTGG

61321 CTGGAGCGGG CCGCCGGATC CGGTGACGTG GGCGCGGTGG GGCTCGGGGA GGCGGGCCAT

61381 CCGCTGCTGG GCGCGGTGGT GCAGCTCCCG GAGACGGGCG GGGTGCAGCT CAGCGGGCGG

61441 CTGTCGGTAC GGGCCCAGCC CTGGCTGGGC GAACACGTCA TCTCCGGGGC GGTGCTGGTG

61501 CCCGGCACGG CCATGGTGGA ACTGGCCGTC CGCGCCGGGG ACGAGACCGG CACCCCGGTG

61561 CTGGAGGAGC TGGTGATCGG GCAGCCGATG GTGCTGCCCG GCGACACCGC CCTGAGCGTC

61621 CAGGTCGTCG TGGGCGCGGA CGAGGGCGGG CGGCGTACGG TGCGGATCTA CTCCCGTACC

61681 GACGGGGGCA GCGACTGGAC CGAGCACGCC ACCGGCACAC TCGCGGCGCA GGGCCCGGCA

61741 CCGCTGGACG GGGCGCGTA CGGAGCCGGG GACGGGGCCG CCGTCCAGTG GCCGCCCGCG

61801 GAAGCCGAGC CGATCCCGGT GGAGGACTTC TACCGCTCGC TCGTCGACGC CGGATACGCG

61861 TACGGTCCGG CGTTCCGTGG GCTCGTCGCC GCGTGGCGCC GGGACGGTGA GATCTTCGGC

61921 GATGTGGCGC TGCCGGAGGC GTCCGTCGCG GAGGCCGAAC GGTTCGGCAT CCACCCGGCG

61981 CTGCTGGACG CCGCGCTGCA CGCGGGCAGC TTCTGCCTGC CCTCGGACCC GGCGCGACAG

62041 GTGACCTTGC TGCCGTTCGC CTGGAACAAC GTGCGTCTGC ACGCGGGCGG CGCGTCCGCG

62101 GTCCGGGTGC ATGTCCGCCC GGTCGGCGAC GACGCCTTCT CGGTACGTCT GACCGACGGC

62161 TCGGGCCAGA CGGTGGCCTC CGTGGACTCG CTCACCCTGC GCGCGGTGGA TCCGGCCCAA
```

-continued

SEQUENCE ID NOS: 1-3

```
62221 CTGGAGATCG GTACGGCCGA CGACGCGCTG TGGACGGTCC GTTGGAGCGA GACCTCCCTG
62281 CCGGACGGCG CGATCTCCTG GGCCGCGCTG GGCGATCCGG CCACCGGTGG CGCCGGGGCC
62341 ATGGGAGACA CCGGAAGCGC GGGAGGCGCC CTTCCCGACG TCCTCGTGGC CGATACGCGC
62401 GCCTGGGCCG AAGACCTCAC CGGGCCGCCG ACCGCGCGGG CCCGCCGGCT CACCGGCCGC
62461 CTGCTGGCGG AGATCCAGCG GTGGGTCGCC GACGACGCGA TGGCCGGGAC CCGGCTGGCC
62521 GTGGTCACCC GCGGTGCGGT CGCGGTGCGC GACGACGCCG AGGTCACCGA CCCGGCCGCC
62581 ACCGCGGTCT GGGGCCTGGT CCGCTCGGCC CAGGCCGAAC ACCCGGGGCG GGTGGCCCTG
62641 GTGGATGCCG ACGGGGTGTG CGAGGAGCTG CCCGCCGGGG TGTGGTCCGG GGAGGAGCCC
62701 CAACTGGCGG TGCGCGGTGG CGCCGTGTGG GTGCCGCGCC TGGCCCGGGT CGAGCCCGGT
62761 CTGCGCGTGC CCGCGCAGGC GTCGTGGCAT CTGGACTCGG CCGAGTACGG CACTCTGGAC
62821 CATCTGGCGC TGCTGCCCGA CGAGGCCGAG CCCGCACCGC TGGAAGCGGG TCAGGTGCGG
62881 ATCGAGGTCC GCGCCGCCGG GCTCAACTTC CGGGATGTCC TGGTGGCTCT CGGCATGTAT
62941 CCGGGCCGGT CGGTGATCGG CACGGAGGGC TCCGGTGTGG TGACCGAGGT CGGTCCGGGC
63001 GTCGCGGAGC TGGCCGTGGG CGACCGGGTG ATGGGCCTGT TCTCCGGCTC GTTCGGGCCG
63061 CTGGCCACCG CCGACGCGCA TACGGTGATC CGGATGCCGG ATGGCTGGTC GTTCGGCACG
63121 GCGGCCGGGG TGCCGGTGGC CTATCTGACG GCGCTGTACG CGTTGCAGGA CCTCGGGAGC
63181 GTTCAGCCGG GCGAGACGGT CCTGGTGCAC GCCGCCGCGG GCGGTGTGGG CATGGCCGCC
63241 GTCCAGCTCG CACAGCACTT CGGCGCCACC GTCCTGGGCA CCGCCCACCC CTCCAAGCAC
63301 CACGCACTCC ACCGGCTTGG CGTGCCCGCC GAACGGCTCG CCTCCAGCCG CGACCTCGGC
63361 TACGCCGCCG CCTTCCCCAC CGCCGACGTC GTGCTCAACT CCCTCACCGG CGAGCACATC
63421 GACGCCTCTC TCGGACTTCT CAATCCCGGC GGCCGGTTCC TGGAGATGGG CAAGACCGAC
63481 CTGCGGGAGC CCGGCGAGGT CGGGGCACGG CATCCGGAGG TCACCTACCG GGCGTTCGAC
63541 CTCGGCGGGG AGGCCCCCGC GGAGCGGGTG CGGGAGTTGC TGCACCAGTT GGTGGAGCTG
63601 TTCGAGGCGG GCCGGATAGA GCCGCTTCCG GTGCGGCAGT GGGACATCAC CCGCGCCCCC
63661 GAGGCGTTCC GCTGGATGAG CCAGGGGCGG CACACCGGCA AGATCGTGCT CACCCTCCCC
63721 CGCGCCCTGG ACCCGGACGG CACCGTCCTG GTCACCGGCG GCACCGGAAC CCTCGGCGCC
63781 ACCGTCGCCC GCCACCTCGT CACCCAGCAC GGCGCACGCC GACTACTGCT GGTCAGCCGC
63841 CGGGGACCGG ACGCACCCGG CGCCACCGAC CTCACCACCG AACTCACCGA ACTCGGCGCC
63901 ACCGTCCACA TCACCGCATG CGACACCGCC GACCGCGACC AACTCGCCAC CACCCTCGCC
63961 GACATCCCGG CCGACCACCC CCTCACCGCC GTGGTCCACA CGGCCGGGAC GCTCGACGAC
64021 GGCATCCTCA CCGCACTCAC CCCGGACCGC CTCGACACCG TCTTCCGCCC CAAGGTCGAC
64081 GCCATCACCC ACCTCCACGA CCTCACCCGC GACCAGGACC TGGCCGCGTT CGTGGTGTAC
64141 TCGTCCGCCG CCGGAGTCCT CGGCGGACCC GGCCAGGGCA ACTACTCCGC CGCCAACGCC
64201 TATCTGGACG GCCTCGCACA GTGGCGGCGT GCGCACGGGC TCCCCGCCAC CTCGCTGGCG
64261 TGGGGCATGT GGGCGCAGAC CAGTGGCATG ACGGCCGGGC TCGGCTCAGG GGATCTGCAC
64321 CGGGTGCGGC GTGGCGGCAT CGTCGGGCTG TCCACGCGCG AGGCGCTGGA CCTGTTCGAC
64381 CGGTCGGTGG CGTCCGGGCT GTCCCTGCTG GTGCCGTTGC GGTTCGACCT CGCCGCCCTC
64441 GGTGCGGAGG CCGCGGAACC GCCGCCGCTG CTGCGGGGGC TGGTCCGGCC GGCCCGGCGT
64501 ACGGCCCGGC CGGTGCCGAA GGCCGGTGAG GGCGGCCTCG TCGAGCGGCT GGCCGGTCTT
```

-continued

SEQUENCE ID NOS: 1-3

```
64561 TCGGCGGCCG AACAGGAGCG TCTGCTGGTC GAGTTGATCC GCGAACAGGC CGCTTCCGTG

64621 CTCGGGTTCC CGACCGTCGA CCCGATCGGG CCGGAGCAGG CATTCCGCGA TATGGGGTTC

64681 GACTCGCTGA CCGCGGTGGA GCTGCGCAAC CGCCTCAACA CGGCCACCGG ACTACGGCTC

64741 CCGGCGACGC TGGTCTTCGA CCACCCGACC CCCTTGGCCA CCGCCGAGCT CCTACGGGAC

64801 GAACTGGGCG GGCGCGCGGT CGAGGCCACG CCCCGCCCGG CCCGGCGCGA CCGGTCGGCT

64861 CCGGACGCGG CCGAGGATCC GGTCGTCGTG GTCGGCATGG CTGCCGCCT GCCCGGCGAC

64921 GTCCGCACCC CCGAGGACCT GTGGCGGCTG GTCGCCGCCG GAACCGACGC GATCGGGCCG

64981 TTCCCGCAGG ACCGGGGCTG GGACCTGGCC GGGCTCTTCG ACTCCGACCC GGACGCCCTG

65041 GGCAAGTCCT ACGTCCGCGA GGGCGGCTTT CTCACCGACG CGGGCGGCTT CGACGCCACG

65101 TTCTTCGGCA TCTCCCCGCG CGAGGCCCTG TCGATGGACC CGCAGCAGCG TGTCCTGCTG

65161 GAGACCGCGT GGGAGACCCT GGAACGCTCC GGGATCGTTC CCACGTCACT GCGCGGACAG

65221 GAGGTCGGGG TCTTCGTCGG GGCCAGCGGC CAGGGGTACG CACCGGTCC TGGCGCGGCT

65281 CCGGAAGGCT TGGAGGGCTA TCTGGGGGTG GGCGGCGCGA CGAGTGTGGC GTCGGGCCGG

65341 TTGTCGTACA CCTTCGGCCT GACCGGTCCG GCGGTCACGG TGGACACGGC GTGCTCCTCC

65401 TCCCTGGTGG CCCTCCACCT CGCGGCACAA GCTCTGCGCT CCGGCGAATG CACGATGGCA

65461 CTCGCGGGCG GTGTCGCGGT GATGGGCCAG CCCGGCGCAT TCGTCGAGTT CTCCCGCCAG

65521 CGCGGTCTCG CGTCCGACGG CCGCTGCAAG TCCTTCGGCG AGGGCGCCGA CGGCACCAAC

65581 TGGTCGGAGG GCGCGGGTCT GGTGCTGCTG GAACGACTGT CCGACGCCCG CCGCAACGGC

65641 CATGAGGTGC TGGCCGTGAT CCGTGGCACC GCGGTGAACC AGGACGGGGC GAGCAACGGC

65701 CTCACCGCTC CGAACGGGCC CTCCCAGCAG CGAGTGATCC GGCAGGCCCT GTCCAATGCC

65761 GGGCTCACAG TGGCCGACGT GGACGCGGTC GAGGCACACG GCACCGGCAC CGCCCTCGGC

65821 GACCCCATCG AGGCACAGGC ACTGCTCGCC ACCTACGGCC AGGACCGCCC GGGGGACGAA

65881 CCCGTGTGGC TCGGCTCGCT GAAGTCCAAC ATCGGCCACA CCCAAGCGGC CGCAGGCATA

65941 TCCAGCGTCA TCAAGATGGT CCTGGCGATG CGGCAGGGCA CGCTTCCCCG GTCCCTGCAC

66001 GCCGACGAAC CCACCACCCA GGTGGACTGG ACGTCGGGCG CGGTGTCCCT GCTGACCGAG

66061 GCACGGCCCT GGCCGGAGAC CGGACACCTC CGCCGCGCCG GGATCTCCTC CTTCGGCGTC

66121 AGCGGGACAA ACGCACATGT GGTCCTGGAG CAGGCCCCGG AAGCGGCCGC ACCGCAGGCG

66181 GACGAGGCCG ACGACATCCC TGGTCTGGTC GCCACCGGCG GGATCGCGCC CTGGGTCCTG

66241 TCGGCCAAGA CCCCCACGGC CCTGCGGGCT CAGGCCCAAC GCCTCCTGGA CCACCTGGAA

66301 TCCGGGGTGG ACGGCCGCCC CCTCGACATC GGCTGGTCCC TGGCCACCAC CCGCACCCTC

66361 CACGACCATC GCGCCATAAT CCTCACCGAC ACCGACACCG ACACGCGCGC CGAGGGCGGT

66421 GAGGCCACGG CCGCCCTGAC CGCCCTCGTG ACCGGACAGC CGCATCCCCG CCTCACGACG

66481 GGCTACGCCA CCACCCAGGG CAAGACCGTG TTCGTTTTCC CGGGGCAGGG GTCGCAGTGG

66541 GTGGGGATGG GGGCACAGCT CCTGGACACT TCGCCCGTCT TCGCGGCCCG GTTGCGCGAG

66601 TGTGCCGACG CGCTGGCCCC GTATACCGAC TGGTCCCTGA TGGACGTCAT CACCGGCGCA

66661 CCCGATGCCC CTTCGCTCGA CCGTGTCGAC GTCGTACAGC CCGCCACCTT CGCCGTCGTC

66721 GTCTCCCTCG CCACCCTCTG GCAATCCATG GGTATCCACC CCGACGCCGT CACCGGCCAC

66781 TCCCAAGGCG AAATCGCCGC AGCCTGCGTC GCCGGACACC TCACCCTCAC CAACGCCGCC
```

-continued

SEQUENCE ID NOS: 1-3

```
66841 AAAATCGTCG CCCTGCGCAG CCAGATCATC GCCGACCACC TCGCCGGACA CGGCGGCATG
66901 ATGTCCCTCG CCACCCCCGC CGACACCATC GACCTCACCA ACTGGCACGG CAAACTCTGG
66961 ATCGCCGCAC ACAACGGCCC CAACGCCACC GTCATCGCAG GCGACGCCGA AGCCCTGCAC
67021 CAACTCCACG CCCACTACAC CGACCAAGGC ATCCGAGCCC GCATCATCCC CGTCGACTAC
67081 GCCTCCCACA CCGGACACGT CGACACCATC AAGAACGAAC TCCACCAAAC CCTGGCCGAC
67141 ACCACCACCG AGCCCGGCAC CCTCCCCTGG CTCTCCACCG TCGACGGGGA GTGGATCGAA
67201 CCCAACACCC TCGACAGCAC CTACTGGTAC CGCAATCTCC GCCAGACCGT GCAGTTCCAC
67261 ACCGCCATCA CCACCCTCGC CGACCAGGGC TACCGCACCT ACATCGAAAT CAGCCCCCAC
67321 CCCGTCCTCA CCACCGCCAT CCAAGAAACC CTCGAAACAC ACAACACCCC CAACGCGATC
67381 GTCACCGGAA CCCTCCGCCG CGACGACGAC ACCCCCACCC GCCTCCTCAC CAACCTCGCC
67441 CACCTCACCA CCCACGGAAC ACCCGTCAAC TGGCCCACCC TCTTCACCGG CACACACCCC
67501 ACCCGCATCA CCCTCCCCAC CTACCCCTTC GAGCAGGAGA CGTTCTGGCT GGACCGCAGC
67561 GGCCCGGGTG ATGTCCGTGC CGTCGGCCTG GAGGACACCG GCCATCCGCT GGTCGGGGCC
67621 GTGGTGAGTG TGCCCGACAC CGACGGTGTG CTGCTCACCG GCGGCTCTC CCTGACCACC
67681 CACCCCTGGC TGGCCGACCA TGCCGTCTCC GGCACCGTCT GCTTCCCGG TACGGCGATG
67741 GTGGAGCTGG CGGTGCGAGC CGGAGACGAG GCGGAGGCCC GCGTACTGGA GGAATTGATC
67801 ATCAGTCGGC CGATGGCGGT GCCGGACGAG GGAACCTTGC ACGTCCAAGT GCTGGTCGGC
67861 GGCGAGGAAG GCGACGAAGG CGGACGCCGC AAGGTGGGGG TCTACTCCCG CCCCGAGGGC
67921 ATACGGCAGT GGACCGAGCA CGCCACCGGC ACACTGCTGA CCGGGGGAAC CGCCACCGCG
67981 GCGGCCACGA CAGCGCATCC GTGGCCGCCC GAGGGGGCCG AACCCGTCGC CCTCGAGGGG
68041 TTCTACGAGC AACTGGCCGA GGCGGGGTAC GAGTACGGCC CGGCGTTCCG GGGCCTGAGC
68101 GCGGTGTGGA AGCGGGACGA CGAGGTGTTC GCCGAGGTGG CCGTGCCGGA GGACCAGACC
68161 GCGGTCGCCG GACGGTTCGG CATCCATCCG GCGCTGCTGG ACGCCACTCT GCATGCCGGG
68221 AACTTCTGCT TCGAGTCCGG CGGCGACCGG CCCACGATGC TGCCGTTCGC CTGGACCGAC
68281 GTGCGGCTCC ATGCCGTGGG CGCCACCGCT GTACGGGTGC GGGCGACGGC GTCCGGCACG
68341 GACGGGCTGT GTGTGCAGAT CACCGATCCG CACGGACTGC CGGTCGCCAC CATTGGCTCG
68401 CTCCAGCTCC GGGAGACCAC ACCCGAGCAG TTGCGGGCCC TCTCCGCCAC CTCAGGTGGC
68461 AATGCCTTGT GGGCGGTCGA ATGGGCCGAA TGCGGGCTCG ACGACACGAC GGAAGCACAG
68521 TGGGCCACAC TCGGAGAGAG CCAACTCCTG GACTCCCCAC TTCACTATGC CGATGTTTCC
68581 CAGGTCGTGG CGGCCGGGGA ACAGCCCGCG GCACTCGTCG CCGACGTGTC CGCATGGGCT
68641 CCCGAGAACA CCGGGCCGCC CATCGACCGC GCCCACGCGC TCTGTGCCCG AGTCCTCGAT
68701 CTGCTGCGGC AATGGGTGGA CCGGCCCGAG CCGGCGGACA CCCGGCTGGT GATCCTGACC
68761 CGCGGTGCCA TGGCGGTCCA CGACACCGCC GAGGTCACGG ATGCGGCCGC CGCCGCGGTC
68821 TGGGGCCTGG TCCGCTCGGC CCAGTCCGAA CACCCGGGCC GGATCCAGCT CATCGACATC
68881 GACGAGCACT CCCACCGCAC CCTGCCGACA GCACTCACCA CCACCGACCA ACCCCAACTC
68941 GCCCTCCGCG ACGCCACCGC CTACACCCCC CACCTGGCCC CGCGCCCAC CCCAACACCC
69001 GGGCCCCTCA CCCTCGCGCC CGAGGGAACC GTCCTCATCA CCGGCGGCAC CGGCACCCTC
69061 GGCGCCCTCA CCGCCCGCCA CCTCATCACC CACCACAAGG CACGCAACCT CCTTCTGGTC
69121 AGCCGCCAGG GTCCGGACGC CCCCGGCGCG GACCGGCTGA GCGAGGAGCT GACCCAGCTC
```

-continued

SEQUENCE ID NOS: 1-3

```
69181 GGTGCCCGTA TCCGCATCGC CGCCTGCGAT GTCGCCGACC GCGACCAGCT CGCCACCGTC
69241 CTCGCCACCA TCCCCGCAGA CCAGCCGCTG ACCGCCGTCA TCCACACCGC CGGCGCCCTC
69301 GACGACGCCC TGCTCACCGA CCTCACCCCG GAACGCCTGG GCACCGTCTT CCGCCCCAAG
69361 GTCGACGCCC TCACCCATCT CCACGACCTC ACCCGCGACC ATGACCTCGC GGCCTTCGTC
69421 ATCTACTCCT CCGCCACCGG TGCGCTCGGC ACCCCGGTC AGGCCAACTA CGCGGCGGCC
69481 AACACCTACG CCGACGCGCT CGCCCAGCAG CGCCACGCCG CCGGGCTCCC CGCCACCTCA
69541 CTCGCCTGGG GCCTGTGGGA AACCACCAGC GCCCTCACGG CCGGGATGTC CACCACCCAT
69601 CAGCAGCGCA CCCGCCACAG CGGTGTCATT CCCCTGACCG ACGCCGACGG CATGCGCCTC
69661 CTCGACACCG CGCTCACCAC CCACCAGCCC CACCTGATCC CCCTCAAGCT CGATCGCACC
69721 GCCCTCCGGA ACAGCGCCGC CTCCCACACC CTCCCGCCCC TGCTCCGCAC CCTGGCGCAA
69781 AGCCACCACC GCCCCACCGC CCACACCACC CCCCGGACCG CCGCCGCCCC GCCCCTCCCC
69841 GAGCAACTCG CCGCCCTCGA TCCGGCCCAG CGGCTCCAGC ACCTCACCGC ATTCGTCCGC
69901 GCCGAAGCCG CGGCCGTGCT CGGACACGCC ACTTCGGACG CGGTGGGACC GGACGATCCG
69961 CTCTTCGAGA TCGGGTTCGA CTCCCTGACC GCGGTGGAAC TGCGCAACCG GCTCAACGCG
70021 GCCACGGGCC TCCAGCTCCC GGCGGCGTTG CTGTTCGACC ACCCCACCCC GGCGATGGCC
70081 GCCGAACACC TCCAGGAACA GCTCGCGCTG AAAGACGCCT CCTGAGGACG CCTCCTGAGA
70141 CGGACAACAG CGTCCCCGGC CGCCGTGGCG GCCGGGGACG CTGCCGTAGG GCGCTCCCCC
70201 GCCCTCCTCA CCAGGCCGCC GCCGTACGCC GTGCAACATG ACTGGTCCCT TCCCCCGGTT
70261 TCTTTGGGGA AGGGACCAGT TTCACTGACG GGTTCCACGG CCCGGCGGCC GTCGCTCGTT
70321 AGGTGTCCGA GGTGACGCTC TCCCCGGCCC GGGCCGCGCG GCGGCGCTCG TCGCCCGCCT
70381 TGATCAGGGC GTACCTGATG CCAGCGCCG CCGCGTTGAC CGCGTGCAGC GCCTCCTGGG
70441 CGGCGGAGTC CGGCTGTTGC TGTCCGGTGG CGGCGGCCGA GGTGGACTGT GCCGCCTCCA
70501 GGCAGGCGAC GCACGCCTCC ACGAGGGCGT CCGGCCGCCC GCCGGCCCGG CCCAGCTCCG
70561 TCAGCAGCCG GGTGATCTCC CGGTGCACTT CGCCGATCGG GTCCGCCACC ATCGGATCAG
70621 CCACCCTCGA GTCAGCCATC CTCGGGTCCG CCGCCATCGG GTCAACGCCC CCGCGCACCG
70681 TCGTCCGCGG GCCCGTGGCC CGTCGGGAGG TCCCCGGCCG GGCCAGGGT GAGGAACCGC
70741 TGCTCCCACA GGGCGAACAC CTCGGTGGCC AGTGCCTCCG AGAGTCCGCC GACGGTCTTG
70801 GCCAGATCCC CGAGGGTGGT GGTGCCGTCC ACCGCGCCGA GCAGTTCGTA CAGCTCGGGC
70861 GAGACCTTCG CGGACGGGCC GCCGTCGTAG TCGAGGTGGA TCTCGTGGGT CCTGGCTCCC
70921 GCCGAGGCGT CCGGACCGGC CGTCCTGCGC TCGACCAGCC GGGTCACCGG GCGGAACCGC
70981 GGCACCAGAA CGCCCAGGTC AGGCGCGGGT TTGCCGCGTA CCAGGCAGTC CTCCACCACC
71041 AGGACGTCCA GGTCGGTGGT CAGGAAGCTG GTGACCACGT CGTCGAGGCT CTGCACGATG
71101 GGTTCGGCGT TGTTGTTGAA GGAGGTGTTG AGGAGCACGG GGGTGCCGGT CAGTTCGCCG
71161 AACCGCCGCA CCAGGCGGTG GAACCGCTCG CCCGATTCGG CGGAGACGAC CTGCACCCGG
71221 GCGGTGCCGT CCACGTGGGT GACCGCGCCG AGTTCCGTAC GCCGCTCCGG CAGCACCGGC
71281 ACCACGAAGG ACATGAACTC GTGGTTGCCG TCCGCGCCGG AGAGGTCGAA GTAGTCGCGG
71341 GCGGCTTCGG CCGTGACCAC CGGGGCGAAC GGCCGGAAGC CCTCGCGCTT CTTCACCATC
71401 GCGTTGATGC GGGTCCGGTT CTCCTCGGGG CGGGCGTCCG CGACGATGCT GCGGTGGCCC
```

-continued

SEQUENCE ID NOS: 1-3

```
71461 AGGGCGCGGG GGCCGAACTC GGAGCGGCCG TACGCCCAGC CGAGCACCTG TCCCTCGGCG

71521 AGGAGTCCGG CCGCCGTCTC CACGGCGTCG TCCGGGAACT CCACATCGAT CAGCGGCGCC

71581 CAGTCGGCCA GCCGGGCCCT GATCTGCTCC CGGCCGCCCA TTGCCGGGCC GAGACTCGCG

71641 CTGAGCAGCC GTTTGCTCGG CCGCTCCAAC GTGCCGAGGC TCGCCGCGGC GGCGTAGGCG

71701 GCGCCCTCGC CCGCGCCCGC GTCGTGCGAG GCGGGGTGCA CGAACACCTC GTCGAAGAGC

71761 CCGGACTTGA GGATCAGCCC GTTGAGGCTG GAGTTGTGGG CGACGCCGCC GCCGAAGCAC

71821 AGGCGGGACT GGCCGCTGGT CTTCGCCCAG TATTCGAGGA TGTGCAGCAC GATCTTCTCG

71881 ACCGTCTCCT GGAGCGCGGC GGCGAAGTCG CGGTGGGCCT GGGTGAACGG CTCGCCCTTG

71941 CGGCGCGGCC GGAAGCCCTC GGCGTAGAAC AGCGGGCTGA CCAGGTTCGG CACCATGATG

72001 TTGCCGTGCA ACTCGTACTC GCCGTTGTCC TGGAGGGTGT AGAGCTTGGC GAAGGTGTCG

72061 CGGTAGGTCT CGGGGTTGCC CCAGGGGGCC AGGCCCATCA CCTTGTACTC GTCGCCGAAG

72121 CCGTAGCCGA GCAGATAGGT GGCGTTCAGA TAGAGCCCGC CGAGCGACTT GGGCACCGGG

72181 TAGTCGGCCA GCTTCTCCAG GTGCGTGCCC TCGGCGCGGT AGACGGTGCC GGAGTGCAGT

72241 TCGCCGCGGC CGTCCAGCAC CAGGACCAGT GCGGAGTCCA TGCCGGAGTG CAGATACGAG

72301 GAGTACGCGT GCGCCTCGTG GTGCGGCACG TACACCAGCT TCTCGTCCGG CAGGTCCCAG

72361 CCCAGGCCCT CCTTCAGCCG CTGCCGGATC AGCTCCCGGG AGTAGCGCAG GGGGGCCCGC

72421 GGATATTCGG TGTAGAGGTG GTTGAGGACG GTGTCGATGT GGTTCTCGGG GAAGTAGTAG

72481 CCCACCGCGT CGACGTCCTC GGGCCGCGCA CCGGCCAGGG CCAGGCACTC ACGGACCGCG

72541 TTGAGGGGAA ATTTGGTTGT CTTCTTGATC CGGTTGAGCC GCTCCTCCTC CACGGCGGCC

72601 ACGAGTTCGC CGTCGCGGAT CAAGGAAGCC GCCGAGTCGT GAAAGAACAC CTCGCCGAGT

72661 TGCGGCACCA CATCGGTGTC CGCGGCGGAG AAGTTGCCGT TGAGCCCGAG CACAAGCACA

72721 GTGATCACCC AAACCAGTCG GAGGCGAACG CGAGGATGCG GGGCGGAAGA CGCCCGCCGG

72781 TCACCGGGAG CGCGGCAGCG CCGGGTCGGC CAGCTCAGGC GCCGTCAGCC GCAGCGTCGT

72841 CGGGGCCGGC TGGAACGCGG GGGTGAGGTG GAGGCGCTCG ACCCCCTCCT CGTCGGGGGC

72901 CGCGAGCGCG GCGGTGCACG CGCAGGTGGT GTCGGCGAAC CCGGCGAAGC GGTAGGCCAC

72961 CTCCATCATC CGGTTGCGAT CGGTGCGCCG GAAGTCGGCG GCCAGGTGCA CCCCGGCCTG

73021 TGCCGCCTGA TCGGCCAGCC AGTTCAGCAG GGTGGACCCG GCGCCGAAGG ACACCACCCG

73081 GCAGGAGGTG GCGAGCAGTT TCAGATGCCA CACCGCGGGG TGCCGTTCCA GCAGCACGAT

73141 GCCGACGGCG CCGTGCGGGC CGAACCGGTC GGCCATCGTG ATGACCAGCA CCTCGTGCGC

73201 GGGGTCGGTG AGCAGTCCGC GCAGTACGGA GTCGGGGTAG TGGACGCCGG TGGCGTTCAT

73261 CTGGCTGGTG CGCAGGGTCA GTTCCTCGAC CCGGGACAGC TCCCGCTCCG TGGCGCGGGA

73321 GATGCCCATC CGTATGTCCA GGGTGCGCAG GAAGTCCTCG TCGGGGCCGC TGAACTCGGC

73381 CCGCTCGGCG TCACGGCGGA ATCCGGACTG GTACATGTTC GGCGCTGCC GGGAGTCCAC

73441 GGTGACCACG GCGGGGCTGA ACTCGGGCAG CCCGGTGAGC CCGGCCAGGT CCTCGGCCGG

73501 GTAGCAGCGC ACCTCGGGGA GCCGGTAGGC GACCTCGGCC CGTTCGGCGG GCTGGTCGTC

73561 GACGAACGCC ATGGCGCGGT CGGCGAAGTT CAGCCGGTCC GCGATGGCGC GTACCGACGC

73621 GGACTTGGGG CCCCAGCCGA TATGCGGCAG TACGAAGTAC TCGGCGAGGC CGAGGGCCTC

73681 CAGGCGCTCC CAGGCGTGGT CGTGGTCGTT CTTGCTGGCG ATGGACTGGA GAATGCCGCG

73741 TTCGTCGAGG GTGGTGATGA CATCGCGCAC CCACTCGAAG GGCAGCACCT CGCCGTCCTC
```

-continued

SEQUENCE ID NOS: 1-3

```
73801 GAGCAGGGTG CCGCGCCACA GTGTGTTGTC CAGGTCCCAG ACGAGACATT TGACGGCCGT
73861 CGGCGGCTCG CTCACGGGCT TCCCCTCCGT CATGCTTGCA CCTTCTTCCG CGTGTGCTGG
73921 GCGAGGACGA GCTGGCAGAT CTCGCTGGTG CCCTCGATGA CTTCCATCAG CTTCGCGTCG
73981 CGGTACGCCC GGGCCACCAC ATGGCCGTCG GATGCGGCGG CCGACGCCAG GAGCTGTACG
74041 GCGCGTGCCG CGCCGTCGGC CGCCTCGCGG GACGCGACGT ACTTCGCGTG CACCGCGTCG
74101 ACCGCCATAT CGGGCGAGCC GGTGTCCCAG GAGGCGCTGG CGTGTTCGCA GGCCCGGGTG
74161 GCGTGCCGCT CCGCGACGTA CAGCTCGGCC AGGTGCCGGG CCACCAACTG GTGCTCGGCG
74221 AGTCTGCGGC CGGACTGTTC CCGGGTGGCG GTGTGCGTGG CGGCGGCGTC CAGGCAGGCG
74281 CGCAGGATGC CGACGCACCC CCACGCCACG GACATGCGCC CGTAGGTGAG CGCCGCGGTG
74341 GTCACCAGGG GCAGTGGCAG TCCGGTGCCG CCGAGTACCT GGCCGGTGGG CACCCGGACG
74401 GCGTCCAGGG TGATGTCCGC GTGGCCGGCG GCGCGGCAGC CCAGCGGGTC GGGCACCCGC
74461 GTGATGCTGA CTCCGGGGGC CCGGGCGGGC ACGACCACGG CCGCGGCGCC GCCACGATAT
74521 TTCCCGAACA CCACCAGCAG ATCGGCGTAG TGGGCGGCGG TGATCCACAC CTTGCGGCCG
74581 GTGACGACCA CGTGTGTGCC GTCATCGGCG ATCTCGGTCT CCATCGCGGC CAGGTCGCTG
74641 CCCGCCCCCG GGCTGCTGAA TCCGACCGCC GCCAGATCAC CGGAGGTCAG CCGGGGCAGA
74701 AAGGTGGACC ACTGTTCCGC GCCACCCAGC CGCCGTACGG TCCACGCCGC CATGCCCTGG
74761 GACGTCATCA CGCTGCGCAG CGAGCTGCAC CGGGCGCCGA CCGCCGCGGT GAGCTCCCCG
74821 TTGGCACGGC TGTCCAGTCC GGCGCCGCCG TGCTCGGCGC CGACCTGCGC GCACAGCACA
74881 CCGGAGGCGC CGAGTTTGAC CAGGAGGTCG CGGGGCAGCT CCCCGGCCAG GTCCCAGGCG
74941 TCCGCCCGGT CCCCGATCAA CCCGCTGACC AGCTCCGTAT GGCTGGTGGC GGCGTCGGTC
75001 ACGGCTGTAC CCCGCGCAGC CGCAGGACCA TCGCGGTCAT CGCGTTGACC GTGCGGAAGT
75061 TGTCCAGCGC CAGGTCGGGG CCGGTGATCA CCACGTCGAA GGTCGACTCC AGGTGCACGA
75121 CCAGCTCCAT GGCGAACATC GAGGACACGG CACCGGAGCT GAACAGATCG GTGTCCGGGT
75181 CCCAGGTCTG CTTGGTGCGC TGTTCGAGGA ACTGCTGCAC CTCCTGCGCC ACCGTCTCGG
75241 CGGTGTGGCT GCCCGGCTCG GATGAGATGG TCACGCCAGT TCCTTCCCGT ATGCGTAGAA
75301 CCCGCGGCCC GACTTGCGGC CCAGGTGGCC GTCGCGGACC TTCTTCAGCA GCAGTTCGCT
75361 CGGCGCGCAC CGGGAGTCGC CGGTGCGCTC GTGCAGCACG CGCAGCGAGT CGGCCAGGTT
75421 GTCCAGGCCG ATCAGGTCCG CGGTGCGCAG CGGCCCGGTG CGGTGGCCCA GGCAGTCCCG
75481 CATGAGTACG TCCACGGCCT CCACCGTGGC CGTGCCCTCC TGCACCACCC GGATCGCGTC
75541 GTTGATCATC GGGTGCAGCA CCCGGCTGGT GACGAACCCC GGCCCGTCGC CGACGACGAC
75601 CGGCTTGCGC TCCAGCGCAC GCAGCAGATC CGTCACGGCG GTCATCACCG CTTCCCCGGT
75661 CCGGGGACCG CGGATCACCT CCACCGTGGG GATCAGATAG GCGGGTTCA TGAAGTGGGT
75721 GCCGACCAGC CGTGCCGGAT CGGCGATATG ACCGGCCAGT TCGTCGATCG GGATGGAGGA
75781 GGTGTTCGAG ATCAGCGGCA CCCGCGCTCC GGTGAGCCCG GCGACCGCTT CGAGCACCTT
75841 GGCCTTGGTG GGGGTGTCCT CGGTGACGGC CTCCACCACC GCGGTGGCGT TCCGGCCGTC
75901 GGCCAGGGAC GCGGTGACCG TCAGCTCGCC CCGCGGGCGG CCGGCCGGCA GGGCTCCCAT
75961 GAGCTGCGCC ATGCGGAGCC GTTCGGTGAC CGCGGCCCGT GTTCGGCCGG CCTTGGCCTC
76021 GTCCACCTCG ACGACCGTCA CCGGGATTCC GTGCCCGACG GCGAGAGAGG TGATTCCCAG
```

-continued

SEQUENCE ID NOS: 1-3

```
76081  TCCCATCGTT CCTGCGCCCA GCACCGTGAG CCGCGGCGCT TCCGCATCTC CGCTCATCAA
76141  TCGCCTCCGC AGCGCGTTGT GAACAACGTG CCGACCATGA CACGCGCTTC CGCGTTCACG
76201  GTATTGTCCG GGCGGTCACC CAAATCCCCT AAGGATCCCC CCTATACCCC CCTCAGCCGG
76261  AATATGAGTT CCAGCATTCT GGAAGACGCC ATTGCGCGGC GCGTCGACGG ATTCTTAGCA
76321  TGGGCCGCAT TGCCTTTCCC TGGTCCTTCC CTTTTCAGCT TTGCGGGGTG CGGAAATCCG
76381  ATGGCTCAGC AAGTCGATGT GACCGAAAAA ATTCTCGGAT ATGTCCGGGA ACTGTCCCTG
76441  CGCGATGACG AGATCCTGGC CGGGCTGCGG GCGGAGACCG CGGGTCTGCC CGCCGCCCAG
76501  GCCATGCAGG TGATGCCCGA GGAGGGCCAG CTCCTCGGGC TGCTGGTACG GCTCGTCGGC
76561  GCCCGTTCGG TGTTGGAGAT CGGCACCTTC ACCGGTTACA GCACGCTGTG CATGGCGCGG
76621  GCCCTGCCGA CCGACGGCAC GCTGGTGACC TGCGACATCA CGGCGAAGTG GCCGGGGCTC
76681  GGCCGCCCGT TCTGGGAGCG CGCCGAGGTG GCGGACCGCA TCGACGTGCG CATCGGTGAC
76741  GCCAAGGAGA CGCTCGCCGG GCTGCGGCGG GAGGGCCGGG AGTTCGACCT GGTCTTCATC
76801  GACGCGGACA AGACCGGATA CGCGCACTAT TACGAGGAGT CGCTGGCGAT GCTCCGGCGC
76861  GGCGGGCTCA TCGTCCTGGA CAACACCCTC TTCTTCGGCC GGGTGACCGA CCCCGCCGCG
76921  CAGGACGCCG ACACCGCCGC CCTGCGCGAG GTGAACAAGC TGCTCCGGGA GGACGGACGC
76981  GTCGAGATCA GCATGCTCAC CGTTGGTGAT GGCATCACGC TCGCGGTCAA ACGCTGACCA
77041  CGTGGCCGGG GTCCGAACGT CTGACGGCCA TGTTCCGGGA TCCTCCCGGG ACATGGCCGT
77101  CCGCGCGGCT CCGCGGTCAG GCGCGCGGCA CCGCGGTCAC GCCAACTCCA TCCGGTCGGC
77161  GTACAGTTCG GTCGGCAGTT GCTCCCGGTG CTTGATGTCC AGCTTGCGGA ACACCCGGGT
77221  CAGATGCTGC TCCACCGTGC TGGCCGTGAC GTACAGCTTC CCGGCGATCT CCCGGTTGGT
77281  ATAGCCCATG GCGGCCAGCG ACGCGACCCG CCGTTCGGAG TGTGTCAGCC GCTCGATCGC
77341  GGTGTCCGAC TTCGGCGTTG GCCCGGTGGC ATGGCCCTGG TCGTCGGCCG GCAGCCACTC
77401  CTCGTACAGC GACGCCGCGT CGCACATCTT CGCCACATGC CAGGCCCGGC GCATGGTCCG
77461  GCGGGCCTGC TTCTTCTCGC CGAGCGCGTG GTACGCCTGG CTGAGGTCCC ACAGGGTGCG
77521  GGCCAGCTCG TACTTGTCCT CCTGCTCGGT GAACAGGCCC ACCGCCTCGT TGAGCAACTG
77581  CGGCCGCCGC TTGGCCGAAC TGGTGGCCGC CAGAAGGCGT AACGACTGTC CGCGGGCCCG
77641  GGCGCCGTCC GTGTGCGGAC GGCTGAGCTG CTGGTACACC AGGATCCGGG CCTGGTCGTG
77701  GTTGCCCTGC GCCAGCCATG CCTCCGCCGC CCCGATCCGC CACGGCACCG GTCGCAGCC
77761  GCTGCTCAGC CCCCAGTCGG TGAGCAGTTC GCCGCAGAGC AGGAAGTCCG CGAGCGCGGC
77821  CTGGTGGCGG CCCGCCGCCA GGAAGTAGTG GCCGCGCGCG TACAGGTAGT GCAGCCCGTA
77881  GGAGCTTTTG AACATGGCGT TGGGCACGGT CTGCGCGACA TGGAACCCCG CCTCCTCGTG
77941  CCGCCCCATC CGCGTACACG CCAGGATGAG GGCGCCGAGC GGCAGTCCGA TGGCGACGCC
78001  CCAGGCGCCG GGGGAGGCGT GGGTGAGGGC GGCGCGGGAC TGCTCCGCGG CCTCGGCTAG
78061  GTCACCGCGG CGCAGTGCGA TCTCCGACCT GGCGGCCGAC AGCACCGCCT GCCGCATCGG
78121  GACGTGCGGT CCACCACCGG TCTCGCCGAG CGCACCCTCG CACCAGGCGG ACGCCAGGTC
78181  GTTCCGGCCG CCGTAGACCA GGGCGAGCAG GGCGAACAGC CCGCCCTGCT CATGGCAGGC
78241  CGGGTCGTGT CCGAGCTGAA GTTCGCGCAG CACCTCCTCG GCCCGGCGGA CGGTGTCATG
78301  GGTCTGCCCG CCGGTGAGCA CGTCGGCCAG GACCGTACCG GCCCGGGGCC ACGCCGCCGC
78361  CCGTGTCGCC GCGGCGCCAC CGTGGTGCGG CGGTGCCGCC CGCCGCTCGG CCAGCCAGGG
```

-continued

SEQUENCE ID NOS: 1-3

```
78421 ATAGGTGCAG GTGAGTGCCG CCTCGATGGC ATGGAGCTGG TCGGTGGCCG CGGGGTCCGC
78481 GCGCAGATGG GCGAGCAGCC CCTCCACCTC GCTCAGTCCC CCCTTCCACA GGAGCTGCAT
78541 GAGCAGGGTG ACGCTGTCGG GGAGGCCGAG CCGGCCGGCC CGGACGGCGC CGTACAGCGG
78601 TGCGTGGTGC CGCGTGGCGG TGGACGGATT GATCTTCCAC TCCGCCTCGG CGAGCTTCGC
78661 CCGCAGGGCG GCGCGGCGCT CTTCGTGCGG GCATTGCTCG AAGGACTGCT CCAGTAAGTC
78721 GACGGCGATG GACGCCTCTT CGCCCACCGC CACCTGCTCG GCCACTTCCA GAAGCACCTC
78781 GGCCGACCAC GAGTCGGGGA TCTGCCCGGC CCGCACCAGA TGACGGGCGA TCGTGGCGGC
78841 GGGCCTGCCC TGGTCGTGCA GCAGCCGCGC GGCCCGCTGG TGCAGGGTCC TGCGGGCCTG
78901 CGCGGGCATG TCGTTGAGCA CGCTCAGCCG GGCCGTCTCC TGCCGGAACG CGCCCTCGTC
78961 CATCAGCCCG GCCCCGGTCA GCGCCGCGAG CACCTGGCTG ATGGGCTCGG GCTCGTGTCC
79021 GGTCAGCCAG GCGAGGTCGG CGGCGGGCAG GGCGGAGCCC ACCACGGCCA GCGCGCGCAC
79081 CACGTCCAGG AAGATCGGCT CATTGCGGTG CAGACAGCTC AGGAAGGACT GGCCGTAGCC
79141 GGTCTGGCGG GCCTCGCCGT ACTCACGGTA GTCGGAGAGC AAGGTGTGCA GCAGCAGCCG
79201 GTTGCCACCG GTGGCGGCGA GGATGTCGCC GACGTGGCGG CGCGCGGTCT CCCCCAGCTC
79261 CGCCACGACC ACTTCGGCCA CCTGACCCGG GGAAAGGGGG CCCAGGCCGA TGCGGCGCAG
79321 GTGCTGGGCG CGCAGCAGTT CGTAGCGGAG CGGCAGGGAC GAGGACAGGC TCAGGTCGTC
79381 GGTGAATACG GCCGCGATGC GCGCCGAGTC CAGGCGCCGT ACCAGTTGCA GGAGGAAGGC
79441 TGCGGAGGCC GGGTCGCTGT GCCGGACATC GTCCACGGCG AGGAGCAGTG GTGTGTGTTC
79501 CGCGTGGTCG ATCAGCGAGG TGCACAGCCG GTGGCACAGC CGGGCGATCC CGGCCCGGTC
79561 CACCGGATCG CCCGGCCCGC GGAGGATGTC CGGCAGCCCC GGTACCTCGG GCGGCCCACC
79621 CGGTGACTTC CAGGCGCCGC GGGCCAATTG CGAGACGACG CCGAAGGGAA GGTCCCGCTC
79681 GCTGGGGGAG CATGTCGCGG TGATGGTGAG ATAGCCGGAT TCCGAGGCTC GTTCGGCGAA
79741 CGACCGGAGC AGGGTCGTCT TCCCGCATGC CAGCGGTCCG TCCACGAGAA GAGCCTCCCC
79801 GGGCCGCACC AAAGAGTCAC CGAATGGATG TCCGAGGTGC ACCGCGGTAT TCAATACCCC
79861 GCCCAGCGGA CGGGAATTCC GCTCGGTATT CACCGGCATG GCATAGCTGT AGGGCATGGT
79921 GATGGTCCCC GATCGAGGTC GACGGAATGC GGACTCGCGG CCCTTGAGTC AGACCAAATT
79981 GTTGATCGGG ACACGATTCC ATCAGCACGC CCCTGCCTGC CTCAACCCCT ACCGGAAGCT
80041 CCGCCCCCTA ACCGCCCCA CCACATCTCG TTCTCCGCAT CGGGCTGTTC AGTTATCCGT
80101 GGCGGCGCC GCACGGTCAA CCCCCTATCG AGTCCGTGCG CCCCTAAAAC GCATGCGGAG
80161 AAAGGTCTCG GTGGCCCGGA CACCGTGAGG CATCACCATG CGGGCGCGCG GGGCATCGCC
80221 GCGAGGGTGG TGCTGACGGT GTCCTCGGGG ATCCGCGCA CCAGTCCGGG CCCCTCGGGG
80281 CCGTCCAGGA CGAACGTCAG CCCGTCGGTG GCCTTCTTGT CCAGGCGCAT CAGCTCCACC
80341 AGCTCGGACA CCGAGACATC CGGCGGCAGC CCGGTCGGCA GGCCGTAGCG GGATACGACG
80401 TCATGGTGCT CGGCGACCCG TTCCGGGCCG ATGCGCCCCA GCGCGCCGGC GAGCCGGCCG
80461 GCGAAGACCG TGCCGATGGC CACGCCCTCG CCGTGGCGCA GTGCGAACCC GGTGGCGCGT
80521 TCCAGCGCAT GCCCCAAGGT GTGTCCGTAG TTGAGGAGGT GGCGCAGGCC GGAGTCGCGT
80581 TCGTCCGCCG CGACGATGCC CGCCTTGAGC GTCACACTGG CCGAGATCTG GTCGAGCAGC
80641 GGCAGCCCGT CGAGGTCGGG CGCGCCGATG AAGTGGCAGC GGGCGATCTC ACCGAGGCCG
```

-continued

SEQUENCE ID NOS: 1-3

```
80701 TTGCGCCATT CCCGGTCGGG CAGGGTTTTC AGATGCTCGA GGTCGCAGAG CACGGCCGCG
80761 GGCTGCCAGT AGGCGCCGAC CAGGTTCTTG CCCTCGGGCA GATTCACCGC GGTCTTCCCG
80821 CCGACGCTCG CGTCCACCTG GGCGAGCAGC GAGGTCGGCA CATGAACGAC CGGGGTGCCC
80881 CGGTGGTAGA GGGCGGCGGC CAGGCCCACC GTGTCGGTCG TGGTGCCGCC GCCACAGGAC
80941 ACCACCACAT CCGAGCGGGT GAGTCCGAAT CCGACGAACC GGCGGCACAG GTCCGTCACG
81001 GCGGCCAGGT CCTTGGCCTC CTCCCCGTCG CGGGCGGGCA CGACGAGCGA GGGCACTCCC
81061 GGGTCGGGGG TCTGCCCGGC GGGCCGCGCG GTGACCACCA CCGCCCTGCG CGCGCCCAGG
81121 GCGGCCACCA CCTGTGGCAG CAGCCGCTGC ACACCGTGGC CGATGTGAAC GGTGTAGGAG
81181 CGTTCGGCCA GCCCGACGGT GACCTGCCGG GCAGGGGACG CGGAGCCGGT GGCCGAAGTG
81241 GAAGTCGACG TGGTCAAGAC TGCCTTCCCA TCGCTGACGC GGCCCCGGCG AGAAGCCGTC
81301 TCGCCGGGGC CGGAATCGGG TGCGGAGCCG TTTTCAGTCC TCGACCGCGA TCGCGGCGGC
81361 CGGGCAGAGG AACGACGCCT CGGCGACGCT GTCGCGCAGC TCGAGCGGCG GCCGCGCATC
81421 CAGCAGGACC ACGGTCCCGT CCTCCTCCCG CTGGTCGAAA ACCTCCGGCG CCGCCAGCGC
81481 GCAATGCCCG GCCGCGCAGC ACTTGTCCTG ATCCACCGAG ACCTTCACCA TCGTGTTCCC
81541 CTCATCATCC TTCTGTCATC CGTTCCGCGG TCACCAGGCG ACGGGCACAC GGGCGACGCC
81601 GAAGTTCATC GACTCGTACA GAAACGCCAG GTCCTCGAGC GGGACCTCCA GGCGCAGCGT
81661 GGGCAGCCGG CGCAGCAGGG TCTCCAGAGC GATCTGGAGC TCGACCCGGG CGAGGGTCTG
81721 CCCCAGGCAC TGGTGCACGC CGAAGCCGAA CGCGACATGC TCGCGGGCGT TGGGCCGGCT
81781 CAGGTCCAGC TCGTGGGCGT CCGCGAAGTG GGGGTCCCGG TTGGCGCTGG GCAGGTTGAT
81841 GATCACCCCT TCACCGGCCG GGATGAGTAC GCCGCCCACC TCGACGTCCT CGACGGCCAC
81901 CCGTCCGGTG CCTTCCTGGA CGATCGTGAT GTACCGGAGC AGTTCGTCCA CCGCGTTGCC
81961 CATCAGCCCG GCATCGGCCC GCAGCCGGGC GAGCTGGTCG GGGTGGTTCA GCAGCAGGAC
82021 GGTGGACAGG GCGATCATGT TGGCGGTGGT CTCGTGCCCG GCCAGCAGCA GCACCAGGGC
82081 GGTGGCGACC ACCTGCTGCT GGGTGAGCCC GCCCGTCGGC TCCTGGTCGA CGATGAGCCG
82141 GCTGAGCAGA TCGTCGCCCG GGTCGGCGCG CTTGGCCGCG CACATCCGGG TCACGTAGTC
82201 CACCATGACG CCGAGCGCGG CGCCCATCTC CTCGGCCGAC GCGGTGAAGT CCATGACGCC
82261 CTGCGACGCC TGCTGGAACT CCGCGAAGTC GGCGTCCGAG ACCCCCAGCA TCACGCCGAT
82321 CACCTGGGAC GGCAGGGGGA AGGCGAAGTC GGCCACCAGG TCGGCCGGCG GGCCCTGGGC
82381 GATCAGCCGG TCCAGGAGGC CGTCGACGAT GCCCTGGATC ATCGGCCGCA TCGCCTCGGT
82441 GCGCCGGATG GTGAAGTTCG CGGTGAGCAT GCGGCGGATC CGGGCGTGCT CCGGATCGTC
82501 CATCCTCCCG AGGTTGAACA CCTCGGCCGG CACCTCGAAC TTCACAAAGC GGGGCATCGC
82561 CTTGTGCGTG CCGTCGGCGC TGAACCTGCT GTCGCCGAGC GCCGCCCGCG CCTCGTGATA
82621 GCCGGTGACG AGAAACGGGG TGCTGCCGTC CCACATCCGC ACCCGCGTGA CGGCGGACCG
82681 CTCGCGCAGT TCCTCGTATC CCGGCGGGGG TGAGAACGGG CATGCAGCAG CCCGCAATTC
82741 GGGGTAGTCG CGTATCTCGT CCATGCCTGT CCGTCCCGTC AGTCGCTTCG TCGCCACCAC
82801 TGCGCCGCCC TACGGATGGA CAAGTCTGGT CCGCGCACCG GATCCCCACT CCCCTAACCA
82861 CTCCCCTATG CCCCCTTGGC TTGGGAGCGG GTATCCCCCC GTGCCCCGGC GGCAGGACGC
82921 TCAGCAGGAG GACGATCCGG TGGCTCCGAT GAGCTGCCAC AGCCGACGCG ACAGCTCCTG
82981 CCGATTTCCG ACCGAGAGCT TTCGGTAGAT GCGGGTCAGA TGCTGCTCCA CGGTGCTGAC
```

-continued

SEQUENCE ID NOS: 1-3

```
83041 CGTGATGTAG AGGCTCTTGG CGATCTGCCG GTTGGACATC CCCGACGCGG CCAGGGTCGC

83101 CACGCGCCAC TCGGCCTCCG AGAGAACGGG CTGCTCCGCG CCTTCGGCCG AGGCGGCGGG

83161 GTCCGACTCC TCGGGCTCCC CGGTATCCCC GGCGGGTTCC GGCAGTCGCG CGTCCGCGGG

83221 GCTCTCGGCG CCATCCACGA CGAGGTCCCT GCGGCTCTCG TGCTGGGCGC TGATCCCGCA

83281 CTCGTCCATC AGCTTCTGCG CCTCATGCCA GGTGCCGCGG GCCTGCTGGG TTTCCCCGGT

83341 GCTGAGGAAG TCCTGGCTGA GCTCGGCGAG CGTACGGGCG AGTTCGAAAC GGTCGCCGTG

83401 CTCGCGCAGA CACTTGGCGG ACTGATACAG GAGCAGCCTG CGCTTGTCCG GGTCTTCGGC

83461 CATGGCCAGA ACGCGCAGCG CCCGGCCGCG GGTGCTCAAG GGGCGGTCGG GCGACAGCTT

83521 GAGTTCCTCC AGGGCGAGTC TTTTGGCCTC CGCCGGCTCC TGGACACGCA GATACGCCTC

83581 GGCGGCGTCG ATACGCCAGG GCGCCAGGTC GCCGAAGTCC ACGGGCCACT GGTCCATCAG

83641 CATCCCGCTC ACCATGAAGT CGTTCAGCGC TGCGTAGGGG CGGTTGGTGG CCAGGCAGTA

83701 CTGTCCACGG GCCCGGAGGT ACTCCAACCC GACAACGCTG TCGAACATTT CCTTCGGCAC

83761 CCAGTAATGC AGATATCGCT GGGCCTCATC GAGTCTGCCG ATGGCGGTGT GGGCCGCCAC

83821 CAGAACGGAG AGCGGCAATC CGATGGCGAC GCCCCAGCCG CGCGGGGGGA TGGACTTCAG

83881 CGCGGTGCCG GCGAGATCGA TGGCCGAGGT GAAGTCCCCA TGGCGGCATC TGATGTAGGC

83941 GCGCATGGCC AGGGCGACGG CGCCGGGCGT CTTCATGTTC AAGTTGCCGG CCGCGGTGAA

84001 AAGCGCGCCG CACAGCCGGT CCGCCGTTTC CGCTTCGCCT CTCGCGGCCA ATGCCCAGAC

84061 CATCCGGCAG GCGTATGCGT AGGCGAACCA GAAGTGGTTG GAGGGCGACA ACAGATGCAT

84121 GGTGTCGGGA GAGAAGTCCG CCACCTGCCG GGGATCCTGG AAATGCCCGA TCTCCATGCC

84181 CAGTTCGTCG ACGGAGAGCT GAAGACCGTG CTCCAGGTTG GCCGCCCACA GTCCGTCGAC

84241 TTCCCCGGCC GAGGAAGCCT GGTCGGGGAA GTCATGGATC AGGGCCGGTT TGAGGAAGGT

84301 GGCCCACTGC CGGGTCACCC GCAGAGCGGC CATGCTGGAG GCGTTATCGG TGTCACCACC

84361 GCCCGAAAGC CACTTGAAGG CTTCTTCCCC ATCGCTGAAC CGGCCGAACC AGAGCACCAT

84421 GAAGAGCAGG AAGCACAGAT ACTGTTCCGG GATGTCCGCG GGGAATTCCT CCCGTATCGC

84481 GGCCATCAGG CGGTCCAGTT CGGGTTCGGC GGTCGCCGGA TTGCTGGACC ATAACGCGCC

84541 GACCAGCGCC ATGAGAATGT CCATGTGCTC GCGCCGGCCG AGGTCCGCGC GGGCGGCGAG

84601 CCGCAGGCCC GCGATCGCTT CCTCCGTACG GCCGTGCTCG AGATTCTTCT GGGCCGCGTG

84661 CCAGAGCACG GTGACGTCTT TTTGGTCGGG CGTTCTGTCG GCGGTGACCA GGAGTTCCGC

84721 CACCGCGATC GGATCGGCCC CGTCGGCATA CAGAAGTTCG GCCGCTTTCG CGCTGAGCCG

84781 GGCCCGGTCC TCCGCCGACA GCGTCTCCAG CGTGATGTAT CGCGCCGCGG GGTGCCGGAA

84841 CCGTCCGTCC TCCAGCAGTC CGGCGGAGTT CATGACGGTG ATGGCCCGGG TCGCGCGTTC

84901 CCGGCCGCAG GCGAGCAGAC TGGCCACCCG CCCCGGGCCG CCGTACCGGT CCAGCACCGC

84961 GAGGGCCTGT GCCACCTGGA GCAACGCCGG ATGGGACAAC AGGCACCCGC GATAGGTCTC

85021 CTGGAACTCC GCGCCGACGG TGACATCCGT CTCCGACCCG CCCGGAGCGG CCTGGAGATG

85081 GTCCCGCAGC AGGGCCTTGA CCAGCCGTGG GTTGCCACCG CTGACGGCGT GGCAGGAGGC

85141 GCGGATCCGG TCGGCCAGGT CGGCGTCGCC GTGCCGCTCC AGCAGGTGTC CGACCCCGGA

85201 TTCCGGGAGT GTATCGATCT TGATCTTGTA GAGCTCATGG AAGCCGTGAG TGCCGACACA

85261 CAACTGATGA CTCTGCCCGC AGGTCATCAC GACGAGCGTA CGGGTGCCGG AGGCATGCCT
```

-continued

SEQUENCE ID NOS: 1-3

```
85321 GGCGATATGC AGCAGGCACA TGAGGGAGGG GTAGTCGGCA TGCTCGGCAT CGTCAACCGC
85381 GATGATCAGT TGCTTGCCGC CCGCGATGCG GTGCAGCACA TCGGATATCT CTCGGACCAG
85441 GCTTCTCAGT ATGCCGGGTT CGGCTTCCGA ATACCGCTCT CCGGCGGTCC TCCAGCGCGC
85501 CACGACGTCC AATTCATCCG TGAACGCGGA CGACCAGATG AGCTGTTCCA CTATATTGAA
85561 CGGGATCGCG GTGTCGTCCG CGAATCCGGA CGCCATAAGA CAGACCGCAC CCGATTCGGC
85621 CGCCTGCTCC TTCAGACTGC CCAATAAGGA GGTCTTTCCG ACACCGGGTC CCCCGGTCAC
85681 TTTGAGAAGC CCGCCGTTTC CTCGTGCTGC CATGTCGAGG ACGCCGCGAA GCTCTGATTG
85741 ATAATCTGTC AGTCCCATAC TCATCAGTCC TCGCTGTGGG GGTGTGTGCG TCTGAGCGAT
85801 GAGTTGATCT CCGCGGTCAT CCCACCCTGC GGAGGAAGCC TTCTCTGACG AGACAGATAA
85861 CCGCTGCGCC GACGGCGGCT GATTCCCTGA TCTGGATCAC CTCCGGTGGG AGCCCATGTC
85921 CTTGACGTTC ATACAAGCAG AGTCACAACC GGAGCGAAAC CGTCCACCGA TCATGATCAG
85981 CCACGGTTTC CAAACCCCGT GCGAACGTGC CCGACTGAGC GGGCGGCCCC GTCCTCGCAC
86041 CCCCGAGAAG GGCGGGACGC CGCCAGTGCC GGCTTGCAGG ATAAACGCGA TGTGCGGCAT
86101 GCCGACGCGA ATGCACCTCA GCCTCTGAAC CGGTTATGGA CCCGGCAGTA TTCCTTACCC
86161 TGTGCAAAGC TGGTGGCTTA CCAGCAGCCG CCCCGGCCGG TCGCCGCTCC ATGCCCGTCC
86221 CAGCGGGCTC CGGAGTGACA AGTGTCCAAC CTGCGGCCAT CCCCCGGTTG CCTCAAAGTC
86281 ATGTCGCATA CCATTCCCGG CAACCTCCTC GCCCCTCAGC AGATAATGCC TGCCCCCGAC
86341 TCGTCGCGGA GATACGGGGA TTGACCCCTA CATGCTCACC GCGCCAGCGC GACCATAAAC
86401 GGCCGCCGCC CCATGATTCC CCTAAACTCT GCGCCGTGAT TTGGCCGGGG TTTATCTGCC
86461 TGCAAAACGG CCGAAACGGG TGCGCCATGG ACCGAACCCG GGACCGTCCC CGCGGCATAC
86521 GATGCCGGAA GTCCTGACTG CTGGCCACAT CAGAGACGAG GGAGCGTGAA CTGTGACCGT
86581 CAAGGGCGCG TTGTTCGACT TCTCCGGGAC TCTGTTCCGA ATCGAGTCCA CCGAGTCCTG
86641 GCTCCGTACC GAGCTGTACG ACGCCCTCTA TGACCGCCAC CTGGAGCCCG CGGCCCGGCA
86701 GCCCTACCCG GACGCCGCCG AGGGGCCGGC CGAGCTGCAC CGGCGCGGGG TGCGGATCGC
86761 GGTGGTCAGC GACATCGGCT GATCCCGAAA GGGATCCCGT GGGGCGAACC CACCGGTTCG
86821 GGGCGATCCC CCCGTGTCGC CCGAACCGGC GGAGACATGC GGCGGCCCTG GAAGGATCGG
86881 CGGACAACCG AACGTCGCCT GAGTATATTG GCTGACAGCC AGCCAACGCA GGAGTTACAG
86941 C
```

AHBA BIOSYNTHETIC GENE CLUSTER DNA (SEQ ID NO. 3)

```
  1 TCCCGGGCCG TGTCGGGTGG CAGGGCCCCG CCGTGCTCGG CGCACTCGGT GTGGGGCAGA
 61 TCGTCACGTT GTTCTTCACC CGGCCGGTCA GATCCGTGCA GGACGCGCTG GCGGAGGAGA
121 CCATCTACCG GATGATCCTG GAGAGCCGCA GTCTGAAGGT GGCGCTGGCT CGGTTCCACA
181 TCACCACGGC GACCTCGCTC CGGCGGCATG ACGATGTCGA CGGGCAATCC CAGGCACTGG
241 CACGGCAGTT GGAGATCCTG GAGAAGATCG ACACAGCCGA CTTCGAACGG CTCAAACAGC
301 TGGGGGTGAC CCCGCGCGCC GAACCACCGG GGCCCGGCCG GTCCCGCAGA AGGAACCGCG
361 CACAGGCTCC CTGAACACCT CCTACTGCCG AGCGAGGGGG GCTCGCCGTC CCGCTAAGGC
421 CCGGCCGTCA GACCTCGACC ACCGGTGTCT GGAGTTCCGT GACCCACTCC TCGCGGTTCT
481 CCGGACACTC CAGGTTGACC TCCCGGGGGT AGCCGGACGA CCGGTAGCCG TTGCCGTCGA
541 TCCAATGGGC CAGGGCCTGG GCCGTGGGCA CCACGGCGTC CATCGGGCCG CGGTGGACGA
```

-continued

SEQUENCE ID NOS: 1-3

```
 601 TGGTCGCGGC CCGGTCGACG GGCGGCAGAT CGAGGATCCG GAGGTCCTCA CCGTCCCGGA
 661 GCGGGGCGGA GACCTGGACG GCGGCGTGGA CGGTGATGGC GCCGCCGCCT TCCGGGGCGT
 721 CCTCGTAGTA CGCGACACCG GGGCCCGTCG GGGTGATGCC CGCCGCATCG AGGCGCCGGA
 781 ACAGCTCGTC GTAGAGGGGT GTGATGACCG GGCCGATGTC CCGGGGGTCG AAGCCGGTGG
 841 CGGTCGCGGT GAGCTCCGCC ACCCGCACTG CCCGGATCTC CTTGATGACG ACGTCGTTCG
 901 TGGGCATGTG TCCTTCGCTT TCGATCGACC GGAGCCTCGC CTCGACCTGC ACCAGCCGTG
 961 CCGCCACGGC GGCCACGGTG GCTTCCAGCT CGGCCCGCCG CAACCGCAGC ATGCCGCGCA
1021 GTTCCTCGGT GCCGGCCTTC TCGTCCACGA TGTCCCGCAC CTGCTGGAGG GTGAAGCCGA
1081 GCTCTTTGAG CGCGATGACC CGGTTCAGGC GGCTGAGCTG GGCGGCCGCG TAGTAGCGGT
1141 AGCCGGTGGC GGGGTCGACA TGGGCCGGGC GCAGCAGTCC GGTGGCGTCG TAGTGGCGCA
1201 GCATCCGGAC CGATACGCGG CCGTGCCGGG CGAAGTCTCC GATGGTGAAC ATGATGTCTC
1261 CGAGTCCAGC GCCTCACACG GTGTGAGGGT CAACCCTCGA TTCAGGCACT ACATTCGACA
1321 ATAGAGAATT CCCGGTCATC GCCCATGGAG GGACGGACAG CGCATGACGG CGTCGGCTCA
1381 TCCGCATACC CGCGTCATGG TGGAACTCGG CGACCGTTCC TATCCCGTCG ACATCGGGCC
1441 GGGTGTCCGG CATGCGCTGT CCGGGGTCGT CGCGGGGCTC GGCGCTCAGC GGGTGGCGAT
1501 GGTCTCCGCC CGGCCGGACG GCTGGCTGCC CGACCCGGGC GTGCCCTCGA TGGTGCTGCG
1561 GGCCCGTGAC GGGGAGGCGG ACAAGTCGCT GGCCACGGTG GAGGAGCTGT GCCGGGAGTT
1621 CGTCCGTTTC GGGCTGACCC GGTCGGATGC GGTTGTCTCC TGCGGTGGCG GGACCACCAC
1681 CGATGTCGTG GGTCTCGCGG CGGCGCTGTA CCACCGGGGT GTGCCCGTGG TGCATCTGCC
1741 GACCTCGCTG CTGGCCCAGG TGGACGCCAG CGTGGGCGGG AAGACGGCGG TGAATCTCCC
1801 CGAGGGGAAG AATCTGGTGG GTGCTTTCTG GCAGCCGTCC GCCGTGTTGT GCGACACCGA
1861 CTATCTGGAG ACGCTGCCCG CAGCGGAAAT GCTCAATGGA TATGGGGAGA TCGCCCGCTG
1921 CCACTTCATC GGCGCCGGTG ATCTGCGCGG GCTGGCGCTG GCGGAGCAGA TCGCGGCGAG
1981 CGTGGCCCTG AAGGCATCGG TGGTCTCCGC GGATGAGCGG GACTCCGGGC TGCGTCATGT
2041 GCTCAATTAC GGCCACACCT TGGGCCATGC GCTGGAAATC GTGACCGATT CCGGCTGCG
2101 GCACGGTGAG GGGGTGGCGA TCGGCACGGT TTTCGCCGGC CGTCTGGCGC TGGCCCTGGG
2161 CCGGATCGAC GAGGCGCGGG CGGCGGAGCA TCTGGAGGTG GTGCGGGGTT ACGGGCTGCC
2221 GTTCGCGCTG CCCGCCGATG CCGATCCGGG TCGCCTGATC GAGGTGATGC GGCTGGACAA
2281 GAAGGCGACG GATGGGCTCA CCTTCGTCCT GGACGGTCCC GGCGGTCCCG AGCTGGTCTC
2341 GGGCCTCGCG GAGGAGACGG TCGCCACGAC GCTGGCCGGG ATGGACCGGG CCGGCTCGGA
2401 CAACCGCCGG TAGAACCGGA CGCGGCTCAG TCCGGCAGCC CCCTGGCCAG CAGAACGGCG
2461 CCGTGCAGTG AGGACAGCCC GCCCAGTCGC GCGGGCCGGA CCGGTGGCAT CGGATGCCCC
2521 GGGCGCCCCA GCGCCGCCGT CCGCTCGGCC ACCATCGCCA CGAGCTCCGG CATCGCCGCG
2581 GCGAACCCTC CGCCGATCAA CACGAGCGCG GGATGGACCA GTTCGCATAC GCCGGTCACG
2641 GCAGCGGCCA GGGCCCTGCC GCTCTCCCGC AGCGCCGCCA TGGCCCATGG CTTCCCGTCG
2701 GCGACGGCCT GGCGCAGCGC GGCGAAGGTC ACGTCCTCGC CCGCCGCCG CGCCGCCGG
2761 CGCAGGGTCG CCGGGCCCGA GGCCGCCGCC TGGACGCAGC CGCGCCGGCC GCAGTCGCAC
2821 AGCGGTCCGT CGCGGTCCAC GACCAGGTGG CCGACTTCGC AGGAGCCGCG GCCCAGGCCG
```

-continued

SEQUENCE ID NOS: 1-3

```
2881  GGGACGGGTT TTCCGTTCAG CACGATGCCA CCACCGATCC CGGTGCCGAC GCCGAGGTAG
2941  AGCAGATCGG GGCAGCCGGC CTCGTGTGCT TCGGCGAGGG CGGCCAGATC GCCGTCGTCG
3001  GCACAGCGCA CCTCGGCGTC GCCGAAAAGC ACGGACAGCG CGCCACCCAG GTCCACTCCG
3061  GCCCAGCCGG GGCGGCCGGG CCAGGCGGTG ACCGTGCCGG TGGCATCGAG GGTGGCGGGC
3121  ATCGCGACCC CGACGCCGGT GAGCCGCTCG GGGCGCCGG TGCATAACTC CGTGACGTGA
3181  TGCGCCAGCA GGTCCAGGTC GAGGGTGGGG TCGCCGGACG TCATGGCGTC CGTACCGTCC
3241  AGCTCGGCCC AGCGGAAGGA GGATTCACTG ATGCTCAGGT CGTCGTGTTC GAGGCGCAGC
3301  GCCACTTTGG TGCCGCCGAC GTCGATTCCC AGATGACTGA TGGTCGCCTC CCGGCTCGTC
3361  GGCTTTGGCG GTGTGGAGTG ACGGCGGAGT GGCCGCTCAG TCCGGCACCT TCTCGAGCAG
3421  GGCGCGTGCG GCGAGCCGGT ATCCCAGGGC GCCGAGCCCG AAGATGACGC CCGCGGCCAG
3481  CGGGCCCGTC ACCGACTCAT GGCGGAACTG CTCGCGGGCC AGACATTCG ACAGATGCAC
3541  CTCTATCCAG GGCCGCGGAT AGTTGGCCAG TGCGTCCCGA AGGCCCAGC CGGCCATCAT
3601  GAGCGCGGCC GGATTGATGA TGGCGCCGAC CGTGTCGTAG TTCCCCTGAA TGGTGTGGAT
3661  GATCTCCGCT TCGCCGTCGA ACTGGTAGGA ATCCACTTTC CAGCCGCGCT CCGCGACCTC
3721  TTCTCCGACC CAGCGCTCGA TGTCCTGCAG CGTATCCGTG CCGTAGATCT CGGGCTGTCG
3781  CTTCCCGAGT ATTCCGAGAT TCGGTCCGTT CACCAACAAC AGTCTGCTCA ATGCACACCT
3841  CGCCATGTGG GGTCGGCTGA ATTACAGCGG CTCATCACGG AAGTGTATTT ATAGCACGGC
3901  CCTCTTGGCC TCGGCCCGAG AGCTTGGTCA ACTCCGTTTT TAAGGGGGCT GTAGGGGGGC
3961  CCTGAGGGGG AATGACGTTT GCTCCGTCGG CCGGTTAGCG TGCTAATGCG TCCGCCGCGG
4021  ACCTGCCTCC ATAACGCATT AAGGGAGTAG GGAAATCATG AGCAATGATG TGCGCCTGGG
4081  ATCCGAGCTG CCCGCATGGC CTCAGTATGG CGACGAGGAG CGCGAGGGGC TCATTCGGGC
4141  CCTGGATCAG GGGCAGTGGT GGCGCATCGG GGGCGGTGAG GTCGACGCCT TCGAGGCGGA
4201  GTTCGCCGCG GCCCACGGCA GCGAGCACGC CCTCGCGGTC ACCAACGGAA CGCACGCGCT
4261  GGAACTCGCC CTCGAGGTAC TCGGCATCGG AGCCGGCACC GAGGTGATCG TTCCCGCGTT
4321  CACCTTCATC TCGTCCTCGC AGGCCGCGCA GCGGCTGGGC GCGGTGGCCG TTCCCGTGGA
4381  CGTGGACCCG GACACCTACT GCATCGATCC GTCGGCGGTC GAGGCGGCCA TCGGCCCGAG
4441  GACCCGCGCG ATCATGCCGG TGCACATGGC GGGTCAGATG TGCGACATGG ACGCGCTGGG
4501  CAAGCTGTCC GCCGACTCGG GGGTGCCGCT GATCCAGGAC GCGGCCCACG CCCACGGAGC
4561  GCAGTGGCGC GGCAAGAAGG TCGGTGAGCT GGGCTCGGTC GCCGCGTTCA GTTTTCAGAA
4621  CGGGAAGCTT ATGACCGCCG GTGAGGGCGG CGCCGTGCTG TTCCCCGACG CCGAGATGTA
4681  CGAGCGGGGC TTCGTCCGGC ACAGCTGCGG ACGTCCGCCC TCCGACCGCG GCTACTTCCA
4741  CCGCACCTCG GGCTCCAACT TCCGGCTGAA CGAGTTCTCC GCCTCGGTGC TGCGCGCCCA
4801  ACTCGGCCGC CTGGAGGACC AGATCACCAC GCGTGAGCAG CGCTGGCCGG TGCTGAGCCG
4861  ACTGCTCGCC GAGATCCCCG TGTCGTACC GCAGTCGCGC GACGACGCG GTGACCGCAA
4921  CCCGCACTAC ATGGCGATGT TCCGGGTGCC GGGTCTCACC GAGGAGCGCC GCGCGAAGAT
4981  CGTCGACCTG CTCATCGAGC GCGGGGTGCC CGCGTTCGTC GCCTTCCGCG CGGTCTACCG
```

-continued

SEQUENCE ID NOS: 1-3

```
5041  TACGGACGCA TTCTGGGAGA TGGCGGCGCC GGACCTGACG GTGGACGAGC TCGCCCGCCG
5101  CTGCCCGCAC TCCGAGGCGC TCACCCGCGA CTGCCTATGG CTGCACCACC GGGTGCTGCT
5161  GGGCAGCGAG GAGCAGATGC ACGAAGTGGC CGCCATCGTC GCCGACGTGC TCGCGAGCTC
5221  ATGAGCGCCC CGCCCGCCGA CGGGACGCCG ATCCGGACCG CCGTGGTGGG GCTGGGGTGG
5281  GCGGCGCGCT CGATCTGGCT GCCCCGGCTC CGCCGCAACC CCGCCTTCAC CGTGATCGCC
5341  GCGGTGGATC CCGACGAGCG CGGCCGCGCG GCCGCCGCCG AGATGGAGGG CGCGGACCGG
5401  CTGCCGGTGC TGGCGGCGGT CCACGACCTC GACCCCGCGG AGGTGGACCT GGCGGTGGTC
5461  GCGGTGCCCA ACCATCTGCA CTGCGATGTC GCCACCGAGC TGCTGGCCAA GGGTATTCCG
5521  GTGTTCCTGG AGAAGCCGGT GTGCCTGACC TCCGAGGAGG CCGAGCGGCT GGCCGCCGCG
5581  GAGCGCTCCG GTGGCGCGGT GCTGCTGGCC GGGAGCGCGG CGCGCTACCG CGCCGATGTG
5641  CGCGGGCTGT ACCGGATCGC CGCCCGGCTG GGCCGTATCC GCCATGTCGA ACTCGCCTGG
5701  GTGCGGGCGC GCGGCGTACC CGACCGGGGC GGCTGGTTCA CCCAGCGGTC GCTCGCGGGC
5761  GGCGGGGCGC TGGTCGACCT GGGCTGGCAT CTGTTCGACA TCGCGGTTCC GCTGCTGGGC
5821  ACCGCCGCGT TCCGGCATGC CATCGGCACC GTGTCGTCCG ACTTCATCAC CCAGCGGTCC
5881  TCGCGGGCCG CGTGGCGGGG CGACGACGAC GGCCCGGTGC TCTCGGGCGG CACCGATGTG
5941  GAGGACACCG CGCGCGGATT CCTCGTCACC GACGACGGCC GTTCGGTCGT GCTGCACGCG
6001  AGTTGGGCCT CGCATGAGGC GCTGGACACC ACGCGGGTCA CGATCGACGG CAGCGCGGGC
6061  AGCGCGACCT TGCACTGCAC CTTCGGATTC AGCCCGAACC GCCTCGAGAA GTCCACCCTG
6121  ACCCGCACCG TCGACGGTAC GACCCGTCCG GTGGCGGTAC CCACCGAACC GATCGGCACC
6181  GAGTACGACC GGCAGCTCGA CATGGTTCCC GCGCAGCTGC GCGACCCGGC GGGGCGGGGC
6241  CGGGTGATCG AGGAGGTCCG ACGGACCATC GGCGCCATCG AACGGGTCTA CACCTCGGCC
6301  CGGATCCCCC AGGAGGTCCG GGAGTCGGTG TCGGCGCCGG TGTGACCGCA CCGGGCGGCT
6361  GTCGCCTCAC CCGCTCGCCT TCGTCATCCC TTGCCGCCCC ATCCCGCTCG TCGTCGTCAT
6421  CCCCTGCCGT CTCACCCTGC TCGCCGTCGT CAACCCCTGC CGTCTCACCC TGCTCGGCGT
6481  CGTCAACCCC TTCTCCGGAC CGCCCTGAGA CCCGGACCGG CCCGAGACCC GGACCGGCGG
6541  TCCGCCGAAC CGGCCCGCAC CACGGGAGTC TTCAATGACC AGCCATCCGA TCAGTCACGG
6601  CGCCCCGCTC TCCGGCGCGA GTACCGCCCC GGTCACCTCG GTGGTCTTCG ACCTCGACGG
6661  TGTCCTCGTC AACAGCTTCG CGGTGATGCG CGAGGCGTTC ACGCTCGCCT ACGCCGAGGT
6721  CGTCGGCGAG GGTGAGCCAC CCTTCGAGGA GTACAACCGG CATCTGGGCC GCTACTTCCC
6781  CGACATCATG CGGATCATGG GTCTTCCGCT GGAGATGGAG GCCCCGTTCG TCCGCGAGAG
6841  CTACCGGCTC GCCCACCTGG TGGAGATGTT CGACGGTGTG CCCGAGCTGC TGTCGGAGTT
6901  ACGCCACCGC GGGCTGCGGC TCGCCGTGGC CACCGGGAAG AGCGGACCCC GGGCGCGTTC
6961  GCTGCTCGAC ACGCTGGGCA TCCGTGGCCA GTTCCACGTG GTCCTCGGCT CCGACGAGGT
7021  GGCGCGGCCC AAGCCCGCGC CGGACATCGT GCTGAAGGCG ATGGACCTGA TGGACGCCGA
7081  TCCCGACCGA ACCGTGATGG TCGGGACGC GGTGACCGAC CTGGCCAGCG CGCGGGGGC
7141  CGGGATCACC GCCGTGGCGG CGATGTGGGG TGAGACCGAC GAGAAGACGC TGCTCGCGGC
```

-continued

SEQUENCE ID NOS: 1-3

```
7201  GGAGCCCGAT GTGATCCTGC ACAAACCCGC CGAACTGCTG GCGCTCTGCC CCGAGGTGAC
7261  GGCTCCGTAG CTCCGCGCGC CACGTCCGTG CAGGTACCTC CACCGGGGCT TTCGCCGCCG
7321  TGTCACACGC CGTGGTGGCT CACCCGGCCC GCGCCTGCCG CCGGTGCGCC CGGCCGGCGT
7381  TCGCCTCCCC GCCGTCTCCC GGCGGTGTGG CCGGTCACTG ATCAAGACGC GCACCCCCGT
7441  ACGTCACCGG CCGGGCGGGG GGTGACGGTG GTGACGTACG GGACACGACG GGCGGTCGCT
7501  GATTGGCCCG CCACCCGCCG TGTCCCGCAT CATCGTTGGG CTCAGCCCGC CAGCCGCACG
7561  GGTTCTGCGG CCTTCTCGGC CGCGGCCAGC AGTGCGGTGA TCTCCTCACG GGCGCGGGCC
7621  ACACGGGAGC GCACGGTGCC GATGGGGCAG CCGGTCGCGG TGGCGGCGTC CGCGTACGGC
7681  AGGCCGAGTA CCGTGGTGAG GAGGAACATC TCGCGGCGCG CCGGGGCGAG CCCAGCCAGC
7741  AGGTCCATCA GCGCCACCCC CTCGTCGAAC CCGGGGAGCC CGACGGGCTG CGCCCGTTCG
7801  GCCACCTCCT GCCAGTCGTC CGACTCCAGG GTGCGGGGGC GGGCGGCGGT CATGCGGTAG
7861  CGGTCGACGA CCACCCGGCG GGCGATCGAC AGCAGCCAGG TGCGGGCCGA TGAGCGGCCG
7921  GCGAAGCGCG AGAGTCCGGT CAGCGCCCGC AGATACGTCT CCTGGGCGAG GTCCTCACAG
7981  CCGTGGGGGT CGGCGCTGAG ATGGAGTACG AAGCGGCGCA CATCGCGGTA GGTGGCGCGG
8041  ATGAAGTGGT CGACCGCGTC GCGGTCGCCG TCACGGGCGG CCAGCGCCCA TGCGGTGACC
8101  TGGCGGTCGT TCGCCGCGGT GGTGAAGCCG TGCATGGCTC TCATCGGTGC GGCGGGCAGC
8161  GTGGCGGAAG GCATCGTCAC ACGTCCTTCG GGTGGCGGTG AACGGCACAC CGGCATGCGC
8221  CACCGGCCGC GCGCGGGCGC GGCGGGGCGG CGAGGAGCCG GCGGTGCCGA CGGATGGGGC
8281  CGACGCCGGG CAGGCGCCGG TACTCCGCCC GTCAACCGGC ACTCACCCCA GGTCGGGGCG
8341  GGGGAAGGAC GGGCGGTTCA GCGGACGGCG AACCGCCTCG GTGGCCCTCT GCGGAGAATG
8401  GCGTGCCGTA GCAGAACTCC GCGCGCCGG CGGGCGAAGG CCGGTGCGGA CGGCCATGCG
8461  GGCAGCGGAG TGGCGCCCGC GCCGAGGATG CGCAGGGCGA GGACGAGCGG GACGAACAGC
8521  AGGGCCGCGA GCGCGCGGCC GAGGCGGAAG GCCGCGCGTT CGCCGCGCCA CAGCCACAGT
8581  CCGCAGACCA GCGCGGCGAG CAGGTGGGCC GCGGCCATGC CCGCCCCGCC GGGGCCCGCC
8641  CAGGGCCACG GCAGATGGCC CATCGACGGC GCGGCGGAGG ACATCGCGTC CGCGCCATGG
8701  TGCATGTGGC CCATGGCGCC GCCGCTCATC GGGGCGGTGC CCATGTCCCG CATACCGGGC
8761  ATCCGGTGGC CCATGGCGCT TCCCGCGGCG GGAGCGACGG TCATCTCCGC GAATCGGAAC
8821  GCCATGTGCA GGCCGAGTTG CGCGACCACC GTCGCACCGG TCACGACCAG CGCTCCGCGC
8881  TCGCGCCCGG CGACCCACCA CGCGGCGGCC GTCGTCGCGG CGAACGCGGC GGCCACGGCC
8941  CACACCGGCA GGGCGTCGCT GGACATCAGC GTGTGCCCGA GCGCGGTCAC CACGACGCAC
9001  ACCGCCGCGA ACACGGCGGC TCGTGCGAGA CGGAAGGGTG GCCCGGCGGA CATGGCAGCC
9061  ATGGTGCCAG CCGTCGCCGG TGCGCGTGAC GACGGCTCAA TCTTCATCAC GCCGGTGACA
9121  AGCGTGGCGT GTGGGCCGCC CCCGAATGTG CTCATGTGAG CCAGTTCACA GATGATGCCC
9181  GGAACTCAGC CGTGTGTGCG GCCGACAACT CAACCGGCGG CCCGATATGC GTCCGCCTCC
9241  CGCCGTTGCC CCGAGCCAGG AGTCGTCCAT GTCCGCTGAA CCGCTCGCCC CGGCCACGGG
9301  CGATTCCCCG GATGATGTCG CCGACAGGGA GCCACGCTCC CTCGCCGAGG CCGAGTCCGG
9361  CGGGTCCGGG TCCGGCGGGT CCGTATGGGC GGGCCTGCGG CCGCTGGTGC TGCGGCTGCA
9421  CTTCTACGCG GGGGTGCTGG TCGCGCCGTT CCTGCTGGTC GCGGCGGTGA CCGGACTGCT
```

-continued

SEQUENCE ID NOS: 1-3

```
 9481 GTACGCCGGA TCGTTCCAGG CCGAGAAGCT GGTCTACGCC CACGAGTTGC GCGTCCCCGT
 9541 CGGCGACCGT GAACTGCCGA TCTCCGCACA GGTGGCAGCC GCGCGCAAGG GCCATCCCGA
 9601 GGGTGAGATC AGCGCCGTAC GGCCCTCCCC CGAGGACGGC GCCACCACCC GGGTGCTGCT
 9661 CTCCGGCGTC AAGGGCGTCG ATCCCGACCA CACATTGGCC GTGTTCGTCG ACCCGTACAC
 9721 CGGGAAGGTG CGCGGGGCGC TGGAGCAGTA CGGCTCCACC GGCGCCCTCC CGCTGCGCAC
 9781 CTGGATCGAT GAGTTCCACC GCGATCTGCA CCTCGGGCAG ACCGGCCGCC TCTACAGCGA
 9841 ACTCGCCGCC AGCTGGCTGT GGGTCATCGC CCTCGGCGGT GTGGTGCTCT GGCTCAGCCG
 9901 TCGCCGTAAG AAGCGCACGC TGCGGGCGGT CGCGCTGCCC GACCGCGCCG CCACCGGCCG
 9961 CAAGCGCACC ATGTCCTTCC ATGGCGCGGT GGGGCTGTGG GTGGCGCTCG GCTGCTGTT
10021 CCTGTCCGCC ACCGGCCTGA CCTGGTCCAC CTACGCGGGG GCCAACGTGG AGGACCTGCG
10081 CACCGCCCTC GGCCAGACCA CCCCGACCGT GTCGGCCACG GTCGGCGGCG GTGAACACGC
10141 CGGACACCAC ATGGGTTCCG GTTCCATGCC GGGCATGGAC ATGGGCGGTA CGGGCGAGGC
10201 GGCCGGGCAC ACCGCCGATG CGGGCCTGGA CACCGTGCTG GCGGCCGCCC GCGCCAAGGA
10261 CCTGGACAAC CCCGTCGAGA TCGTCCCGCC CGCCGAGCCG GGCAGTGCGT ATGTCGTCAG
10321 CCAGATCCAG CGGAGCTGGC CCGAGAAGCA GGACTCGGTG GCCGTCGACC CGGCCACGGG
10381 CGAGGTGACC GACGTCCAGC GGTTCGCCGA CTACCCGGTG CTCGCCAAGC TCACCCGCTG
10441 GGGCATCGAC CTCCACACCG GAAACCTCTT CGGCCTCGTC AATCAGATCG CCCTGGCCGC
10501 TCTCGCGCTC GCGCTGATCC TTCTGATCGT CTGGGGCTAT CGCATGTGGT GGCAGCGCGG
10561 TCGCGCCTCC GCCTTCGGCC GCCCGATCCC CCGCGGCGCG TGGCGGCGGG TACCGCTGTA
10621 CGTCCTCGTC CCCCTGGCCG CGGCCACCGC CGTGATCGGC TACTACCTGC CCCTCCTCGG
10681 TATCCCGCTC GCGACCTTCC TGGCCGTCGA CATCGTCGCG GGCGAGATCG CCCGCCGGCG
10741 CCGCGCCGCC CCCGCCGCCT GACCATCGCT TTGCCATCTC GGCAACAAGC TTTGCGCTCA
10801 C
```

Although the present invention has been described in detail with reference to specific embodiments, those of skill in the art will recognize that modifications and improvements are within the scope and spirit of the invention, as set forth in the claims which follow. All publications and patent documents cited herein are incorporated herein by reference as if each such publication or document was specifically and individually indicated to be incorporated herein by reference. Citation of publications and patent documents is not intended as an admission that any such document is pertinent prior art, nor does it constitute any admission as to the contents or date of the same. The invention having now been described by way of written description and example, those of skill in the art will recognize that the invention can be practiced in a variety of embodiments and that the foregoing description and examples are for purposes of illustration and not limitation of the following claims.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07671190B2). An electronic copy of the "Sequence Listing" will also be available from the USPTO upon request and payment of the fee set forth in 37 CFR 1.19(b)(3).

The invention claimed is:

1. An isolated nucleic acid molecule comprising a polynucleotide sequence encoding the polypeptide amino acid sequence depicted in SEQ ID NO:150.

2. The isolated nucleic acid molecule according to claim 1 wherein said polynucleotide comprises the sequence of nucleotides from position 4058 to position 5221 of SEQ ID NO:3.

3. A recombinant vector comprising the isolated nucleic acid molecule of claim 1.

4. An isolated recombinant host cell comprising the vector of claim 3.

5. A method of making an isolated polypeptide comprising:
 (a) culturing the isolated recombinant host cell of claim 4 under conditions such that said polypeptide is expressed; and
 (b) recovering said polypeptide.

6. The isolated nucleic acid molecule of claim 1 wherein said nucleic acid sequence further comprises a heterologous nucleic acid sequence.

7. An isolated nucleic acid molecule comprising a polynucleotide, the nucleic acid sequence of which is at least 95.0% identical to the polynucleotide sequence of claim 2, and wherein said polynucleotide encodes a polypeptide that functions as an AHBA (3-amino-5-hydroxy benzoic acid) synthase.

8. An isolated nucleic acid molecule comprising a polynucleotide that encodes a polypeptide comprising an amino acid sequence that is at least 95.0% identical to SEQ ID NO:150, and wherein said polypeptide functions as an AHBA (3-amino-5-hydroxy benzoic acid) synthase.

9. An isolated nucleic acid molecule, wherein said molecule comprises at least 500 contiguous nucleotides of the sequence of nucleotides from position 4058 to position 5221 of SEQ ID NO:3.

10. An isolated nucleic acid molecule that comprises the exact complement of the sequence of nucleotides from position 4058 to position 5221 of SEQ ID NO:3.

* * * * *